United States Patent
Reddy et al.

(10) Patent No.: US 8,293,747 B2
(45) Date of Patent: Oct. 23, 2012

(54) HETEROCYCLIC AMIDE COMPOUNDS AS PROTEIN KINASE INHIBITORS

(75) Inventors: Panduranga Adulla P. Reddy, Walpole, MA (US); Lianyun Zhao, Burlington, MA (US); Praveen K. Tadikonda, Norwood, MA (US); Tzu Tshin Wong, Belmont, MA (US); Shuyi Tang, Belmont, MA (US); Luis E. Torres, Medford, MA (US); David F. Cauble, Jr., Cambridge, MA (US); Timothy J. Guzi, Sudbury, MA (US); M. Arshad Siddiqui, Newton, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 252 days.

(21) Appl. No.: 12/669,334

(22) PCT Filed: Jul. 17, 2008

(86) PCT No.: PCT/US2008/008749
§ 371 (c)(1),
(2), (4) Date: Jul. 15, 2010

(87) PCT Pub. No.: WO2009/014637
PCT Pub. Date: Jan. 29, 2009

(65) Prior Publication Data
US 2010/0286135 A1    Nov. 11, 2010

Related U.S. Application Data

(60) Provisional application No. 60/950,709, filed on Jul. 19, 2007.

(51) Int. Cl.
| | |
|---|---|
| *A61K 31/506* | (2006.01) |
| *C07D 401/14* | (2006.01) |
| *A61K 31/496* | (2006.01) |
| *A61K 31/497* | (2006.01) |
| *A61K 31/519* | (2006.01) |
| *C07D 405/14* | (2006.01) |
| *C07D 409/14* | (2006.01) |
| *C07D 413/14* | (2006.01) |
| *C07D 417/14* | (2006.01) |
| *C07D 471/04* | (2006.01) |
| *C07D 487/04* | (2006.01) |
| *C07D 491/04* | (2006.01) |

(52) U.S. Cl. .................... 514/252.18; 544/295; 544/121; 544/263; 544/280; 544/357; 544/362; 544/363; 544/364; 546/194

(58) Field of Classification Search .................... None
See application file for complete search history.

(56) References Cited

U.S. PATENT DOCUMENTS
2005/0222410 A1* 10/2005 Stokes et al. .................. 544/124
2006/0089403 A1*  4/2006 Fertig et al. ................... 514/448

FOREIGN PATENT DOCUMENTS
| WO | 01/55115 | * | 8/2001 |
| WO | 2006/053227 | * | 5/2006 |
| WO | 2008/106692 | * | 9/2008 |

OTHER PUBLICATIONS

Vandromme et al. SynLett. No. 20, pp. 3423-3426 (2006).*

* cited by examiner

*Primary Examiner* — Emily Bernhardt
(74) *Attorney, Agent, or Firm* — Peter Haeberli; David A. Muthard

(57) ABSTRACT

The present invention relates to novel heterocyclic amide compounds of Formula I: as disclosed herein or a pharmaceutically acceptable salt, solvate, ester, prodrug or stereoisomer thereof. Also disclosed are compositions comprising said compounds, and methods for using said compounds for treating or preventing a proliferative disease, an anti-proliferative disorder, inflammation, arthritis, a neurological or neurodegenerative disease, a cardiovascular disease, alopecia, a neuronal disease, an ischemic injury, a viral disease or a fungal disease.

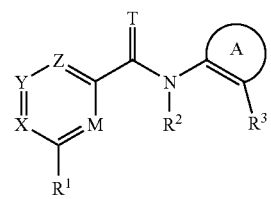

(I)

2 Claims, No Drawings

HETEROCYCLIC AMIDE COMPOUNDS AS PROTEIN KINASE INHIBITORS

CROSS-REFERENCE TO RELATED APPLICATIONS

This application claims the priority of U.S. Provisional Application No. 60/950,709, filed Jul. 19, 2007.

FIELD OF THE INVENTION

The present invention relates to compounds useful as protein kinase inhibitors, regulators or modulators, pharmaceutical compositions comprising the compounds, and methods of treatment using the compounds and compositions to treat various diseases such as cancer, inflammation, arthritis, viral diseases, neurodegenerative diseases such as Alzheimer's disease, cardiovascular diseases, and fungal diseases.

BACKGROUND OF THE INVENTION

Protein kinases are a family of enzymes that catalyze phosphorylation of proteins, in particular the hydroxyl group of specific tyrosine, serine, or threonine residues in proteins. Protein kinases are pivotal in the regulation of a wide variety of cellular processes, including metabolism, cell proliferation, cell differentiation, and cell survival. Uncontrolled proliferation is a hallmark of cancer cells, and can be manifested by a deregulation of the cell division cycle in one of two ways—making stimulatory genes hyperactive or inhibitory genes inactive. Protein kinase inhibitors, regulators or modulators alter the function of kinases such as cyclin-dependent kinases (CDKs), mitogen activated protein kinase (MAPK/ERK), glycogen synthase kinase 3 (GSK3beta), Checkpoint (Chk) (e.g., CHK-1, CHK-2 etc.) kinases, AKT kinases, PDK-1, JNK, and the like. Examples of protein kinase inhibitors are described in WO02/22610 A1 and by Y. Mettey et al., in *J. Med. Chem.*, 46:222-236 (2003).

The cyclin-dependent kinases are serine/threonine protein kinases, which are the driving force behind the cell cycle and cell proliferation. Misregulation of CDK function occurs with high frequency in many important solid tumors. Individual CDK's, such as, CDK1, CDK2, CDK3, CDK4, CDK5, CDK6 and CDK7, CDK8 and the like, perform distinct roles in cell cycle progression and can be classified as either GIS, or G2M phase enzymes. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over—or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development of cancer treatments.

A number of adenosine 5'-triphosphate (ATP) competitive small organic molecules as well as peptides have been reported in the literature as CDK inhibitors for the potential treatment of cancers. U.S. Pat. No. 6,413,974, col. 1, line 23-col. 15, line 10 offers a good description of the various CDKs and their relationship to various types of cancer. Flavopiridol (shown below) is a nonselective CDK inhibitor that is currently undergoing human clinical trials, A. M. Sanderowicz et al., *J. Clin. Oncol.* 16:2986-2999 (1998).

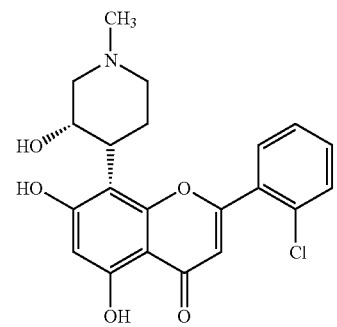

Other known inhibitors of CDKs include, for example, olomoucine (J. Vesely et al., *Eur. J. Biochem.*, 224:771-786 (1994)) and roscovitine (I. Meijer et al., *Eur. J. Biochem.*, 243:527-536 (1997)). U.S. Pat. No. 6,107,305 describes certain pyrazolo[3,4-b] pyridine compounds as CDK inhibitors. An illustrative compound from the '305 patent is:

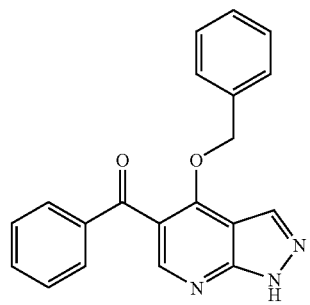

K. S. Kim et al., *J. Med. Chem.* 45:3905-3927 (2002) and WO 02/10162 disclose certain aminothiazole compounds as CDK inhibitors.

Another series of protein kinases are those that play an important role as a checkpoint in cell cycle progression. Checkpoints prevent cell cycle progression at inappropriate times, such as in response to DNA damage, and maintain the metabolic balance of cells while the cell is arrested, and in some instances can induce apoptosis (programmed cell death) when the requirements of the checkpoint have not been met. Checkpoint control can occur in the G1 phase (prior to DNA synthesis) and in G2, prior to entry into mitosis.

One series of checkpoints monitors the integrity of the genome and, upon sensing DNA damage, these "DNA damage checkpoints" block cell cycle progression in $G_1$ & $G_2$ phases, and slow progression through S phase. This action enables DNA repair processes to complete their tasks before replication of the genome and subsequent separation of this genetic material into new daughter cells takes place. Inactivation of CHK1 has been shown to transduce signals from the DNA-damage sensory complex to inhibit activation of the cyclin B/Cdc2 kinase, which promotes mitotic entry, and abrogate G.sub.2 arrest induced by DNA damage inflicted by either anticancer agents or endogenous DNA damage, as well as result in preferential killing of the resulting checkpoint defective cells. See, e.g., Peng et al., *Science*, 277:1501-1505 (1997); Sanchez et al., *Science*, 277:1497-1501 (1997); Nurse, *Cell*, 91:865-867 (1997); Weinert, *Science*, 277:1450-1451 (1997); Walworth et al., *Nature*, 363:368-371 (1993); and Al-Khodairy et al., *Molec. Biol. Cell.*, 5:147-160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK1 as a pivotal target in DNA-damage checkpoint control. The elucidation of inhibitors of this and functionally related kinases such as CDS1/CHK2, a kinase recently discovered to cooperate with CHK1 in regulating S phase progression (see Zeng et al., *Nature*, 395:507-510 (1998); Matsuoka, *Science*, 282:1893-1897 (1998)), could provide valuable new therapeutic entities for the treatment of cancer.

Another group of kinases are the tyrosine kinases. Tyrosine kinases can be of the receptor type (having extracellular, transmembrane and intracellular domains) or the non-receptor type (being wholly intracellular). Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3 and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, IR, and IR-R. The PDGF subfamily includes the PDGF-alpha and beta receptors, CSFIR, c-kit and FLK-II. The FLK family is comprised of the kinase insert domain receptor (KDR), fetal liver kinase-1(FLK-1), fetal liver kinase-4 (FLK-4) and the fms-like tyrosine kinase-1 (flt-1). For detailed discussion of the receptor-type tyrosine kinases, see Plowman et al., *DN&P* 7(6):334-339, 1994.

At least one of the non-receptor protein tyrosine kinases, namely, LCK, is believed to mediate the transduction in T-cells of a signal from the interaction of a cell-surface protein (Cd4) with a cross-linked anti-Cd4 antibody. A more detailed discussion of non-receptor tyrosine kinases is provided in Bolen, *Oncogene*, 8:2025-2031 (1993). The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, *Oncogene*, 8:2025-2031 (1993).

In addition to its role in cell-cycle control, protein kinases also play a crucial role in angiogenesis, which is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. On the other hand, unwanted angiogenesis is a hallmark of several diseases, such as retinopathies, psoriasis, rheumatoid arthritis, age-related macular degeneration, and cancer (solid tumors). Protein kinases which have been shown to be involved in the angiogenic process include three members of the growth factor receptor tyrosine kinase family; VEGF-R2 (vascular endothelial growth factor receptor 2, also known as KDR (kinase insert domain receptor) and as FLK 1); FGF-R (fibroblast growth factor receptor); and TEK (also known as Tie-2).

VEGF-R2, which is expressed only on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al, *Cancer Res.*, 56:3540-3545 (1996)), as has been shown with mutants of VEGF-R2 which fail to mediate signal transduction. Millauer et al, *Cancer Res.*, 56:1615-1620 (1996). Furthermore, VEGF-R2 appears to have no function in the adult beyond that of mediating the angiogenic activity of VEGF. Therefore, a selective inhibitor of the kinase activity of VEGF-R2 would be expected to exhibit little toxicity.

Similarly, FGFR binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. Yoshiji et al., *Cancer Research*, 57: 3924-3928 (1997). Unlike VEGF-R2, however, FGF-R is expressed in a number of different cell types throughout the body and may or may not play important roles in other normal physiological processes in the adult. Nonetheless, systemic administration of a small molecule inhibitor of the kinase activity of FGF-R has been reported to block bFGF-induced angiogenesis in mice without apparent toxicity. Mohammad et al., *EMBO Journal*, 17:5996-5904 (1998).

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre et al., *Science*, 277:55-60 (1997).

The kinase, JNK, belongs to the mitogen-activated protein kinase (MAPK) superfamily. JNK plays a crucial role in inflammatory responses, stress responses, cell proliferation, apoptosis, and tumorigenesis. JNK kinase activity can be activated by various stimuli, including the proinflammatory cytokines (TNF-alpha and interleukin-1), lymphocyte costimulatory receptors (CD28 and CD40), DNA-damaging chemicals, radiation, and Fas signaling. Results from the JNK knockout mice indicate that JNK is involved in apoptosis induction and T helper cell differentiation.

Pim-1 is a small serine/threonine kinase. Elevated expression levels of Pim-1 have been detected in lymphoid and myeloid malignancies, and recently Pim-1 was identified as a prognostic marker in prostate cancer. K. Peltola, "Signaling in Cancer: Pim-1 Kinase and its Partners", Annales Universitatis Turkuensis, Sarja—Ser. D Osa—Tom. 616, (Aug. 30, 2005), http://kirjasto.utu.fi/julkaisupalvelut/annaalit/2004/D616.html Pim-1 acts as a cell survival factor and may prevent apoptosis in malignant cells. K. Petersen Shay et al., *Molecular Cancer Research* 3:170-181 (2005).

Aurora kinases (Aurora-A, Aurora-B, Aurora-C) are serine/threonine protein kinases that have been implicated in human cancer, such as colon, breast and other solid tumors. Aurora-A (also sometimes referred to as AIK) is believed to be involved in protein phosphorylation events that regulate the cell cycle. Specifically, Aurora-A may play a role in controlling the accurate segregation of chromosomes during mitosis. Misregulation of the cell cycle can lead to cellular proliferation and other abnormalities. In human colon cancer tissue, Aurora-A, Aurora-B, Aurora-C have been found to be overexpressed (see Bischoff et al., EMBO J., 17:3052-3065 (1998); Schumacher et al., J. Cell Biol. 143:1635-1646 (1998); Kimura et al., J. Biol. Chem., 272:13766-13771 (1997)).

c-Met is a proto-oncogene that encodes for a tyrosine kinase receptor for hepatocyte growth factor/scatter factor (HGF/SF). The c-Met protein is expressed mostly in epithelial cells, and due to its function it is also known as hepatocyte growth factor receptor, or HGFR. When HGF/SF activates c-Met, the latter in turn may activate a number of kinase pathways, including the pathway Ras to Raf to Mek to the mitogen-activated protein kinase ERK1 to the transcription factor ETS1. Met signaling has been implicated in the etiology and malignant progression of human cancers (see Birchmeier et al., Nature Reviews Molecular Cell Biology, 4.915-925 (2003); Zhang et al., Journal of Cellular Biochemistry, 88:408-417 (2003); and Paumelle et al,m Oncogene, 21:2309-2310 (2002)).

The AGC sub-family of kinases phosphorylate their substrates at serine and threonine residues and participate in a variety of well-known signaling processes, including, but not limited to cyclic AMP signaling, the response to insulin, apoptosis protection, diacylglycerol signaling, and control of protein translation (Peterson et al., Curr. Biol. 1999, 9, R521). This sub-family includes PKA, PKB (c-Akt), PKC, PRK1, 2, $p70^{S6K}$, and PDK.

AKT (also known as PKB or Rac-PK beta), a serine/threonine protein kinase, has been shown to be overexpressed in several types of cancer and is a mediator of normal cell functions [(Khwaja, A., Nature 1999, 401, 33-34); (Yuan, Z. Q., et al., Oncogene 2000, 19, 2324-2330); (Namikawa, K., et al., J. Neurosci. 2000, 20, 2875-2886,)]. AKT comprises an N-terminal pleckstrin homology (PH) domain, a kinase domain and a C-terminal "tail" region. Three isoforms of human AKT kinase (AKT-1,-2 and-3) have been reported so far [(Cheng, J. Q., Proc. Natl. Acad. Sci. USA 1992, 89, 9267-9271); (Brodbeck, D. et al., J. Biol. Chem. 1999, 274, 9133-9136)]. The PH domain binds 3-phosphoinositides, which are synthesized by phosphatidyl inositol 3-kinase (PI3K) upon stimulation by growth factors such as platelet derived growth factor (PDGF), nerve growth factor (NGF) and insulin-like growth factor (IGF-1) [(Kulik et al., Mol. Cell. Biol., 1997, 17, 1595-1606,); (Hemmings, B. A., Science, 1997, 275, 628-630)]. Lipid binding to the PH domain promotes translocation of AKT to the plasma membrane and facilitates phosphorylation by another PH-domain-containing protein kinases, PDK1 at Thr308, Thr309, and Thr305 for the AKT isoforms 1, 2 and 3, respectively. A second, as of yet unknown, kinase is required for the phosphorylation of Ser473, Ser474 or Ser472 in the C-terminal tails of AKT-1,-2 and-3 respectively, in order to yield a fully activated AKT enzyme.

Once localized to the membrane, AKT mediates several functions within the cell including the metabolic effects of insulin (Calera, M. R. et al., J. Biol. Chem. 1998, 273, 7201-7204) induction of differentiation and/or proliferation, protein synthesis and stress responses (Alessi, D. R. et al., Curr. Opin. Genet. Dev. 1998, 8, 55-62,).

Manifestations of altered AKT regulation appear in both injury and disease, the most important role being in cancer. The first account of AKT was in association with human ovarian carcinomas where expression of AKT was found to be amplified in 15% of cases (Cheng, J. Q. et al., Proc. Natl. Acad. Sci. U.S.A. 1992, 89, 9267-9271). It has also been found to be overexpressed in 12% of pancreatic cancers (Cheng, J. Q. et al., Proc. Natl. Acad. Sci. U.S.A. 1996, 93, 3636-3641). It was demonstrated that AKT-2 was over-expressed in 12% of ovarian carcinomas and that amplification of AKT was especially frequent in 50% of undifferentiated tumours, suggesting that AKT may also be associated with tumour aggressiveness (Bellacosa, et al., Int. J. Cancer 1995, 64, 280-285).

PKA (also known as cAMP-dependent protein kinase) has been shown to regulate many vital functions including energy metabolism, gene transcription, proliferation, differentiation, reproductive function, secretion, neuronal activity, memory, contractility and motility (Beebe, S. J., Semin. Cancer Biol. 1994, 5, 285-294). PKA is a tetrameric holoenzyme, which contains two catalytic subunits bound to a homo-dimeric regulatory subunit (which acts to inhibit the catalytic subunits). On binding of cAMP (enzyme activation), the catalytic subunits dissociate from the regulatory subunits to yield the active serine/threonine kinase (McKnight, G. S. et al., Recent Prog.

Horm. Res. 1988, 44, pp. 307). Three isoforms of the catalytic subunit (C-α, C-β and C-γ) have been reported to date (Beebe, S. J. et al., J. Biol. Chem. 1992, 267, 25505-25512) with the C-α subunit being the most extensively studied, primarily because of its elevated expression in primary and metastatic melanomas (Becker, D. et al., Oncogene 1990, 5, 1133). To date, strategies to modulate the activity of the C-α subunit involve the use of antibodies, molecules that block PKA activity by targeting regulatory dimers and antisense oligonucleotides expression.

The ribosomal protein kinases $p70^{S6K}$-1 and-2 are also members of the AGC sub-family of protein kinases and catalyze the phosphorylation and subsequent activation of the ribosomal protein S6, which has been implicated in the translational up-regulation of mRNAs coding for the components of the protein synthetic apparatus. These mRNAs contain an oligopyrimidine tract at their 5' transcriptional start site, termed a 5'TOP, which has been shown to be essential for their regulation at the translational level (Volarevic, S. et al., Prog. Nucleic Acid Res. Mol. Biol. 2001, 65, 101-186). $p70^{S6K}$ dependent S6 phosphorylation is stimulated in response to a variety of hormones and growth factors primarily via the PI3K pathway (Coffer, P. J. et al., Biochem. Biophys. Res. Commun, 1994 198, 780-786), which may be under the regulation of mTOR, since rapamycin acts to inhibit $p70^{S6K}$ activity and blocks protein synthesis, specifically as a result of a down-regulation of translation of these mRNA's encoding ribosomal proteins (Kuo, C. J. et al., Nature 1992, 358, 70-73).

In vitro PDK1 catalyses the phosphorylation of Thr252 in the activation loop of the p70 catalytic domain, which is indispensable for p70 activity (Alessi, D. R., Curr. Biol., 1998, 8, 69-81). The use of rapamycin and gene deletion studies of dp70S6K from Drosophila and $p70^{S6K}1$ from mouse have established the central role p70 plays in both cell growth and proliferation signaling.

The 3-phosphoinositide-dependent protein kinase-1 (PDK1) plays a key role in regulating the activity of a number of kinases belonging to the AGC subfamily of protein kinases (Alessi, D. et al., *Biochem. Soc. Trans* 2001, 29, 1). These include isoforms of protein kinase B (PKB, also known as AKT), p70 ribosomal S6 kinase (S6K) (Avruch, J. et al., *Prog. Mol. Subcell. Biol.* 2001, 26, 115), and p90 ribosomal S6 kinase (Frodin, M. et al., *EMBO J.* 2000, 19, 2924-2934). PDK1 mediated signaling is activated in response to insulin and growth factors and as a consequence of attachment of the cell to the extracellular matrix (integrin signaling). Once activated these enzymes mediate many diverse cellular events by phosphorylating key regulatory proteins that play important roles controlling processes such as cell survival, growth, proliferation and glucose regulation [(Lawlor, M. A. et al., *J. Cell Sci.* 2001, 114, 2903-2910), (Lawlor, M. A. et al., *EMBO J.* 2002, 21, 3728-3738)]. PDK1 is a 556 amino acid protein, with an N-terminal catalytic domain and a C-terminal pleckstrin homology (PH) domain, which activates its substrates by phosphorylating these kinases at their activation loop (Belham, C. et al., *Curr. Biol.* 1999, 9, R93-R96). Many human cancers including prostate and NSCL have elevated PDK1 signaling pathway function resulting from a number of distinct genetic events such as PTEN mutations or over-expression of certain key regulatory proteins [(Graff, J. R., *Expert Opin. Ther. Targets* 2002, 6, 103-113), (Brognard, J., et al., *Cancer Res.* 2001, 61, 3986-3997)]. Inhibition of PDK1 as a potential mechanism to treat cancer was demonstrated by transfection of a PTEN negative human cancer cell line (U87MG) with antisense oligonucleotides directed against PDK1. The resulting decrease in PDK1 protein levels led to a reduction in cellular proliferation and survival (Flynn, P., et al., *Curr. Biol.* 2000, 10, 1439-1442). Consequently the design of ATP binding site inhibitors of PDK1 offers, amongst other treatments, an attractive target for cancer chemotherapy.

The diverse range of cancer cell genotypes has been attributed to the manifestation of the following six essential alterations in cell physiology: self-sufficiency in growth signaling, evasion of apoptosis, insensitivity to growth-inhibitory signaling, limitless replicative potential, sustained angiogenesis, and tissue invasion leading to metastasis (Hanahan, D. et al., *Cell* 2000, 100, 57-70). PDK1 is a critical mediator of the PI3K signalling pathway, which regulates a multitude of cellular function including growth, proliferation and survival. Consequently, inhibition of this pathway could affect four or more of the six defining requirements for cancer progression. As such it is anticipated that a PDK1 inhibitor will have an effect on the growth of a very wide range of human cancers.

Specifically, increased levels of PI3K pathway activity has been directly associated with the development of a number of human cancers, progression to an aggressive refractory state (acquired resistance to chemotherapies) and poor prognosis. This increased activity has been attributed to a series of key events including decreased activity of negative pathway regulators such as the phosphatase PTEN, activating mutations of positive pathway regulators such as Ras, and overexpression of components of the pathway itself such as PKB, examples include: brain (gliomas), breast, colon, head and neck, kidney, lung, liver, melanoma, ovarian, pancreatic, prostate, sarcoma, thyroid [(Teng, D. H. et al., *Cancer Res.*, 1997 57, 5221-5225), (Brognard, J. et al., *Cancer Res.*, 2001, 61, 3986-3997), (Cheng, J. Q. et al., *Proc. Natl. Acad. Sci.* 1996, 93, 3636-3641), (*Int. J. Cancer* 1995, 64, 280), (Graff, J. R., *Expert Opin. Ther. Targets* 2002, 6, 103-113), (*Am. J. Pathol.* 2001, 159, 431)].

Additionally, decreased pathway function through gene knockout, gene knockdown, dominant negative studies, and small molecule inhibitors of the pathway have been demonstrated to reverse many of the cancer phenotypes in vitro (some studies have also demonstrated a similar effect in vivo) such as block proliferation, reduce viability and sensitize cancer cells to known chemotherapies in a series of cell lines, representing the following cancers: pancreatic [(Cheng, J. Q. et al., *Proc. Natl. Acad. Sci.* 1996, 93, 3636-3641), (*Neoplasia* 2001, 3, 278)], lung [(Brognard, J. et al., *Cancer Res.* 2001, 61, 3986-3997), (*Neoplasia* 2001, 3, 278)], ovarian [(Hayakawa, J. et al., *Cancer Res.* 2000, 60, 5988-5994), (*Neoplasia* 2001, 3, 278)], breast (*Mol. Cancer Ther.* 2002, 1, 707), colon [(*Neoplasia* 2001, 3, 278), (Arico, S. et al., *J. Biol. Chem.* 2002, 277, 27613-27621)], cervical (*Neoplasia* 2001, 3, 278), prostate [(*Endocrinology* 2001, 142, 4795), (Thakkar, H. et al. *J. Biol. Chem.* 2001, 276, 38361-38369), (Chen, X. et al., *Oncogene* 2001, 20, 6073-6083)] and brain (glioblastomas) [(Flynn, P. et al., *Curr. Biol.* 2000, 10, 1439-1442)].

Mitogen-activiated protein kinase-activated protein kinase 2(MAPKAP K2 or MK2) mediates multiple p38 MAPK-dependent cellular responses. MK2 is an important intracellular regulator of the production of cytokines, such as tumor necrosis factor alpha (TNFa), interleukin 6 (Il-6) and interferon gamma (IFNg), that are involved in many actute and chronic inflammatory diseases, e.g. theumatoid arthritis and inflammatory bowel disease. MK2 resides in the nucleus of non-stimulated cells and upon stimulation, it translocates to the cytoplasm and phosphorylates and activates tuberin and HSP27. MK2 is also implicated in heart failure, brain ischemic injury, the regulation of stress resistance and the production of TNF-□ (see Deak et al., *EMBO*. 17:4426-4441 (1998); Shi et al., *Biol. Chem.* 383:1519-1536 (2002); Staklatvala., *Curr. Opin. Pharmacol.* 4:372-377 (2004), and Shiroto et al., *J. Mol. Cardiol.* 38:93-97 (2005)).

International Publication WO 2005/115146 refers to piperazin derivatives and their use in controlling pests.

International Publication WO 2004/002948 refers to amide compounds that are effective in inhibiting interleukin-4 production in type-2 helper T cells useful for treating allergic diseases. International Publication WO 2006/113140 refers to compounds useful for bradykinin B1 receptor antagonism. International Publication WO 2003/045921 refers to heterocyclic amide compounds as apolipoprotein B inhibitors. U.S. Provisional Applications Serial Nos. 60/855,421 and 60/855,422 both filed on Oct. 31, 2006 refer to Anilinopiperazine derivatives and methods of use therefore. U.S. application Ser. No. 11/758,243 filed Jun. 5, 2007 refers to Imidazopyrazines as protein kinase inhibitors.

There is a need for effective inhibitors of protein kinases in order to treat or prevent disease states associated with abnormal cell proliferation. Moreover, it is desirable for kinase inhibitors to possess both high affinities for the target kinase as well as high selectivity versus other protein kinases. Small-molecule compounds that may be readily synthesized and are potent inhibitors of cell proliferation are those, for example, that are inhibitors of one or more protein kinases, such as CHK1, CHK2, VEGF (VEGF-R2), Pim-1, PDK-1, CDKs or CDK/cyclin complexes and both receptor and non-receptor tyrosine kinases.

SUMMARY OF THE INVENTION

In its many embodiments, the present invention provides a novel class of heterocyclic amide compounds, pharmaceutical compositions comprising one or more said compounds, and methods for using said compounds for treating or preventing a proliferative disease, an anti-proliferative disorder, inflammation, arthritis, a neurological or neurodegenerative disease, a cardiovascular disease, alopecia, a neuronal disease, an ischemic injury, a viral disease or a fungal disease.

Accordingly, in one aspect, the present invention provides compounds of Formula (I):

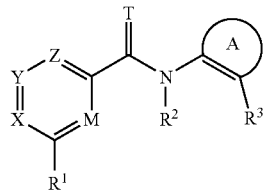

Formula I or a pharmaceutically acceptable salt, or ester thereof;
wherein:

ring A is selected from the group consisting of aryl, and heteroaryl, wherein when each of said aryl and heteroaryl has two substituents on adjacent carbon atoms, said substituents, may optionally be taken together with the carbon atoms to which they are attached to form a five- to six-membered aryl, heterocyclyl, heterocyclenyl, or heteroaryl ring;

M is N or N-oxide;

X, Y, and Z independently are selected from the group consisting of N, N-oxide, and C(R), with the proviso that no more than only one of X, Y, and Z can be N or N-oxide;

T is O, S, or —$NR^4$;

each R independently is selected from the group consisting of H, alkyl, alkenyl, alkynyl, cycloalkyl, heterocyclyl, heterocyclenyl, aryl, heteroaryl, —$NR^4R^5$, hydroxy, alkoxy, —$SR^4$, —S(=O)$R^4$, —S(=O)$_2R^4$, —C(=O)$R^4$, —C(=O)$OR^4$, —C(=O)$NR^4R^5$, —C(=O)$NR^4S(=O)_2R^4$, —C(=O)$NR^4S(=O)_2R^4$, —C(=O)$NR^4S(=O)_2NR^4R^5$, —C(=O)$NR^4S(=O)_2NR^4R^5$, —S(=O)$_2R^4R^5$, —S(=O)$R^4R^5$, —S(=O)$_2NR^4R^5$, —S(=O)$_2OR^4$, —$NR^4C(=O)NR^4R^5$, —$NR^4C(=O)R^4$, —$NR^4C(=O)OR^4$, —$NR^4S(=O)_2NR^4R^5$, —$NR^4S(=O)_2NR^4R^5C(=O)NR^4R^5$, —$NR^4OR^4$, and —$NR^4NR^4R^5$;

$R^1$ is selected from the group consisting of —C(=O)$N(R^4)$aryl, —C(=O)$N(R^4)$heteroaryl, —C(=O)$N(R^4)$heterocyclyl, —C(=O)$N(R^4)$heterocyclenyl, —$N(R^4)C(=O)$aryl, —$N(R^4)C(=O)$heteroaryl, —$N(R^4)C(=O)$heterocyclyl, —$N(R^4)C(=O)$heterocyclenyl, —$N(R^4)C(=O)N(R^4)$aryl, aryl, heterocyclyl, heterocyclenyl, and heteroaryl, wherein each of the $R^1$ heterocyclyl, heterocyclenyl, and heteroaryl, contains at least one nitrogen ring atom, and wherein when each of the $R^1$ heterocyclyl, heterocyclenyl, aryl, heteroaryl, and the "heterocyclyl", "heterocyclenyl", "aryl" and "heteroaryl" portions of —C(=O)$N(R^4)$aryl, —C(=O)$N(R^4)$heteroaryl, —C(=O)$N(R^4)$heterocyclyl, —C(=O)$N(R^4)$heterocyclenyl, —$N(R^4)C(=O)$aryl, —$N(R^4)C(=O)$heteroaryl, —$N(R^4)C(=O)$heterocyclyl, and —$N(R^4)C(=O)$heterocyclenyl has two substituents on adjacent carbon atoms, said substituents, may optionally be taken together with the carbon atoms to which they are attached to form a five- to six-membered cycloalkyl, cycloalkenyl, aryl, heterocyclyl, heterocyclenyl, or heteroaryl ring;

$R^2$ is H or alkyl;

$R^3$ is selected from the group consisting of heterocyclyl, heterocyclenyl, aryl, heteroaryl, —$OR^4$, —$SR^4$, —S(=O)$R^4$, —S(=O)$_2R^4$, and —$NR^4R^5$;

each of $R^4$ and $R^5$ independently is selected from the group consisting of H, alkyl, alkenyl, alkynyl, cycloalkyl, heterocyclyl, heterocyclenyl, aryl, and heteroaryl;

with the proviso that when $R^1$ is morpholinyl, R is other than optionally substituted alkoxy, or optionally substituted —N(alkyl)$_2$.

In another aspect, the present invention provides compounds of Formula (I):

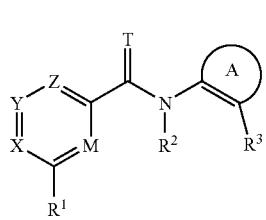

Formula I or a pharmaceutically acceptable salt, or ester thereof;
wherein:

ring A is selected from the group consisting of aryl, and heteroaryl, wherein when each of said aryl and heteroaryl has two substituents on adjacent carbon atoms, said substituents, may optionally be taken together with the carbon atoms to which they are attached to form a five- to six-membered aryl, heterocyclyl, heterocyclenyl, or heteroaryl ring;

M is N or N-oxide;

X, Y, and Z independently are selected from the group consisting of N, N-oxide, and C(R), with the proviso that no more than only one of X, Y, and Z can be N or N-oxide;

T is O, S, or —$NR^4$;

each R independently is selected from the group consisting of H, alkyl, alkenyl, alkynyl, cycloalkyl, heterocyclyl, heterocyclenyl, aryl, heteroaryl, —$NR^4R^5$, hydroxy, alkoxy, —$SR^4$, —S(=O)$R^4$, —S(=O)$_2R^4$, —C(=O)$R^4$, —C(=O)$OR^4$, —C(=O)$NR^4R^5$, —C(=O)$NR^4S(=O)_2R^4$, —C(=O)$NR^4S(=O)_2R^4$, —C(=O)$NR^4S(=O)_2NR^4R^5$, —C(=O)$NR^4S(=O)_2NR^4$, $R^5$, —S(=O)$_2R^4R^5$, —S(=O)$R^4R^5$, —S(=O)$_2NR^4R^5$, —S(=O)$_2OR^4$, —$NR^4C(=O)NR^4R^5$, —$NR^4C(=O)R^4$, —$NR^4C(=O)OR^4$, —$NR^4S(=O)_2NR^4R^5$, —$NR^4S(=O)_2NR^4R^5C(=O)NR^4R^5$, —$NR^4OR^4$, and —$NR^4NR^4R^5$;

$R^1$ is selected from the group consisting of —C(=O)$N(R^4)$aryl, —C(=O)$N(R^4)$heteroaryl, —C(=O)$N(R^4)$heterocyclyl, —C(=O)$N(R^4)$heterocyclenyl, —$N(R^4)C(=O)$aryl, —$N(R^4)C(=O)$heteroaryl, —$N(R^4)C(=O)$heterocyclyl, —$N(R^4)C(=O)$heterocyclenyl, aryl, heterocyclyl, heterocyclenyl, and heteroaryl, wherein each of the $R^1$ heterocyclyl, heterocyclenyl, and heteroaryl, contains at least one nitrogen ring atom, and wherein when each of the $R^1$ heterocyclyl, heterocyclenyl, aryl, heteroaryl, and the "heterocyclyl", "heterocyclenyl", "aryl" and "heteroaryl" portions of —C(=O)$N(R^4)$aryl, —C(=O)$N(R^4)$heteroaryl, —C(=O)$N(R^4)$heterocyclyl, —C(=O)$N(R^4)$heterocyclenyl, —$N(R^4)C(=O)$aryl, —$N(R^4)C(=O)$heteroaryl, —$N(R^4)C(=O)$heterocyclyl, and —$N(R^4)C(=O)$heterocyclenyl has two substituents on adjacent carbon atoms, said substituents, may optionally be taken together with the carbon atoms to which they are attached to form a five- to six-membered cycloalkyl, cycloalkenyl, aryl, heterocyclyl, heterocyclenyl, or heteroaryl ring;

$R^2$ is H or alkyl;

$R^3$ is selected from the group consisting of heterocyclyl, heterocyclenyl, aryl, heteroaryl, —$OR^4$, —$SR^4$, —S(=O)$R^4$, —S(=O)$_2R^4$, and —$NR^4R^5$;

each of $R^4$ and $R^5$ independently is selected from the group consisting of H, alkyl, alkenyl, alkynyl, cycloalkyl, heterocyclyl, heterocyclenyl, aryl, and heteroaryl;

with the proviso that when $R^1$ is morpholinyl, R is other than optionally substituted alkoxy, or optionally substituted —N(alkyl)$_2$.

In one aspect, the compounds of Formula I can be useful as protein kinase inhibitors.

In another aspect, the compounds of Formula I can be useful for treating or preventing proliferative disease, an antiproliferative disorder, inflammation, arthritis, a neurological or neurodegenerative disease, a cardiovascular disease, alopecia, a neuronal disease, an ischemic injury, a viral disease or a fungal disease (each being a "Condition").

In another aspect, the present invention provides pharmaceutical compositions comprising at least one compound of Formula I and a pharmaceutically acceptable carrier. The compositions can be useful for treating or preventing a Condition in a patient.

In still another aspect, the present invention provides methods for treating a Condition in a patient, the method comprising administering to a patient an effective amount of at least one compound of Formula I.

In another aspect, the present invention provides methods for treating a cancer in a patient, the method comprising administering to a patient an effective amount of at least one compound of Formula I and at least one additional anticancer agent which is not a compound of Formula I.

DETAILED DESCRIPTION OF THE INVENTION

In an embodiment, the present invention provides compounds of Formula (I) and or pharmaceutically acceptable salts, solvates, esters and prodrugs thereof. The compounds of formula I can be useful for treating or preventing a Condition in a patient.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, heterocyclyl, heteroaryl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)—cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, heterocyclyl, heteroaryl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond.

Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkyiheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

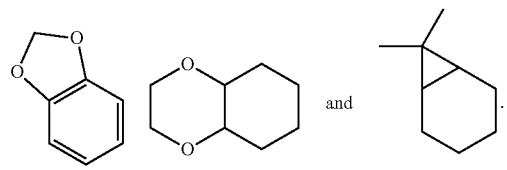

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocycly1" may also mean a single moiety (e.g., carbonyl) which simultaneously replaces two available hydrogens on the same carbon atom on a ring system. Example of such moiety is pyrrolidone:

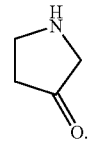

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

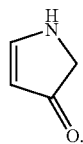

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

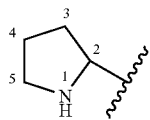

there is no —OH attached directly to carbons marked 2 and 5.

It should also be noted that tautomeric forms such as, for example, the moieties:

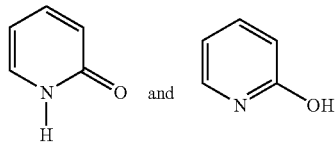

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I-VI, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design,* (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1\text{-}C_8)$alkyl, $(C_2\text{-}C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1\text{-}C_2)$alkylamino$(C_2\text{-}C_3)$alkyl (such as β-dimethylaminoethyl), carbamoyl-$(C_1\text{-}C_2)$alkyl, N,N-di $(C_1\text{-}C_2)$alkylcarbamoyl-(C1-C2)alkyl and piperidino-, pyrrolidino- or morpholino$(C_2\text{-}C_3)$ alkyl, and the like.

Similarly, if a compound of Formula (I) contains an alcohol functional group, a prodrug can be formed by the replacement of the hydrogen atom of the alcohol group with a group such as, for example, $(C_1\text{-}C_6)$alkanoyloxymethyl, 1-$((C_1\text{-}C_6)$alkanoyloxy)ethyl, 1-methyl-1$((C_1\text{-}C_6)$alkanoyloxy)ethyl, $(C_1\text{-}C_6)$alkoxycarbonyloxymethyl, N—$(C_1\text{-}C_6)$alkoxycarbonylaminomethyl, succinoyl, $(C_1\text{-}C_6)$alkanoyl, α-amino$(C_1\text{-}C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1\text{-}C_6)$alkyl$)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1\text{-}C_{10})$alkyl, $(C_3\text{-}C_7)$ cycloalkyl, benzyl, or R-carbonyl is a natural α-aminoacyl or natural α-aminoacyl, —$C(OH)C(O)OY^1$ wherein Y' is H, $(C_1\text{-}C_6)$alkyl or benzyl, —$C(OY^2)Y^3$ wherein $Y^2$ is $(C_1\text{-}C_4)$ alkyl and $Y^3$ is $(C_1\text{-}C_6)$alkyl, carboxy $(C_1\text{-}C_6)$alkyl, amino $(C_1\text{-}C_4)$alkyl or mono-N— or di-N,N—$(C_1\text{-}C_6)$alkylaminoalkyl, —$C(Y^4)Y^5$ wherein $Y^4$ is H or methyl and $Y^5$ is mono-N— or di-N,N—$(C_1\text{-}C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical . association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I-VI can form salts which are also within the scope of this invention. Reference to a compound of Formula I-VI herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I-VI contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I-VI may be formed, for example, by reacting a compound of Formula I-VI with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book (Food & Drug Administration*, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I-VI, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I-VI, and of the salts, solvates, esters and prodrugs of the compounds of Formula I, are intended to be included in the present invention.

The following abbreviations are used below and have the following meanings:
Boc is tert-butoxycarbonyl, dba is dibenzylideneacetone, DMF is N,N-dimethylformamide, DMSO is dimethylsulfoxide, EtOAc is ethyl acetate, LCMS is liquid chromatography mass spectrometry, MeOH is methanol, NMR is nuclear magnetic resonance, PBS is phosphate buffered saline, SPA is scintillation proximity assay, Tf is triflate, TFA is trifluoroacetic acid and Xantphos is 9,9-Dimethyl-4,5-bis(diphenylphosphino)xanthene. Me4Si is tetramethyl silane, DIEA is di isopropyl ethylamine,SGC is silicagel column, TMSCHN2 is trimethylsilyl diazomethane, BBr3 is tribromoborane,m-CPBA is m-chloro perbenzoic acid, CDI is carbodiimidazole,HATU is 2-(1H-azabenzotriazol-1-yl-1,13,3-tetramethyl uranium hexafluorophosphate, NaH is sodium hydride,SiO2 is silica,CBZ is benzyloxy carbonyl, Tos is p-toluene sulfonyl,CH3CN is acetonitrile.

Heterocyclic Amide Compounds of the Invention

The present invention provides a compound of Formula I:

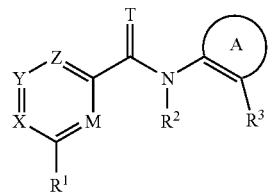

Formula I or a pharmaceutically acceptable salt, solvate, ester, prodrug, or stereoisomer thereof; wherein ring A, M, X, Y, Z, T, $R^1$, $R^2$, and $R^3$ are as defined above for formula (I).

In one embodiment, in Formula I, ring A, in addition to the substituents $-NR^2C(=T)-$(ring comprising M, X, Y, and Z) and $R^3$ as shown, may, optionally with said five- to six-membered aryl, heterocyclyl, heterocyclenyl, or heteroaryl ring, is optionally substituted with one or more substituents selected from the group consisting of halo, cyano, hydroxy, alkoxy, aryloxy, alkyl, $-NR^4R^5$, haloalkyl, haloalkoxy, nitro, aryl, $-C(=O)R^4$, $-C(=O)OR^4$, $-C(=O)NR^4R^5$, $-OC(=O)R^4$, and $-NR^4C(=O)R^4$.

In another embodiment, in Formula I, each of the $R^1$ aryl, heterocyclyl, heterocyclenyl, and heteroaryl, and the "heterocyclyl", "heterocyclenyl", "aryl" and "heteroaryl" portions of $-C(=O)N(R^4)$aryl, $-C(=O)N(R^4)$heteroaryl, $-C(=O)N(R^4)$heterocyclyl, $-C(=O)N(R^4)$heterocyclenyl, $-N(R^4)C(=O)$aryl, $-N(R^4)C(=O)$heteroaryl, $-N(R^4)C(=O)$heterocyclyl, and $-N(R^4)C(=O)$heterocyclenyl optionally with said five- to six-membered cycloalkyl, cycloalkenyl, aryl, heterocyclyl, heterocyclenyl, or heteroaryl ring, is optionally substituted with one or more susbstituents selected from the group consisting of halo, hydroxy, alkoxy, aryloxy, alkyl, $-NR^4R^5$, haloalkyl, haloalkoxy, nitro, aryl, heteroaryl, $-C(=O)R^4$, $-C(=O)OR^4$, $-C(=O)NR^4R^5$, $-OC(=O)R^4$, $-NR^4C(=O)R^4$, $-O$-alkyl-O-alkyl, $-O$-alkyl-O-alkyl-O-alkyl, $-O$-alkyl-heterocyclyl, $-S-R^4$, heterocyclyl, and $-S(=O)_2-R^4$.

In another embodiment, in Formula I, X, Y, and Z are C(R).
In another embodiment, in Formula I, T is O.
In another embodiment, in Formula I, ring A is heteroaryl.
In another embodiment, in Formula I, ring A is pyridyl.
In another embodiment, in Formula I, R is H.
In another embodiment, in Formula I, $R^2$ is H.
In yet another embodiment, in Formula I, $R^3$ is heterocyclyl.

In another embodiment, the compound of formula I is represented by the formula II

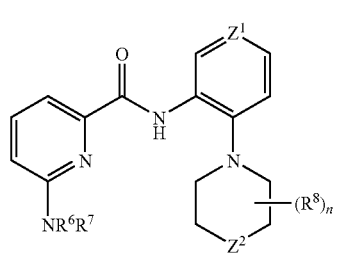

Formula II or a pharmaceutically acceptable salt, solvate, ester, or prodrug thereof, wherein:
$Z^1$ is CH or N;
$Z^2$ is $CH_2$ or NH
$R^6$ and $R^7$ independently are selected from the group consisting of H, heteroaryl, $-C(=O)$aryl, and $-C(=O)$heteroaryl and, or $R^6$ and $R^7$ together with the nitrogen atom to which they are shown attached is heterocyclyl, wherein when said heterocyclyl has two substituents on adjacent carbon atoms, said substituents together with the carbon atoms to which they are attached form a five- to six-membered heterocyclyl, aryl or heteroaryl;
$R^8$ is selected from the group consisting of alkyl, $-NH_2$, $-NH(alkyl)$, and $-N(alkyl)_2$; and
n is 0, 1, or 2.

In another embodiment, in Formula II, —NR$^6$R$^7$ heterocyclyl, optionally with said five- to six-membered heterocyclyl, aryl or heteroaryl is optionally substituted with one or more substituents selected from the group consisting of alkoxy, —O-alkyl-O-alkyl, —O-alkyl-O-alkyl-O-alkyl, —O-alkyl-heterocyclyl, —S-alkyl, heterocyclyl, —C(=O)OH, —C(=O)Oalkyl, —S(=O)$_2$-heterocyclyl, halo, and alkyl.

In another embodiment, in Formula II, Z$^1$ is N.

In another embodiment, in Formula II, Z$^1$ is CH.

In another embodiment, in Formula II, Z$^2$ is CH$_2$.

In another embodiment, in Formula II, Z$^2$ is NH.

In another embodiment, in Formula II, Z$^1$ is N, and Z$^2$ is NH.

In another embodiment, in Formula II, Z$^1$ is N and Z$^2$ is CH$_2$.

In a further embodiment, in Formula II, Z$^1$ is CH and Z$^2$ is CH$_2$.

In one another embodiment, in Formula II, Z$^1$ is N, Z$^2$ is NH, and n is 0.

In another embodiment, in Formula II, Z$^1$ is N and Z$^2$ is CH$_2$, and n is 1.

In another embodiment, in Formula II, Z$^1$ is CH and Z$^2$ is CH$_2$, and n is 1.

In another embodiment, in Formula II, R$^8$ is —NH$_2$.

In another embodiment, in Formula II, Z$^1$ is N and Z$^2$ is CH$_2$, n is 1, and R$^8$ is —NH$_2$.

In another embodiment, in Formula II, Z$^1$ is CH and Z$^2$ is CH$_2$, and n is 1, and R$^8$ is —NH$_2$.

In another embodiment, in Formula II, —NR$^6$R$^7$ is —NHC(=O)aryl. In another embodiment, in Formula II, —NR$^6$R$^7$ is —NHC(=O)aryl, wherein the "aryl" of said —NHC(=O)aryl is is optionally substituted with 1 or more substituents selected from the group consisting of alkyl, alkoxy, haloalkoxy, haloalkyl, and halo.

In another embodiment, in Formula II, said —NR$^6$R$^7$ heterocyclyl optionally with said five- to six-membered heterocyclyl, aryl or heteroaryl is a heterocyclyl optionally fused to either a benzene or pyridine ring. In another embodiment, in Formula II, —NR$^6$R$^7$ is —NH(2-pyrazinyl). In another embodiment, in Formula II, —NR$^6$R$^7$ is selected from the group consisting of:

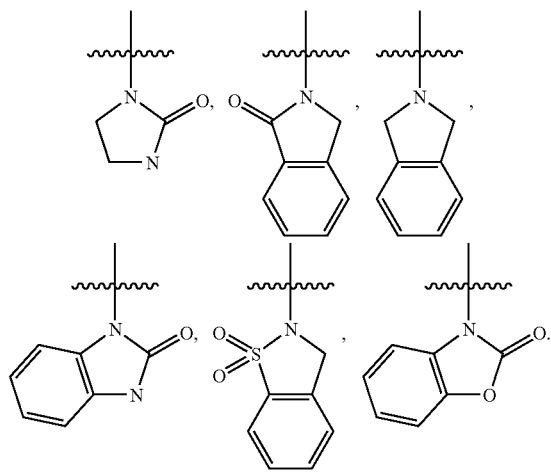

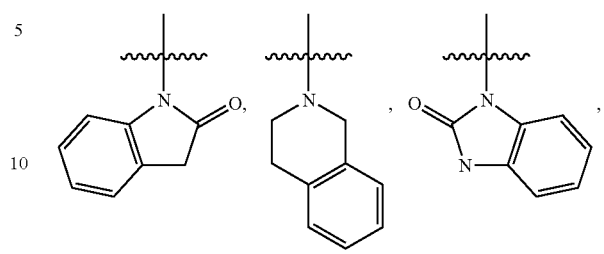

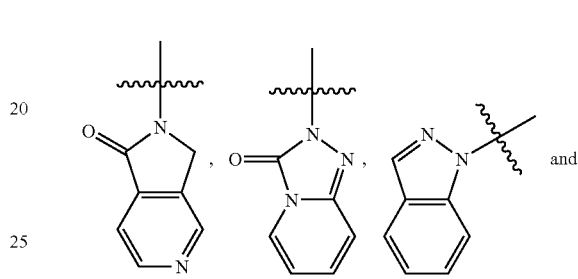

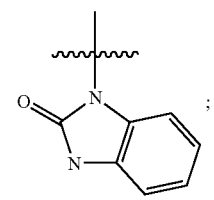

each of which is optionally substituted.

In one another embodiment, in Formula II, said —NR$^6$R$^7$ heterocyclyl optionally with said five- to six-membered heterocyclyl, aryl or heteroaryl is a heterocyclyl optionally fused to either a benzene or pyridine ring, wherein said five- to six-membered heterocyclyl with said optionally fused benzene or pyridine ring is optionally substituted with one or more substituents selected from the group consisting of methyl, methoxy, 4-piperidinyl, —C(=O)OH, —C(=O)OCH$_3$, —S(=O)$_2$-pyrrolidinyl, fluoro, chloro, —CH$_2$CH$_2$-(1-morpholinyl), —OCH$_2$CH$_2$-(1-morpholinyl), —CH$_2$CH$_2$—N(CH$_3$)$_2$, and —OCH$_2$CH$_2$—N(CH$_3$)$_2$.

In one another embodiment, in Formula II, said —NR$^6$R$^7$ heterocyclyl optionally with said five- to six-membered heterocyclyl, aryl or heteroaryl is a heterocyclyl optionally fused to either a benzene or pyridine ring, wherein said five- to six-membered heterocyclyl with said optionally fused benzene or pyridine ring is optionally substituted with one or more substituents selected from the group consisting of methyl, methoxy, 4-piperidinyl, -C(=O)OH, —C(=O)OCH$_3$, —S(=O)$_2$-pyrrolidinyl, fluoro, chloro, —CH$_2$CH$_2$-(1-morpholinyl), —OCH$_2$CH$_2$-(1-morpholinyl), —CH$_2$CH$_2$—N(CH$_3$)$_2$, —OCH$_2$CH$_2$OCH$_3$ and —OCH$_2$CH$_2$—N(CH$_3$)$_2$.

In another embodiment, the compound of Formula II is selected from the group consisting of:

25
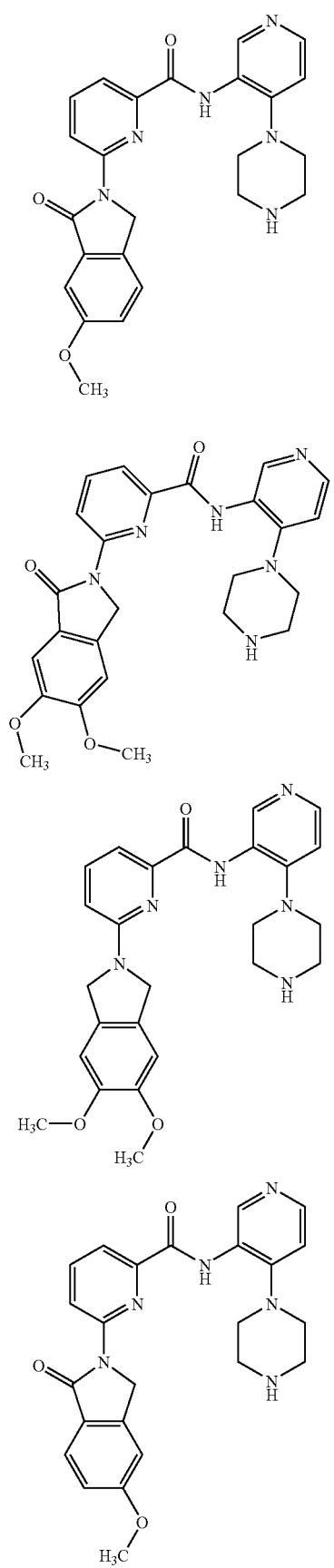
26
-continued
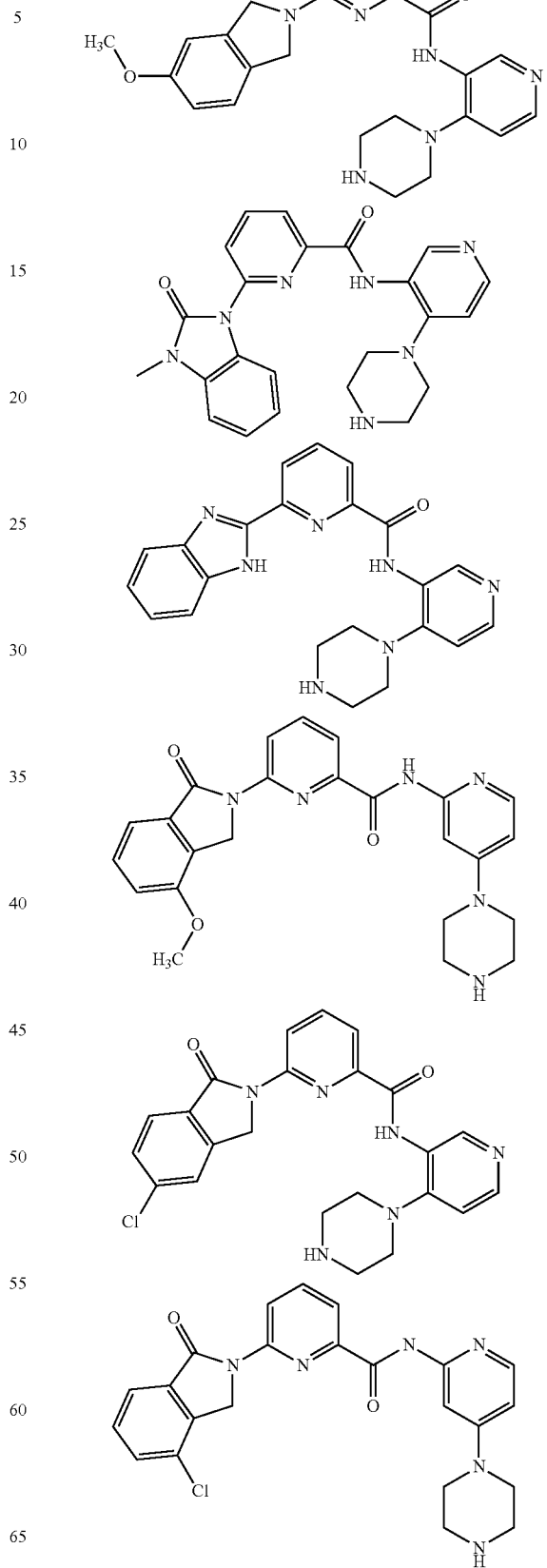

27
-continued
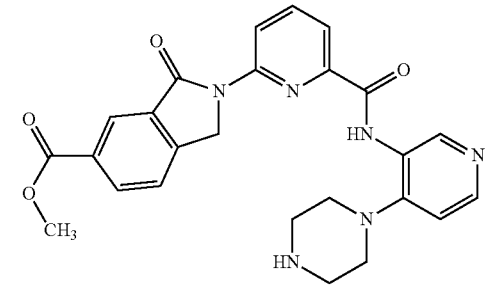
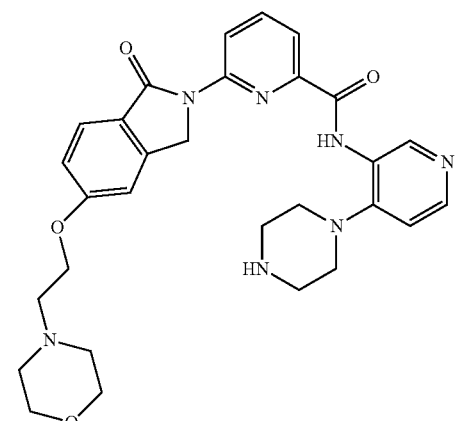
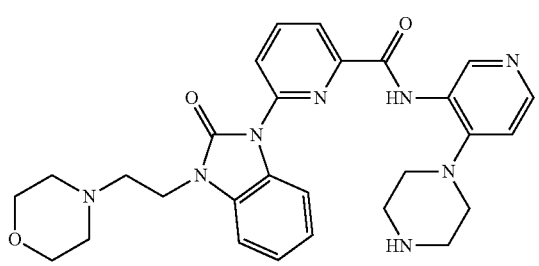
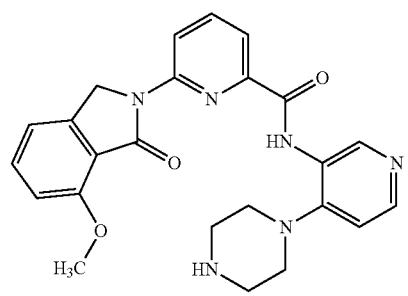
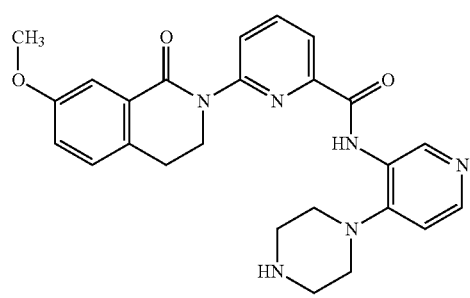
28
-continued
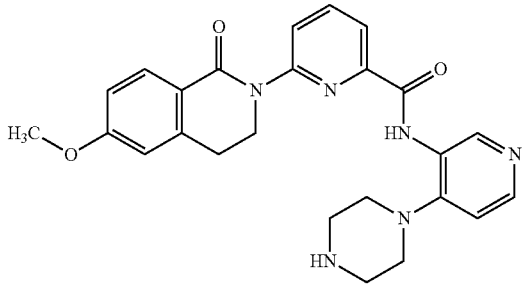
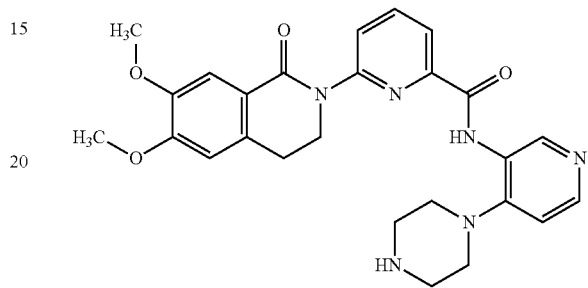
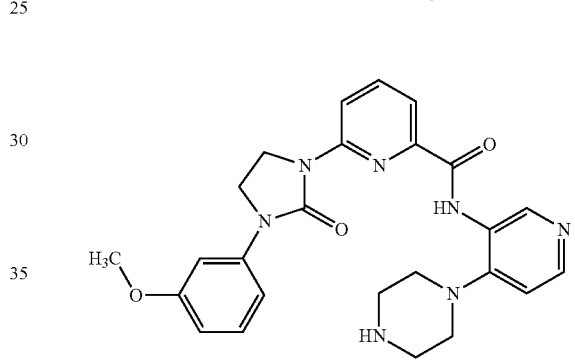
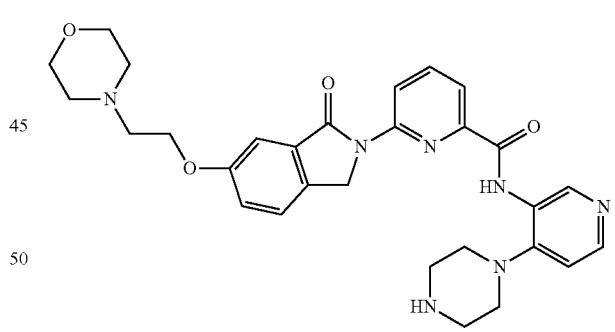
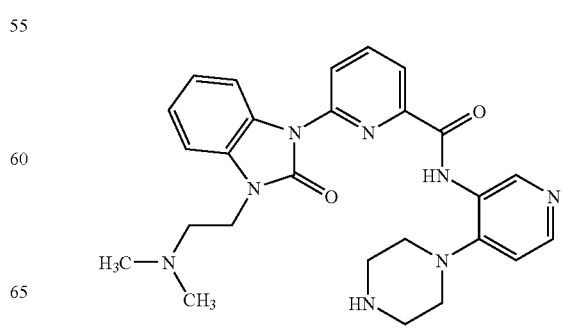

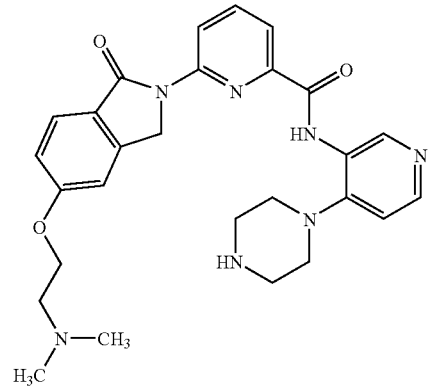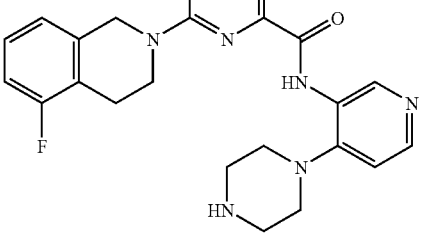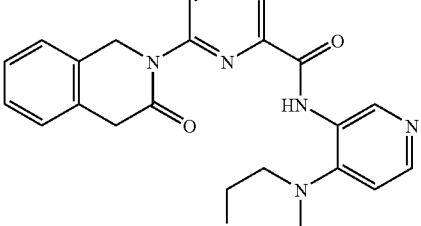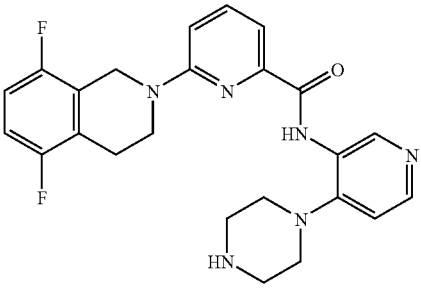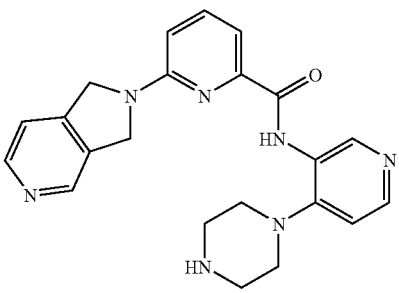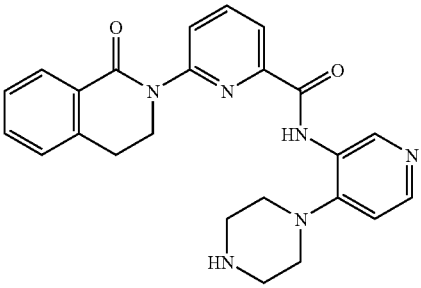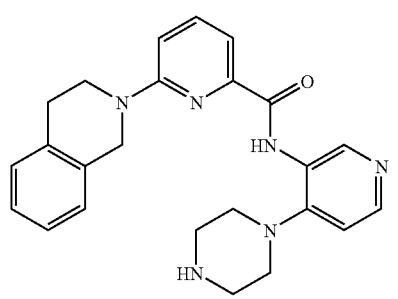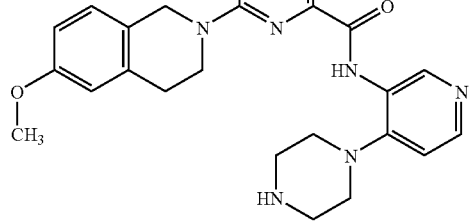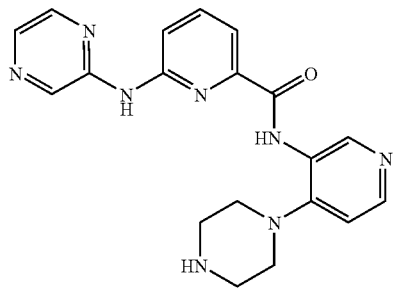

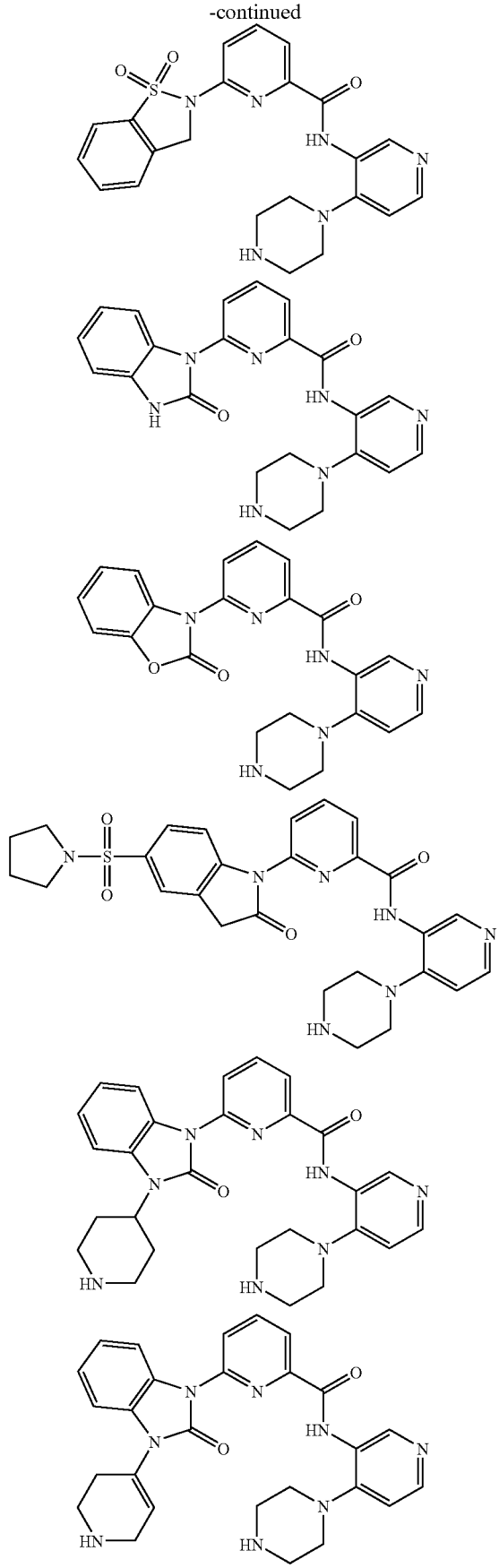
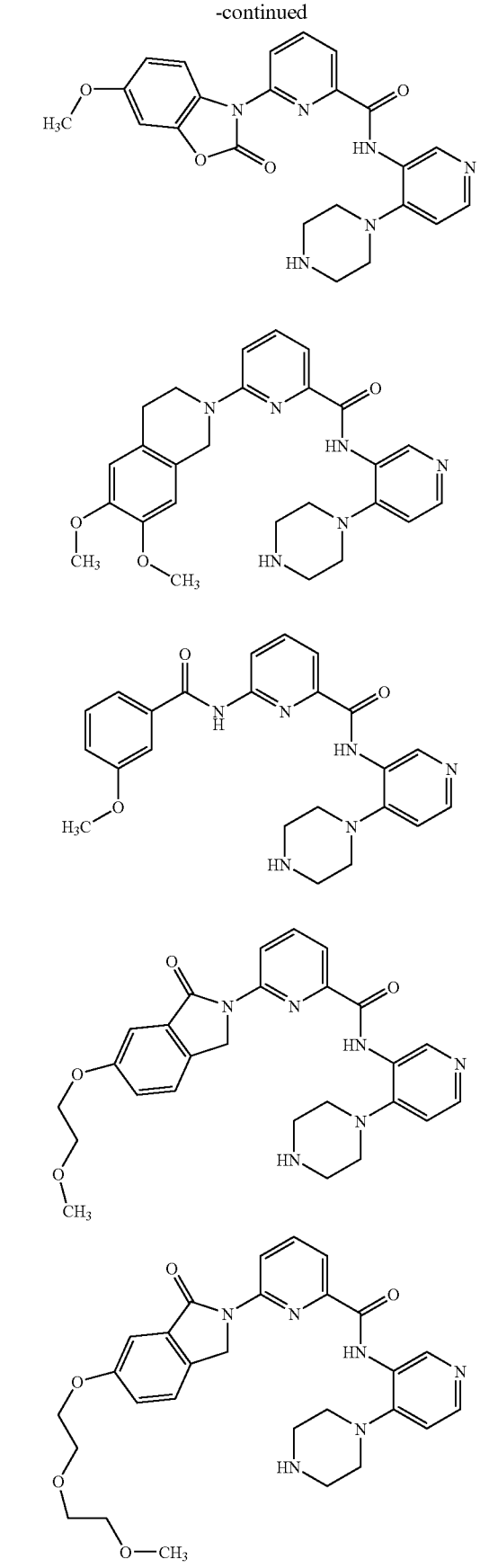

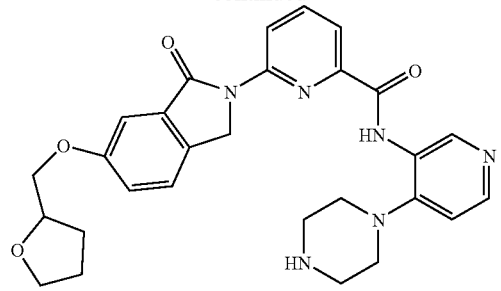
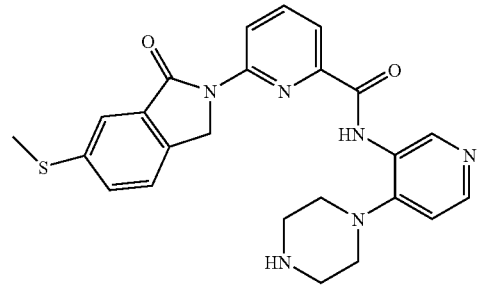
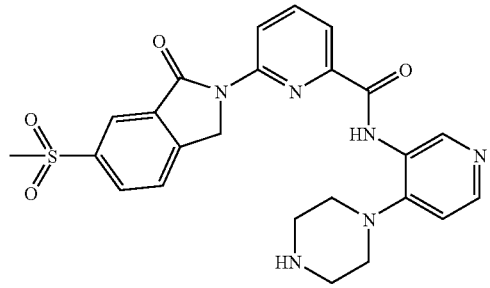
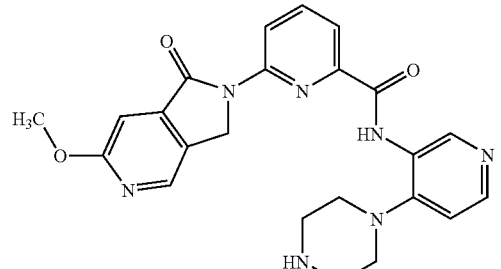
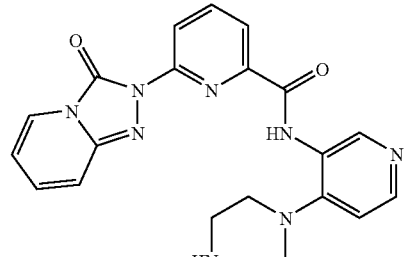
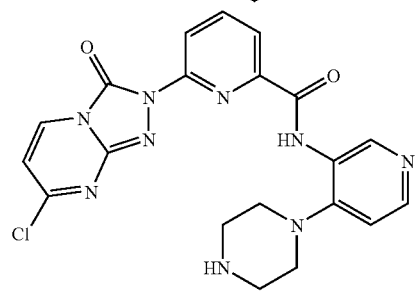
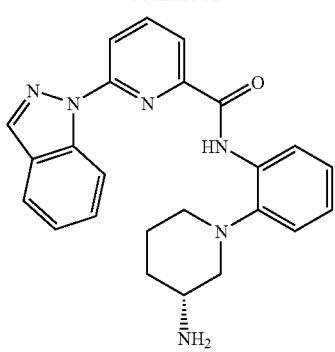
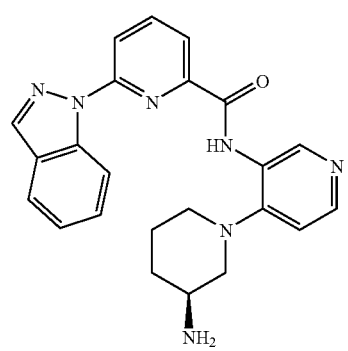
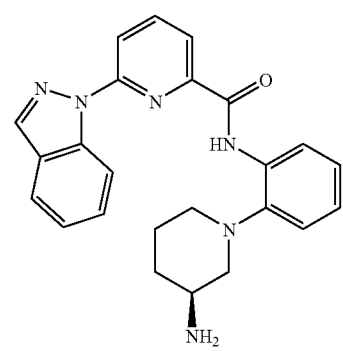
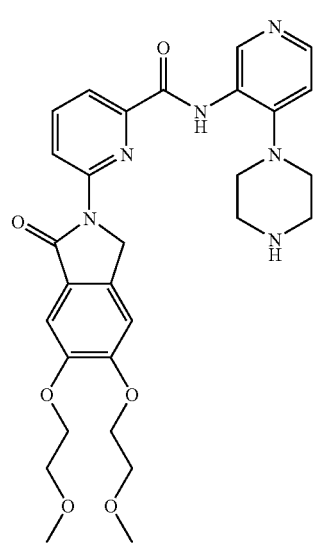

-continued

[chemical structure]

[chemical structure]

and

[chemical structure]

;

or a pharmaceutically acceptable salt, or ester thereof.

In another embodiment, the compound of formula I is represented by the formula IIA:

Formula IIA

[chemical structure]

wherein:
Z$^1$ is CH or N;
Z$^2$ is CH$_2$ or NH
each R$^2$ independently is H or alkyl;

R$^{6a}$ is selected from the group consisting of aryl and heteroaryl;

R$^8$ is selected from the group consisting of alkyl, —NH$_2$, —NH(alkyl), and —N(alkyl)$_2$; and n is 0, 1, or 2.

In another embodiment, in Formula II, Z$^1$ is N.

In another embodiment, in Formula IIA, Z$^1$ is CH.

In another embodiment, in Formula IIA, Z$^2$ is CH$_2$.

In another embodiment, in Formula IIA, Z$^2$ is NH.

In another embodiment, in Formula IIA, Z$^1$ is N, and Z$^2$ is NH.

In another embodiment, in Formula IIA, Z$^1$ is N and Z$^2$ is CH$_2$.

In a further embodiment, in Formula IIA, Z$^1$ is CH and Z$^2$ is CH$_2$.

In one another embodiment, in Formula IIA, Z$^1$ is N, Z$^2$ is NH, and n is 0.

In another embodiment, in Formula IIA, Z$^1$ is N and Z$^2$ is CH$_2$, and n is 1.

In another embodiment, in Formula IIA, Z$^1$ is CH and Z$^2$ is CH$_2$, and n is 1.

In another embodiment, in Formula IIA, R$^{6a}$ is aryl.

In another embodiment, in Formula IIA, R$^{6a}$ aryl is phenyl.

In another embodiment, in Formula IIA, R$^{6a}$ phenyl is optionally substituted with one or more substituents selected from the group consisting of methoxy, trifluoromethyl, fluoro, and chlroro.

In another embodiment, the compound of Formula IIA is selected from the group consisting of:

[chemical structure]

[chemical structure]

37
-continued

38
-continued

-continued

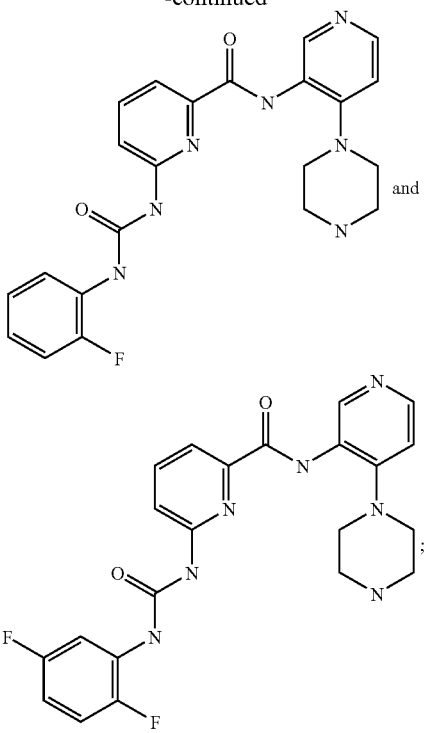

or a pharmaceutically acceptable salt, or ester thereof.

In another embodiment, the compound of formula I is represented by the formula III:

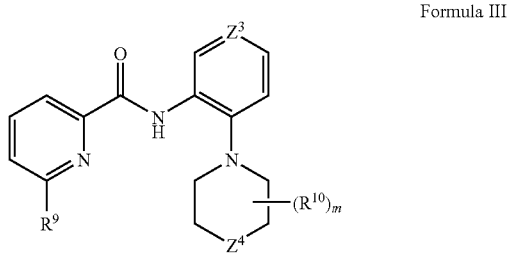

Formula III or a pharmaceutically acceptable salt, solvate, ester, or prodrug thereof, wherein in Formula III:

$Z^3$ is CH or N;

$Z^4$ is $CH_2$ or NH;

$R^9$ is —C(=O)NH(aryl), aryl or heteroaryl, wherein said $R^9$ aryl or heteroaryl is attached to the pyridine ring through a carbon atom, wherein when said aryl or heteroaryl has two substituents or adjacent carbon atoms, said substituents may optionally be taken together with the carbon atoms to which they are attached to form a five- to six-membered heterocyclyl, aryl or heteroaryl;

$R^{10}$ is selected from the group consisting of alkyl, —$NH_2$, —NH(alkyl), and —N(alkyl)$_2$; and m is 0, 1, or 2.

In another embodiment, in Formula III, said $R^9$ aryl or heteroaryl, optionally with said five- to six-membered heterocyclyl, aryl or heteroaryl, is optionally substituted with one or more substitutents selected from the group consisting of heterocyclyl, alkoxy, aryl, and alkyl.

In another embodiment, in Formula III, $Z^1$ is N.

In another embodiment, in Formula III, $Z^1$ is CH.

In another embodiment, in Formula III, $Z^1$ is $CH_2$.

In another embodiment, in Formula III, $Z^2$ is NH.

In another embodiment, in Formula III, $Z^1$ is N, and $Z^2$ is NH.

In another embodiment, in Formula III, $Z^1$ is N and $Z^2$ is $CH_2$.

In another embodiment, in Formula III, $Z^1$ is CH and $Z^2$ is $CH_2$.

In another embodiment, in Formula III, $Z^1$ is N, $Z^2$ is NH, and n is 0.

In another embodiment, in Formula III, $Z^1$ is N and $Z^2$ is $CH_2$, and n is 1.

In another embodiment, in Formula III, $Z^1$ is CH, $Z^2$ is $CH_2$, and n is 1.

In another embodiment, in Formula III, $R^9$ is —C(=O)NHaryl.

In another embodiment, in Formula III, $R^9$ is —C(=O)NHaryl, wherein said aryl of —C(=O)NHaryl is optionally substituted with 1 or more substituents selected from the group consisting of halo, haloalkyl, alkoxy, haloalkoxy, and alkyl.

In another embodiment, in Formula III, $R^9$ is aryl or heteroaryl, and is selected from the group consisting of: phenyl, 4-pyridyl, 2-(6-(1-piperizinyl))pyridyl, benzofuranyl, benzothiophenyl, benzimidazolyl, benzo(dihydro)furanyl, 3-pyridyl, 2-thiophenyl, 3-thiopehyl, 5-pyrimidinyl, benzopyrrolyl, benzomorpholinyl, benzopyridyl, phenyl, 3-pyrrolyl, and oxazolyl, each of which is optionally substituted.

In another embodiment, in Formula III, $R^9$ is aryl or heteroaryl, and is selected from the group consisting of: phenyl, 4-pyridyl, 2-(6-(1-piperizinyl))pyridyl, benzofuranyl, benzothiophenyl, benzimidazolyl, benzo(dihydro)furanyl, 3-pyridyl, 2-thiophenyl, 3-thiopehyl, 5-pyrimidinyl, benzopyrrolyl, benzomorpholinyl, benzopyridyl, phenyl, 3-pyrrolyl, and oxazolyl, each of which is optionally substituted, wherein said $R^9$ benzofuranyl, benzothiophenyl, benzimidazolyl, benzo(dihydro)furanyl, benzopyrrolyl, benzomorpholinyl, and benzopyridyl is selected from the group consisting of:

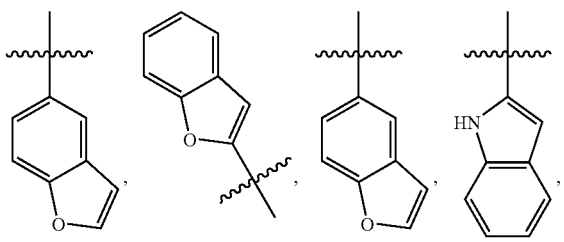

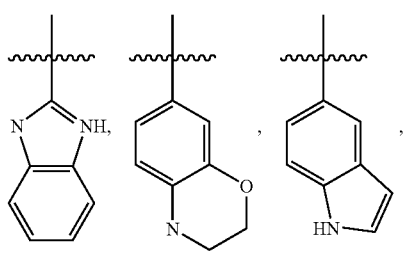

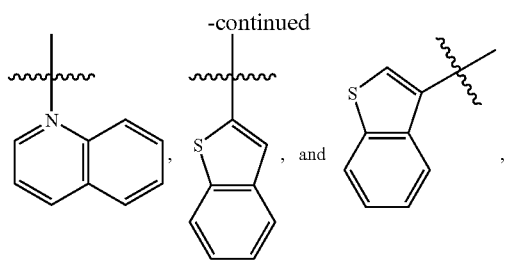

each of which is optionally substituted.

In another embodiment, in Formula III, said R⁹ aryl or heteroaryl, optionally with said five- to six-membered heterocyclyl, aryl or heteroaryl, is optionally substituted with one or more substitutents selected from the group consisting of 1-piperazinyl, methoxy, methyl, 1-morpholinyl, —CH$_2$-(1-morpholinyl), and phenyl.

In another embodiment, the compound of Formula III is selected from the group consisting of:

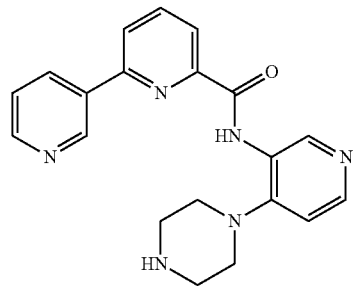

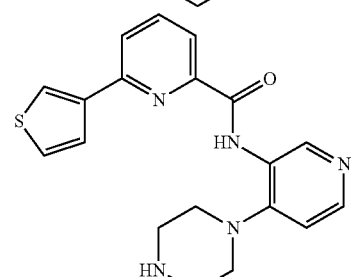

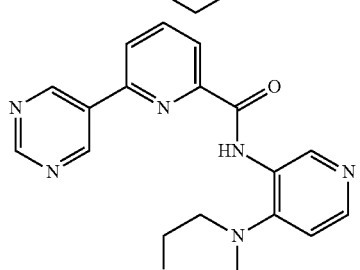

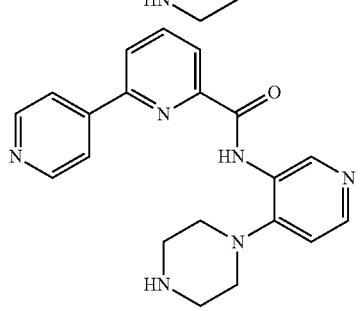

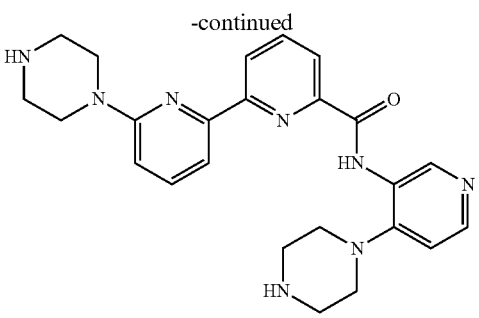

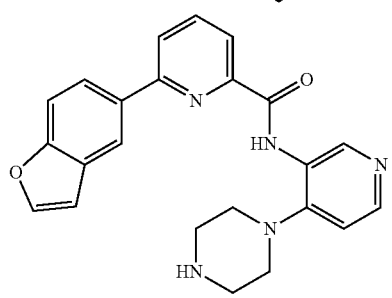

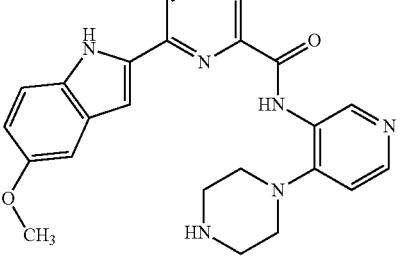

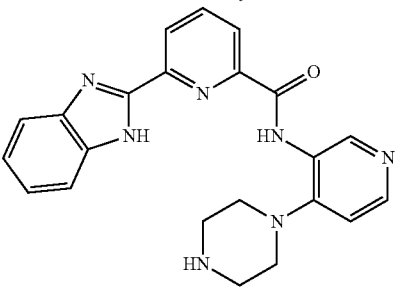

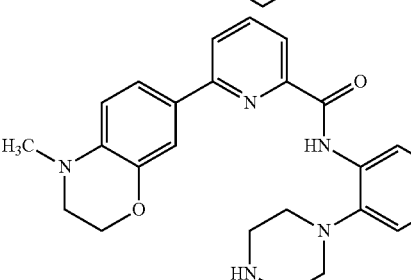

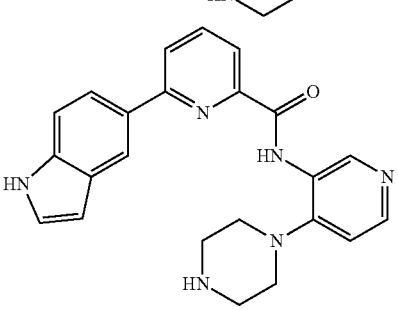

43
-continued
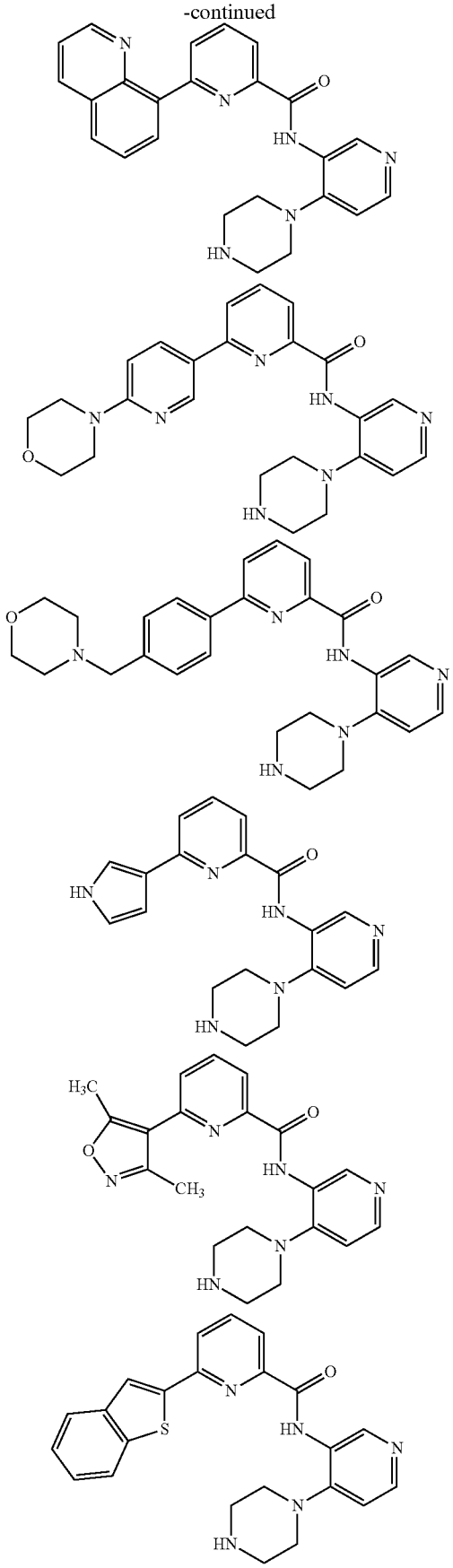
44
-continued
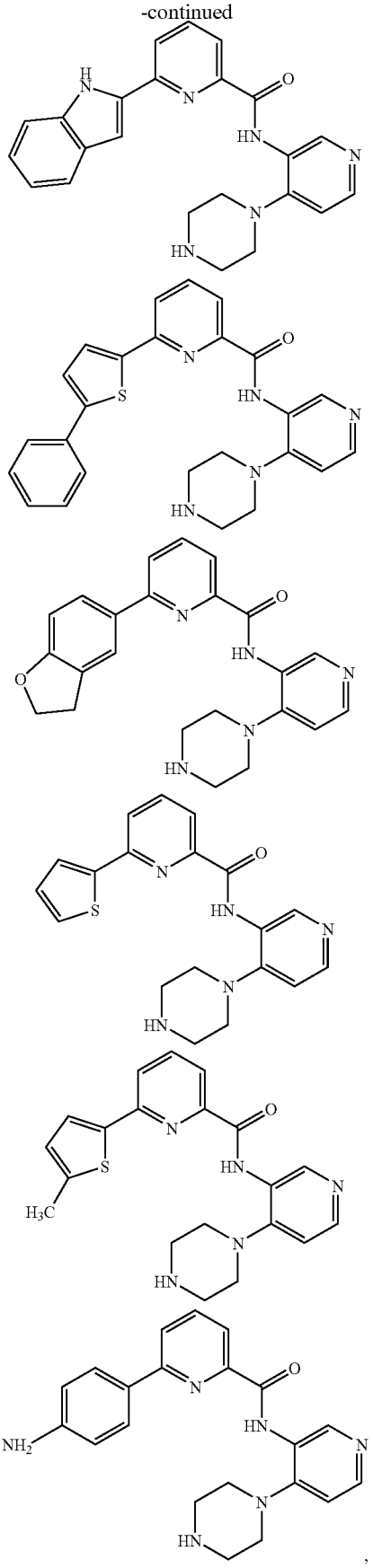

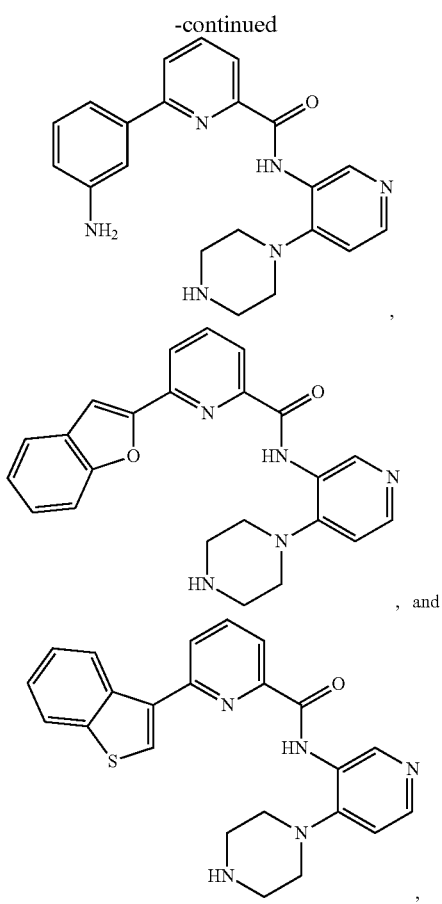

, and

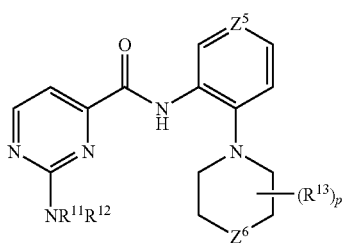

, or a pharmaceutical acceptable salt, solvate, ester, or prodrug thereof.

In another embodiment, the compound of formula I is represented by the formula IV:

Formula IV

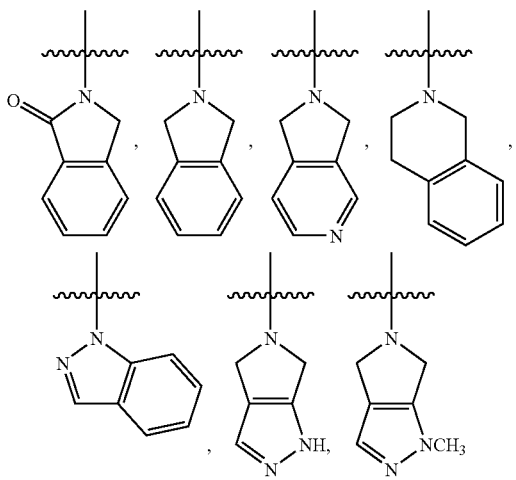

or a pharmaceutically acceptable salt, or ester thereof, wherein:

$Z^5$ is CH or N;

$Z^6$ is $CH_2$ or NH;

$R^{11}$ and $R^{12}$ independently are H and alkyl, wherein said alkyl is optionally substituted with an aryl, or wherein $R^{11}$ and $R^{12}$ together with the nitrogen atom to which they are shown attached is heterocyclyl, wherein when said heterocyclyl has two substituents on adjacent carbon atoms, said substituents may optionally be taken together with the carbon atoms to which they are attached to form a five- to six-membered heterocyclyl, aryl or heteroaryl;

$R^{13}$ is selected from the group consisting of alkyl, $-NH_2$, $-NH(alkyl)$, and $-N(alkyl)_2$; and p is 0, 1, or 2.

In another embodiment, in Formula IV, said $-Nr^{11}R^{12}$ heterocyclyl, optionally with said five- to six-membered heterocyclyl, aryl or heteroaryl is optionally substituted with one or more substituents selected from the group consisting of alkoxy, halo, alkyl, heterocyclyl and aryl.

In another embodiment, in Formula IV, $Z^5$ is N.

In another embodiment, in Formula IV, $Z^5$ is CH.

In another embodiment, in Formula IV, $Z^5$ is $CH_2$.

In another embodiment, in Formula IV, $Z^5$ is NH.

In another embodiment, in Formula IV, $Z^5$ is N, and $Z^6$ is NH.

In another embodiment, in Formula IV, $Z^5$ is N and $Z^6$ is $CH_2$.

In another embodiment, in Formula IV, $Z^5$ is CH and $Z^6$ is $CH_2$.

In another embodiment, in Formula IV, $Z^5$ is N, $Z^6$ is NH, and p is 0.

In another embodiment, in Formula IV, $Z^5$ is N, $Z^6$ is $CH_2$, and p is 1.

In another embodiment, in Formula IV, $Z^5$ is CH, $Z^6$ is $CH_2$, and p is 1.

In another embodiment, in Formula IV, $R^{13}$ is $-NH_2$.

In another embodiment, in Formula IV, $Z^5$ is N, $Z^6$ is $CH_2$, p is 1, and $R^{13}$ is $-NH_2$.

In another embodiment, in Formula IV, $Z^5$ is CH, $Z^6$ is $CH_2$, p is 1, and $R^{13}$ is $-NH_2$.

In another embodiment, in Formula IV, $R^{11}$ and $R^{12}$ independently are H, and alkyl.

In another embodiment, in Formula IV, said $R^{11}$ and $R^{12}$ alkyl independently is alkyl-aryl.

In another embodiment, in Formula IV, said $R^{11}$ and $R^{12}$ alkyl independently is alkyl-aryl, wherein the "aryl" portion of said alkyl-aryl is optionally substituted with one or more substituents selected from the group consisting of halo and alkoxy.

In another embodiment, in Formula IV, $R^{11}$ and $R^{12}$ independently are selected from the group consisting of: H, methyl, $-CH_2$-(3-fluorophenyl), (3-methoxyphenyl), $-CH_2$-phenyl, $-CH_2CH_2$-phenyl, $-CH_2CH_2$-(3-methoxyphenyl), and $-CH_2CH_2$-(3-fluorophenyl).

In another embodiment, in Formula IV, said $-R^{11}R^{12}$ is selected from the group consisting of: pyrrolidinyl, piperidinyl,

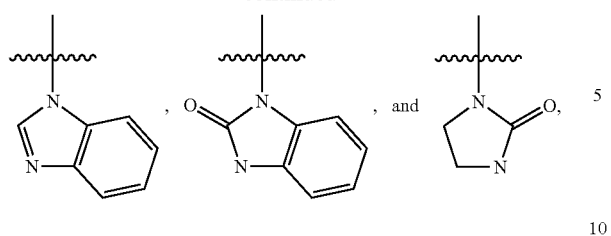

each of which is optionally substituted.

In another embodiment, in Formula IV, said —NR$^9$R$^{10}$ heterocyclyl, optionally with said five- to six-membered heterocyclyl, aryl or heteroaryl is optionally substituted with one or more substituents selected from the group consisting of methoxy, fluoro, chloro, —CH$_2$CH$_2$N(CH$_3$)$_2$, —OCH$_2$CH$_2$-(1-morpholinyl), 2-methoxyphenyl, phenyl, and 1-pyrrolidinyl.

In another embodiment, the compound of Formula IV is selected from the group consisting of:

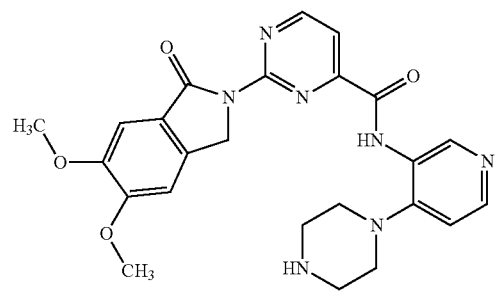

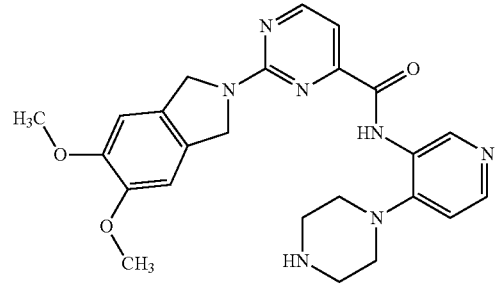

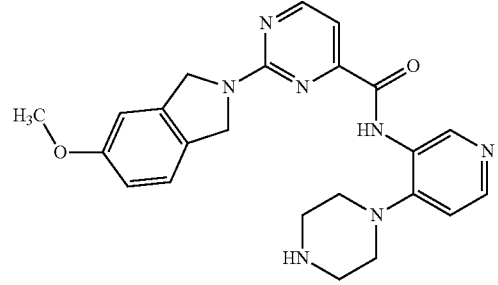

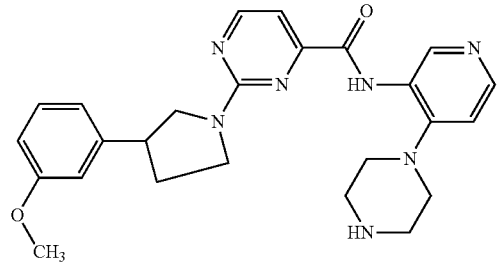

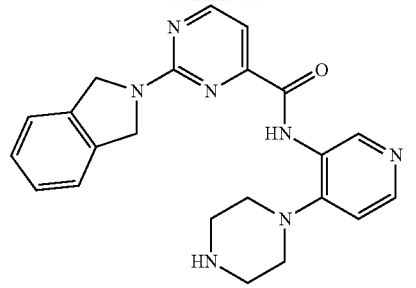

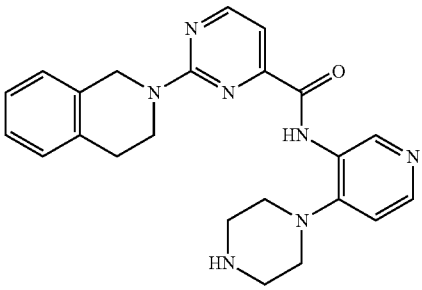

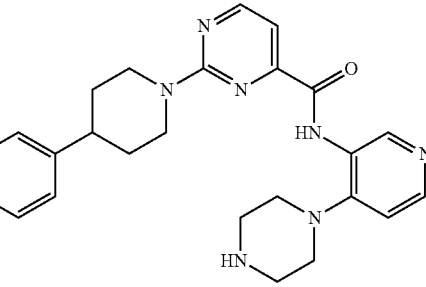

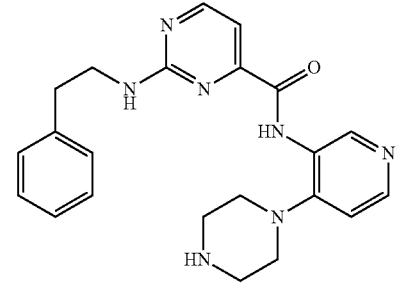

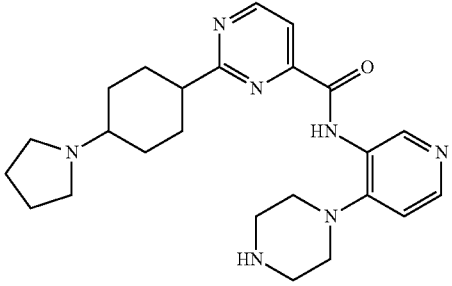

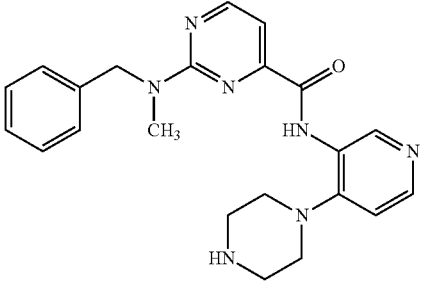

-continued
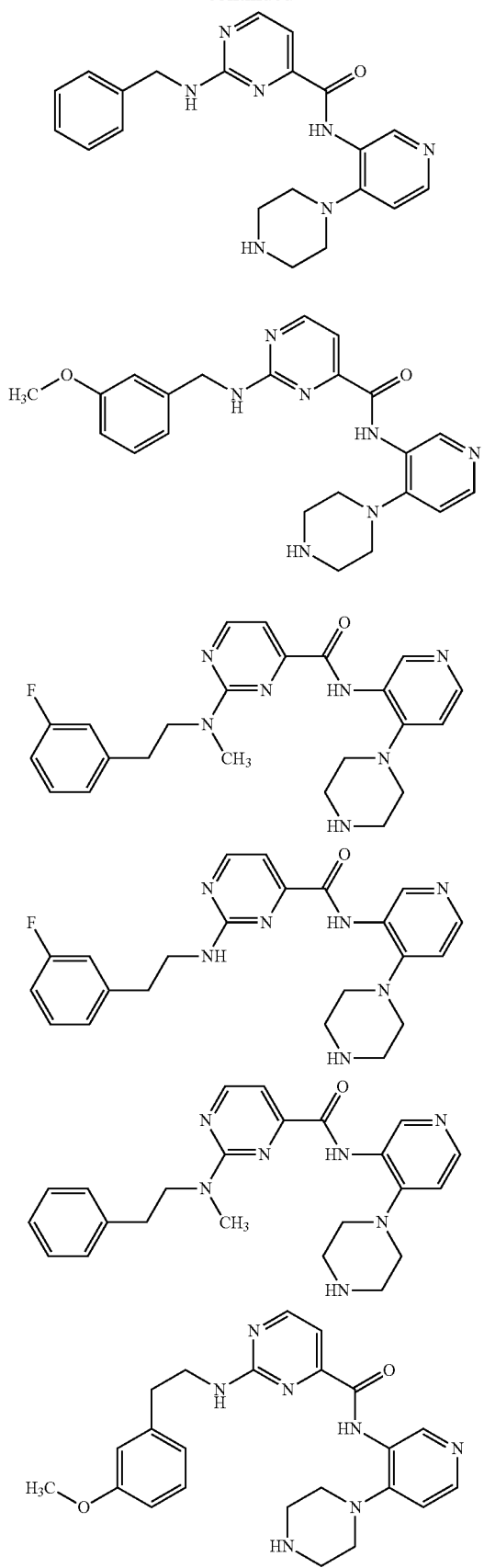
-continued
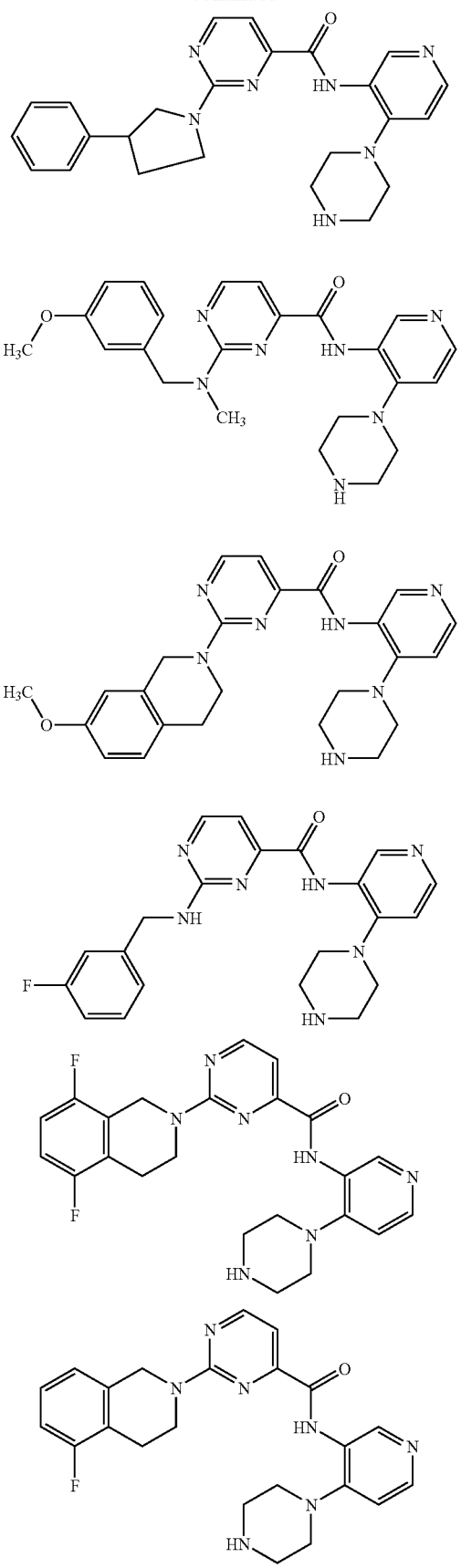

51
-continued
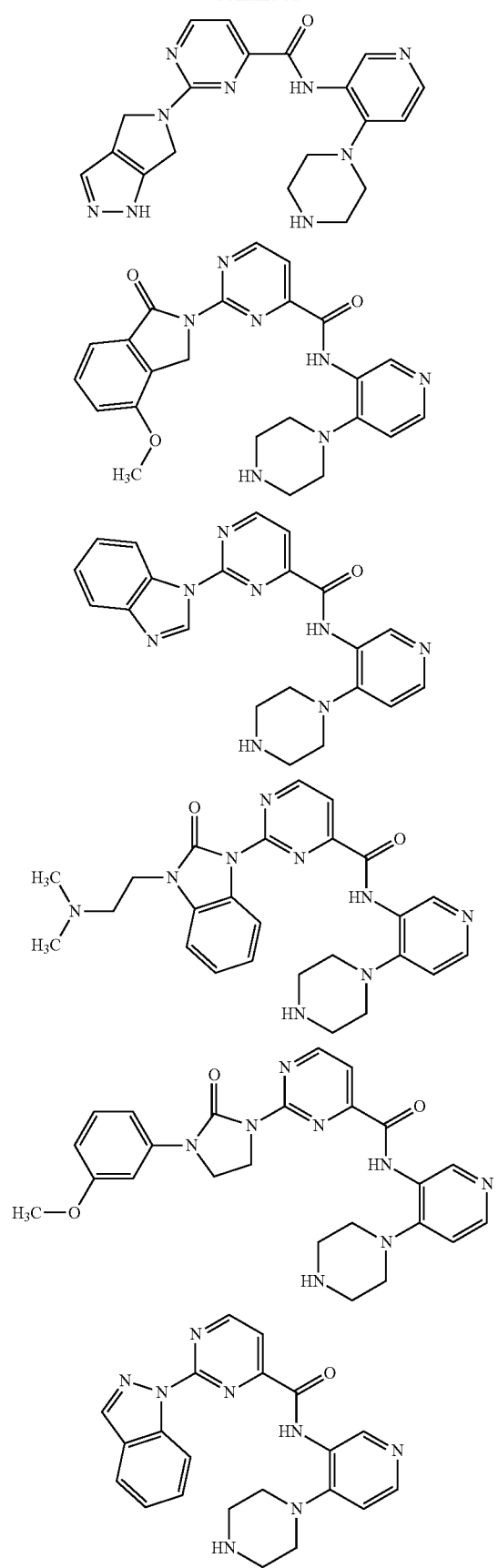
52
-continued
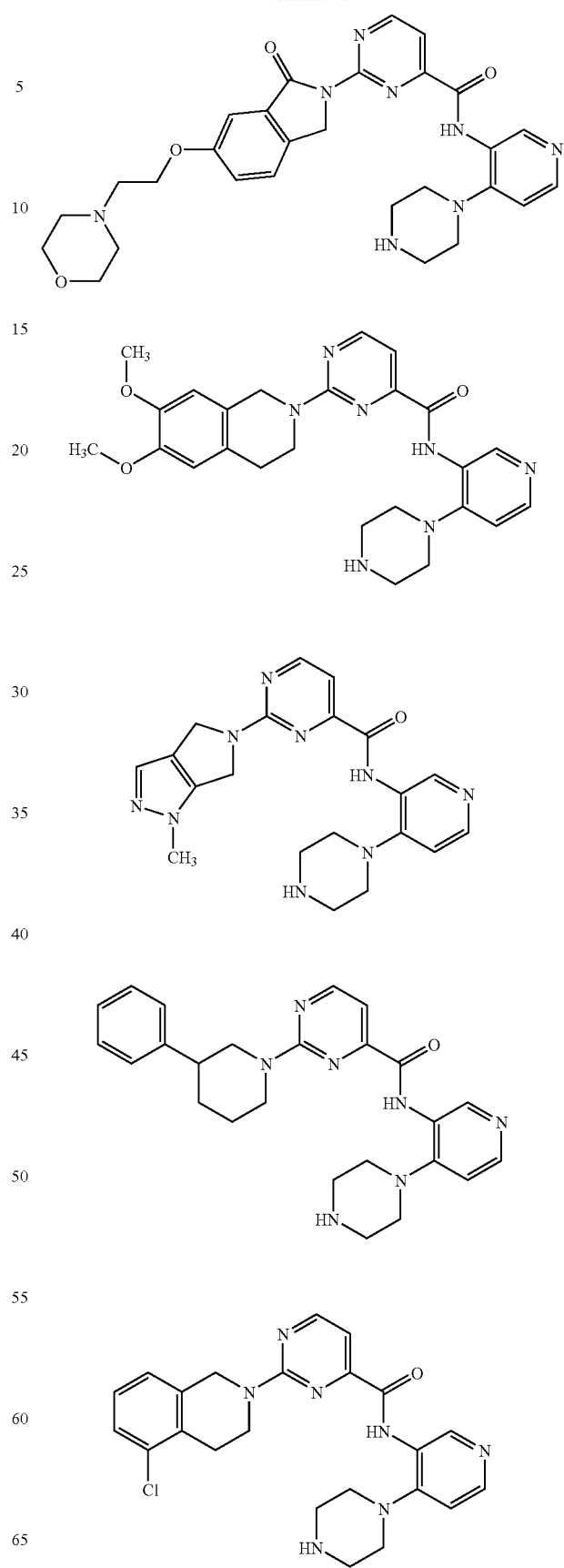

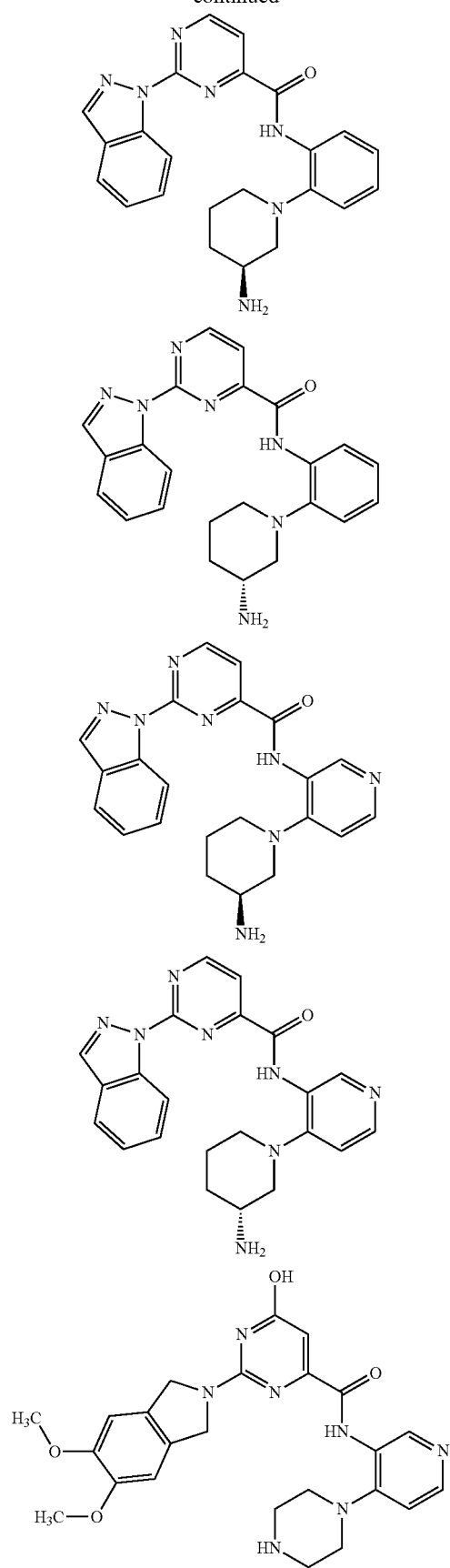

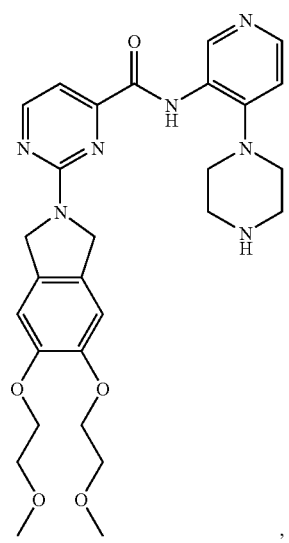
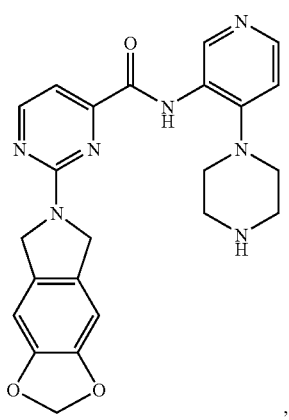
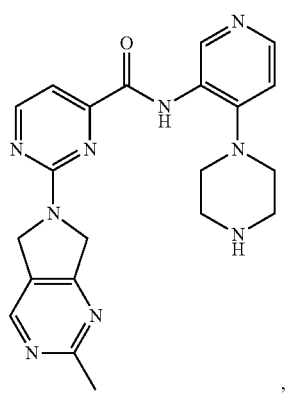
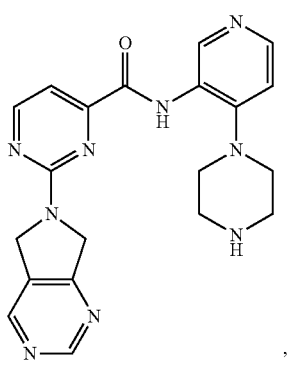
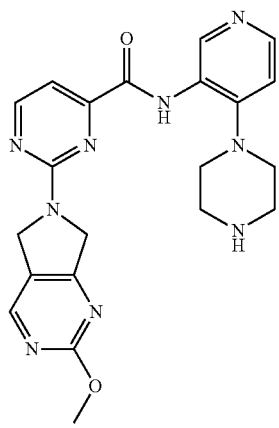
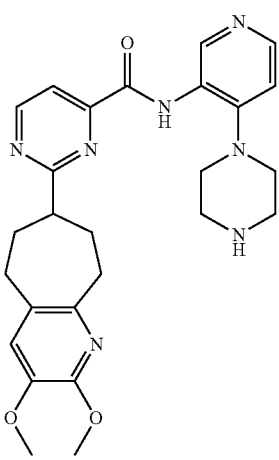
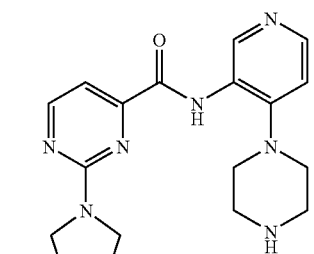

-continued

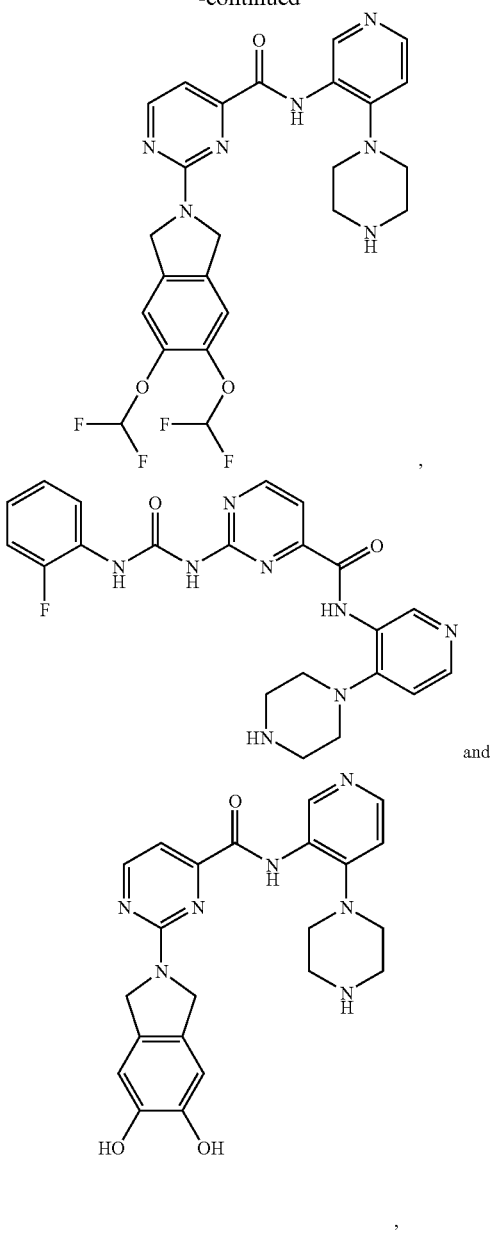

, or a pharmaceutically acceptable salt, solvate, ester, or prodrug thereof.

In another embodiment, the compound of formula I is represented by the formula IV(A):

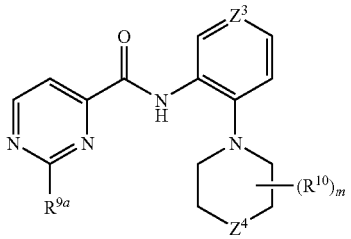

Formula IV(A)

or a pharmaceutically acceptable salt, or ester thereof, wherein in Formula III:

$Z^3$ is CH or N;

$Z^4$ is $CH_2$ or NH;

$R^{9a}$ is —N($R^2$)—C(=O)—N($R^2$)-aryl, aryl or heteroaryl, wherein each $R^2$ independently is H or alkyl, wherein said $R^{9a}$ aryl or heteroaryl is attached to the pyrimidine ring through a carbon atom, wherein when each of said "aryl" and "heteroaryl" in any of the aforementioned $R^{9a}$ groups has two substituents on adjacent carbon atoms, said substituents may optionally be taken together with the carbon atoms to which they are attached to form a first five- to six-membered heterocyclyl, aryl or heteroaryl; wherein when said five-to-six-membered heterocylclyl, aryl or heteroaryl has two substituents or adjacent carbon atoms, said substituents may optionally be taken together with the carbon atoms to which they are attached to form a second five- to six-membered heterocyclyl, aryl or heteroaryl;

$R^{10}$ is selected from the group consisting of alkyl, —$NH_2$, —NH(alkyl), and —N(alkyl)$_2$; and m is 0, 1, or 2.

In another embodiment, in formula IV(A), $R^{9a}$ aryl or heteroaryl, or the "aryl" portion of said —N($R^2$)—C(=O)N($R^2$)-aryl optionally with said first and second five- to six-membered heterocyclyl, aryl or heteroaryl, is optionally substituted with one or more substitutents selected from the group consisting of heterocyclyl, heteroaryl, alkoxy, alkyl, aryloxy, dialkylamino, halo, —S(=O)$_2$alkyl, —S-alkyl, —C(=O)alkyl, —NHC(=O)alkyl, —O-alkyl-cycloalkyl, —C(=O)N(alkyl)$_2$, —NHC(=O)NH(alkyl), and —C(=O)NH(alkyl).

In another embodiment, in formula IV(A), $Z^1$ is N.

In another embodiment, in formula IV(A), $Z^1$ is CH.

In another embodiment, in formula IV(A), $Z^2$ is $CH_2$.

In another embodiment, in formula IV(A), $Z^2$ is NH.

In another embodiment, in formula IV(A), $Z^1$ is N, and $Z^2$ is NH.

In another embodiment, in formula IV(A), $Z^1$ is N and $Z^2$ is $CH_2$.

In another embodiment, in formula IV(A), $Z^1$ is CH and $Z^2$ is $CH_2$.

In another embodiment, in formula IV(A), $Z^1$ is N, $Z^2$ is NH, and n is 0.

In another embodiment, in formula IV(A), $Z^1$ is N, $Z^2$ is $CH_2$, and n is 1.

In another embodiment, in formula IV(A), $Z^1$ is CH, $Z^2$ is $CH_2$, and n is 1.

In another embodiment, in formula IV(A), $R^{9a}$ aryl or heteroaryl, or the "aryl" portion of said —N($R^2$)—C(=O)$R^2$-aryl, optionally with said first and second five- to six-membered heterocyclyl, aryl and heteroaryl is selected from the group consisting of: phenyl, indolyl, furanyl, morpholinyl, pyridyl, indazolyl, pyrimidinyl, benzofuranyl, benzothiophenyl, benzopyridyl, benzothiazolyl, isoindolyl, benzimidazolyl, oxazolyl,

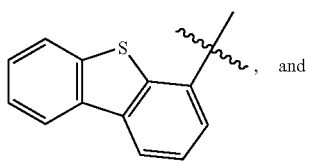

-continued

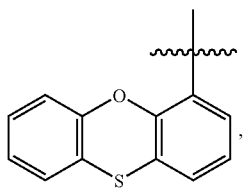

each of which is optionally substituted.

In another embodiment, in formula IV(A), $R^{9a}$ aryl or heteroaryl, or the "aryl" portion of said —N($R^2$)—C(=O)N$R^2$-aryl, optionally with said first and second five- to six-membered heterocyclyl, aryl or heteroaryl, is optionally substituted with one or more substituents selected from the group consisting of 1-pyrrolidinyl, methoxy, 1-morpholinyl, —N(CH$_3$)$_2$, bromo, fluoro, phenoxy, —S(=O)$_2$CH$_3$, —S—CH$_3$, methyl, isopropoxy, —C(=O)OCH$_3$, —NH—C(=O)—CH$_3$, —O—CH$_2$-cyclopropyl, —C(=O)—N(CH$_2$CH$_3$)$_2$, —NH—C(=O)NHCH$_2$CH$_3$, and —C(=O)NCH$_3$.

In another embodiment, the compound of formula IV(A) is selected from the group consisting of:

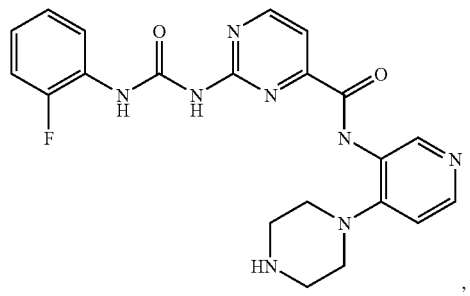

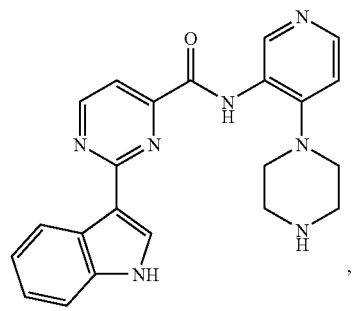

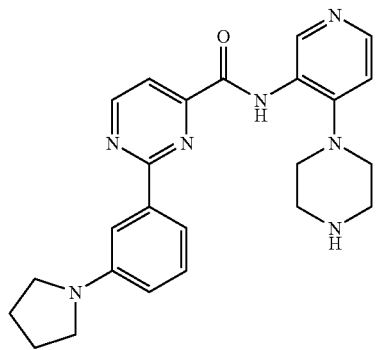

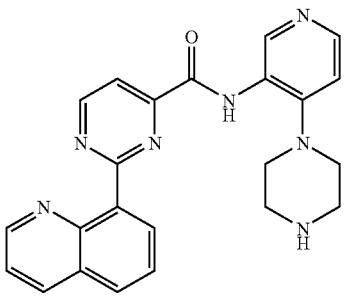

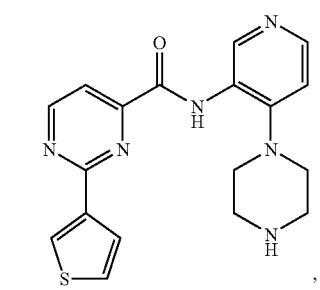

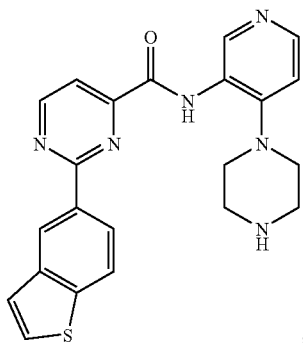

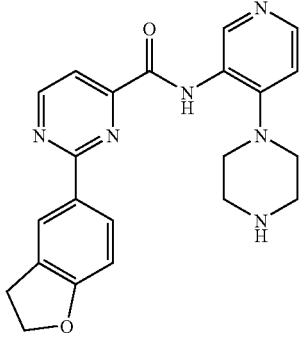

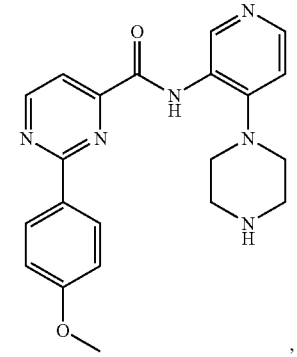

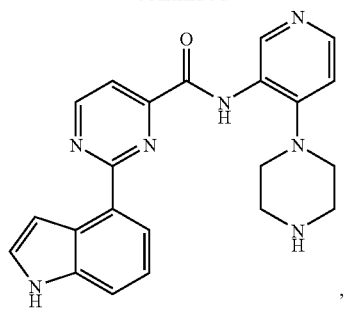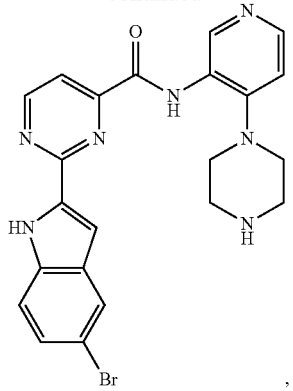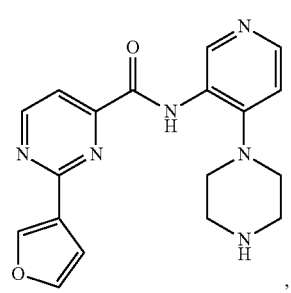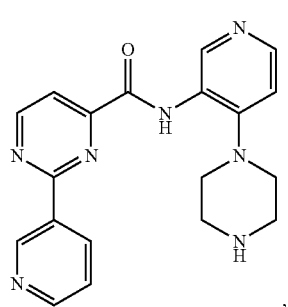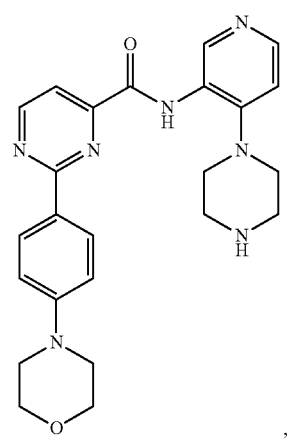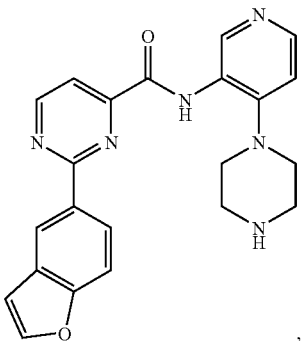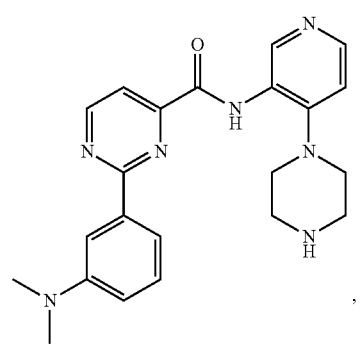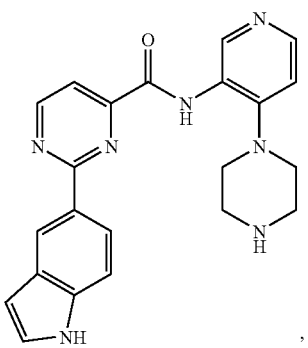

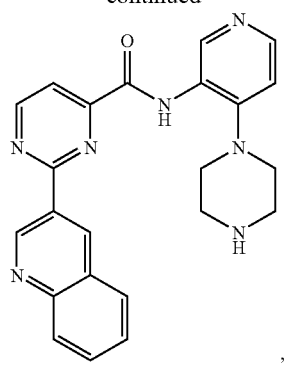
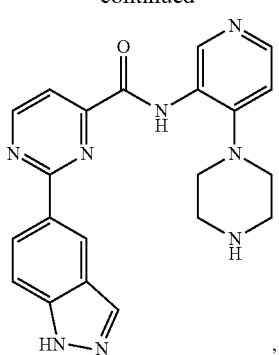
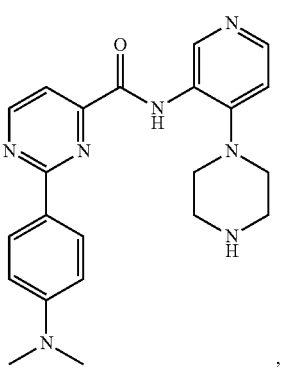
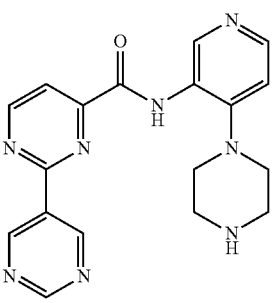
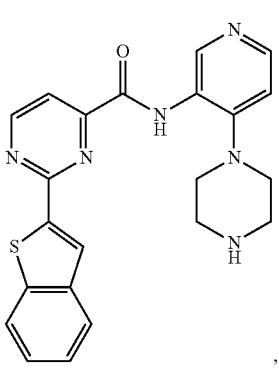

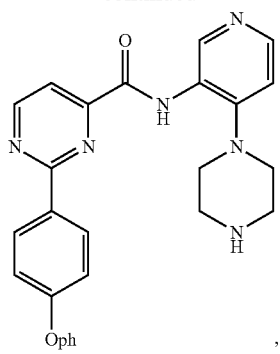
,
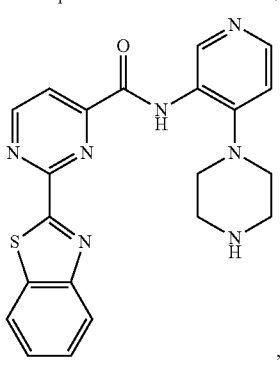
,
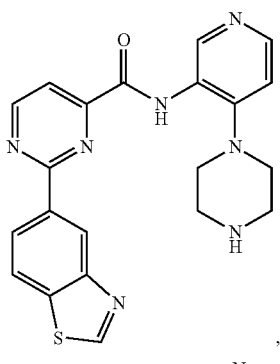
,
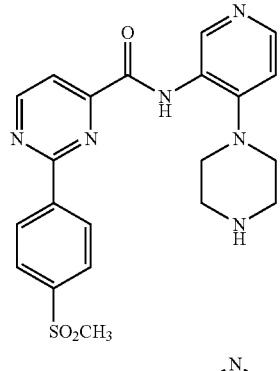
,
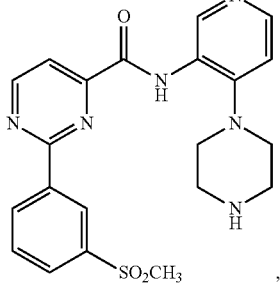
,
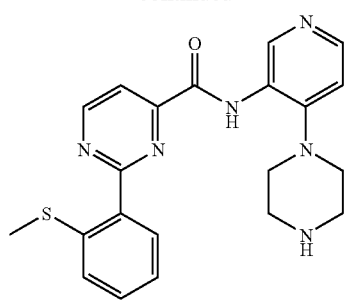
,
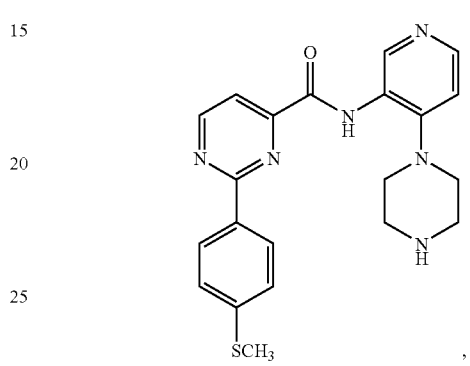
,
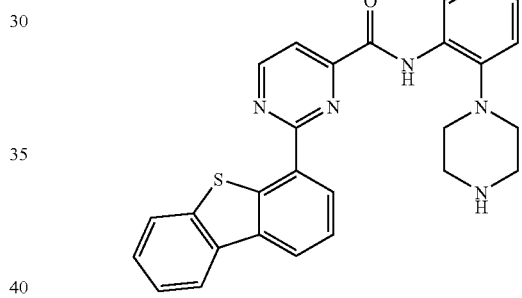
,
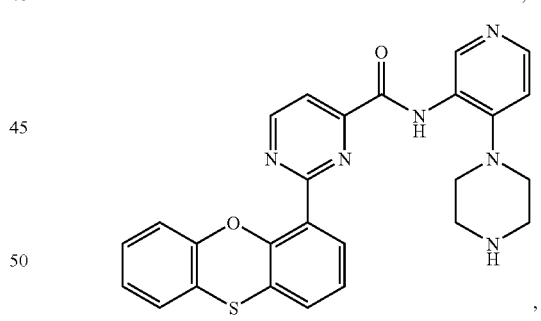
,
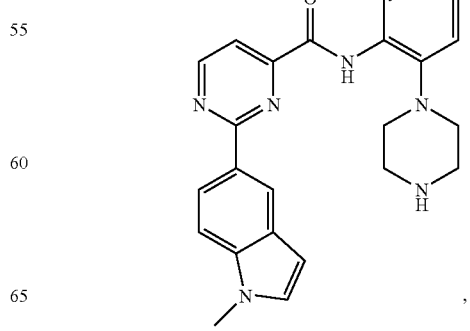
,

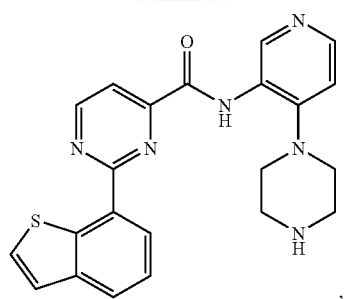
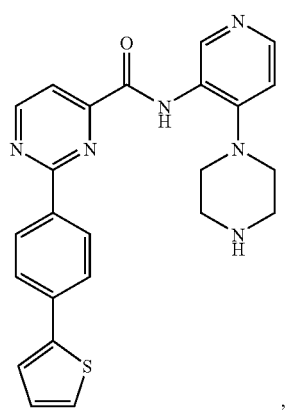
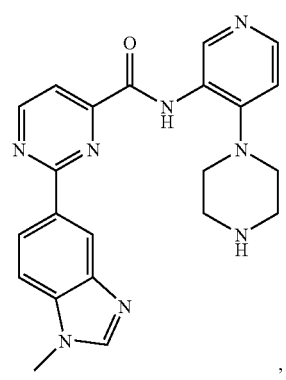
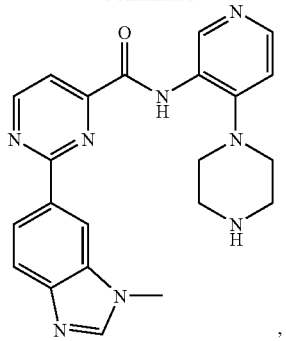
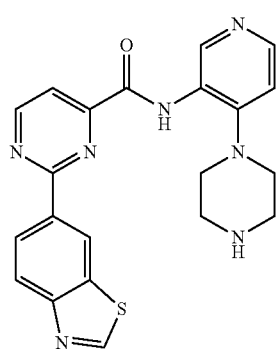
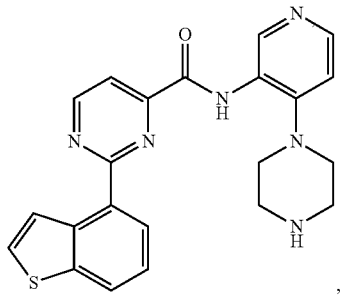
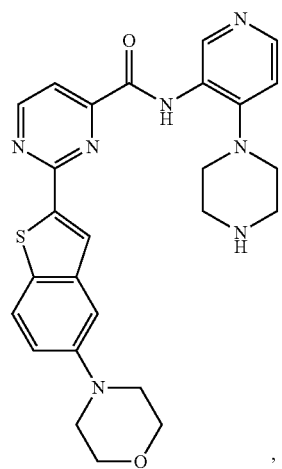

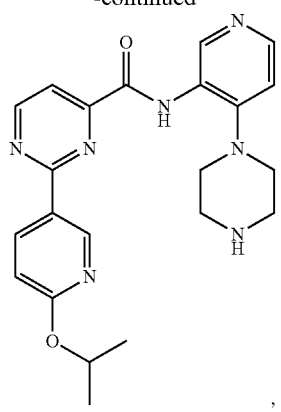
,
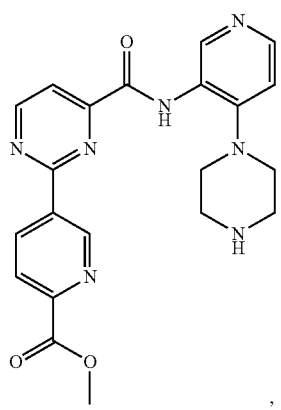
,
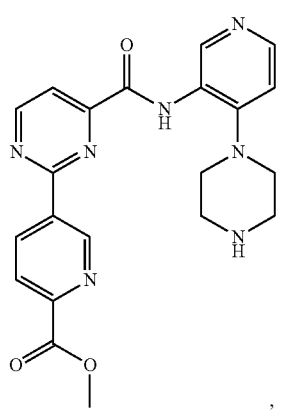
,
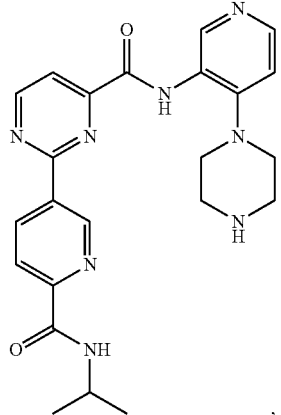
,
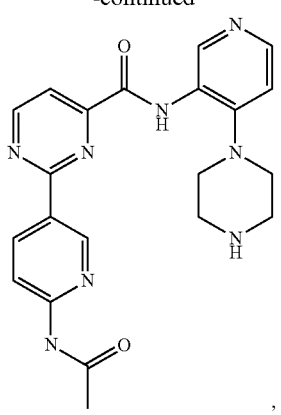
,
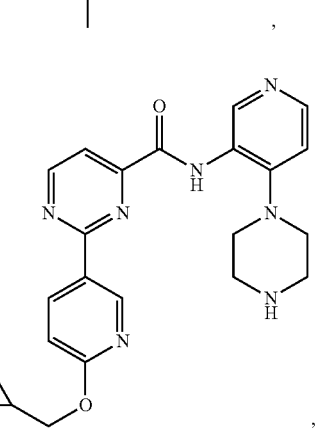
,
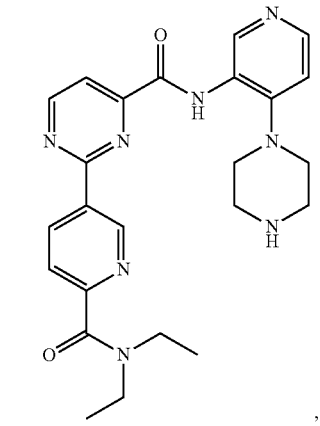
,
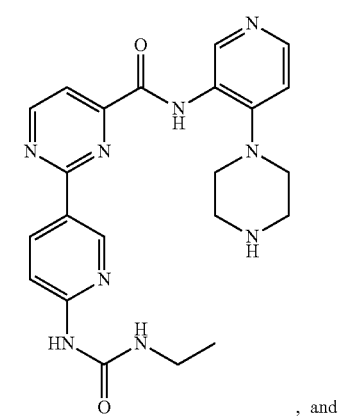
, and or a pharmaceutically acceptable salt thereof.

In another embodiment, the compound of Formula I is represented by formula V:

Formula V or a pharmaceutically acceptable salt, solvate, ester, or prodrug thereof, wherein:

$Z^7$ is CH or N;
$Z^8$ is $CH_2$ or NH;
$R^{14}$ and $R^{15}$ together with the nitrogen atom to which they are shown attached is heterocyclyl, wherein when said heterocyclyl has two substituents on adjacent carbon atoms, said substituents together with the carbon atoms to which they are attached form a five- to six-membered heterocyclyl, aryl or heteroaryl;
$R^{16}$ is selected from the group consisting of alkyl, $-NH_2$, $-NH(alkyl)$, and $-N(alkyl)_2$; and
q is 0, 1, or 2.

In another embodiment, in Formula V, said $-NR^{14}R^{15}$ heterocyclyl, optionally with said five- to six-membered heterocyclyl, aryl or heteroaryl is optionally substituted with one or more substituents selected from the group consisting of alkoxy, halo, alkyl, and aryl.

In another embodiment, in Formula V, $Z^7$ is N.
In another embodiment, in Formula V, $Z^7$ is CH.
In another embodiment, in Formula V, $Z^8$ is $CH_2$.
In another embodiment, in Formula V, $Z^8$ is NH.
In another embodiment, in Formula V, $Z^7$ is N, and $Z^8$ is NH.
In another embodiment, in Formula V, $Z^7$ is N and $Z^8$ is $CH_2$. In another embodiment, in Formula V, $Z^7$ is CH and $Z^8$ is $CH_2$.
In another embodiment, in Formula V, q is 0.
In another embodiment, in Formula V, $Z^7$ is N, $Z^8$ is NH, and q is 0.
In another embodiment, in Formula V, q is 1.
In another embodiment, in Formula V, $Z^7$ is N, $Z^8$ is $CH_2$, and q is 1.

In another embodiment, in Formula V, $Z^7$ is CH, $Z^8$ is $CH_2$, and q is 1.
In another embodiment, in Formula V, $R^{16}$ is $-NH_2$.
In another embodiment, in Formula V, $Z^7$ is N, $Z^8$ is $CH_2$, q is 1, and $R^{16}$ is $-NH_2$.
In another embodiment, in Formula V, $Z^7$ is CH, $Z^8$ is $CH_2$, q is 1, and $R^{16}$ is $-NH_2$.
In another embodiment, in Formula V, $-NR^{14}R^{15}$ is a benzo-fused pyrrolidine that is optionally substituted.
In another embodiment, the compound of Formula V is or a pharmaceutically acceptable salt, solvate, ester, or prodrug thereof.

In another embodiment, the compound of formula I is represented by Formula VI:

Formula VI or a pharmaceutically acceptable salt, solvate, ester, or prodrug thereof, wherein:

$Z^9$ is CH or N;
$Z^{19}$ is $CH_2$ or NH;
$R^{17}$ and $R^{18}$ together with the nitrogen atom to which they are shown attached is heterocyclyl, wherein when said heterocyclyl has two substituents on adjacent carbon atoms, said substituents together with the carbon atoms to which they are attached form a five- to six-membered heterocyclyl, aryl or heteroaryl;
$R^{19}$ is selected from the group consisting of alkyl, $-NH_2$, $-NH(alkyl)$, and $-N(alkyl)_2$, and
r is 0, 1, or 2.

In another embodiment, in Formula VI, said $-NR^{14}R^{15}$ heterocyclyl, optionally with said five- to six-membered heterocyclyl, aryl or heteroaryl is optionally substituted with one or more substituents selected from the group consisting of alkoxy, halo, alkyl, and aryl.

In another embodiment, in Formula VI, $Z^9$ is N.
In another embodiment, in Formula VI, $Z^9$ is CH.
In another embodiment, in Formula VI, $Z^{10}$ is $CH_2$.
In another embodiment, in Formula VI, $Z^{10}$ is NH.
In another embodiment, in Formula VI, $Z^9$ is N, and $Z^{10}$ is NH In another embodiment, in Formula VI, $Z^9$ is N and $Z^{10}$ is $CH_2$.

In another embodiment, in Formula VI, $Z^9$ is CH and $Z^{10}$ is $CH_2$.

In another embodiment, in Formula VI, q is 0.

In another embodiment, in Formula VI, $Z^9$ is N, $Z^{10}$ is NH, and q is 0.

In another embodiment, in Formula VI, q is 1.

In another embodiment, in Formula VI, $Z^9$ is N, $Z^{10}$ is $CH_2$, and q is 1.

In another embodiment, in Formula VI, $Z^9$ is CH, $Z^{10}$ is $CH_2$, and q is 1.

In another embodiment, in Formula VI, $R^{19}$ is —$NH_2$.

In another embodiment, in Formula VI, $Z^9$ is N, $Z^{10}$ is $CH_2$, q is 1, and
$R^{19}$ is —$NH_2$.

In another embodiment, in Formula VI, $Z^9$ is CH, $Z^{10}$ is $CH_2$, q is 1, and $R^{19}$ is —$NH_2$.

In another embodiment, in Formula VI, —$NR^{17}R^{18}$ is selected from the group consisting of:

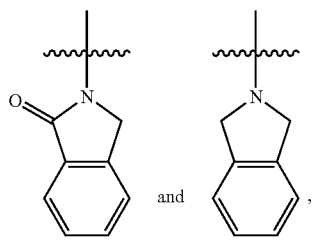

each of which is optionally substituted.

In another embodiment, in Formula VI, said —$NR^{13}R^{14}$ heterocyclyl, optionally with said five- to six-membered heterocyclyl, aryl or heteroaryl is optionally substituted with one or more alkoxy substituents.

In another embodiment, in Formula VI, said —$NR^{13}R^{14}$ heterocyclyl, optionally with said five- to six-membered heterocyclyl, aryl or heteroaryl is optionally substituted with one or more alkoxy substituents, wherein said alkoxy is methoxy.

In another embodiment, the compound of Formula VI is selected from the group consisting of:

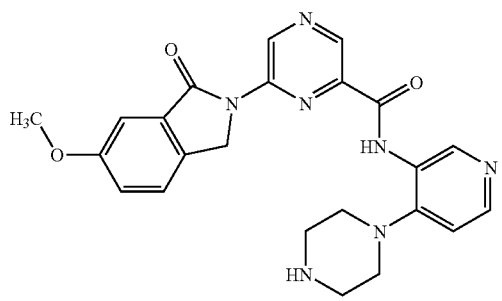

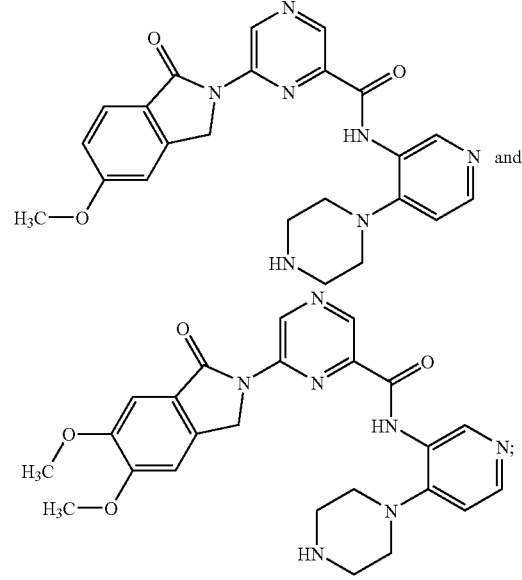

or a pharmaceutically acceptable salt, solvate, ester, or prodrug thereof.

In another embodiment, the compound of formula I is represented by Formula VII:

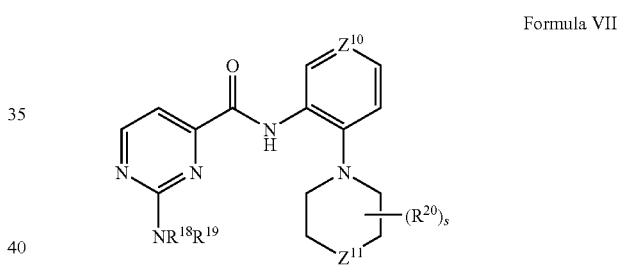

Formula VII or a pharmaceutically acceptable salt thereof, wherein:
$Z^{10}$ is CH or N;
$Z^{11}$ is $CH_2$ or NH;
$R^{18}$ and $R^{19}$ together with the nitrogen atom to which they are shown attached is heteroaryl, wherein when said heterocyclyl has two substituents on adjacent carbon atoms, said substituents together with the carbon atoms to which they are attached form a five- to six-membered heterocyclyl, aryl or heteroaryl;
$R^{20}$ is selected from the group consisting of alkyl, —$NH_2$, —NH(alkyl), and —N(alkyl)$_2$; and
s is 0, 1, or 2.

In another embodiment, in Formula VII, said —$NR^{17}R^{18}$ heteroaryl, optionally with said five- to six-membered heterocyclyl, aryl or heteroaryl is optionally substituted with one or more substituents selected from the group consisting of heteroaryl, and aryl.

In another embodiment, in Formula VII, $Z^{10}$ is N.
In another embodiment, in Formula VII, $Z^{11}$ is CH.
In another embodiment, in Formula VII, $Z^{10}$ is $CH_2$.
In another embodiment, in Formula VII, $Z^{11}$ is NH.
In another embodiment, in Formula VII, $Z^{10}$ is N, and $Z^{11}$ is NH.
In another embodiment, in Formula VII, $Z^{10}$ is N and $Z^{11}$ is $CH_2$.

In another embodiment, in Formula VII, $Z^{10}$ is CH and $Z^{11}$ is $CH_2$.

In another embodiment, in Formula VII, $Z^{10}$ is N, $Z^{11}$ is NH, and s is 0.

In another embodiment, in Formula VII, $Z^{10}$ is N, $Z^{11}$ is $CH_2$, and s is 1.

In another embodiment, in Formula VII, $Z^{10}$ is CH, $Z^{11}$ is $CH_2$, and s is 1.

In another embodiment, in Formula VII, In another embodiment, in

Formula VII, $Z^{10}$ is N, $Z^{11}$ is $CH_2$, s is 1, and $R^{19}$ is —$NH_2$.

In another embodiment, in Formula VII, $Z^{10}$ is CH, $Z^{11}$ is $CH_2$, s is 1, and $R^{19}$ is —$NH_2$.

In another embodiment, in Formula VII, —$NR^{18}R^{19}$ is pyrrazzolyl which is optionally substituted.

In another embodiment, in Formula VII, said —$NR^{13}R^{14}$ heteroaryl, optionally with said five- to six-membered heterocyclyl, aryl or heteroaryl is optionally substituted with one or more substitutents selected from the group consisting of optionally substituted thiophenyl, and optionally substituted aryl.

In another embodiment, the compound of Formula VII is selected from the group consisting of:

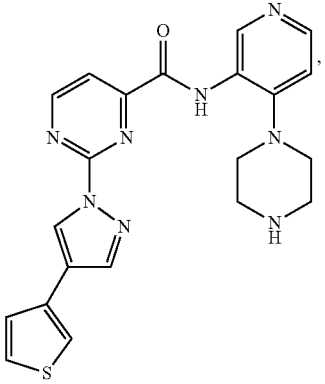

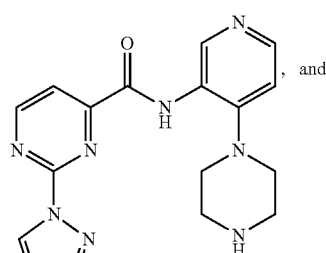

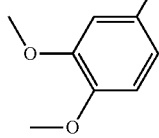

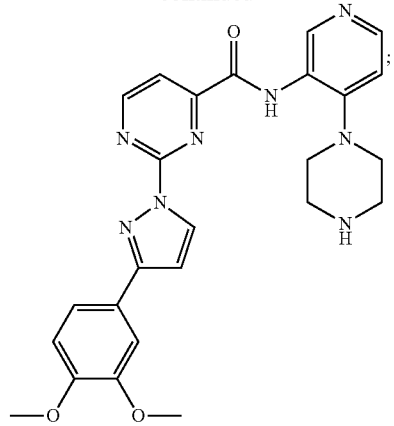

or a pharmaceutically acceptable salt thereof.

In another embodiment, the compound of formula I is represented by Formula VIII:

Formula VIII

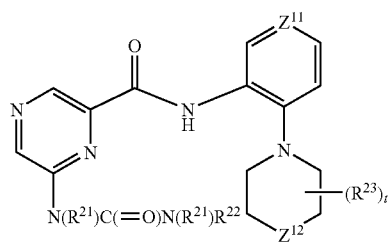

or a pharmaceutically acceptable salt thereof, wherein:
$Z^{11}$ is CH or N;
$Z^{12}$ is $CH_2$ or NH;
each $R^{21}$ independently is H or alkyl;
$R^{22}$ is aryl, wherein when said aryl has two substituents on adjacent carbon atoms, said substituents together with the carbon atoms to which they are attached form a five- to six-membered heterocyclyl, aryl or heteroaryl;
$R^{23}$ is selected from the group consisting of alkyl, —$NH_2$, —NH(alkyl), and —N(alkyl)$_2$; and
t is 0, 1, or 2.

In another embodiment, in formula VIII, said $R^{22}$ aryl, optionally with said five- to six-membered heterocyclyl, aryl or heteroaryl is optionally substituted with a halo.

In another embodiment, in formula VIII, $Z^{11}$ is N.
In another embodiment, in formula VIII, $Z^{12}$ is CH.
In another embodiment, in formula VIII, $Z^{12}$ is $CH_2$.
In another embodiment, in formula VIII, $Z^{12}$ is NH.
In another embodiment, in formula VIII, $Z^{11}$ is N, and $Z^{12}$ is NH.
In another embodiment, in formula VIII, $Z^{11}$ is N and $Z^{12}$ is $CH_2$.
In another embodiment, in formula VIII, $Z^{11}$ is CH and $Z^{12}$ is $CH_2$.
In another embodiment, in formula VIII, $Z^{11}$ is N, $Z^{12}$ is NH, and t is 0.
In another embodiment, in formula VIII, $Z^{11}$ is N, $Z^{12}$ is $CH_2$, and t is 1.
In another embodiment, in formula VIII, $Z^{11}$ is N, $Z^{12}$ is $CH_2$, and t is 1.
In another embodiment, in formula VIII, $R^{22}$ is phenyl which is optionally substituted.

In another embodiment, the compound of formula VIII is:

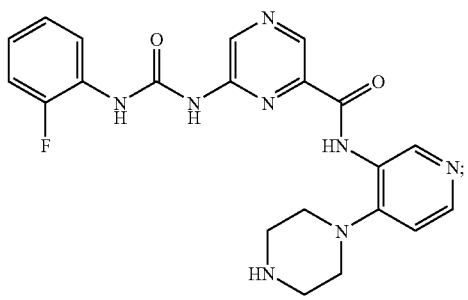

or a pharmaceutically acceptable salt thereof.

Methods for Making the Compounds of Present Invention

General Methods

Solvents, reagents, and intermediates that are commercially available were used as received. Reagents and intermediates that are not commercially available were prepared in the manner as described below. $^1$H NMR spectra were obtained on a Varian AS-400 (400 MHz) and are reported as ppm down field from Me$_4$Si with number of protons, multiplicities, and coupling constants in Hz indicated parenthetically. Where LC/MS data are presented, analyses were performed using an Applied Biosystems API-100 mass spectrometer and Shimadzu SCL-10A LC column: Altech platinum C18, 3 micron, 33 mm×7 mm ID; gradient flow: 0 min-10% CH$_3$CN, 5 min-95% CH$_3$CN, 7 min-95% CH$_3$CN, 7.5 min-10% CH$_3$CN, 9 min- stop. MS data were obtained using Agilent Technologies LC/MSD SL or 1100 series LC/MSD mass spectrometer. Final compounds were purified by PrepLC using the column of Varian Pursuit XRs C18 10 u 250×21.2 mm and an eluent mixture of mobile phase A and B. The mobile phase A is composed of 0.1% TFA in H$_2$O and the mobile phase B is composed of CH$_3$CN (95%)/H$_2$O(5%)/TFA (0.1%). The mixture of mobile phase A and B was eluted through the column at a flow rate of 20 mL/min at room temperature. The purity of all the final discrete compounds was checked by LCMS using a Higgins Haisil HL C18 5 u150×4.6 mm column and an eluent mixture of mobile phase A and B, wherein mobile phase A is composed of 0.1% TFA in H$_2$O and the mobile phase B is composed of CH$_3$CN (95%)/H$_2$O (5%)/TFA (0.1%). The column was eluted at a flow rate of 3 mL/min at a temperature of 60° C. Intermediate compounds were characterized by LCMS using a Higgins Haisil HL C18 5u 50×4.6 mm column and an eluent mixture of mobile phase A and B, wherein mobile phase A is composed of 0.1% TFA in H$_2$O and the mobile phase B is composed of CH$_3$CN (95%)/H$_2$O (5%)/TFA (0.1%). The column was eluted at a flow rate of 3 mL/min at a column temperature of 60° C.

Methods useful for making the compounds of formula I-VI are set forth below in various schemes Scheme 1 illustrates a method for making the intermediate amine compounds of formula 4.

Scheme 1

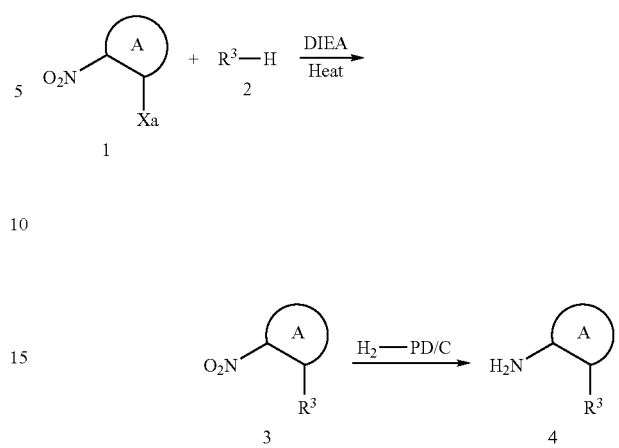

wherein $X^a$ is F or Cl, and $R^3$, and ring A are as defined above for the compounds of formula (I).

A nitro-substituted aryl or heteroaryl derivative of formula 1 can be coupled with a piperizine compound of formula 2 in the presence of diisopropylethylamine (DIEA) heating or by using a microwave-assisted process to provide the coupled compound 3. The nitro group of a compound of formula 3 can then be reduced using an appropriatemethod to provide the intermediate amine compounds of formula 4.

Example

Preparation of Intermediate 6

Scheme 2

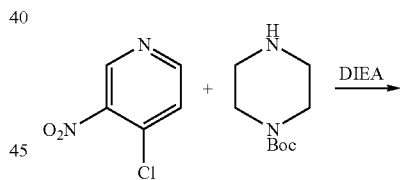

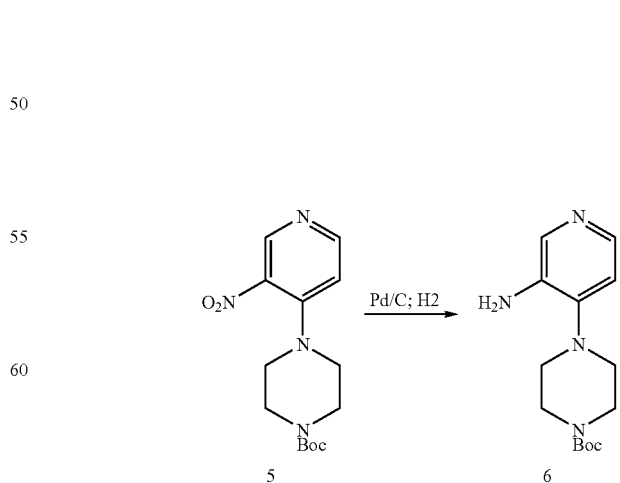

Intermediate 5:

3-Nitro-4-Chloro pyridine (10 mmol) dissolved in dichloromethane (25 mL) and diethyl iso propyl amine (20 mmol) followed Boc piperazine(10 mmol) was added to the above solution while cooling at 0° C. and the reaction mixture was stirred at room temperature for overnight. The dichloromethane was evaporated under vacuum. The resulting solid is extracted in to dichloromethane and washed with citric acid and brine solution. The evaporation of dichloromethane gave a yellow solid, 4-(3-Nitro-pyridin-4-yl)-piperazine-1-carboxylic acid tert-butyl ester which is used for next step without purification.

Intermediate 6:

3-Nitro-4-boc piperizinyl pyridine was dissolved in ethyl acetate and few drops of acetic acids was added. The resulting solution was subjected Pd/C(10%, 10 mol %) and was kept under hydrogen atmosphere at room temperature. Overnight stirring and monitored the reaction progress until the reaction is complete. The reaction solution was filtered through celite and concentrated to give the product, 4-(3-Amino-pyridin-4-yl)-piperazine-1-carboxylic acid tert-butyl ester in good yield (80%)

Interrmediate 7:

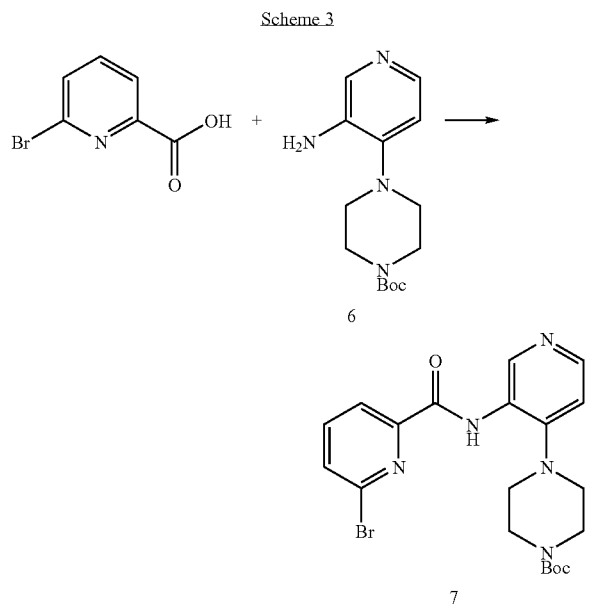

A mixture of 4-(3-Amino-pyridin-4-yl)-piperazine-1-carboxylic acid tert-butyl ester (5.9 g, 21.2 mmol), 6-Bromo-pyridine-2-carboxylic acid (19.3 g, 95.5 mmol), O-(7-Azabenzotriazol-1-yl)-N,N,N',N'-tetramethyluronium hexafluorophosphate (12.1 g, 31.8 mmol), Diisopropyl ethyl amine (11.1 ml, 63.6 mmol) in DMF (106 ml) was stirred at room temperature overnight. Solvent was removed under vacuo, resulting oil taken up in ethyl acetate. Organic layer was washed with dilute hydrochloric acid, dilute sodium hydroxide solution followed by brine and dried over anhydrous sodium sulfate. Solvent was removed to yield thick oil which was purified by column chromatography (SiO2, 10% methanol/dichloromethane) to yield compound 5 (8.3 g of beige solid, 85%). HPLC-MS $t_R$=3.25 min (UV$_{254\ nm}$); Mass calculated for formula $C_{20}H_{24}BrN_5O_3$, 462.34, observed LCMS m/z 462 & 464 (M+H).

Methods for Making the benzolactam Derivatives

Example

Prepration of Intermediate 10

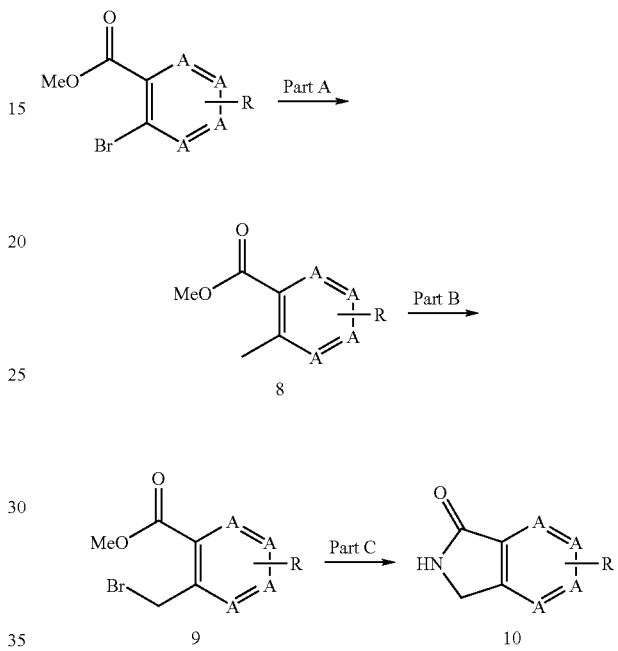

Intermediate 8 (Part A):

Methyl2-bromo-5-methoxy aryl carboxylate (81.61 mmol), trimethylboroxine (13.36 mL, 97.93 mmol), Pd(dppf)Cl$_2$ (1.0 g, 1.36 mmol), dioxane (350 mL), water (50 mL), and Cs$_2$CO$_3$ (22.5 g, 163 mmol) were stirred at 110° C. (oil bath) under nitrogen for 16 hours. After cooling, the solid was removed by filtration. The solution was concentrated and purified by SGC (10:1 EtOAc/hexanes) to give 8

Intermediate 9:

Compound 8 (4.4 g, 24.2 mmol) was dissolved in carbon tetrachloride (80 mL) and N-bromosuccinimide (4.48 g, 24.2 mmol) and benzoyl peroxide (276 mg, 1.13 mmol) were added. The reaction mixture was stirred at reflux for 3 hours and then solids were filtered and washed with ether. The combined organic layers were washed with water, dried over sodium sulfate, and concentrated to provide the desired product 9)

Intermediate 10:

Compound 9 (, 124.0 mmol) was dissolved in 7 M ammonia in MeOH (150 mL) and stirred in a sealed pressure flask at 60° C. overnight. The reaction mixture was cooled and the solvent was removed under reduced pressure. The residue was suspended in ethyl acetate and stirred for 30 minutes. The solids were filtered and dissolved in dichloromethane. The dichloromethane was washed with water, dried over sodium sulfate, and concentrated to provide the desired product 10

Example

Preparation of Intermediate 13

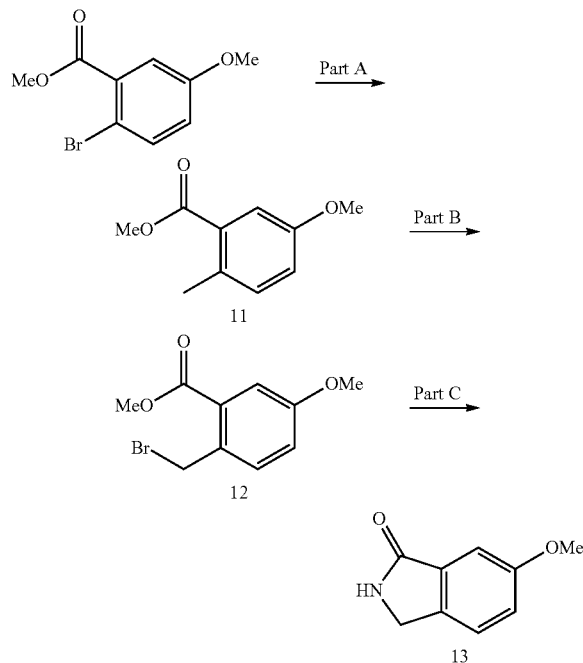

Scheme 5

Intermediate 11:

Methyl 2-bromo-5-methoxy benzoate (20.0 g, 81.61 mmol), trimethylboroxine (13.36 mL, 97.93 mmol), Pd(dppf)Cl$_2$ (1.0 g, 1.36 mmol), dioxane (350 mL), water (50 mL), and Cs$_2$CO$_3$ (22.5 g, 163 mmol) were stirred at 110° C. (oil bath) under nitrogen for 16 hours. After cooling, the solid was removed by filtration. The solution was concentrated and purified by SGC (10:1 EtOAc/hexanes) to give 11 (12.1 g, 80%). Mass calculated for formula C$_{10}$H12NO$_3$, 180.20, observed LCMS m/z 181.20 (M+H).NMR (H$^1$); 2.35(3H, CH3) 3.73(3H, —OCH3),3.88(3 H, CO2-CH3),6.86-7.5(m, 3H,Aromatic)

Intermediate 12:

Compound 11 (4.4 g, 24.2 mmol) was dissolved in carbon tetrachloride (80 mL) and N-bromosuccinimide (4.48 g, 24.2 mmol) and benzoyl peroxide (276 mg, 1.13 mmol) were added. The reaction mixture was stirred at reflux for 3 hours and then solids were filtered and washed with ether. The combined organic layers were washed with water, dried over sodium sulfate, and concentrated to provide the desired product 12 (6.1 g, 98%). Mass calculated for formula C$_{10}$H$_{11}$BrO$_3$ 259.10, observed LCMS m/z 260 (M+H), NMR (H$^1$); 4.50 (2H,CH2-Br) 3.73(3H, —OCH3),3.88(3 H, CO2-CH3), 6.86-7.5(m,3H,Aromatic) Intermediate 13 :

Compound 12 (32.0 g, 124.0 mmol) was dissolved in 7 M ammonia in MeOH (150 mL) and stirred in a sealed pressure flask at 60° C. overnight. The reaction mixture was cooled and the solvent was removed under reduced pressure. The residue was suspended in ethyl acetate and stirred for 30 minutes. The solids were filtered and dissolved in methylene chloride. The methylene chloride was washed with water, dried over sodium sulfate, and concentrated to provide the desired product 13 (13.5 g, 67%). Mass calculated for formula C$_9$H$_9$NO$_2$, 163.17, observed LCMS m/z 164.2 (M+H), NMR (H$^1$); 4.20 (2H,CH2) 3.73(3H, —OCH3),3.88,6.86-7.5(m,3H,Aromatic), 8.0(NH)

Compounds 14-19 in Table-1 could be synthesized by essentially following similar experimental procedures described above in the examples

TABLE 1

| Compound | Structure | Exact mass | MS m/z (M + H) | HPLC MS $t_R$ |
|---|---|---|---|---|
| 14 | 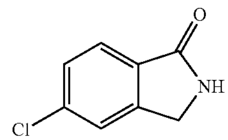 | 167.0 | 168.1 | 1.09 |
| 15 | 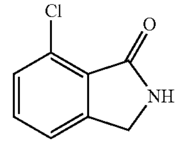 | 167.0 | 168.0 | 1.08 |
| 16 | 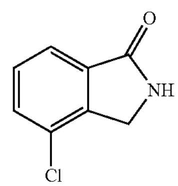 | 167.0 | 168.1 | 1.09 |
| 17 | 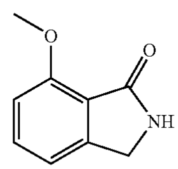 | 163.1 | 164.1 | 0.82 |
| 18 | 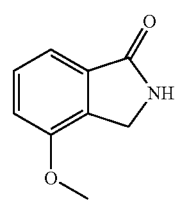 | 163.1 | 164.1 | 0.92 |
| 19 | 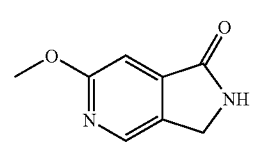 | 164.1 | 165.20 | 0.85 |

Intermediate 20:

Scheme 6

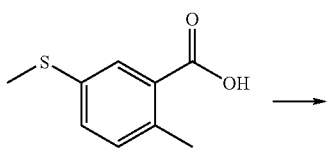

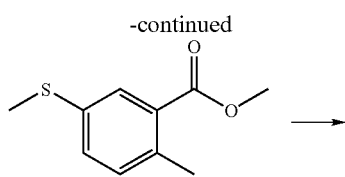

To a solution of compound 20 (40 mg, 0.223 mmol) in 5 ml of DCM was added 0.223 mg of MCPBA. Reaction mixture was stirred at room temperature for 3 hours. Crude was washed with water and organic concentrated under vacuo.); mass calculated for formula C9H9NO2S 195.04 observed LCMS m/z 196.42 (M+H) Product was used without further purifications.

Intermediate 24:

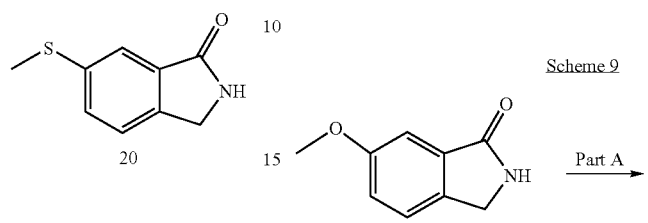

To a solution of 2-Methyl-5-methylsulfanyl-benzoic acid (250 mg, 1.37 mmol) in 10 ml of 1:1 benzene/methanol mixture was added 2.74 mmol of TMSCHN2. Reaction was stirred at room temperature for 0.5 hr. Solvent was removed to give 250 mg of compound 20 as a yellow oil (93%). Material was used without further purifications. NMR (H$^1$); 2.48(s, 3H,CH3) 2.54(s, 3H, SCH3),3.88(s, 3 H, CO2-CH3),7.10-7.8(m,3H,Aromatic)

Intermediate 21:

Scheme 7

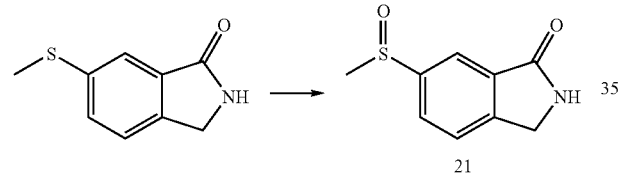

To a solution of 20 (1.034 g, 5.27 mmol) in carbon tetrachloride (15 ml) was added N-bromo succinamide (0.935 g, 5.27 mmol) and benzoyl peroxide (47 mg, 0.19 mmol). Mixture was heated at reflux overnight. Solution was cooled over ice and solid filtered off. Removal of solvent yields yellow oil which was stirred in excess 7M NH$_3$ in methanol in a pressure vessel at 70° C. overnight. Solvent was removed and resulting crude was purified on flash column (SiO2, Hexane/ethyl acetate) afforded compound 21 as a off-white solid (158 mg, 17%). NMR (H$^1$); 2.51(s, 3H, SCH3), 4.3(s, 2 H, -CH2), 7.44-7.5(m,3H,Aromatic)

Example 22

Scheme 8

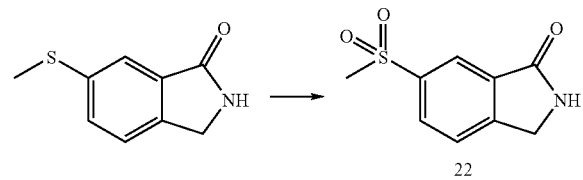

Intermediate 23:

Example Compound 13 (150 mg, 0.92 mmol) was dissolved in DCM (20 mL) and cooled to -78° C. To this mixture, BBr$_3$ (1M, 1.2 mL) was added dropwise. After 1 hour, the mixture was warmed to room temperature and stirred for another 2 hours. Then, another portion of BBr$_3$ (1M, 1.2 mL) was added and the resulting mixture was heated to reflux and stirred overnight. After cooling to room temperature, EtOAc (100 mL) was added and the organics washed with water, brine and dried over Na$_2$SO$_4$. After concentration, the residue was used in the next step without further purification. HPLC-MS t$_R$=0.58 min (UV$_{254\ nm}$); mass calculated for formula C$_8$H$_7$NO$_2$ 149.0, observed LCMS m/z 150.1 (M+H).

Intermediate 24:

Example Compound 23 (50 mg, 0.33 mmol) was added to the mixture of Cs$_2$CO$_3$ (326 mg, 1.0 mmol), 2-dimethylaminoethyl chloride (HCl salt, 50 mg) in DMF (5 mL). The resulting mixture was heated to 60° C. and stirred overnight. After cooling to room temperature, the base was removed by filtration and the solvent was removed with concentration. The residue was with column (silica gel, DCM/MeOH=95:5 to DCM/MeOH/Et3N=90:5:5) to give the product 24 (53 mg) as yellowish solid. HPLC-MS t$_R$=0.56 min (UV$_{254\ nm}$); mass calculated for formula C$_{12}$H$_{16}$N$_2$O$_2$ 220.1, observed LCMS m/z 221.1 (M+H).

Intermediate 25

Compound 25 in Table 2 was prepared with the same procedure described in the procedure above for intermediate 24.

TABLE 2

| Compound # | Compound No. | Exact mass | MS m/z (M + H) | HPLC MS $t_R$ |
|---|---|---|---|---|
| 25 | 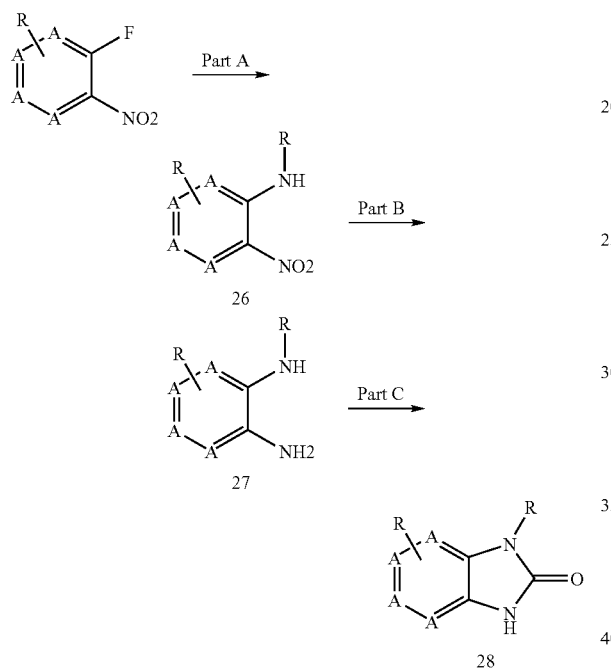 | 262.1 | 263.1 | 0.59 |

Intermediate 28

Scheme 10

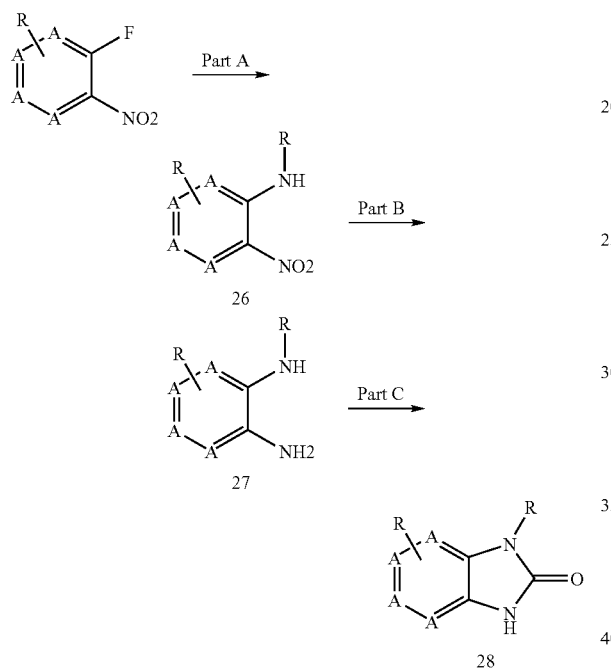

Preparation of Intermediate 31:

Scheme 11

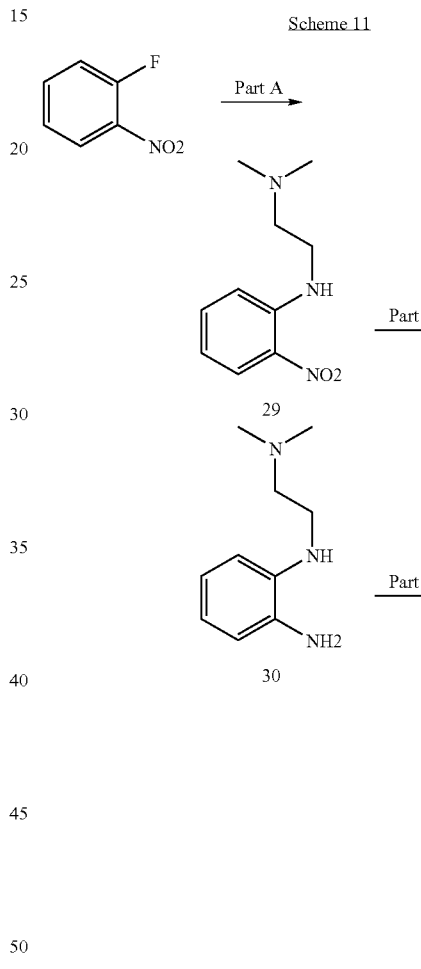

Intermediate 26:

2-fluoronitroarene (6 g, 43 mmol) was dissolved in dry THF (80 mL) with $K_2CO_3$ (12 g, 86 mmol). The mixture was cooled to 0° C., and amine (4.6 g, 88 mmol) was added. The resulting mixture was warmed to room temperature and stirred for 24 hours. The mixture was filtrated through celite and concentrated. The residue was used in the next step without further purification.

Intermediate 27:

The nitro compound 26 (7.8 g, crude) was dissolved in THF (50 mL) and Pd/C (10%, 1 g) was added under argon. The mixture was treated with $H_2$ (40 psi) and stirred for 2 hours. The mixture was filtrated through celite and concentrated under reduced vacuum to give the crude product 27, which was used in the next step without any further purification.

Intermediate 28:

Compound 27 (7.0 g, crude) was dissolved in DMF (20 mL) and CDI (6.5 g, 40 mmol). The mixture was heated up to 110° C. and stirred for 2 hours. After cooling to room temperature, the DMF was removed by concentration under reduced pressure. The residue was purified with column (silica gel, DCM/MeOH=95:5 to DCM/MeOH/$Et_3N$=90:5:5) to give the product 28 (5.2 g) as yellowish solid Intermediate 29:

2-fluoronitrobenzene (6 g, 43 mmol) was dissolved in dry THF (80 mL) with $K_2CO_3$ (12 g, 86 mmol). The mixture was cooled to 0° C., and amine (4.6 g, 88 mmol) was added. The resulting mixture was warmed to room temperature and stirred for 24 hours. The mixture was filtrated through celite and concentrated. The residue was used in the next step without further purification. HPLC-MS $t_R$=0.77 min (UV$_{254\ nm}$), mass calculated for formula $C_{10}H_{15}N_3O_2$ 209.1, observed LCMS m/z 210.1 (M+H).

Intermediate 30:

The nitro-compound 29 (7.8 g, crude) was dissolved in THF (50 mL) and Pd/C (10%, 1 g) was added under argon. The mixture was treated with $H_2$ (40 psi) and stirred for 2 hours. The mixture was filtrated through celite and concentrated under reduced vacuum to give the crude product 30, which was used in the next step without any further purification. HPLC-MS $t_R$=0.39 min (UV$_{254\ nm}$); mass calculated for formula $C_{10}H_{17}N_3$ 179.1, observed LCMS m/z 180.1 (M+H).

Intermediate 31:

Compound 30 (7.0 g, crude) was dissolved in DMF (20 mL) and CDI (6.5 g, 40 mmol). The mixture was heated up to 110° C. and stirred for 2 hours. After cooling to room temperature, the DMF was removed by concentration under reduced pressure. The residue was purified with column (silica gel, DCM/MeOH=95:5 to DCM/MeOH/Et$_3$N=90:5:5) to give the product 31 (5.2 g) as yellowish solid HPLC-MS $t_R$=0.57 min (UV$_{254\ nm}$); mass calculated for formula $C_{11}H_{15}N_3O$ 205.1, observed LCMS m/z 206.1 (M+H).

Compound 32 in Table 3 was prepare with the same procedure as described for intermediate 31

TABLE 3

| Compound # | Structure | Exact mass | MS m/z (M + H) | HPLC MS $t_R$ |
|---|---|---|---|---|
| 32 | 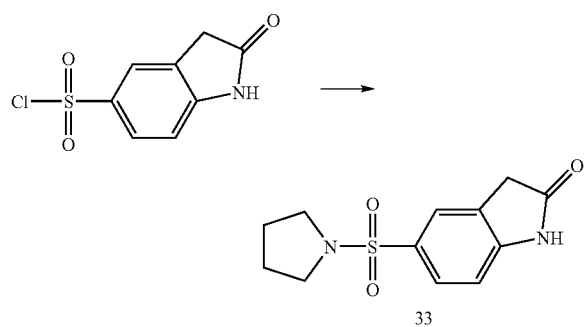 | 247.1 | 248.2 | 0.55 |

Intermediate 33:

Scheme 12

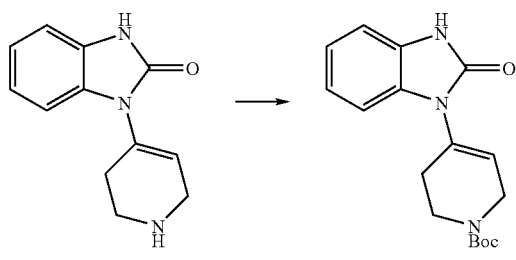

33

Into a solution of 2-Oxo-2,3-dihydro-1H-indole-5-sulfonyl chloride (800 mg, 3.45 mmol) in 5 mL DCM was added triethylamine (0.97 mL, 6.90 mmol) followed by Pyrrolidine (0.34 mL, 4.14 mmol). Reaction mixture was stirred at room temperature for 2 hours. Solid formed were filtered and washed with DCM. Organic layer collected and removed in vacuo. Resulting oil was dissolved in ethyl acetate and washed with water and brine, then dried over anhydrous sodium sulfate. Removal of solvent yielded yellow solid that was of sufficient purity to be used as is. HPLC-MS $t_R$=1.05 min (UV$_{254\ nm}$); Mass calculated for formula $C_{12}H_{14}N_2O_3S$, 266.32, observed LCMS m/z 267.30 (M+H).

Intermediate 34:

Scheme 13

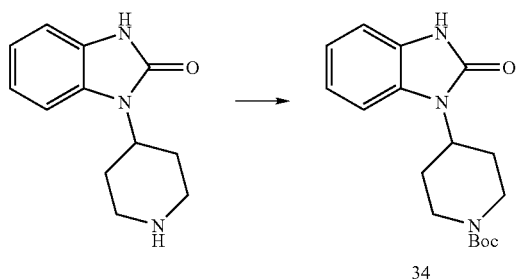

34

Into a solution of 1-Piperidin-4-yl-1,3-dihydro-benzoimidazol-2-one (1.0 g, 4.6 mmol in 10 mL) was added a solution of Di-tert-butyl dicarbonate (1.26 mL) and Diisopropyl ethyl amine (1.6 mL) in 10 ml DCM. Mixture was stirred at room temperature for one hour. Mixture was washed with water and dried over anhydrous sodium sulfate. Removal of solvent yield white solid of good purity (95%). HPLC-MS $t_R$=1.61 min (UV$_{254\ nm}$); Mass calculated for formula $C_{17}H_{23}N_3O_3S$, 317.38, observed LCMS m/z 340.20 (M+Na).

Intermediate 35:

Scheme 14

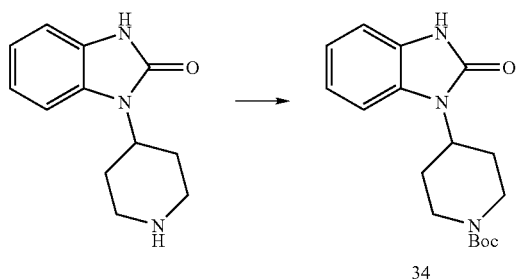

35

Into a solution of 1,3-Dihydro-1-(1,2,3,6-tetrahydro-4-pyridinyl)-2H-benzimidazole-2-one (4.6 mmol in 10 mL) was added a solution of Di-tert-butyl dicarbonate (1.26 mL) and Diisopropyl ethyl amine (1.6 mL) in 10 ml DCM. Mixture was stirred at room temperature for one hour. Mixture was washed with water and dried over anhydrous sodium sulfate. Removal of solvent yield white solid of good purity (95%). HPLC-MS $t_R$=1.68 min (UV$_{254\ nm}$); Mass calculated for formula $C_{17}H_{21}N_3O_3S$, 315.38, observed LCMS m/z 316.20 (M+H).

Intermediate 41:

Scheme 15

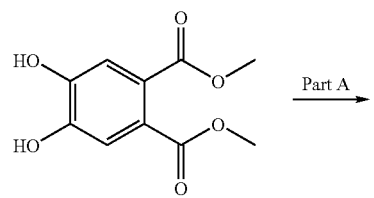

Part A

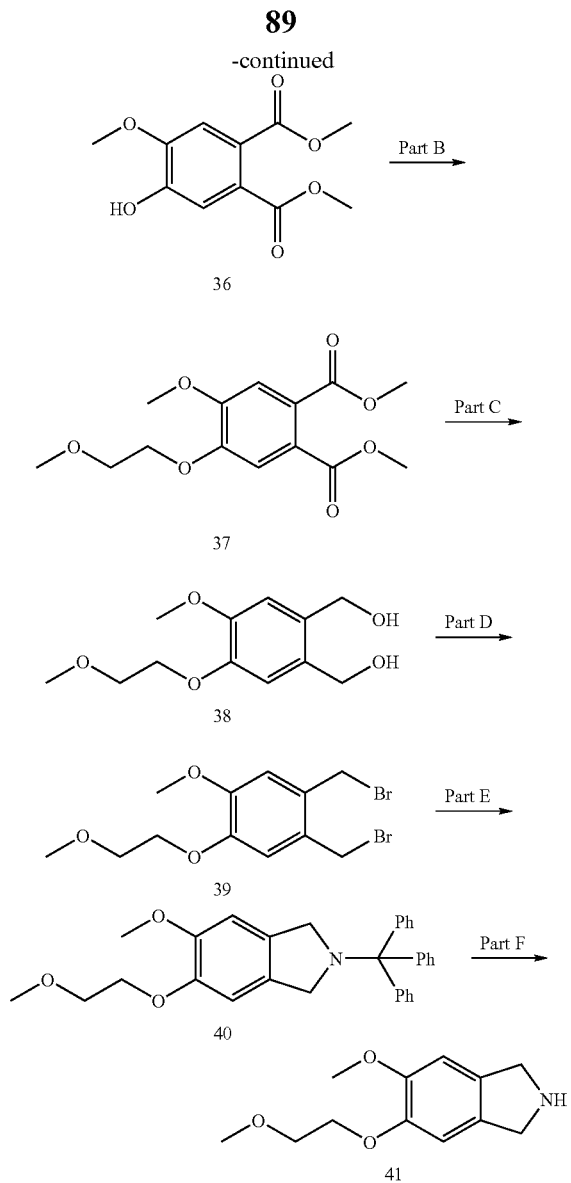

with column (silica gel, 30% EtOAc in Hexane) gave the product 37 (288 mg) as brown solid. HPLC-MS tR=1.60 min (UV254 nm); mass calculated for formula $C_{14}H_{18}O_7$ 298.1, observed LCMS m/z 299.2 (M+H).

Part C:

The compound 37 (288 mg, 0.966 mmol) was dissolved in THF (15 mL) and cooled to 0° C. LiAlH$_4$ (1 M in THF, 4.0 mL) was added. The mixture was allowed to warm to room temperature and then refluxed overnight. After cooling to room temperature, H$_2$O (152 uL) was added carefully followed by 15% NaOH (152 uL) and H$_2$O (456 uL). The mixture was stirred for another 30 min, and the solid was filtered off and was with THF. The organics was concentrated under vacuum and purified with column (silica gel, EtOAc ~2% MeOH in EtOAc) gave the product 38 (155 mg). HPLC-MS tR=1.00 min (UV254 nm); mass calculated for formula $C_{12}H_{18}O_5$ 242.1, observed LCMS m/z 225.1 (M−OH).

Part D:

The compound 38 (155 mg, 0.64 mmol) was dissolved in THF (15 mL) and PPh$_3$ (504 mg, 1.92 mmol) was added. The mixture was cooled to 0° C. and CBr$_4$ (467 mg, 1.4 mmol) was added. The resulting mixture was allowed to warm to room temperature and stirred for 2 hours. The solid was filtered off and the solvent was removed under vacuum. The residue was purified with column (silica gel, 15% EtOAc in hexane) gave the product 39 (192 mg).

Part E:

The dibromo compound 39 (192 mg, 0.52 mmol) was dissolved in DMF (5 mL). DIEA (260 uL, 1.5 mmol) and tritylamine (148 mg, 0.57 mmol) was added and the mixture was heated to 60° C. and stirred for 2 hours. DMF was removed under vacuum and the residue was taken up with EtOAc (60 mL). The organics was washed with water and brine and dried over Na$_2$SO$_4$. After concentration, the residue was purified with column (silica gel, 30% EtOAc/Hexane) gave the product 40 (211 mg).

Part F:

The compound 40 (211 mg, 0.45 mmol) was dissolved in the mixture of MeOH/CHCl$_3$ (5 mL/5 mL) and cooled to 0° C. TFA (10 mL) was added carefully. After 5 min at 0° C., the mixture was warmed to room temperature and stirred for another 30 min. After concentration, the residue was taken in ether and 1 N HCl. The aqueous was extracted with ether and then basified with 4 N NaOH to pH ~10. The mixture was extracted with DCM (40 mL×3). The combined organic phase were dried and concentrated. The crude product 41 (95 mg) was used in the next step directly without further purification. HPLC-MS tR=0.78 min (UV254 nm); mass calculated for formula $C_{12}H_{17}NO_3$ 223.1, observed LCMS m/z 224.2 (M−OH).

Part A:

The diethyl-3,4-dihydroxy-o-phthalate (1.77 g, 7.8 mmol) was dissolved in DMF (10 mL) and Cs$_2$CO$_3$ (2.55 g, 7.8 mmol) was added. To the mixture, MeI (1.2 g, 8.6 mmol) was added and the resulting mixture was stirred at room temperature overnight. The mixture was diluted with EtOAc and washed with water and brine, dried over Na$_2$SO$_4$. After concentration, the crude product was purified with column (silica gel, 15% to 30% EtOAc in Hexane) gave the product 36 (698 mg) as brown solid and recovered the starting material (369 mg). HPLC-MS tR=1.12 min (UV254 nm); mass calculated for formula $C_{11}H_{12}O_6$ 240.1, observed LCMS m/z 241.1 (M+H).

Part B:

The compound 36 (390 mg, 1.6 mmol) was dissolved in THF (10 mL). 2-Methoxyethanol (152 mg, 2.0 mmol), and PPh$_3$ (525 mg, 2.0 mmol) were added to the mixture and the resulting mixture was cooled to 0° C. DIAD (404 mg, 2.0 mmol) was added dropwise. The mixture was allowed to warm to room temperature and stirred overnight. Ether (50 mL) was added and the solid was filtered off. The solvent was removed under reduced pressure and the residue was purified Example 46

Example 51

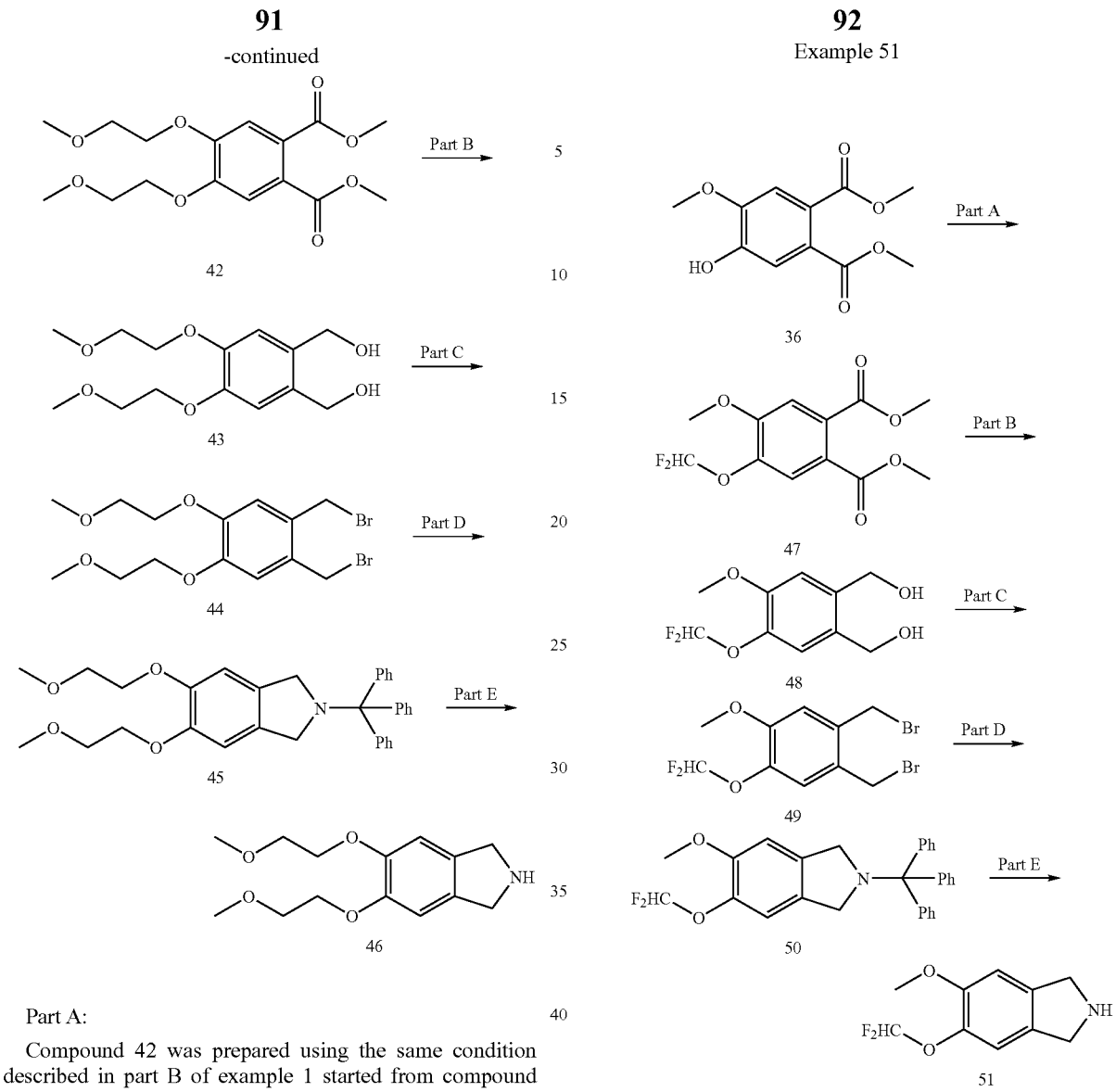

Part A:

Compound 42 was prepared using the same condition described in part B of example 1 started from compound diester of 3,4-dihydroxy-o-phthalate. HPLC-MS tR=1.45 min (UV254 nm); mass calculated for formula $C_{16}H_{22}O_8$ 342.1, observed LCMS m/z 343.1 (M+H).

Part B:

Compound 43 was prepared using the same condition described in part C of example 41 started from compound 42. HPLC-MS tR=0.90 min (UV254 nm); mass calculated for formula $C_{14}H_{22}O_6$ 286.1, observed LCMS m/z 269.2 (M−OH).

Part C:

Compound 44 was prepared using the same condition described in part D of example 41 started from compound 43.

Part D:

Compound 45 was prepared using the same condition described in part E of example 41 started from compound 44.

Part E:

Compound 46 was prepared using the same condition described in part F of example 41 started from compound 45. HPLC-MS tR=0.80 min (UV254 nm); mass calculated for formula $C_{14}H_{21}NO_4$ 267.1, observed LCMS m/z 268.1 (M+H).

Part A:

Compound 36 (240 mg, 1.0 mmol) was dissolved in DMF (5 mL). $Cs_2CO_3$ (325 mg, 1.0 mmol) was added. The mixture was cooled to 0° C. and $BrCHF_2$ was blown in for 5 min. The resulting mixture was allowed to warm to room temperature and stirred overnight. EtOAc (60 mL) was added and then washed with water and brine and dried over $Na_2SO_4$. After concentration, the residue was purified with column (15-30% EtOAc in hexane) gave the product 47 (271 mg). HPLC-MS tR=1.69 min (UV254 nm); mass calculated for formula $C_{12}H_{12}F_2O_6$ 290.1, observed LCMS m/z 291.1 (M+H).

Part B:

Compound 48 was prepared using the same condition described in part C of example 41 started from compound xxx. HPLC-MS tR=1.06 min (UV254 nm); mass calculated for formula $C_{10}H_{12}F_2O_4$ 234.1, observed LCMS m/z 257.0 (M+Na).

Part C:

Compound 49 was prepared using the same condition described in part D of example 41 started from compound 48.

Part D:
Compound 50 was prepared using the same condition described in part E of example 41 started from compound 49

Part E:
Compound 51 was prepared using the same condition described in part F of example 41 started from compound 50. HPLC-MS tR=0.98 min (UV254 nm); mass calculated for formula $C_{10}H_{11}F_2NO_2$ 215.1, observed LCMS m/z 216.1 (M+H).

Example 52

By essentially the same procedure given in Preparative Example 46, compound 52 given in Column 2 of Table 4 can be prepared starting from Diethyl-3,4-dihydroxy-o-phthalate and $BrCHF_2$.

TABLE 4

| Compound # | Column 2 | Exact mass | MS m/z (M + H) | HPLC MS $t_R$ |
|---|---|---|---|---|
| 52 | F₂HC-O-...-NH (F₂HC-O-) | 251.1 | 252.2 | 0.93 |

Example 55

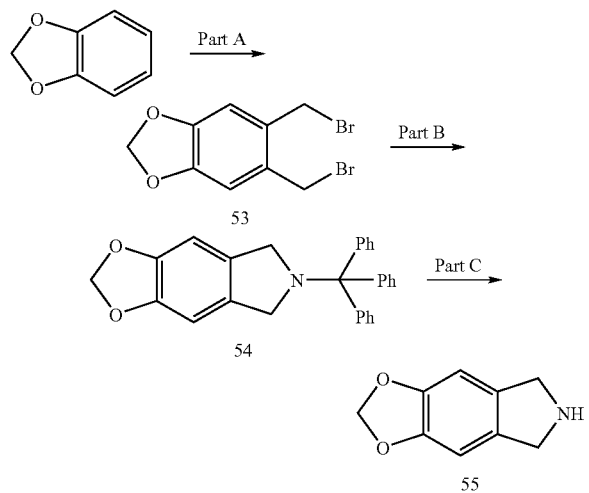

Part A
The benzodioxole (2.66 mL, 20 mmol) was mixed with paraformaldehyde (2.83 g, 94 mmol) in 33% HBr in HOAc (27 mL) at 0° C. The mixture was allowed to warm to room temperature and stirred for overnight. The solvent was removed under vacuum and the residue was purified with column (silica gel, 15% EtOAc in hexane) gave the product 53 (4.5 g) as white solid.

Part B:
Compound 54 was prepared using the same condition described in part E of example 41 started from compound 53.

Part C:
Compound 55 was prepared using the same condition described in part F of example 41 started from compound 54.

HPLC-MS tR=0.54 min (UV254 nm); mass calculated for formula $C_9H_9NO_2$ 163.1, observed LCMS m/z 164.1 (M+H).

Example 59

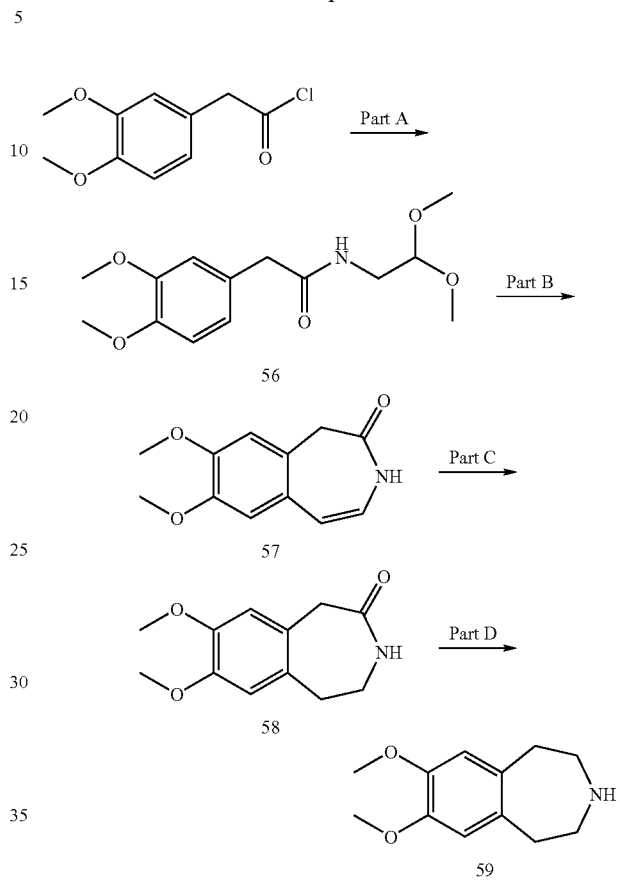

Part A:
To the solution of 3,4-dimethoxy phenyl acetyl chloride (5.0 g, 23.29 mmol) in DCM (30 mL), $Et_3N$ (3.24 mL, 23.29 mmol) was added at 0° C. followed by aminoacetaldehyde dimethyl acetal (2.51 mL, 23.9 mmol). The mixture was allowed to warm to room temperature and stirred for one hour. EtOAc (300 mL) was added and the organics was washed with water, brine and dried over $Na_2SO_4$. After concentration, the crude product 56 (6.5 g) was used in the next step without further purification.

Part B:
The crude product 56 from last step was dissolved in HOAc (30 mL) and concentrated HCl (30 mL) was added. The mixture was stirred at room temperature overnight. The acid was removed under reduced pressure. Water (100 mL) was added and the solid was collected(compound 57) with filtration and dried under air (4.4 g). HPLC-MS tR=1.05 min (UV254 nm); mass calculated for formula $C_{12}H_{13}NO_3$ 219.1, observed LCMS m/z 220.1 (M+H).

Part C:
The compound 57 (4.4 g) was dissolved in HOAc (100 mL) and 10% Pd/C (1 g) was added under nitrogen. The mixture was stirred under hydrogen (5 bar) at room temperature overnight. The Pd/C was filtered off and the filter was concentrated. The residue 58 (3.5 g) was used in the next step directly without further purification. HPLC-MS tR=0.91 min (UV254 nm); mass calculated for formula $C_{12}H_{15}NO_3$ 221.1, observed LCMS m/z 222.1 (M+H).

Part D:

The lactam 58 (3.5 g, 15.8 mmol) was dissolved in THF (100 mL) and the solution was heated to 45° C. LiAlH$_4$ (1 N in THF, 32 mL) was added carefully and the resulting mixture was refluxed for 20 hours. After cooling to room temperature, H$_2$O (1.2 mL) was added carefully followed by 15% NaOH (1.2 mL) and H$_2$O (3.6 mL). The mixture was stirred for another 30 min, and the solid was filtered off and was with THF. The organics was concentrated under vacuum and the crude product 59 (2.13 g) was used in the reaction without any further purification. HPLC-MS tR=0.62 min (UV254 nm); mass calculated for formula C$_{12}$H$_{17}$NO$_2$ 207.1, observed LCMS m/z 208.1 (M+H).

Example 62

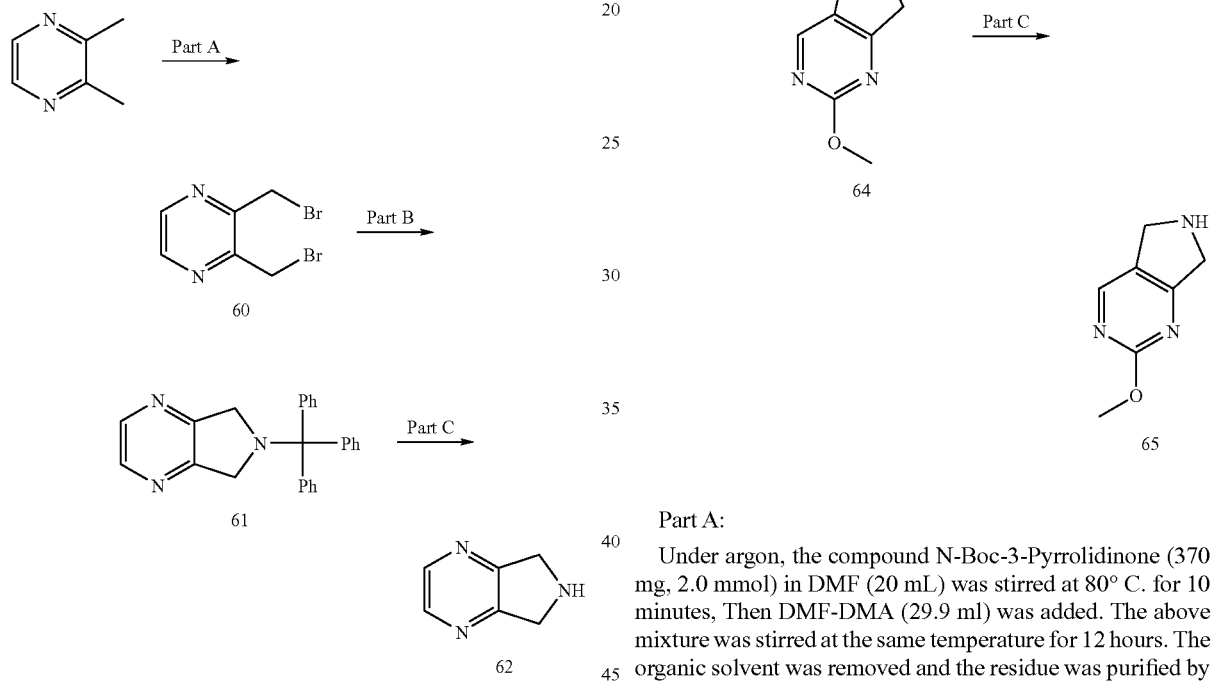

Example 65

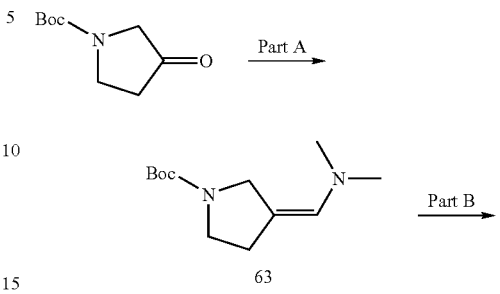

Part A:

Under argon, the compound 2,3-dimethylpyrazine (216 mg, 2.0 mmol) was dissolved in CCl$_4$ (10 mL), 2,2'-azobis(2-methylpropionitrile) (33 mg, 0.2 mmol) and NBS (356 mg, 2.0 mmol) were added. The mixture was refluxed for 16 hours. The mixture was filtered and washed with CCl$_4$. The filtrate was concentrated and purified with column (silica gel, EtOAc) gave the product 60 (457 mg) as yellow solid. HPLC-MS tR=1.34 min (UV254 nm); mass calculated for formula C$_6$H$_6$Br$_2$N$_2$ 263.9, observed LCMS m/z 264.9 (M+H).

Part B:

Compound 61 was prepared using the same condition described in part E of example 41 started from compound 69.

Part C:

Compound 62 was prepared using the same condition described in part F of example 41 started from compound 61. HPLC-MS tR=0.22 min (UV254 nm); mass calculated for formula C$_6$H$_7$N$_3$ 121.1, observed LCMS m/z 122.1 (M+H).

Part A:

Under argon, the compound N-Boc-3-Pyrrolidinone (370 mg, 2.0 mmol) in DMF (20 mL) was stirred at 80° C. for 10 minutes, Then DMF-DMA (29.9 ml) was added. The above mixture was stirred at the same temperature for 12 hours. The organic solvent was removed and the residue was purified by column gave compound 63.

Part B:

Under argon, methyl carbamate (514 mg, 4.65 mmol) and NaOEt (21% in EtOH, 2.02 mL) were stirred for 15 minutes. Then the compound 63 (372 mg, 1.55 mmol) was added. The mixture was stirred at 85° C. for 3.5 hours. The reaction mixture was quenched by 5% citric acid and evaporated to dryness. The residue was dissolved in EtOAc and washed with saturated NaHCO$_3$ solution, brine and dried. After concentration The residue was purified by column gave compound 64. HPLC-MS tR=1.48 min (UV254 nm); mass calculated for formula C$_{12}$H$_{17}$N$_3$O$_3$ 251.1, observed LCMS m/z 252.1 (M+H).

Part C:

Compound 64 was dissolved in 4N HCl in 1,4-dioxane and stirred at room temperature for 15 minutes. After concentration, the residue 65 was used in the next step directly without further purification. HPLC-MS tR=0.27 min (UV254 nm); mass calculated for formula C$_{12}$H$_{17}$N$_3$O$_3$ 151.1, observed LCMS m/z 152.1 (M+H).

Intermediate 68:

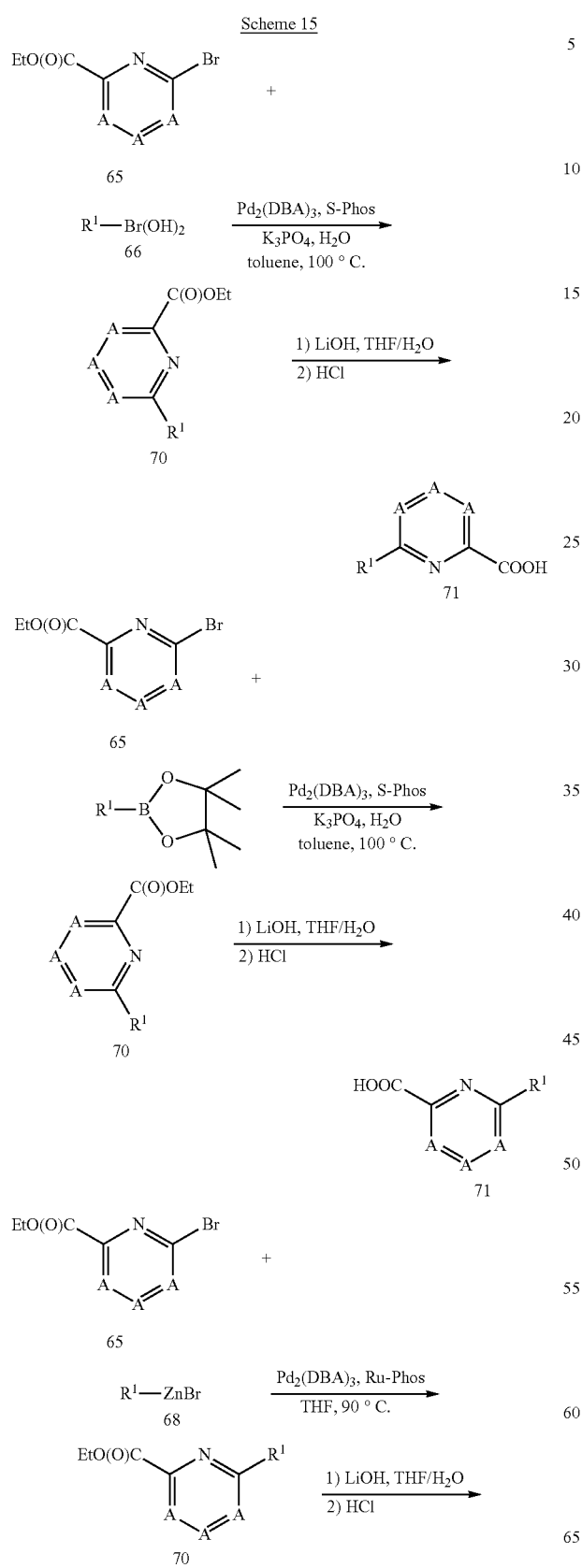

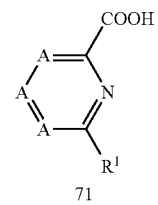

wherein $R^1$ is as defined above for the compounds of formula (I). (When $R^1$ is attached to a nitrogen in Scheme 6 above, it has, in one embodiment, the same meaning as $R^6$ and $R^7$ of Formula II, $R^{11}$ and $R^{12}$ of Formula IV, $R^{14}$ and $R^{15}$ of Formula V and $R^{17}$ and $R^{18}$ of Formula VI)

2-Bromoheteroaryl-6-carboxylic acid ethyl ester (65) can be reacted with (i) a boronic acid compound of formula 66, (ii) a boronic pinacol ester compound of formula 67, or (iii) a zinc bromide compound of formula 68 or (iv) amines (40) using appropriate palladium coupling conditions or Cu catalyst with diamine (Buchwald/Hartwig reaction conditions to make a 2-substituted heteroaryl-6-ester intermediate of formula 69. The compounds of formula 60 can then be hydrolyzed using LiOH, for example, to provide the 2-substituted heteroaryl-6-carboxylic acid compounds of formula 71.

Example 74

Following scheme 16 illustrates a method for making the compounds of formula (I).

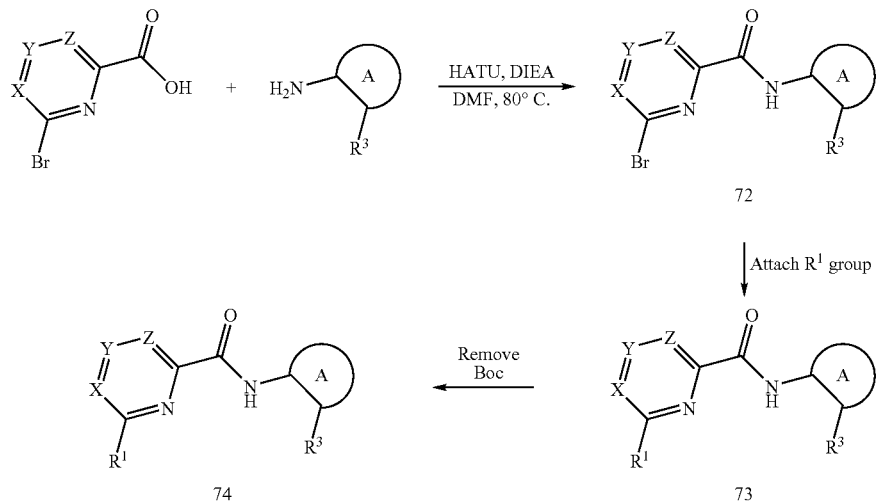

Scheme 16 wherein $R^1$, $R^2$, $R^3$, and ring A are as defined above for the compounds of formula (I).

A 2-bromo-heteroaryl-6-carboxylic acid can be coupled with an amine compound of formula 65 using 2-(1H-7-aza-benzotriazol-1-yl)-1,1,3,3-tetramethyl uronium hexafluorophosphate (HATU) in the presence of N,N-diisopropylethylamine to provide the amido intermediates of formula 72. A compound of formula 72 can then be coupled with an $R^1$ group using a palladium-catalyzed process described in above Scheme to provide the compounds of formula 73. Removal of the Boc protecting group from a compound of formula 73 using an acid, such as TFA or formic acid, provides the Anilinopiperazine Derivatives (75) of formula (I).

Example

Preparation of Intermediate 74

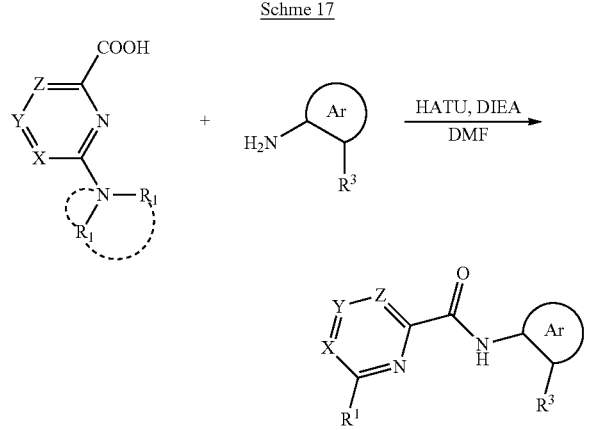

Schme 17

An a 2-substituted-heteroaryl-6-carboxylic acid of formula 71 can be coupled with an amine using the HATU-mediated coupling method set forth in Scheme to give compound of the structure 74,

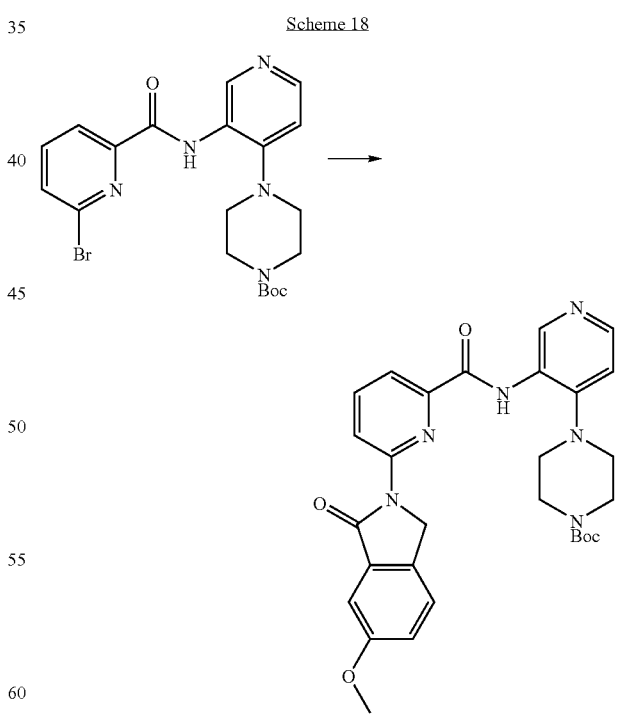

Scheme 18

A mixture of 4-{3-[(6-Bromo-pyridine-2-carbonyl)-amino]-pyridin-4-yl}-piperazine-1-carboxylic acid tert-butyl ester (xxx, 100 mg, 0.22 mmol), the 6-methoxy-2,3-dihydro-isoindol-1-one, 1.2 equivalent, Tris(dibenzylideneacetone)dipalladium(0) (20 mg, 0.02 mmol), Xantphos (26 mg, 0.04 mmol), Potassium Phosphate (139 mg, 0.66 mmol) in 5 ml of Dioxane was heated to 85° C. for 16 hours. Resulting suspension was passed through a filter to remove insoluble solid. Organic layer was concentrated in vacuo. The crude compound was purified by Prep-LC to yield compound 76.

HPLC-MS tR=3.84 min (UV254 nm); Mass calculated for formula $C_{29}H_{32}N_6O_5$, 544.17, observed LCMS m/z 545.20.

By essentially following the procedure described for the preparation of intermediate 76 above, the compounds 77-124, given in Table 5 below could be prepared.

TABLE 5

| Compound # | Structure | MW | LCMS MH+ m/z | HPLC MS $t_R$ |
|---|---|---|---|---|
| 77 | 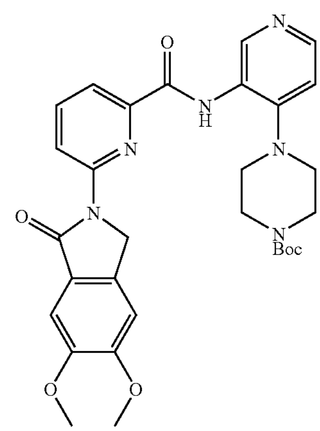 | 574.25 | 575.25 | 3.60 |
| 78 | 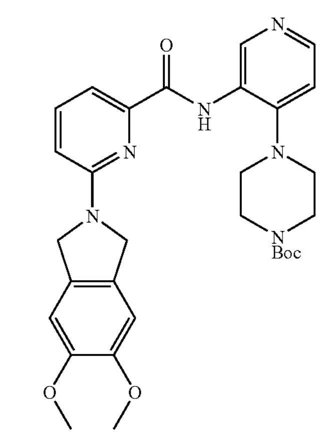 | 560.27 | 561.27 | 3.75 |
| 79 | 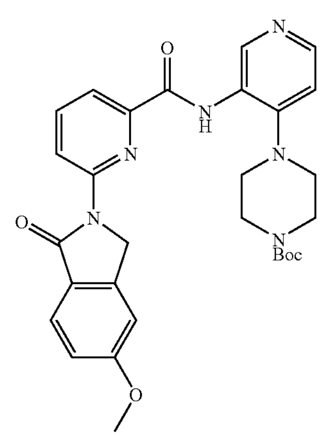 | 544.24 | 545.25 | 3.80 |

TABLE 5-continued

| Compound # | Structure | MW | LCMS MH+ m/z | HPLC MS $t_R$ |
|---|---|---|---|---|
| 80 | 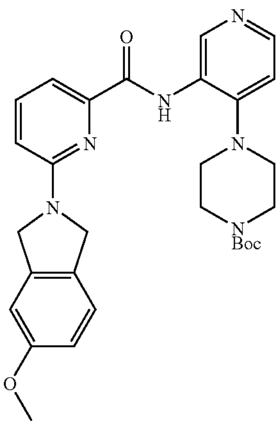 | 530.26 | 531.26 | 3.65 |
| 81 | 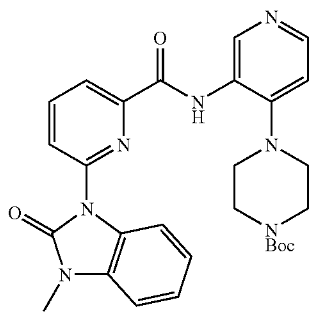 | 529.24 | 530.24 | 3.40 |
| 82 | 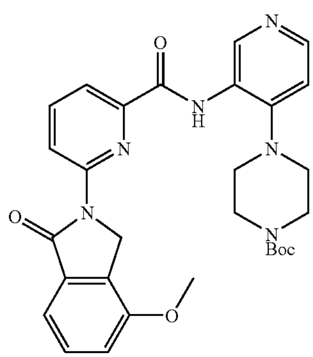 | 544.24 | 545.24 | 3.84 |
| 83 | 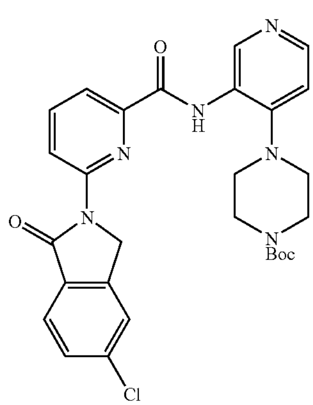 | 548.19 | 549.19 | 3.99 |

TABLE 5-continued

| Compound # | Structure | MW | LCMS MH+ m/z | HPLC MS $t_R$ |
|---|---|---|---|---|
| 84 | 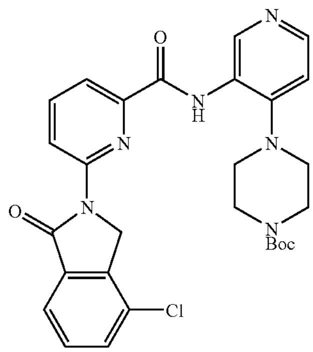 | 548.19 | 549.19 | 3.87 |
| 85 | 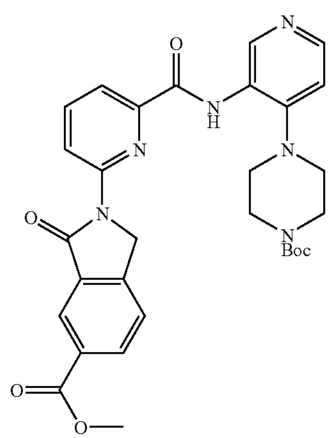 | 572.24 | 573.24 | 3.76 |
| 86 | 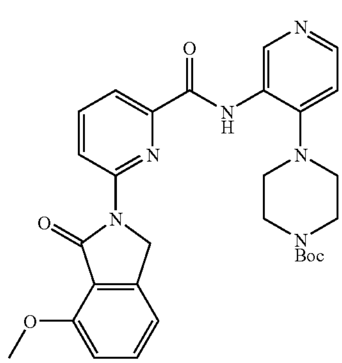 | 544.24 | 545.24 | 3.53 |

TABLE 5-continued
| Compound # | Structure | MW | LCMS MH+ m/z | HPLC MS t_R |
|---|---|---|---|---|
| 87 | 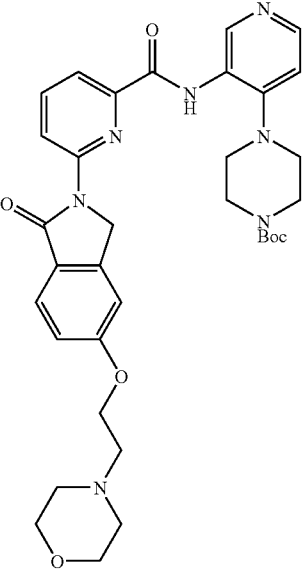 | 643.31 | 644.31 | 2.86 |
| 88 | 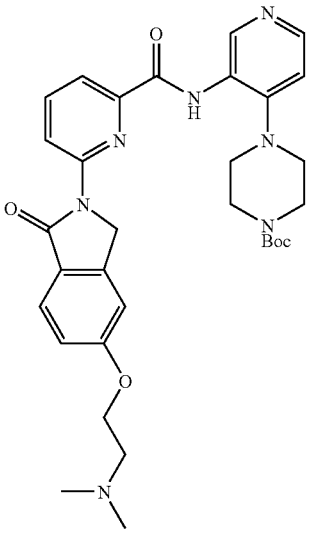 | 601.30 | 602.30 | 2.78 |

TABLE 5-continued

| Compound # | Structure | MW | LCMS MH+ m/z | HPLC MS $t_R$ |
|---|---|---|---|---|
| 89 | 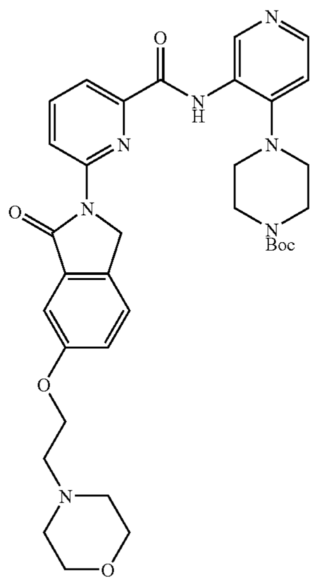 | 643.31 | 644.31 | 2.72 |
| 90 | 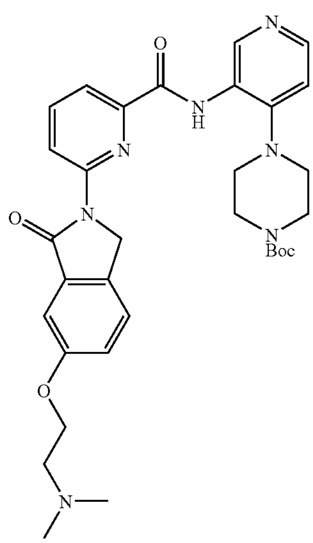 | 601.30 | 602.30 | 2.73 |
| 91 | 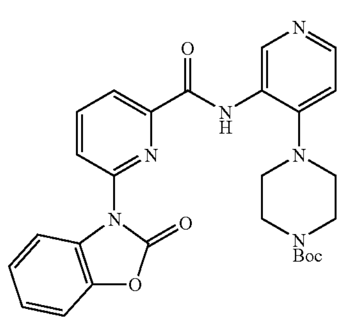 | 516.21 | 517.21 | 3.48 |

TABLE 5-continued

| Compound # | Structure | MW | LCMS MH+ m/z | HPLC MS $t_R$ |
|---|---|---|---|---|
| 92 | 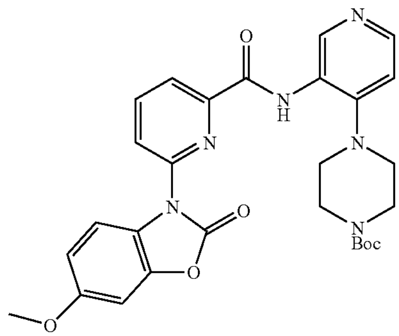 | 546.22 | 547.22 | 3.57 |
| 93 | 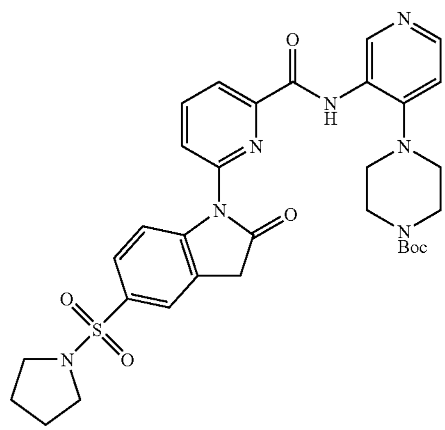 | 647.25 | 648.25 | 3.39 |
| 94 | 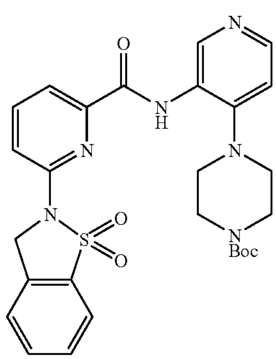 | 550.20 | 551.20 | 3.46 |
| 95 | 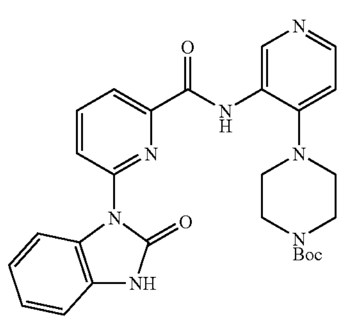 | 515.23 | 516.23 | 3.13 |

TABLE 5-continued

| Compound # | Structure | MW | LCMS MH+ m/z | HPLC MS $t_R$ |
|---|---|---|---|---|
| 96 | 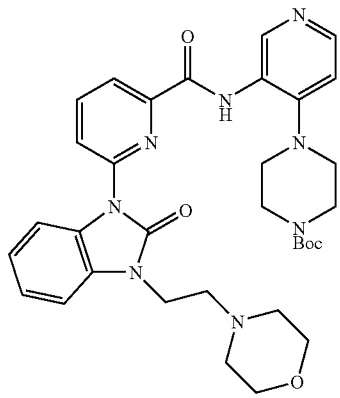 | 628.31 | 629.31 | 2.62 |
| 97 | 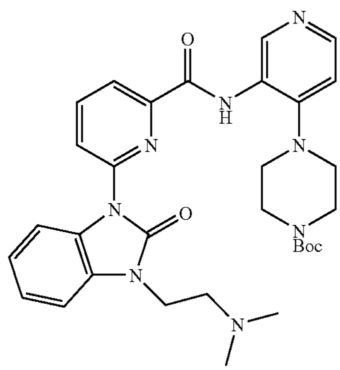 | 586.30 | 587.30 | 2.56 |
| 98 | 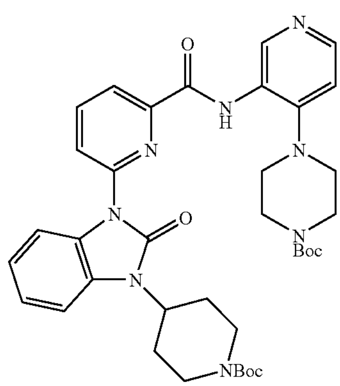 | 698.35 | 699.35 | 4.28 |
| 99 | 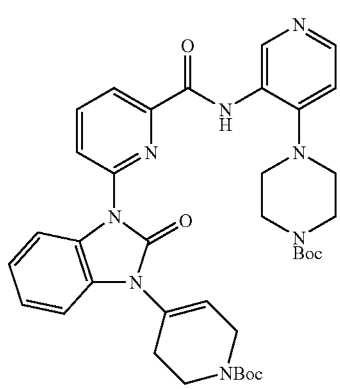 | 696.34 | 697.34 | 4.32 |

TABLE 5-continued
| Compound # | Structure | MW | LCMS MH+ m/z | HPLC MS $t_R$ |
|---|---|---|---|---|
| 100 | 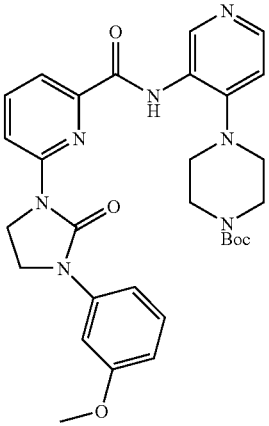 | 573.27 | 574.27 | 3.90 |
| 101 | 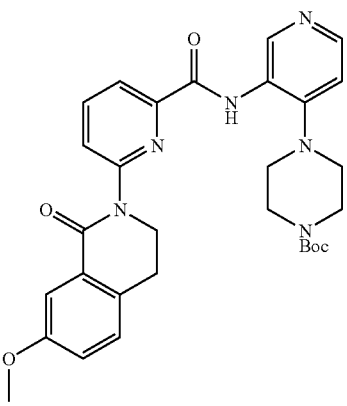 | 558.26 | 559.26 | 3.67 |
| 102 | 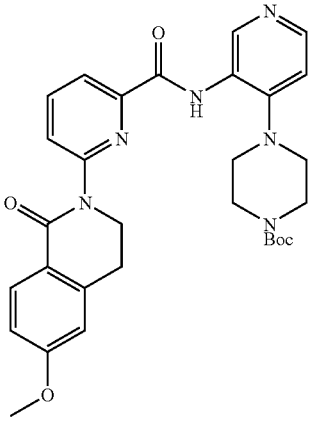 | 558.26 | 559.26 | 3.63 |

TABLE 5-continued

| Compound # | Structure | MW | LCMS MH+ m/z | HPLC MS $t_R$ |
|---|---|---|---|---|
| 103 | 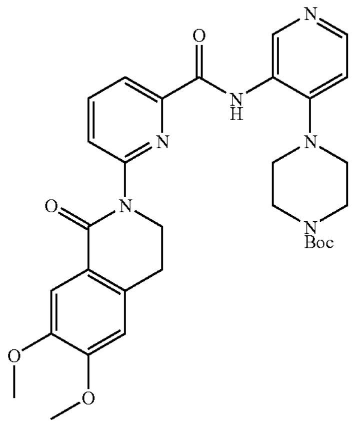 | 588.27 | 589.27 | 3.44 |
| 104 | 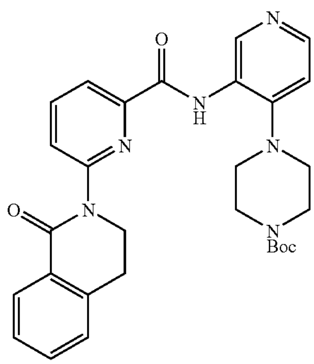 | 528.25 | 529.25 | 3.63 |
| 105 | 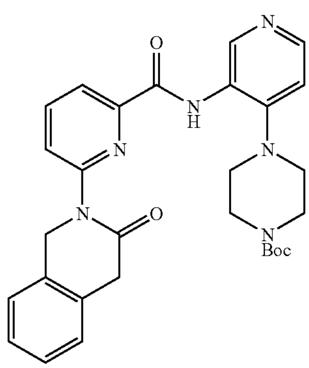 | 528.25 | 529.25 | 3.51 |
| 106 | 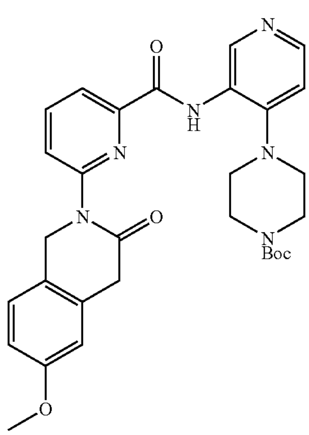 | 558.26 | 559.26 | 3.54 |

TABLE 5-continued

| Compound # | Structure | MW | LCMS MH+ m/z | HPLC MS $t_R$ |
|---|---|---|---|---|
| 107 | 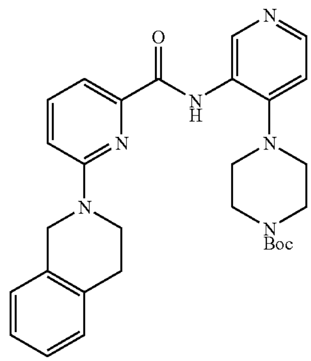 | 514.27 | 515.27 | 4.20 |
| 108 | 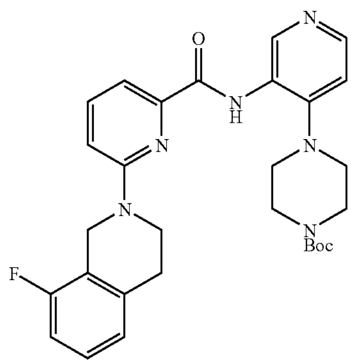 | 532.26 | 533.26 | 4.23 |
| 109 | 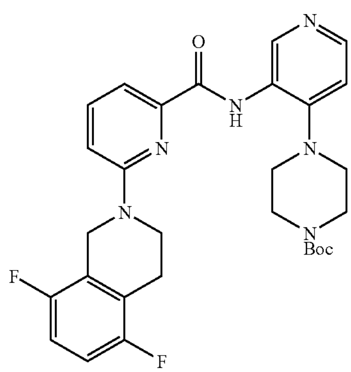 | 550.25 | 551.25 | 4.27 |
| 110 | 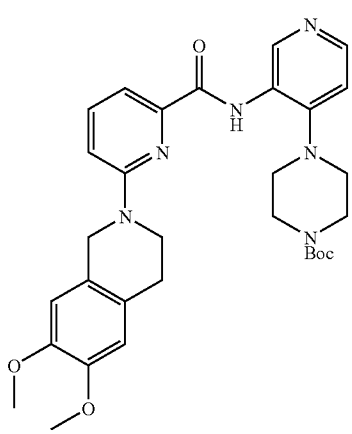 | 574.29 | 575.29 | 3.85 |

TABLE 5-continued
| Compound # | Structure | MW | LCMS MH+ m/z | HPLC MS $t_R$ |
|---|---|---|---|---|
| 111 | 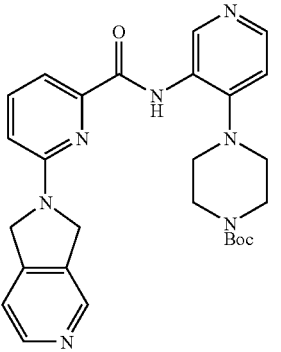 | 501.25 | 502.25 | 2.53 |
| 112 | 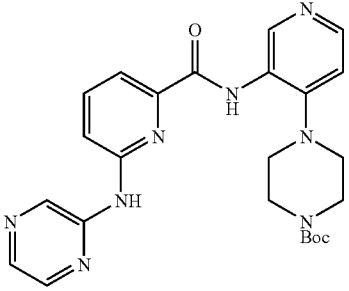 | 476.23 | 477.23 | 3.11 |
| 113 | 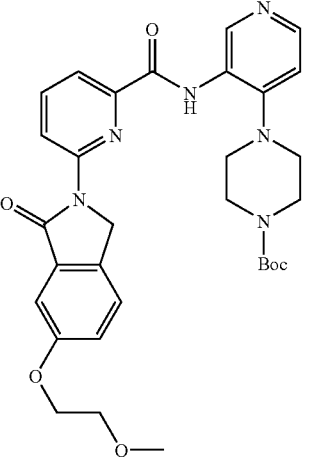 | 588.22 | 589.22 | 3.11 |

TABLE 5-continued

| Compound # | Structure | MW | LCMS MH+ m/z | HPLC MS $t_R$ |
| --- | --- | --- | --- | --- |
| 114 | 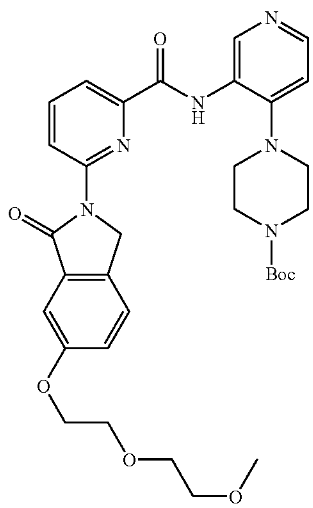 | 632.24 | 633.24 | 3.21 |
| 115 | 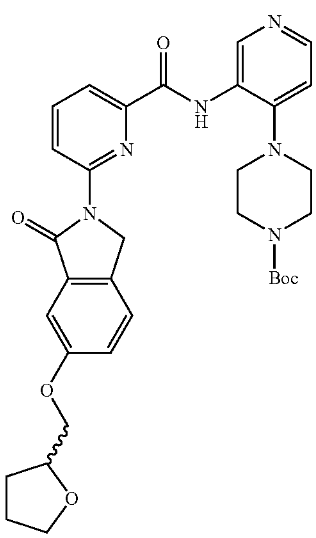 | 614.23 | 615.23 | 3.35 |
| 116 | 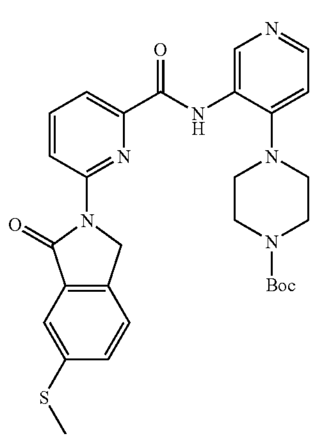 | 560.17 | 561.17 | 3.21 |

TABLE 5-continued

| Compound # | Structure | MW | LCMS MH+ m/z | HPLC MS $t_R$ |
|---|---|---|---|---|
| 117 | 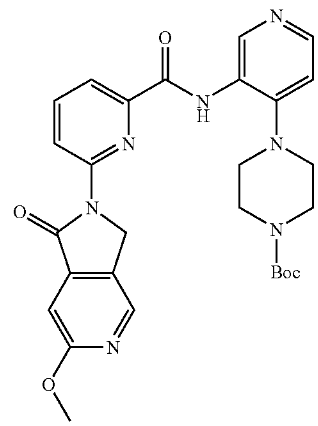 | 545.19 | 546.19 | .69 |
| 118 | 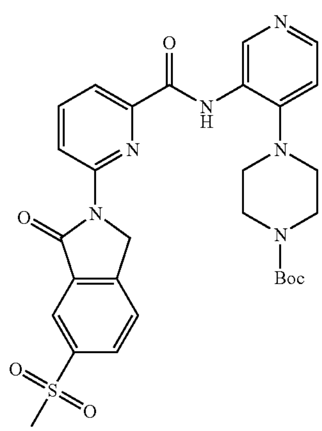 | 593.15 | 593.16 | 2.62 |
| 119 | 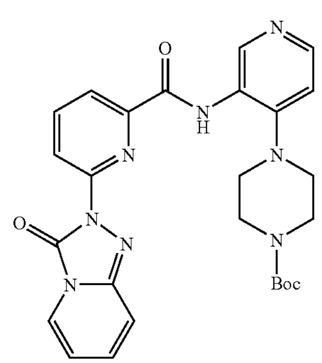 | 516.17 | 517.17 | 2.58 |

TABLE 5-continued

| Compound # | Structure | MW | LCMS MH+ m/z | HPLC MS $t_R$ |
|---|---|---|---|---|
| 120 | 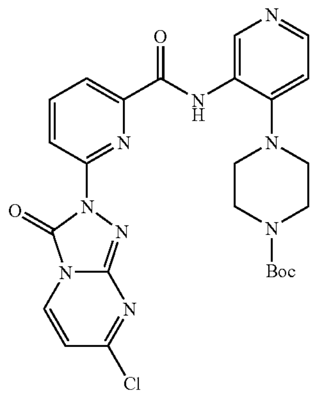 | 551.13 | 552.13 | 2.58 |
| 121 | 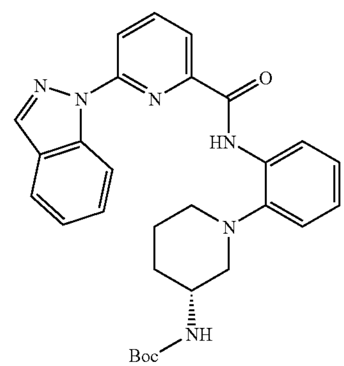 | 512.20 | 513.20 | 4.57 |
| 122 | 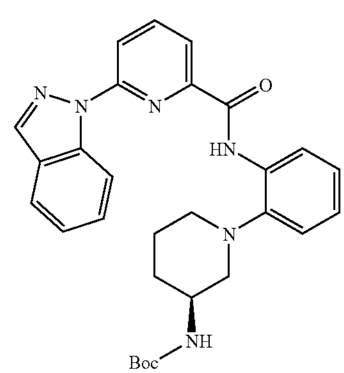 | 512.20 | 513.20 | 4.56 |

TABLE 5-continued

| Compound # | Structure | MW | LCMS MH+ m/z | HPLC MS $t_R$ |
|---|---|---|---|---|
| 123 | 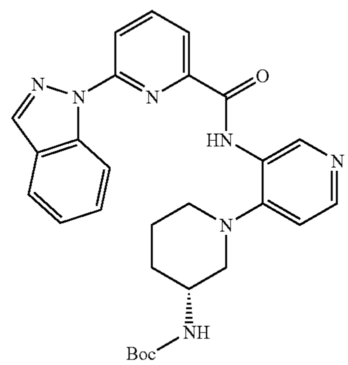 | 513.20 | 514.20 | 3.16 |
| 124 | 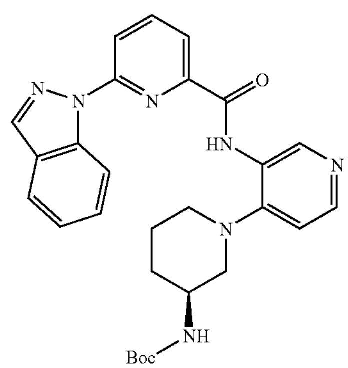 | 513.20 | 514.20 | 3.16 |

Compound 125:

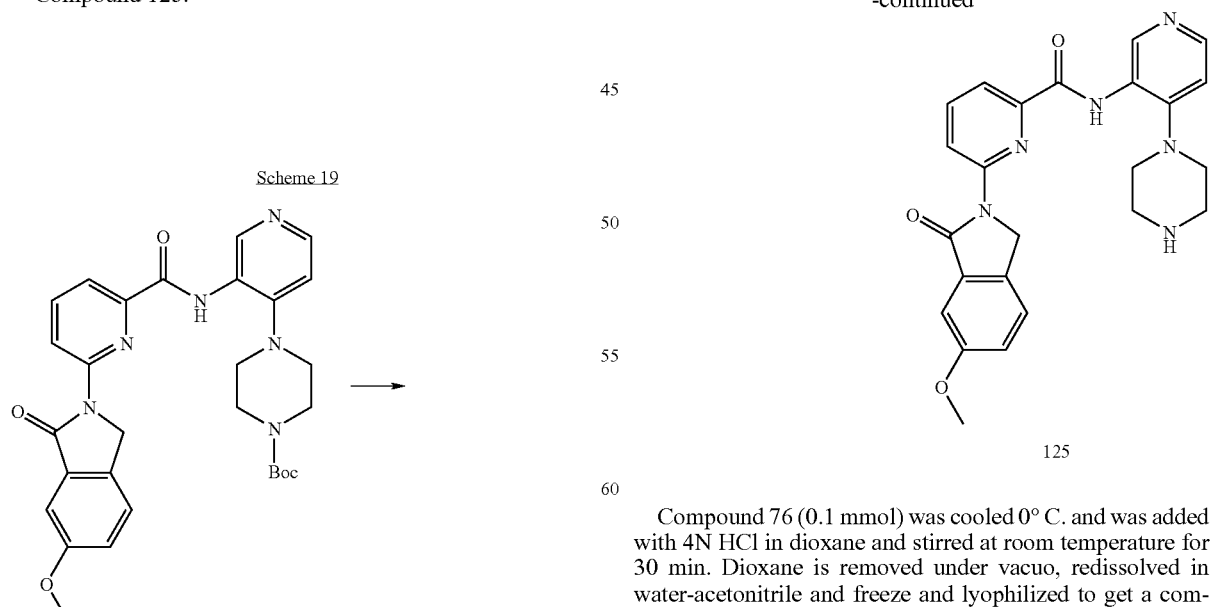

-continued

125

Compound 76 (0.1 mmol) was cooled 0° C. and was added with 4N HCl in dioxane and stirred at room temperature for 30 min. Dioxane is removed under vacuo, redissolved in water-acetonitrile and freeze and lyophilized to get a compound 125 as powder. HPLC-MS tR=0.75 min (UV254 nm); Mass calculated for formula $C_{24}H_{24}N_6O_3$, 444.20.17, observed LCMS m/z 445.20

Compounds 126-186

By essentially following the procedure described for Intermediate 91, the compounds in Table 6 could be synthesized

TABLE 6

| Compound # | Structure | MW | LCMS m/z (M + H) | HPLC MS $t_R$ |
|---|---|---|---|---|
| 126 | 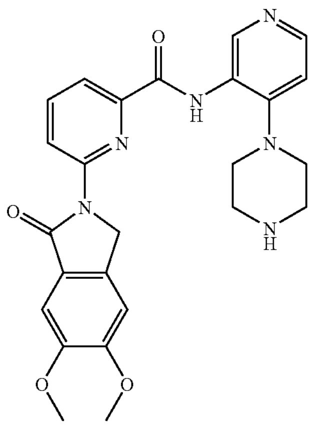 | 474.20 | 475.20 | 0.70* |
| 127 | 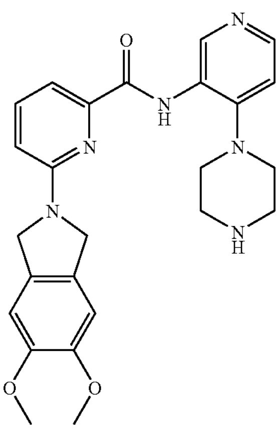 | 460.22 | 461.22 | 1.05* |
| 128 | 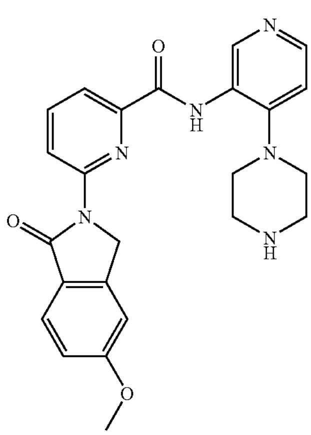 | 444.20 | 445.20 | 0.90* |

TABLE 6-continued

| Compound # | Structure | MW | LCMS m/z (M + H) | HPLC MS $t_R$ |
|---|---|---|---|---|
| 129 | 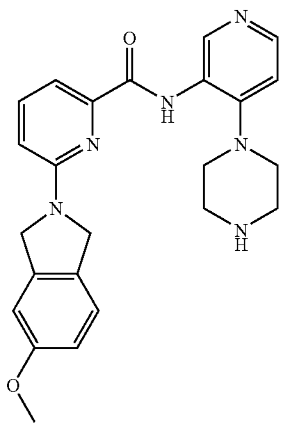 | 430.21 | 431.20 | 0.85* |
| 130 | 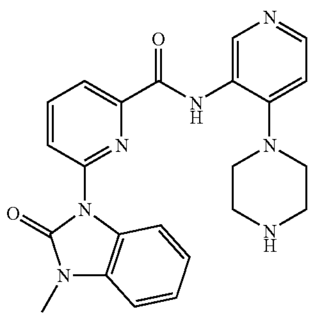 | 429.19 | 430.19 | 0.85* |
| 131 | 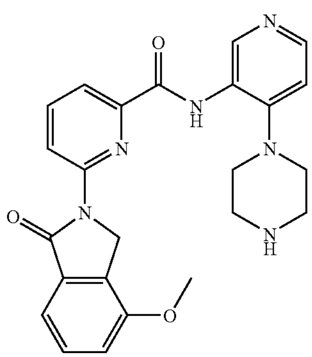 | 444.19 | 445.19 | 2.16 |
| 132 | 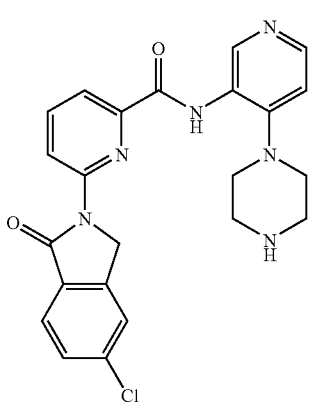 | 448.14 | 449.14 | 2.24 |

TABLE 6-continued

| Compound # | Structure | MW | LCMS m/z (M + H) | HPLC MS $t_R$ |
|---|---|---|---|---|
| 133 | 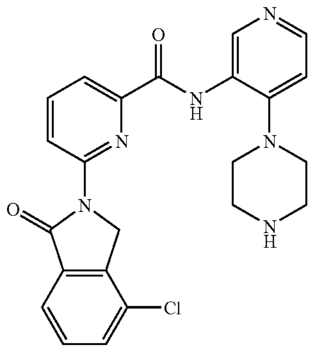 | 448.14 | 449.14 | 2.16 |
| 134 | 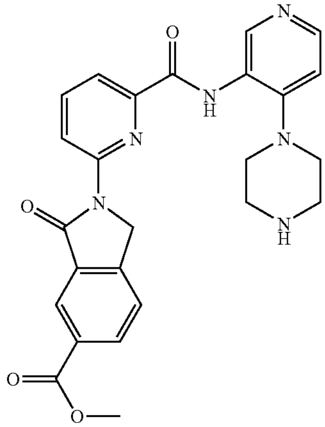 | 472.19 | 473.19 | 2.09 |
| 135 | 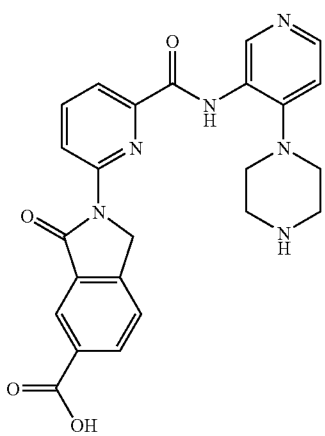 | 458.17 | 459.17 | 1.75 |
| 136 | 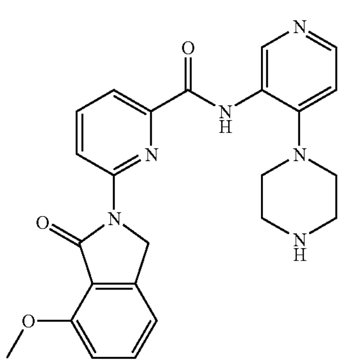 | 444.10 | 445.10 | 2.05 |

TABLE 6-continued
| Compound # | Structure | MW | LCMS m/z (M + H) | HPLC MS $t_R$ |
|---|---|---|---|---|
| 137 | 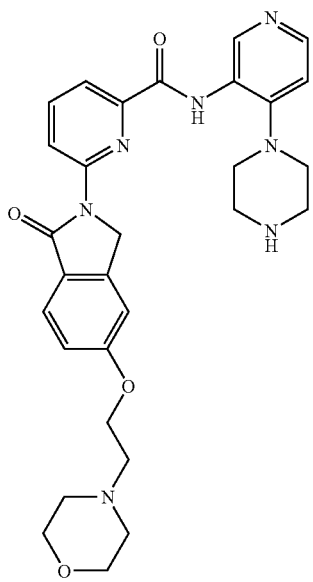 | 543.26 | 544.26 | 0.69 |
| 138 | 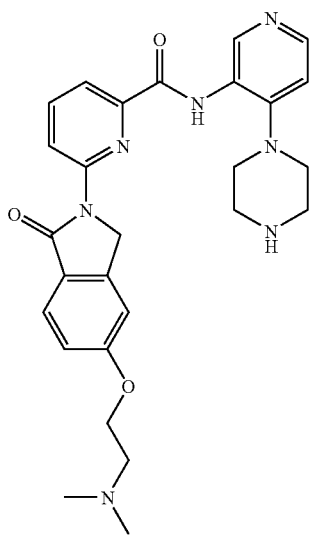 | 501.25 | 502.25 | 0.70 |

TABLE 6-continued
| Compound # | Structure | MW | LCMS m/z (M + H) | HPLC MS $t_R$ |
|---|---|---|---|---|
| 139 | 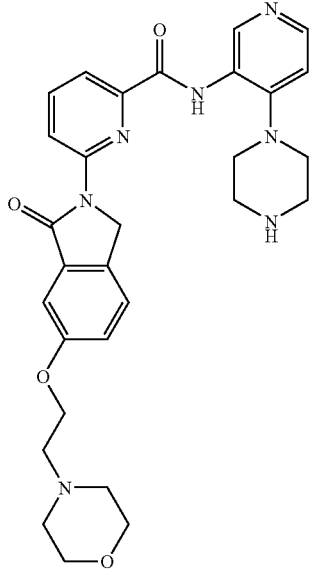 | 543.26 | 544.26 | 0.69 |
| 140 | 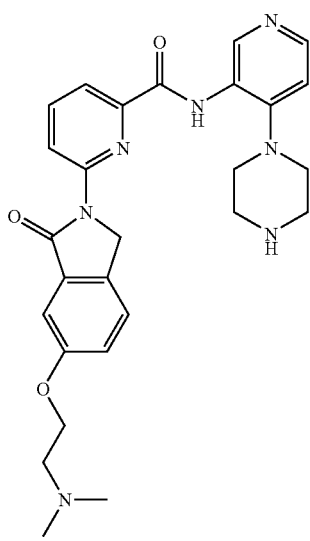 | 501.25 | 502.25 | 0.7 |
| 141 | 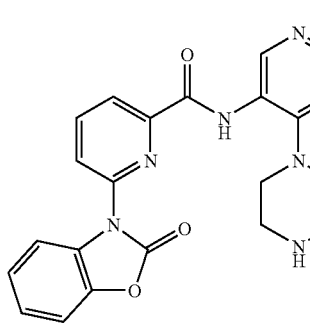 | 416.16 | 417.16 | 0.73 |

TABLE 6-continued

| Compound # | Structure | MW | LCMS m/z (M + H) | HPLC MS $t_R$ |
|---|---|---|---|---|
| 142 | 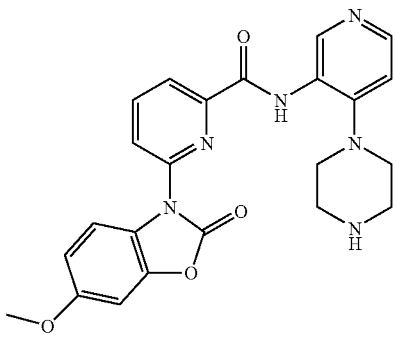 | 446.17 | 447.17 | 2.02 |
| 143 | 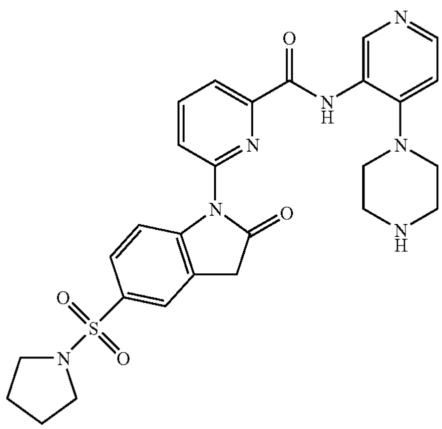 | 547.20 | 548.20 | 1.86 |
| 144 | 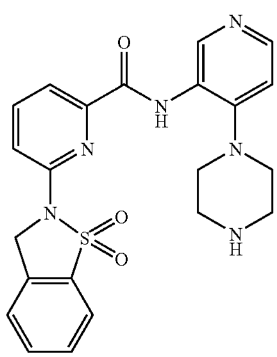 | 450.15 | 451.15 | 0.74 |
| 145 | 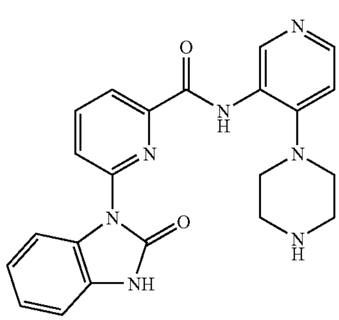 | 415.18 | 416.18 | 0.74 |

TABLE 6-continued

| Compound # | Structure | MW | LCMS m/z (M + H) | HPLC MS $t_R$ |
|---|---|---|---|---|
| 146 | 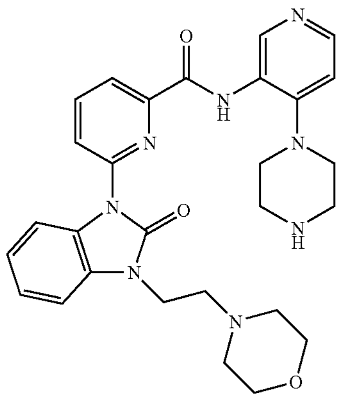 | 528.26 | 529.26 | 0.69 |
| 147 | 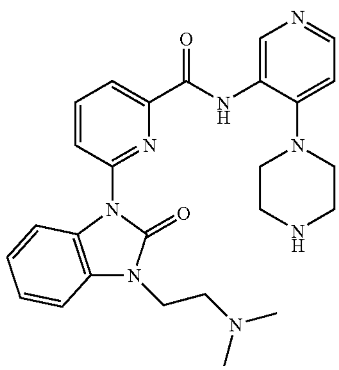 | 486.25 | 487.25 | 0.70 |
| 148 | 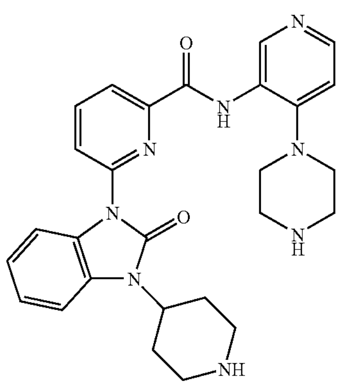 | 498.20 | 499.20 | 1.90 |
| 149 | 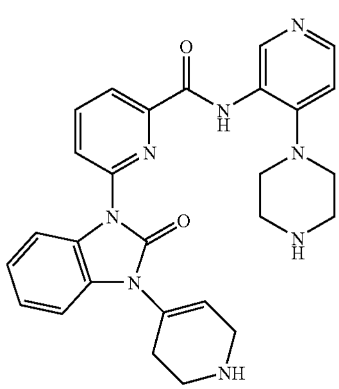 | 496.20 | 497.20 | 1.74 |

TABLE 6-continued

| Compound # | Structure | MW | LCMS m/z (M + H) | HPLC MS $t_R$ |
|---|---|---|---|---|
| 150 | 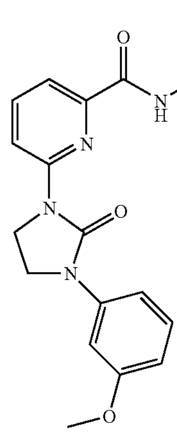 | 473.22 | 474.22 | 2.30 |
| 151 | 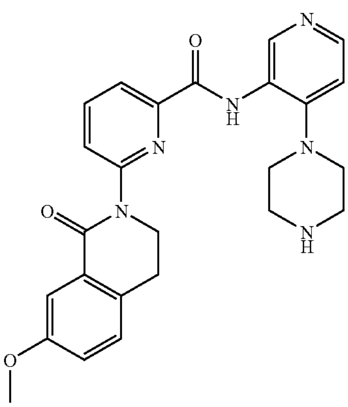 | 458.21 | 459.21 | 2.06 |
| 152 | 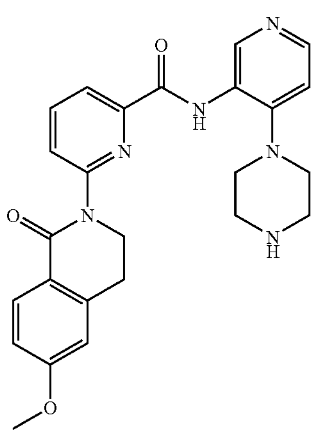 | 458.21 | 459.21 | 2.13 |

TABLE 6-continued

| Compound # | Structure | MW | LCMS m/z (M + H) | HPLC MS $t_R$ |
|---|---|---|---|---|
| 153 | 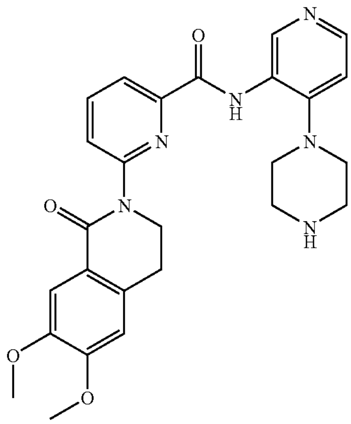 | 488.22 | 489.22 | 2.09 |
| 154 | 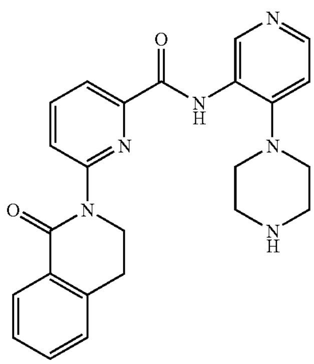 | 428.49 | 429.49 | 1.72 |
| 155 | 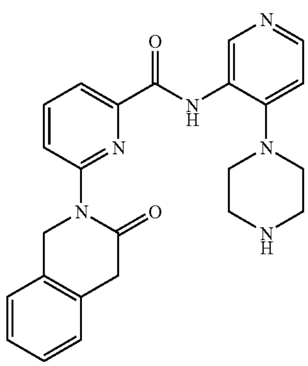 | 428.20 | 429.20 | 1.72 |
| 156 | 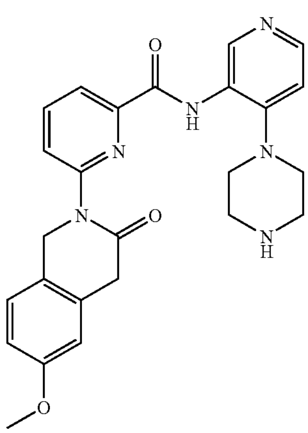 | 458.21 | 459.21 | 1.78 |

TABLE 6-continued

| Compound # | Structure | MW | LCMS m/z (M + H) | HPLC MS $t_R$ |
|---|---|---|---|---|
| 157 | 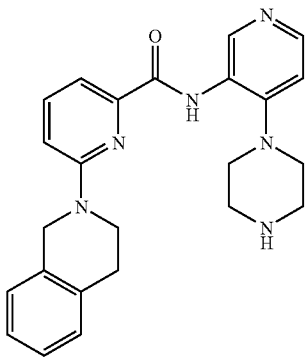 | 414.22 | 415.22 | 2.32 |
| 158 | 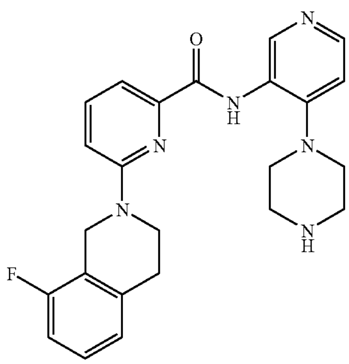 | 432.21 | 433.21 | 2.39 |
| 159 | 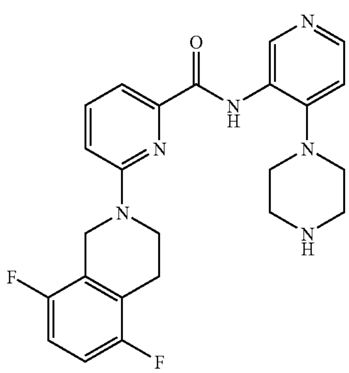 | 450.20 | 451.20 | 2.36 |
| 160 | 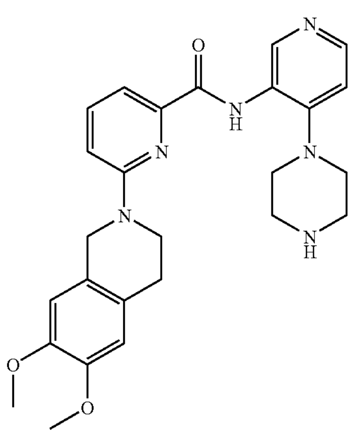 | 474.24 | 475.24 | 2.25 |

TABLE 6-continued

| Compound # | Structure | MW | LCMS m/z (M + H) | HPLC MS t_R |
|---|---|---|---|---|
| 161 | 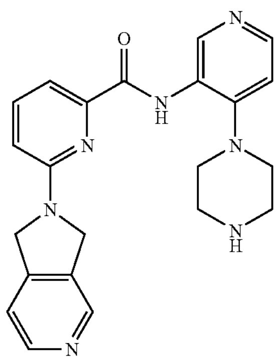 | 401.20 | 402.20 | 0.71 |
| 172 | 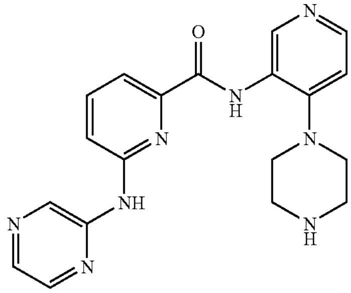 | 376.18 | 377.18 | 0.74 |
| 173 | 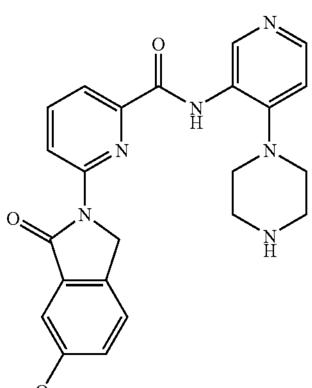 | 488.54 | 489.20 | 2.25 |

TABLE 6-continued

| Compound # | Structure | MW | LCMS m/z (M + H) | HPLC MS $t_R$ |
|---|---|---|---|---|
| 174 | 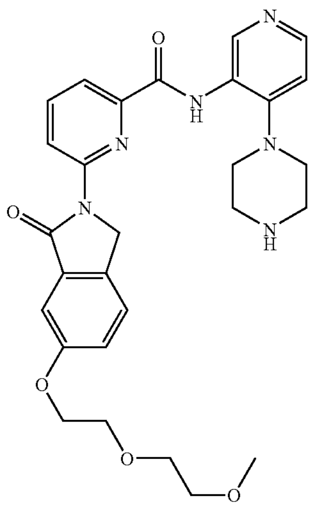 | 532.59 | 533.20 | 2.40 |
| 175 | 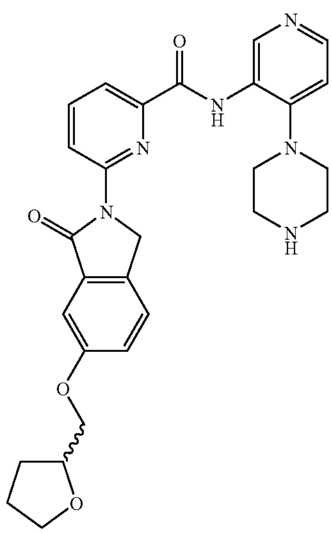 | 514.58 | 515.10 | 2.50 |
| 176 | 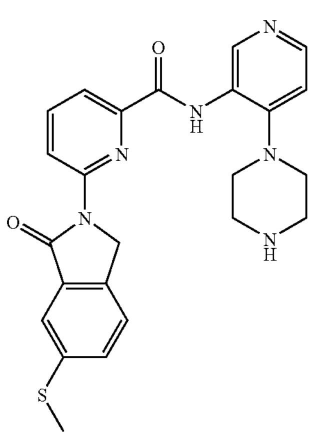 | 460.55 | 461.25 | 2.25 |

TABLE 6-continued

| Compound # | Structure | MW | LCMS m/z (M + H) | HPLC MS $t_R$ |
|---|---|---|---|---|
| 177 | 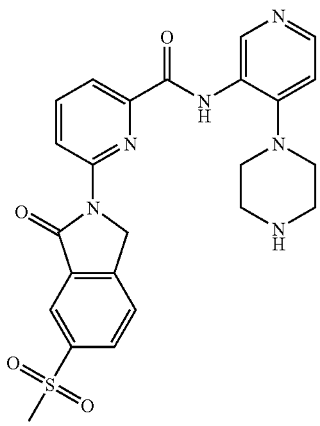 | 492.55 | 493.15 | 1.85 |
| 178 | 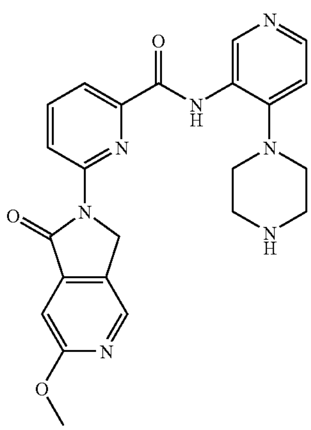 | 445.47 | 446.20 | 1.75 |
| 179 | 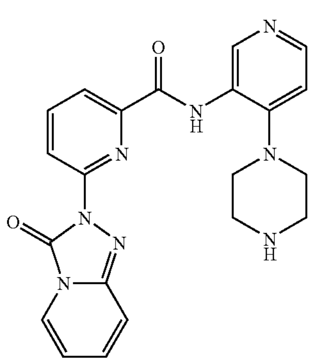 | 416.44 | 417.10 | 1.60 |

TABLE 6-continued

| Compound # | Structure | MW | LCMS m/z (M + H) | HPLC MS $t_R$ |
|---|---|---|---|---|
| 180 | 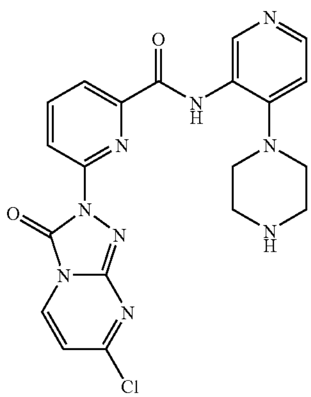 | 451.87 | 452.15 | 2.10 |
| 181 | 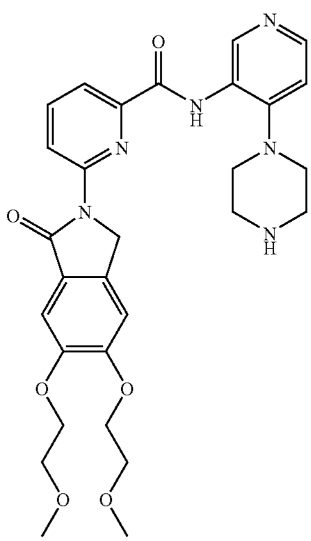 | 562.25 | 563.35 | 2.23 |
| 182 | 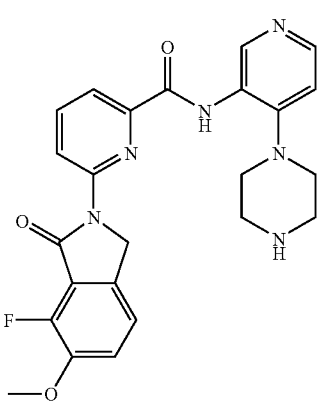 | 462.18 | 463.33 | 1.9 |

TABLE 6-continued

| Compound # | Structure | MW | LCMS m/z (M + H) | HPLC MS $t_R$ |
|---|---|---|---|---|
| 183 | 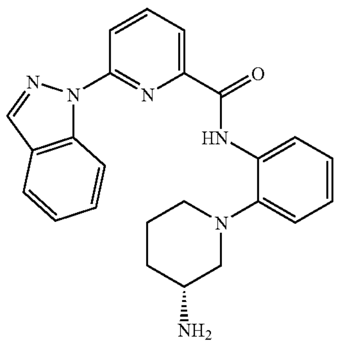 | 412.20 | 413.20 | 3.57 |
| 184 | 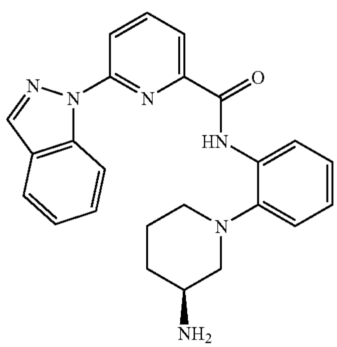 | 412.20 | 413.20 | 3.56 |
| 185 | 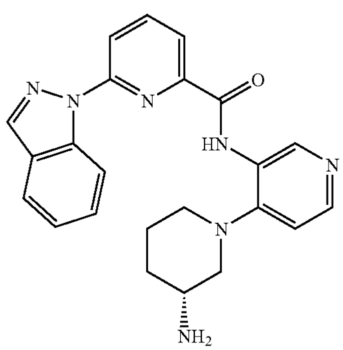 | 413.20 | 414.20 | 2.16 |
| 186 | 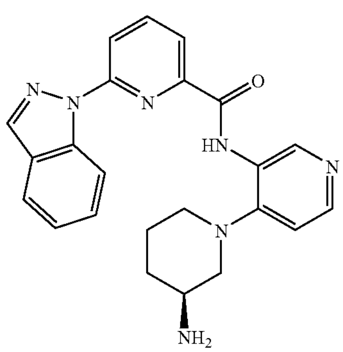 | 413.20 | 414.20 | 2.16 |

Compounds 187-199 shown in the table-7 are essentially made using the similar procedure described in scheme-16

TABLE 7

| Compound # | Structure | MW | LCMS m/z (M + H) | HPLC MS $t_R$ |
|---|---|---|---|---|
| 187 | 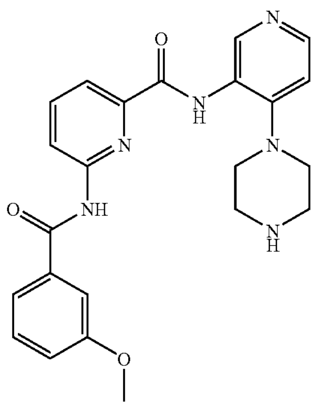 | 432.18 | 433.20 | 2.10 |
| 188 | 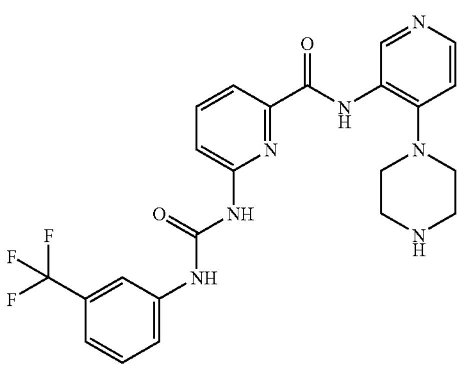 | 485.18 | 456.20 | 3.10 |
| 189 | 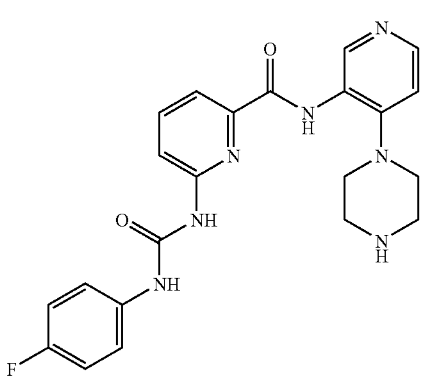 | 435.18 | 436.20 | 2.54 |

TABLE 7-continued

| Compound # | Structure | MW | LCMS m/z (M + H) | HPLC MS $t_R$ |
|---|---|---|---|---|
| 190 | 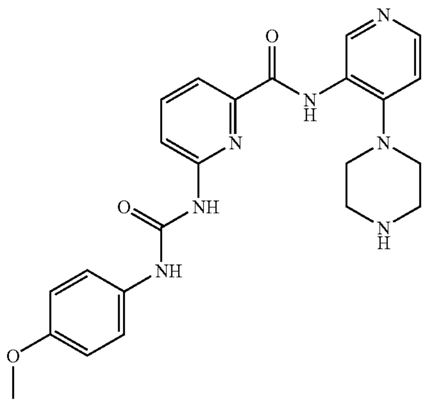 | 447.20 | 448.10 | 2.20 |
| 191 | 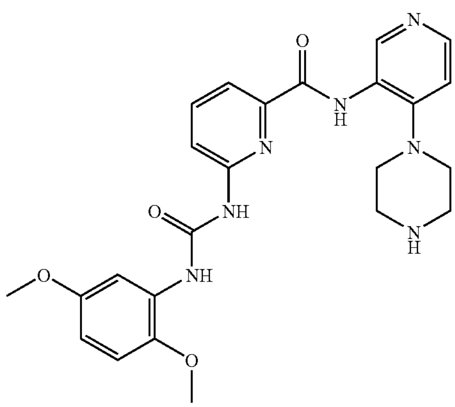 | 477.21 | 478.10 | 2.00 |
| 192 | 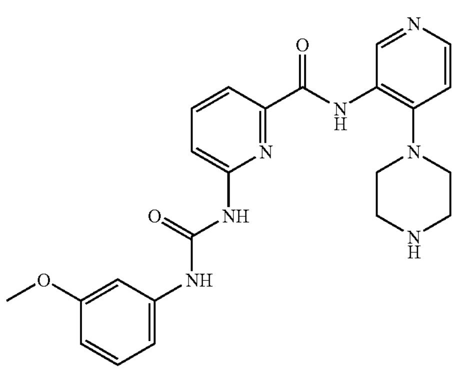 | 447.20 | 448.10 | 2.20 |
| 193 | 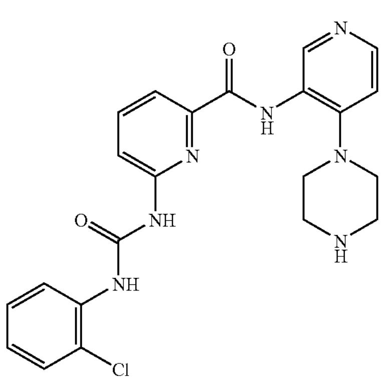 | 451.15 | 416.10 | 2.75 |

TABLE 7-continued

| Compound # | Structure | MW | LCMS m/z (M + H) | HPLC MS $t_R$ |
|---|---|---|---|---|
| 194 | 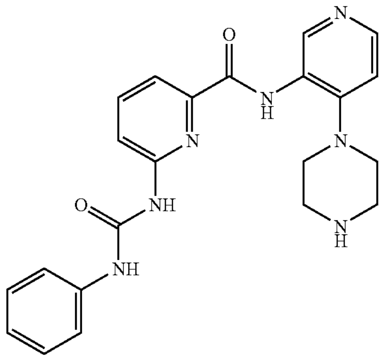 | 417.19 | 418.20 | 2.10 |
| 195 | 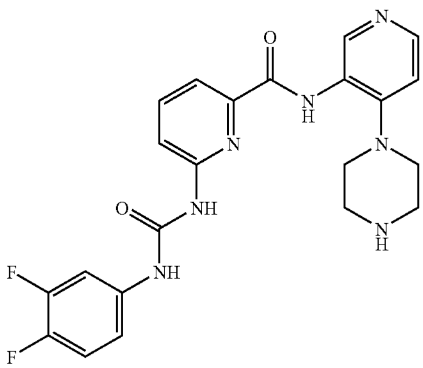 | 453.17 | 454.20 | 3.10 |
| 196 | 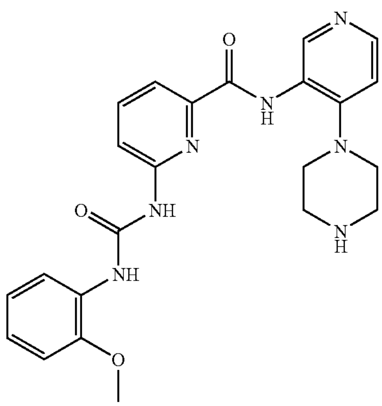 | 447.20 | 448.10 | 2.20 |
| 197 | 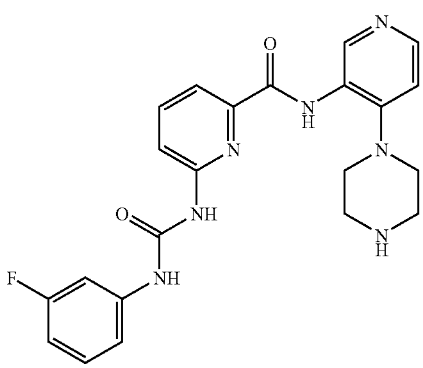 | 435.18 | 436.20 | 2.54 |

TABLE 7-continued

| Compound # | Structure | MW | LCMS m/z (M + H) | HPLC MS $t_R$ |
|---|---|---|---|---|
| 198 | 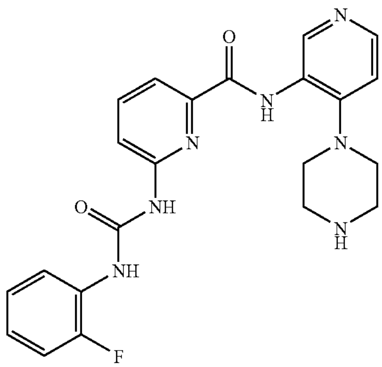 | 435.18 | 436.20 | 2.54 |
| 199 | 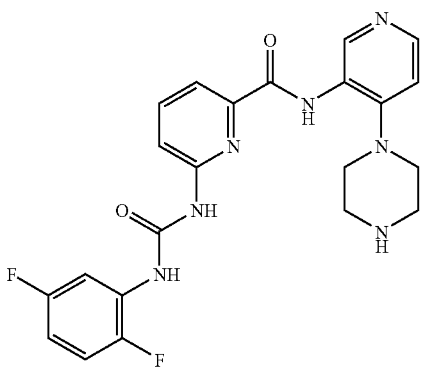 | 453.17 | 454.20 | 3.10 |

Intermediate 200

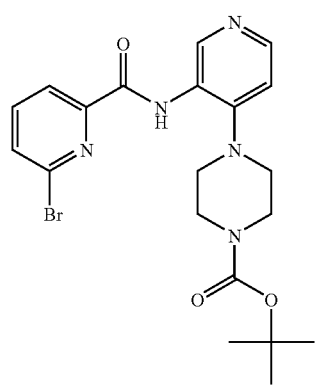

Scheme 20

→

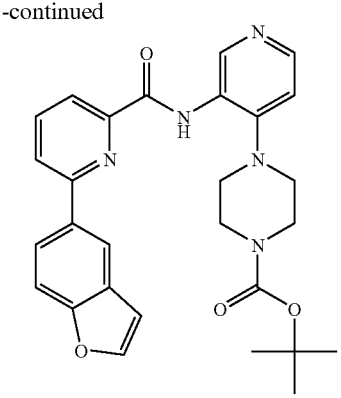

200

A mixture of 4-{3-[(6-Bromo-pyridine-2-carbonyl)-amino]-pyridin-4-yl}-piperazine-1-carboxylic acid tert-butyl ester (0.15 mmol), 5-(4,4,5,5-Tetramethyl-[1,3,2]dioxaborolan-2-yl)-benzofuran (0.3 mmol), 1,1'-Bis(diphenylphosphino)ferrocene palladium(II) chloride (0.075 mmol), potassium phosphate (0.45 mmol) in 5 mL of dioxane was heated in sealed vessel at 90° C. overnight. Crude mixture was passed through filter. Organic layer collected and concentrated under vacuo. Crude was purified by Prep-LC to yield compound 200. with MH+ m/z of 500.22 having retention time of 3.88 min. HPLC-MS tR=3.84 min (UV254 nm); Mass calculated for formula $C_{28}H_{29}N_5O_4$, 499.22, observed LCMS m/z 500.22

Intermediates 201-248

Examples 201-222, given in Table 8 could be synthesized, essentially following the procedure described in example 95.

TABLE 8

| Compound # | Structure | MW | LCMS MH+ m/z | HPLC MS $t_R$ |
|---|---|---|---|---|
| 201 | 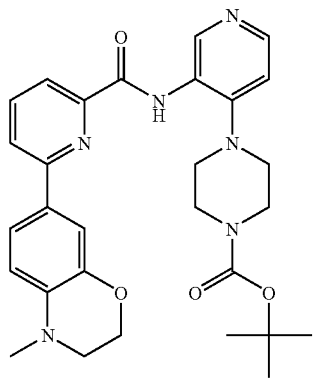 | 530.26 | 531.26 | 3.83 |
| 202 | 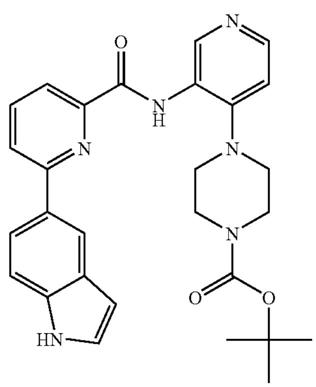 | 498.24 | 499.24 | 3.64 |
| 203 | 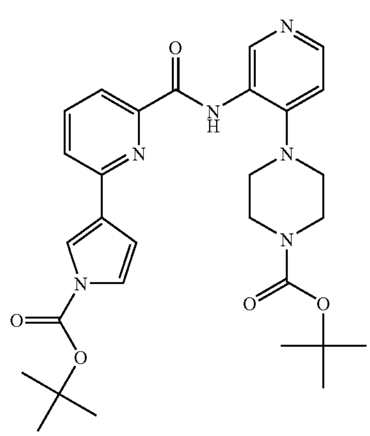 | 548.27 | 549.28 | 4.12 |

TABLE 8-continued
| Compound # | Structure | MW | LCMS MH+ m/z | HPLC MS t_R |
|---|---|---|---|---|
| 204 | 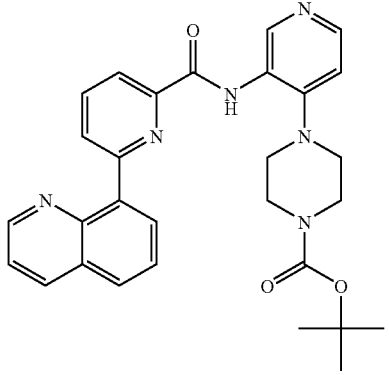 | 510.24 | 511.24 | 3.12 |
| 205 | 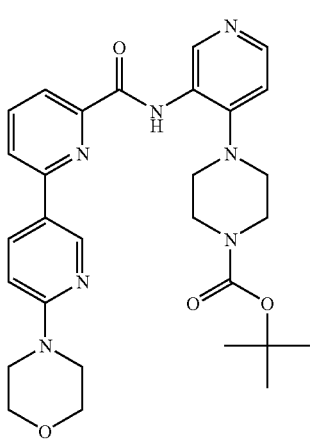 | 545.28 | 546.28 | 2.76 |
| 206 | 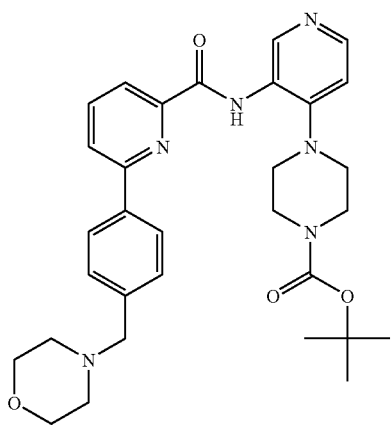 | 558.30 | 559.30 | 2.63 |

TABLE 8-continued

| Compound # | Structure | MW | LCMS MH+ m/z | HPLC MS $t_R$ |
|---|---|---|---|---|
| 207 | 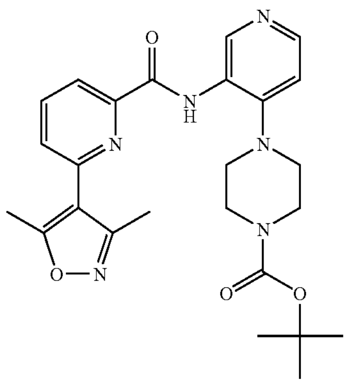 | 478.23 | 479.23 | 3.18 |
| 208 | 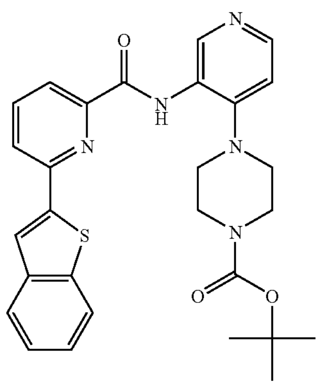 | 515.20 | 516.20 | 4.10 |
| 209 | 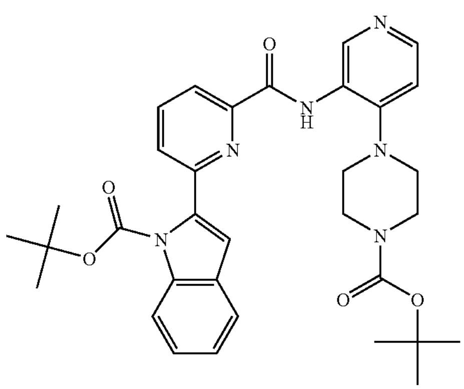 | 598.29 | 599.29 | 4.42 |
| 210 | 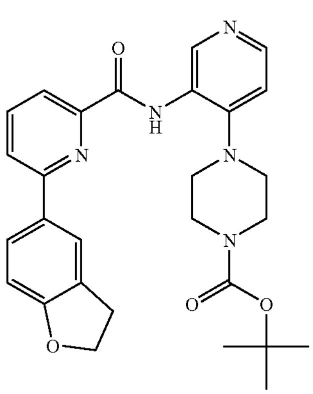 | 501.24 | 502.24 | 3.76 |

TABLE 8-continued

| Compound # | Structure | MW | LCMS MH+ m/z | HPLC MS $t_R$ |
|---|---|---|---|---|
| 211 | 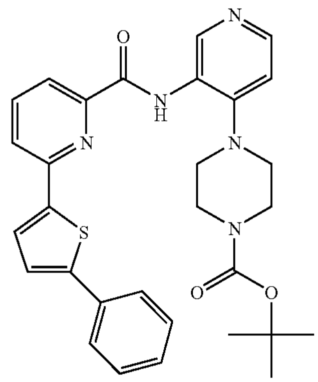 | 541.21 | 542.22 | 4.34 |
| 212 | 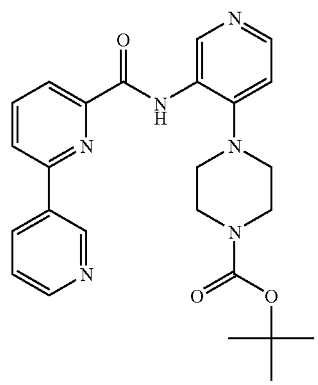 | 460.22 | 461.22 | 2.45 |
| 213 | 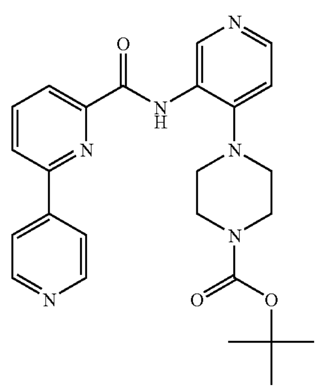 | 460.22 | 461.22 | 2.29 |
| 214 | 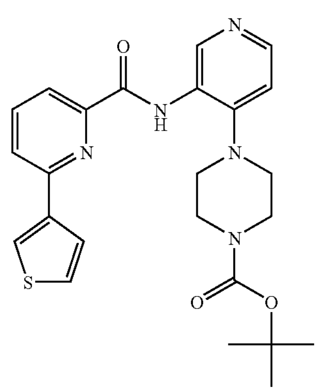 | 465.18 | 466.18 | 3.63 |

TABLE 8-continued

| Compound # | Structure | MW | LCMS MH+ m/z | HPLC MS $t_R$ |
|---|---|---|---|---|
| 215 | 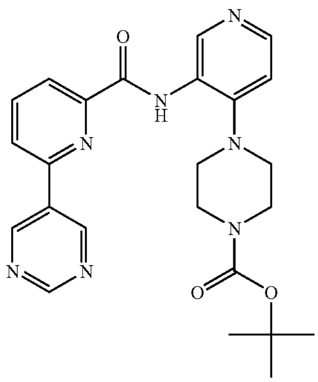 | 461.22 | 462.22 | 2.85 |
| 216 | 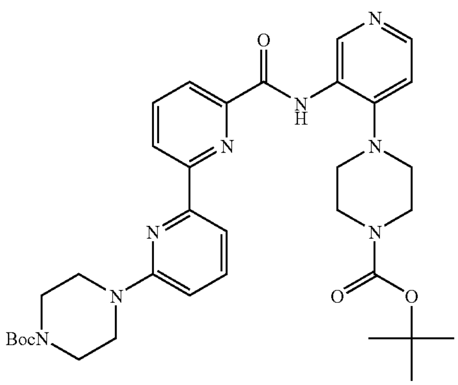 | 644.34 | 645.34 | 4.49 |
| 217 | 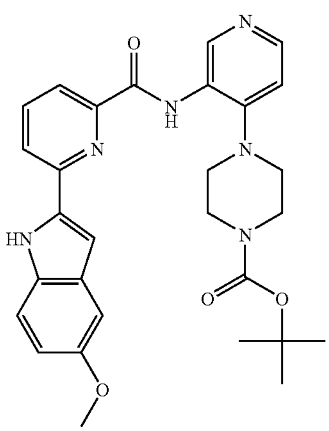 | 528.25 | 529.25 | 3.90 |
| 218 | 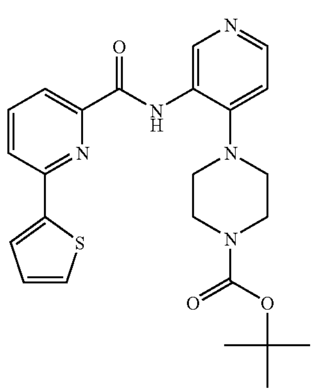 | 465.18 | 466.18 | 3.64 |

TABLE 8-continued

| Compound # | Structure | MW | LCMS MH+ m/z | HPLC MS $t_R$ |
|---|---|---|---|---|
| 219 | 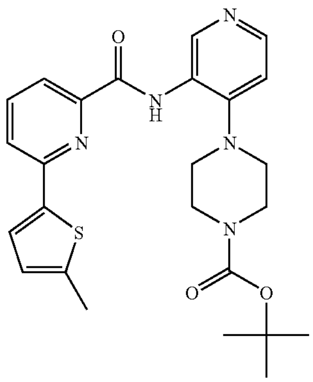 | 479.20 | 480.19 | 3.90 |
| 220 | 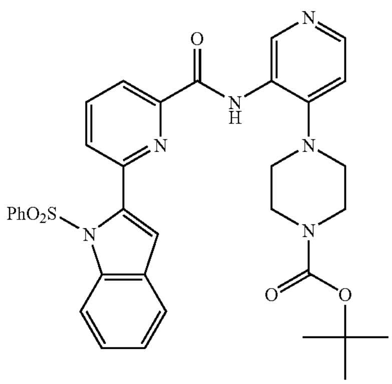 | 638.23 | 639.25 | 4.50 |
| 221 | 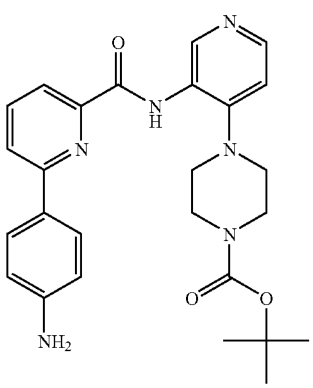 | 474.24 | 475.20 | 2.90 |
| 222 | 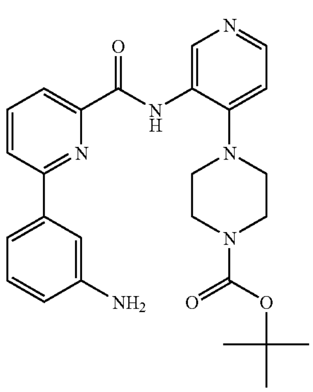 | 474.24 | 475.20 | 2.90 |

Compound 223:

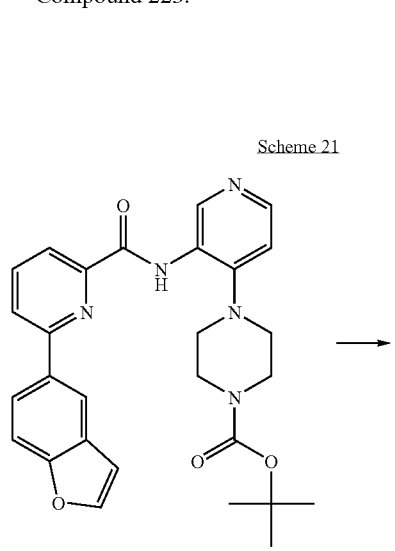

Scheme 21

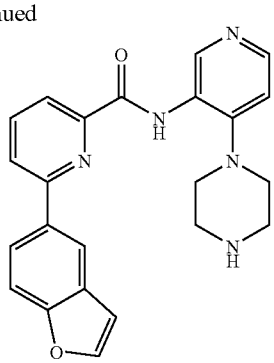

223

Intermediate 200 (0.1 mmol) was cooled 0° C. and was added with 4N HCl in dioxane and stirred at room temperature for 30 min. Dioxane is removed under vacuo, redissolved in water-acetonitrile and freeze dried and lyophilized to get a compound 223 as powder. HPLC-MS tR=2.62 min (UV254 nm); Mass calculated for formula $C_{23}H_{21}N_5O_2$, 399.17, observed LCMS m/z 400.20

Compounds 224-248, listed in Table 9, can be synthesized by essentially following the procedure described for the preparation of compound 223 (scheme-21).

TABLE 9

| Compound # | Structure | MW | LCMS MH+ m/z | HPLC MS $t_R$ |
|---|---|---|---|---|
| 224 | 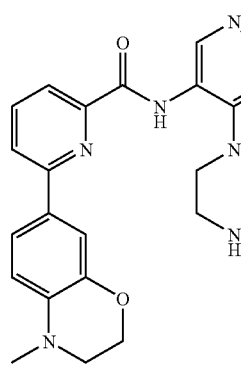 | 430.21 | 431.21 | 2.29 |
| 225 | 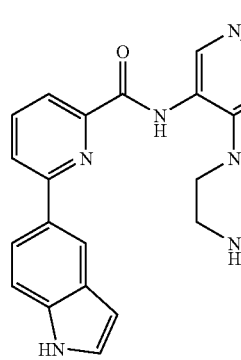 | 398.19 | 399.19 | 1.96 |

TABLE 9-continued

| Compound # | Structure | MW | LCMS MH+ m/z | HPLC MS $t_R$ |
|---|---|---|---|---|
| 226 | 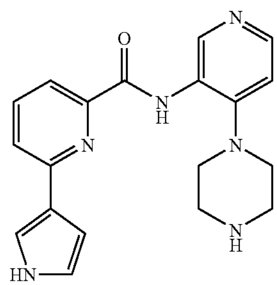 | 348.17 | 349.17 | 0.71 |
| 227 | 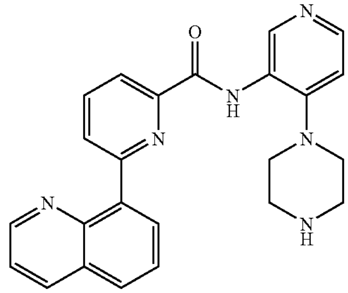 | 410.19 | 411.19 | 0.71 |
| 228 | 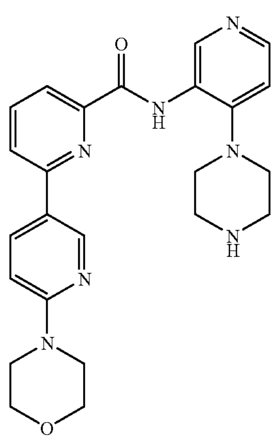 | 445.22 | 446.22 | 0.75 |
| 229 | 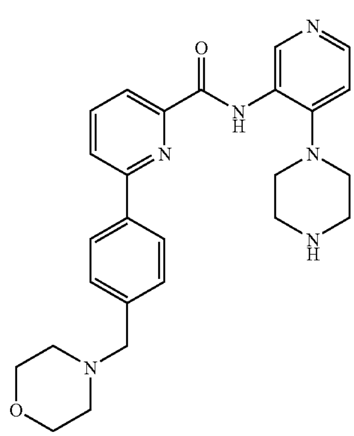 | 458.24 | 459.24 | 0.71 |

TABLE 9-continued

| Compound # | Structure | MW | LCMS MH+ m/z | HPLC MS $t_R$ |
|---|---|---|---|---|
| 230 | 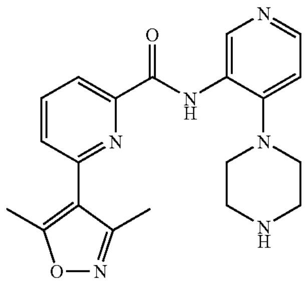 | 378.18 | 379.20 | 1.85 |
| 231 | 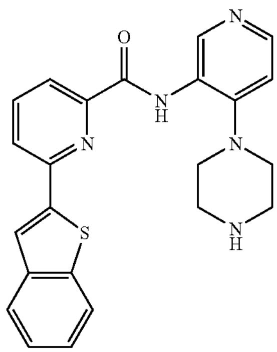 | 415.15 | 416.10 | 2.50 |
| 232 | 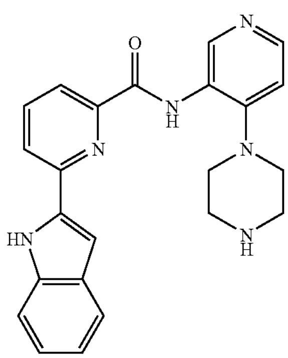 | 398.24 | 399.20 | 1.96 |
| 233 | 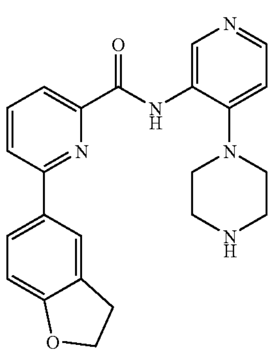 | 401.19 | 402.20 | 1.80 |

TABLE 9-continued

| Compound # | Structure | MW | LCMS MH+ m/z | HPLC MS $t_R$ |
|---|---|---|---|---|
| 234 | 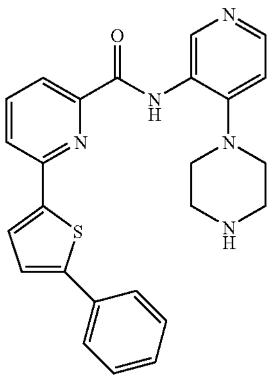 | 441.16 | 442.20 | 2.65 |
| 235 | 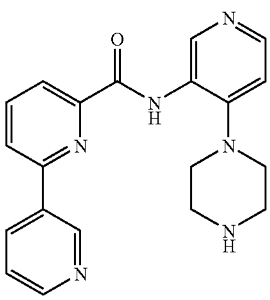 | 360.17 | 361.17 | 0.73 |
| 236 | 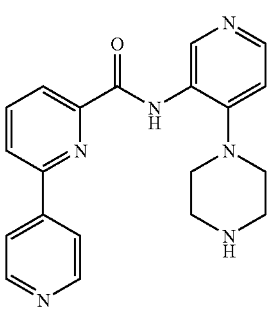 | 360.17 | 361.20 | 0.47 |
| 237 | 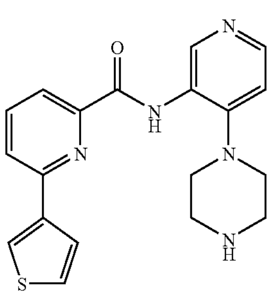 | 365.13 | 366.13 | 0.74 |

TABLE 9-continued

| Compound # | Structure | MW | LCMS MH+ m/z | HPLC MS t$_R$ |
|---|---|---|---|---|
| 238 | 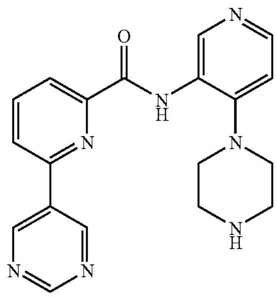 | 361.17 | 362.17 | 0.74 |
| 239 | 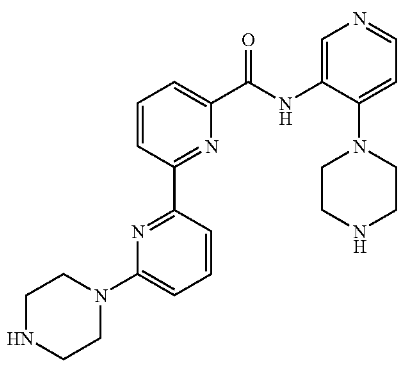 | 444.24 | 445.30 | 0.62 |
| 240 | 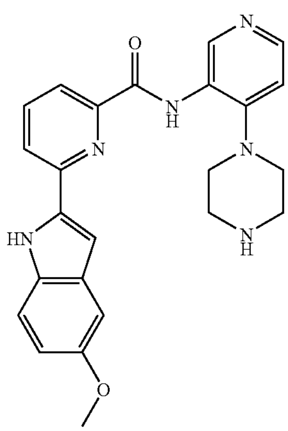 | 428.20 | 429.20 | 2.32 |
| 241 | 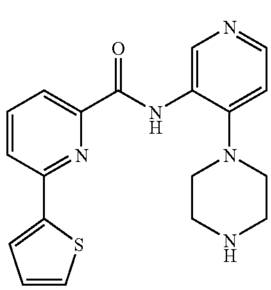 | 365.13 | 366.20 | 1.85 |

TABLE 9-continued
| Compound # | Structure | MW | LCMS MH+ m/z | HPLC MS t_R |
|---|---|---|---|---|
| 242 | 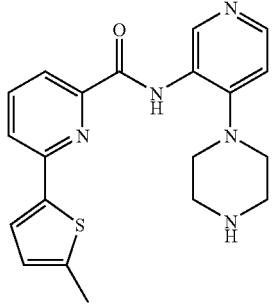 | 379.15 | 380.20 | 2.00 |
| 243 | 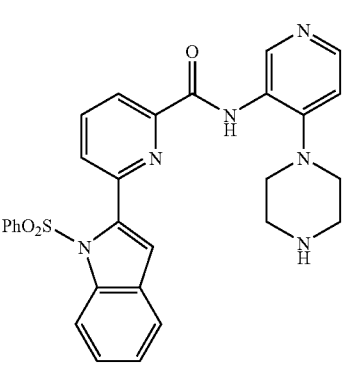 | 538.18 | 539.25 | 2.25 |
| 244 | 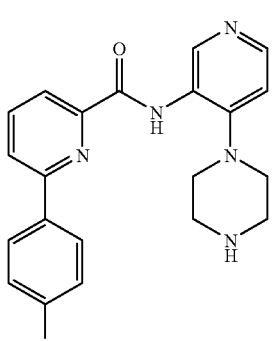 | 374.19 | 375.20 | 1.80 |
| 245 | 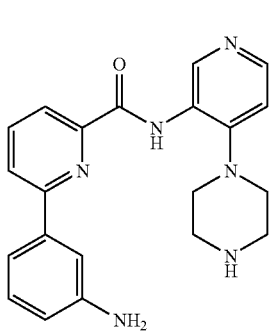 | 374.19 | 375.20 | 1.80 |

TABLE 9-continued
| Compound # | Structure | MW | LCMS MH+ m/z | HPLC MS $t_R$ |
|---|---|---|---|---|
| 246 | 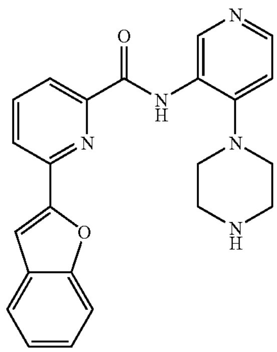 | 399.45 | 400.17 | 2.13 |
| 247 | 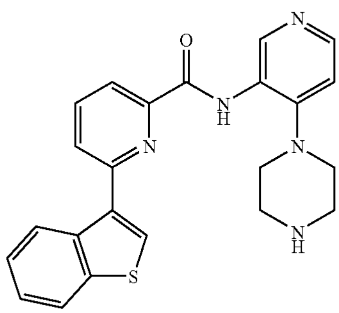 | 415.51 | 416.15 | 2.21 |
| 248 | 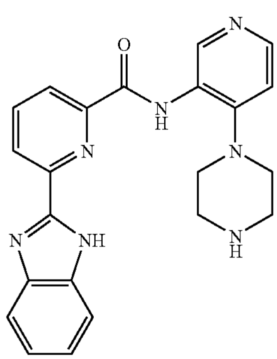 | | | |
Compound 251:
Scheme 22
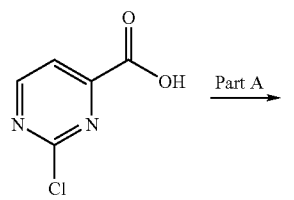 Part A →
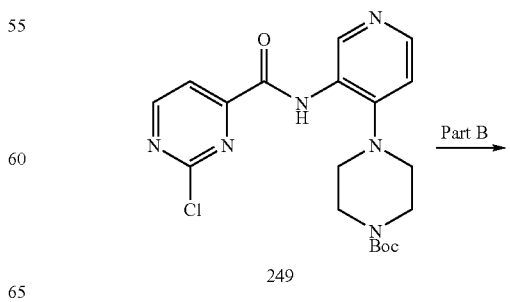
Part B →
249

-continued

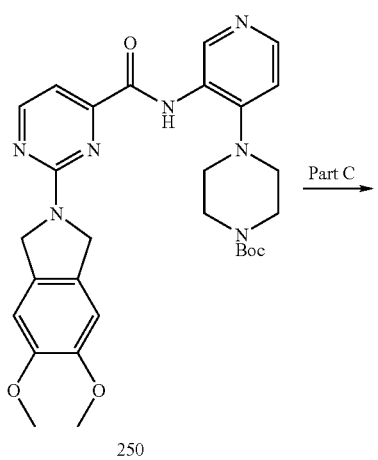

250

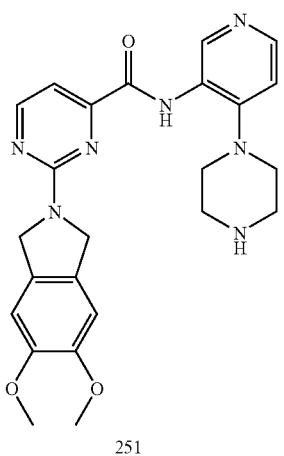

251

Compound 249:

The compound, 2-chloropyrimidine-4-carboxylic acid (317 mg, 2.0 mmol) was dissolved in DMF (5 mL), DIEA (350 uL, 2.0 mmol) and HATU (760 mg, 2.0 mmol) were added at room temperature followed by the addition of 4-(3-Amino-pyridin-4-yl)-piperazine-1-carboxylic acid tert-butyl ester (556 mg, 2.0 mmol). The mixture was stirred at room temperature over night. The mixture was diluted with EtOAc and washed with water, brine and dried over $Na_2SO_4$. After concentration, the crude product was purified with column (silica gel, EtOAc) gave the product 249 (620 mg) as brown solid. HPLC-MS $t_R$=1.18 min ($UV_{254}$ nm); mass calculated for formula $C_{19}H_{23}ClN_6O_3$ 418.2, observed LCMS m/z 419.2 (M+H).

Compound 250:

2-chloropyrimidine derivative 249 (50 mg) and isoindoline (50 mg) were dissolved in Acetonitrile (5 mL) and the mixture was heated to 80° C. and stirred for 1 hour. The solvent was removed by concentration and the residue was purified by Prep-LC gave compound 250. HPLC-MS $t_R$=1.63 min ($UV_{254\,nm}$); mass calculated for formula $C_{29}H_{35}N_7O_5$ 561.3, observed LCMS m/z 562.3 (M+H).

Compound 251:

Compound 250 was dissolved in 10% TFA in DCM and stirred at room temperature overnight. After concentration, the residue was purified by Prep-LC gave the compound 251. HPLC-MS $t_R$=0.89 min ($UV_{254\,nm}$); mass calculated for formula $C_{24}H_{27}N_7O_3$ 461.2, observed LCMS m/z 462.2 (M+H).

Compounds 252-288:

By essentially the same procedure given for the preparation of compounds 252-288, compounds 252-288 (set forth in Table 10 below) can be prepared from compound 2-chloropyrimidine-4-carboxylic acid.

TABLE 10

| Compound # | Structure | Exact mass | MS m/z (M + H) | HPLC MS $t_R$ |
|---|---|---|---|---|
| 252 | 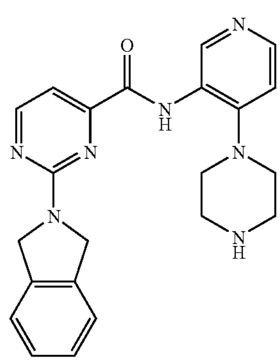 | 401.2 | 402.2 | 0.93 |

TABLE 10-continued

| Compound # | Structure | Exact mass | MS m/z (M + H) | HPLC MS $t_R$ |
|---|---|---|---|---|
| 253 | 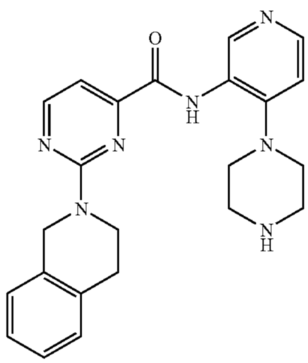 | 415.2 | 416.2 | 1.01 |
| 254 | 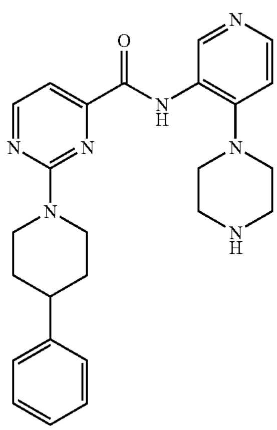 | 443.2 | 444.2 | 1.34 |
| 255 | 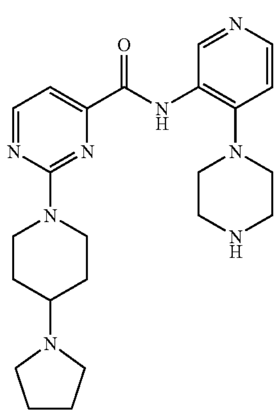 | 436.3 | 437.4 | 0.20 |
| 256 | 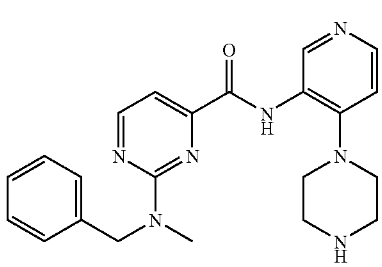 | 403.2 | 404.2 | 0.96 |

TABLE 10-continued

| Compound # | Structure | Exact mass | MS m/z (M + H) | HPLC MS $t_R$ |
|---|---|---|---|---|
| 257 | 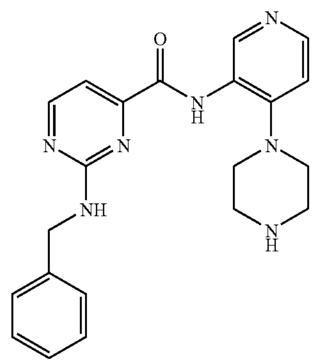 | 389.2 | 390.2 | 0.83 |
| 258 | 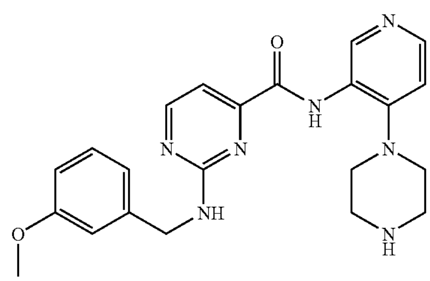 | 419.2 | 420.2 | 1.06 |
| 259 | 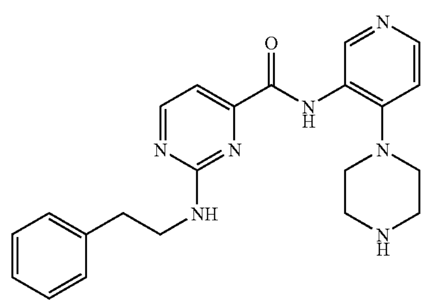 | 403.2 | 404.2 | 1.12 |
| 260 | 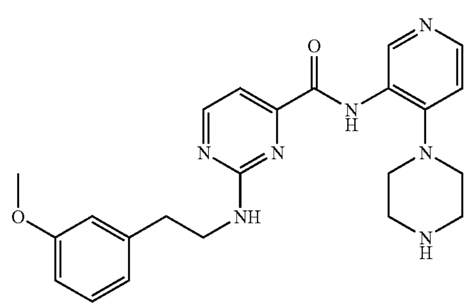 | 433.2 | 434.2 | 1.13 |
| 261 | 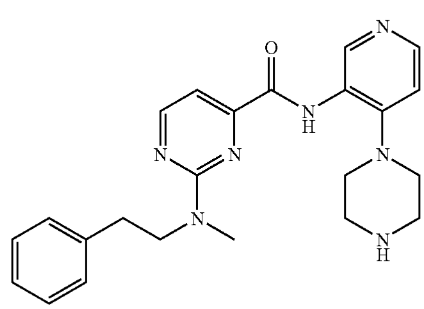 | 417.2 | 418.3 | 1.22 |

TABLE 10-continued

| Compound # | Structure | Exact mass | MS m/z (M + H) | HPLC MS $t_R$ |
|---|---|---|---|---|
| 262 | 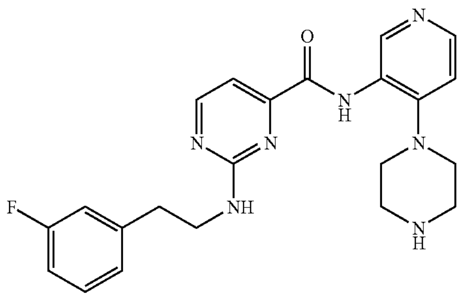 | 421.2 | 422.2 | 1.15 |
| 263 | 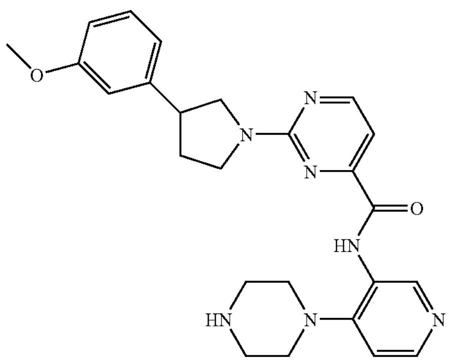 | 459.2 | 460.2 | 1.07 |
| 264 | 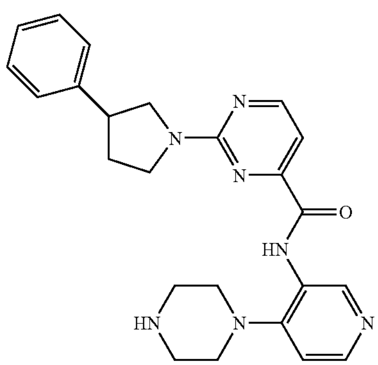 | 429.2 | 430.2 | 1.07 |
| 265 | 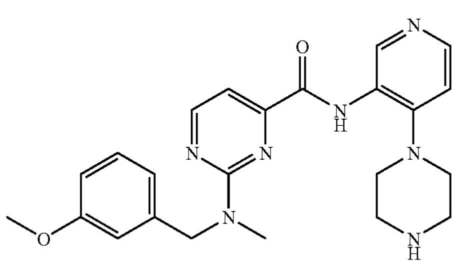 | 433.2 | 434.2 | 1.08 |

TABLE 10-continued

| Compound # | Structure | Exact mass | MS m/z (M + H) | HPLC MS t$_R$ |
|---|---|---|---|---|
| 266 | 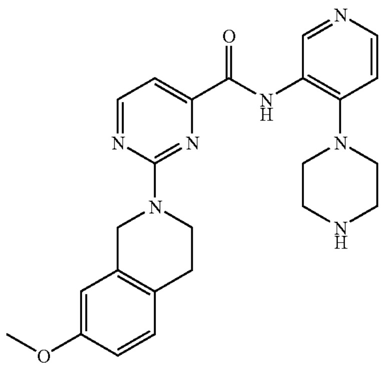 | 445.2 | 446.2 | 1.05 |
| 267 | 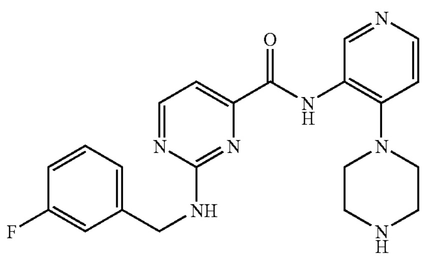 | 407.2 | 408.3 | 0.91 |
| 268 | 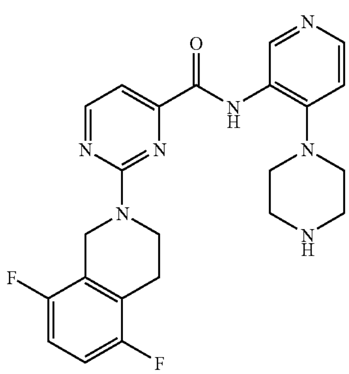 | 451.2 | 452.2 | 1.08 |
| 269 | 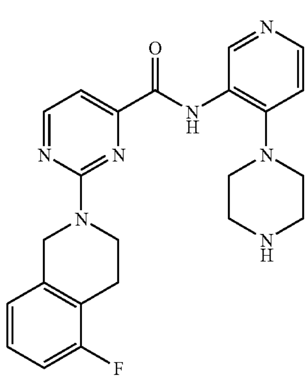 | 433.2 | 434.2 | 1.08 |

TABLE 10-continued

| Compound # | Structure | Exact mass | MS m/z (M + H) | HPLC MS $t_R$ |
|---|---|---|---|---|
| 270 | 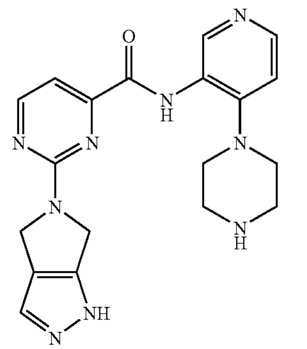 | 391.2 | 392.2 | 0.66 |
| 271 | 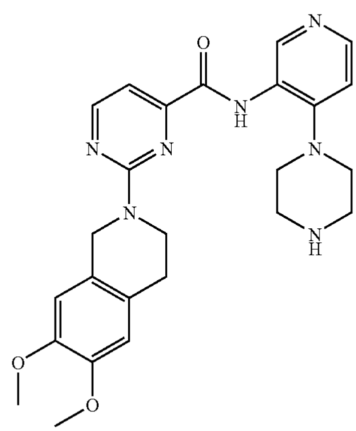 | 475.2 | 476.2 | 1.16 |
| 272 | 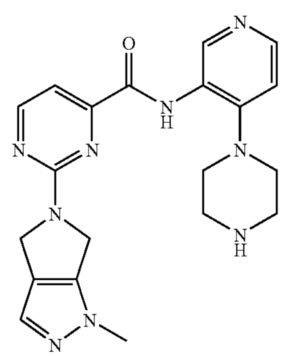 | 405.2 | 406.3 | 0.87 |
| 273 | 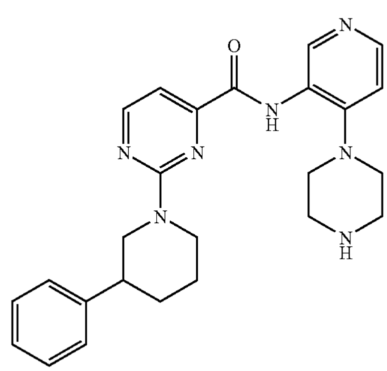 | 443.2 | 444.2 | 1.36 |

TABLE 10-continued

| Compound # | Structure | Exact mass | MS m/z (M + H) | HPLC MS t$_R$ |
|---|---|---|---|---|
| 274 | 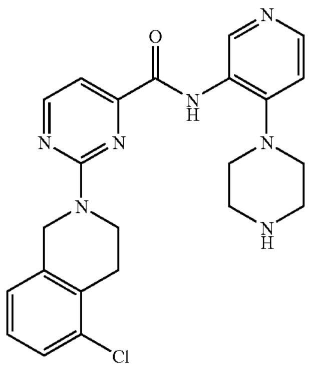 | 449.2 | 450.1 | 1.19 |
| 275 | 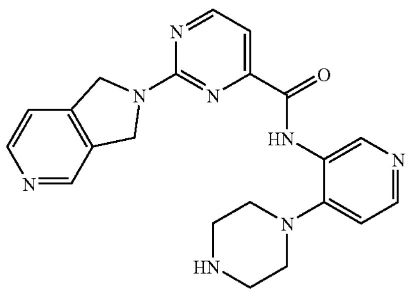 | 402.2 | 403.20 | 1.20 |
| 276 | 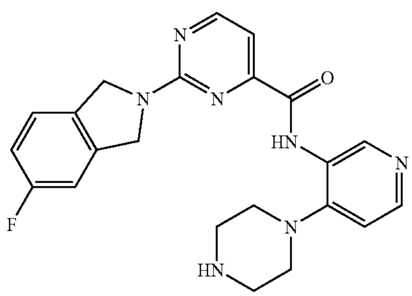 | 419.45 | 420.20 | 1.40 |
| 277 | 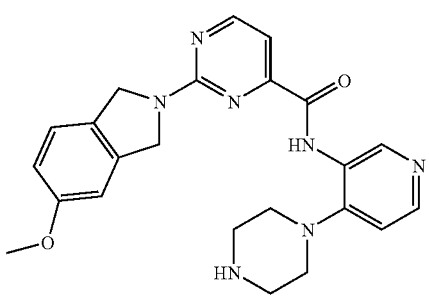 | 431.49 | 432.20 | 1.36 |
| 278 | 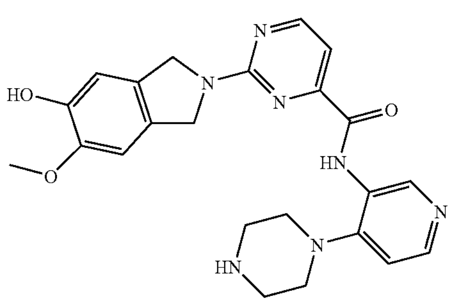 | 447.49 | 448.20 | 1.20 |

TABLE 10-continued

| Compound # | Structure | Exact mass | MS m/z (M + H) | HPLC MS $t_R$ |
|---|---|---|---|---|
| 279 | 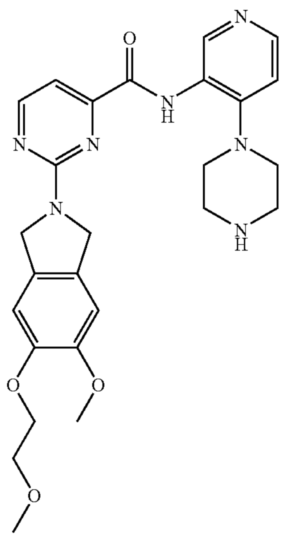 | 505.2 | 506.2 | 0.96 |
| 280 | 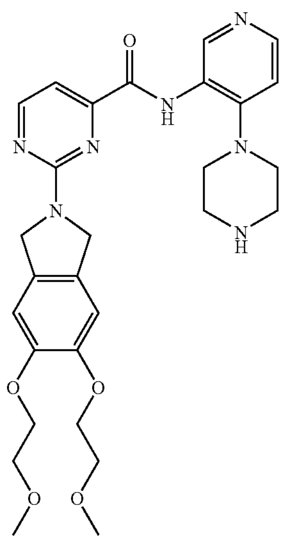 | 549.3 | 550.3 | 1.17 |
| 281 | 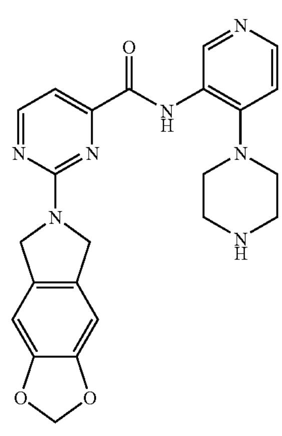 | 445.2 | 446.2 | 1.13 |

TABLE 10-continued

| Compound # | Structure | Exact mass | MS m/z (M + H) | HPLC MS $t_R$ |
|---|---|---|---|---|
| 282 | 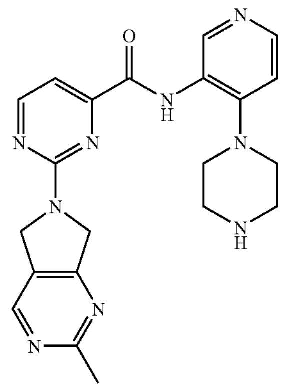 | 417.2 | 418.2 | 0.68 |
| 283 | 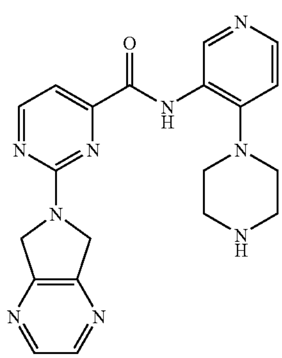 | 403.2 | 404.2 | 0.67 |
| 284 | 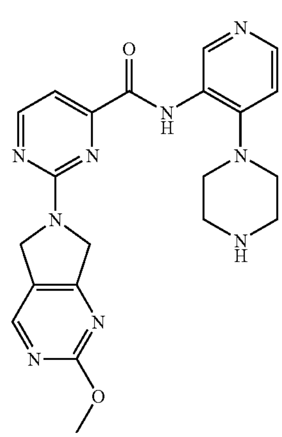 | 433.2 | 434.2 | 0.75 |

TABLE 10-continued

| Compound # | Structure | Exact mass | MS m/z (M + H) | HPLC MS $t_R$ |
|---|---|---|---|---|
| 285 | 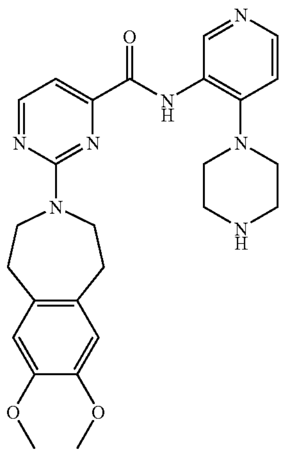 | 489.2 | 490.2 | 1.12 |
| 286 | 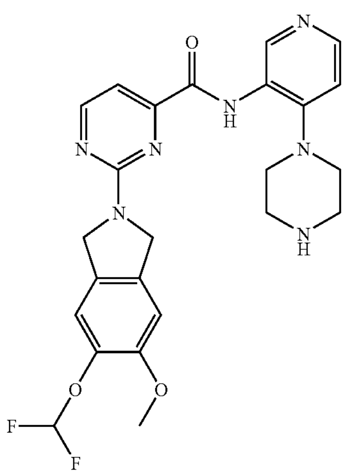 | 497.2 | 498.2 | 1.25 |
| 287 | 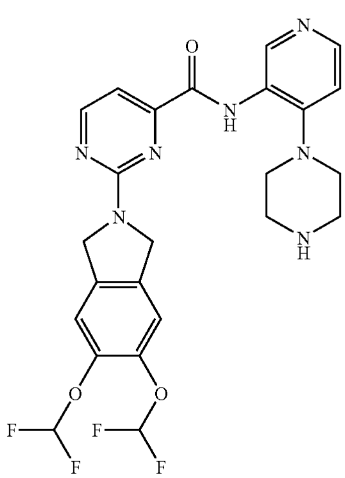 | 533.2 | 534.2 | 1.20 |

TABLE 10-continued

| Compound # | Structure | Exact mass | MS m/z (M + H) | HPLC MS $t_R$ |
|---|---|---|---|---|
| 288 | 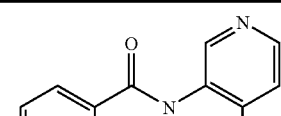 | 433.19 | 434.20 | 1.00 |

Preparation of Compound 290:

Scheme 23

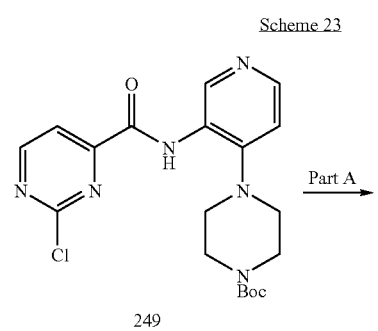

249

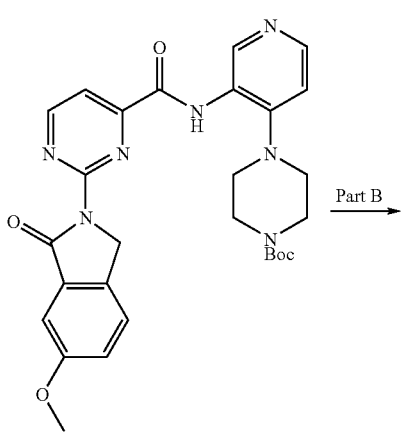

289

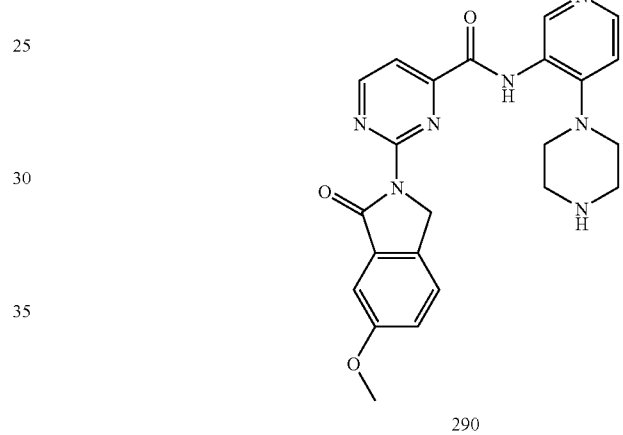

290

Compound 289:

To a 25 ml round bottom flask charged with compound 249 (84 mg, 0.2 mmol), lactam (49 mg, 0.3 mmol), Pd$_2$(dba)$_3$ (18 mg, 0.02 mmol), Xant-phos (23 mg, 0.04 mmol) and K$_3$PO$_4$ (106 mg, 0.5 mmol) was added dioxane (5 mL). The mixture was thoroughly degassed by alternately connected the flask to vacuum and Argon. This resulting mixture was then heated at 80° C. overnight, diluted by EtOAc (40 ml) and washed with brine. After concentration, the residue was purified with Prep-LC to give the product 289. HPLC-MS $t_R$=1.45 min (UV$_{254\ nm}$); mass calculated for formula C$_{28}$H$_{31}$N$_7$O$_5$ 545.2, observed LCMS m/z 546.3 (M+H).

Compound 290:

The compound 289 (10 mg) was treated with HCl (4N in dioxane, 4 mL) and stirred at room temperature for 10 min. After concentration, the residue was dried with lypholization gave compound 290. HPLC-MS $t_R$=0.85 min (UV$_{254\ nm}$); mass calculated for formula C$_{23}$H$_{23}$N$_7$O$_3$ 445.2, observed LCMS m/z 446.1 (M+H).

Examples 291-295

By following essentially the same procedure set forth above for compound 290, compounds 291-295 (set forth below in Table 11) can be prepared from compound 249.

TABLE 11

| Compound # | Structure | Exact mass | MS m/z (M + H) | HPLC MS $t_R$ |
|---|---|---|---|---|
| 291 | 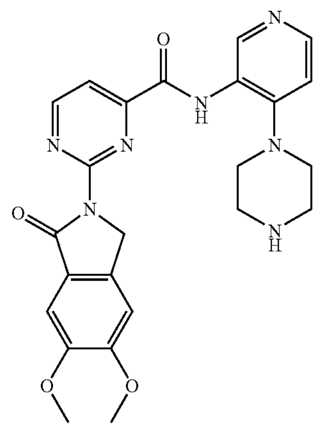 | 475.2 | 476.2 | 0.81 |
| 292 | 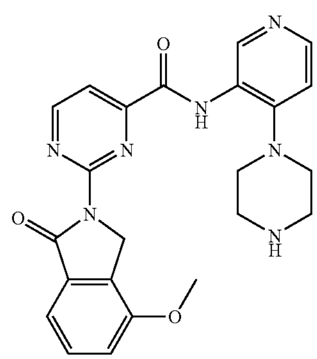 | 445.2 | 446.1 | 0.89 |
| 293 | 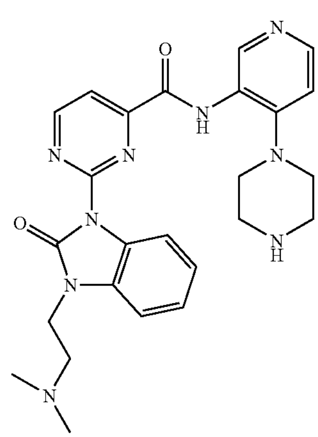 | 487.2 | 488.3 | 0.83 |

TABLE 11-continued

| Compound # | Structure | Exact mass | MS m/z (M + H) | HPLC MS $t_R$ |
|---|---|---|---|---|
| 294 | 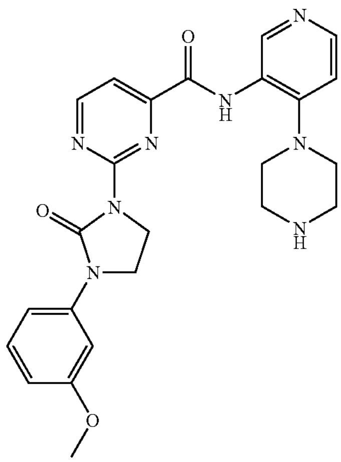 | 474.2 | 475.3 | 1.08 |
| 295 | 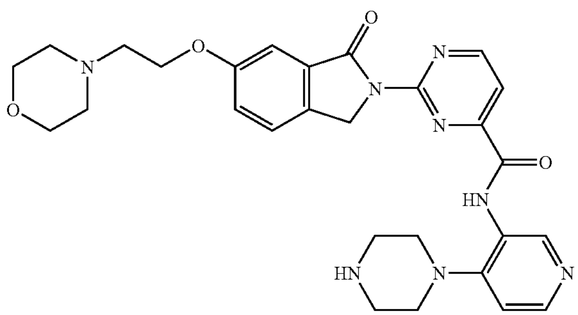 | 544.2 | 545.3 | 0.85 |

Preparation of Compound 297:

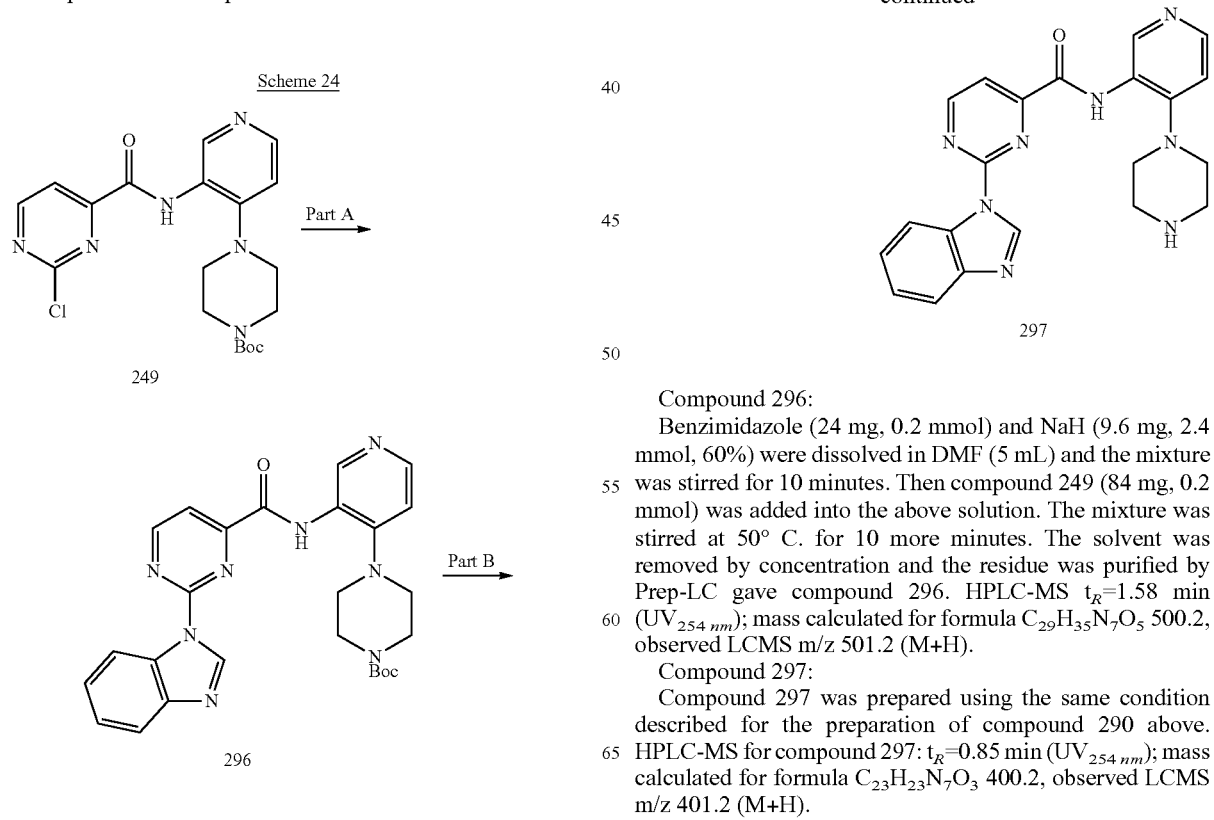

Compound 296:

Benzimidazole (24 mg, 0.2 mmol) and NaH (9.6 mg, 2.4 mmol, 60%) were dissolved in DMF (5 mL) and the mixture was stirred for 10 minutes. Then compound 249 (84 mg, 0.2 mmol) was added into the above solution. The mixture was stirred at 50° C. for 10 more minutes. The solvent was removed by concentration and the residue was purified by Prep-LC gave compound 296. HPLC-MS $t_R$=1.58 min (UV$_{254\,nm}$); mass calculated for formula $C_{29}H_{35}N_7O_5$ 500.2, observed LCMS m/z 501.2 (M+H).

Compound 297:

Compound 297 was prepared using the same condition described for the preparation of compound 290 above. HPLC-MS for compound 297: $t_R$=0.85 min (UV$_{254\,nm}$); mass calculated for formula $C_{23}H_{23}N_7O_3$ 400.2, observed LCMS m/z 401.2 (M+H).

Compound 298-309:

By essentially the same procedure set forth for the preparation of compounds 297, compounds 298-309 (set forth below in Table 12) can be prepared from compound 249

TABLE 12

| Compound # | Structure | Exact mass | MS m/z (M + H) | HPLC MS $t_R$ |
|---|---|---|---|---|
| 298 | 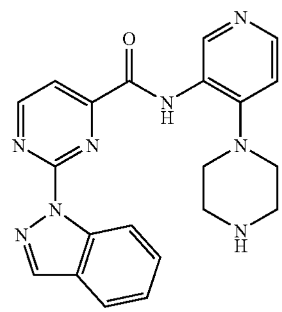 | 400.2 | 401.2 | 0.96 |
| 299 | 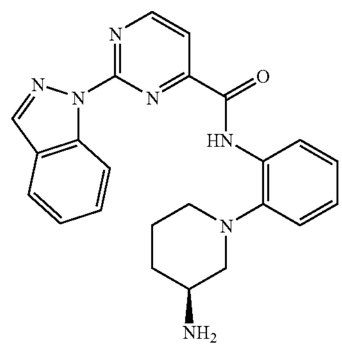 | 413.20 | 414.2 | 3.65 |
| 300 | 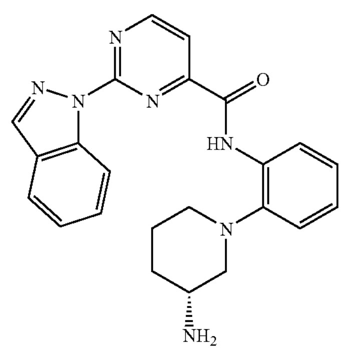 | 413.20 | 414.2 | 3.65 |
| 301 | 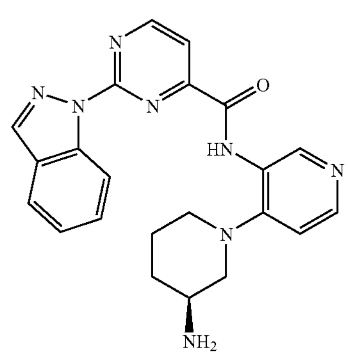 | 414.20 | 415.2 | 2.16 |

TABLE 12-continued
| Compound # | Structure | Exact mass | MS m/z (M + H) | HPLC MS $t_R$ |
|---|---|---|---|---|
| 302 | 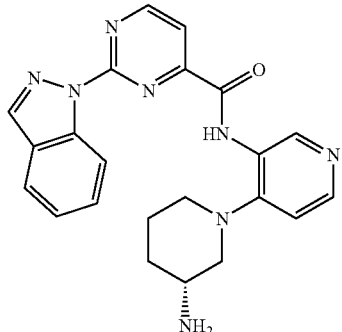 | 414.20 | 415.2 | 2.16 |
| 303 | 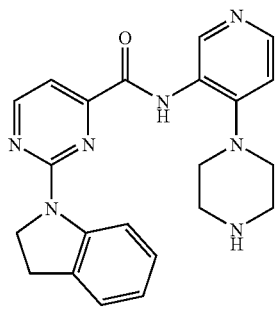 | 401.2 | 402.2 | 1.19 |
| 304 | 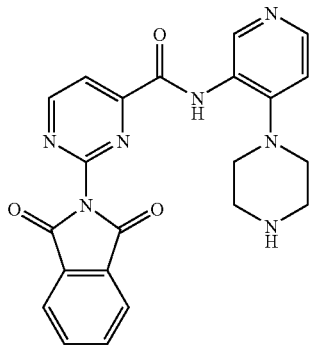 | 429.2 | 430.1 | 0.65 |

TABLE 12-continued

| Compound # | Structure | Exact mass | MS m/z (M + H) | HPLC MS $t_R$ |
|---|---|---|---|---|
| 305 | 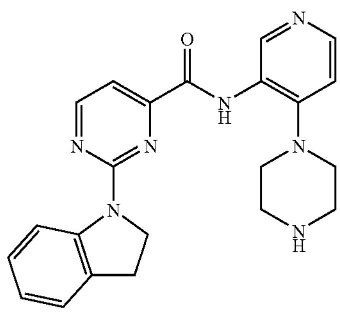 | 401.20 | 402.10 | 1.00 |
| 306 | 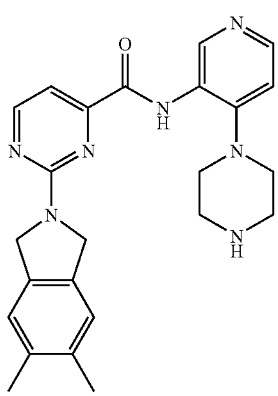 | 429.23 | 430.20 | 1.35 |
| 307 | 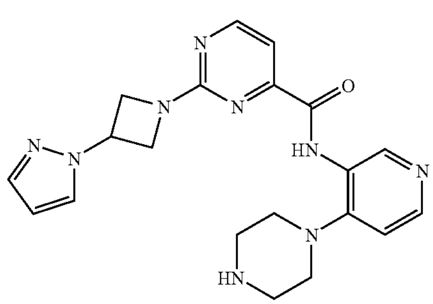 | 405.20 | 406.20 | 1.20 |

TABLE 12-continued
| Compound # | Structure | Exact mass | MS m/z (M + H) | HPLC MS $t_R$ |
|---|---|---|---|---|
| 308 | 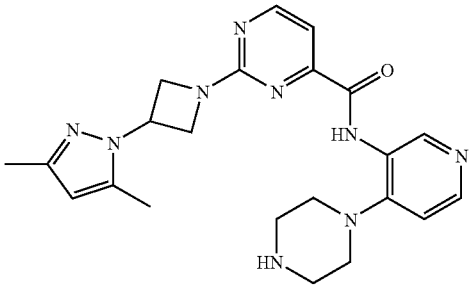 | 433.23 | 434.10 | 1.30 |
| 309 | 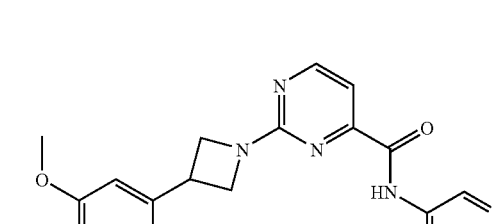 | 475.23 | 476.20 | 1.20 |
Compound 310:
Compound in table-13 could be essentially prepared from the intermediate 249 and corresponding urea
TABLE 13
| Compound # | Structure | Exact mass | MS m/z (M + H) | HPLC MS $t_R$ |
|---|---|---|---|---|
| 310 | 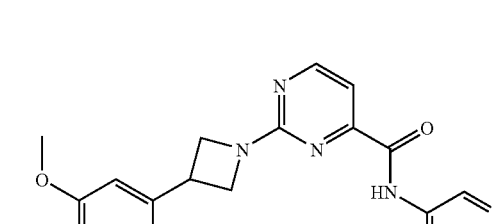 | 436.18 | 437.20 | 1.75 |

Compound 312:

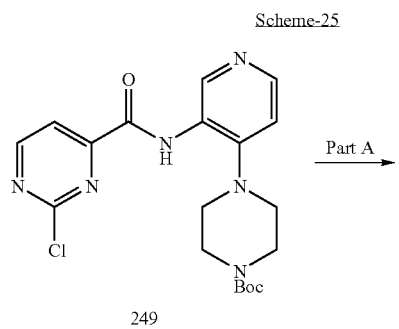

Scheme-25

249

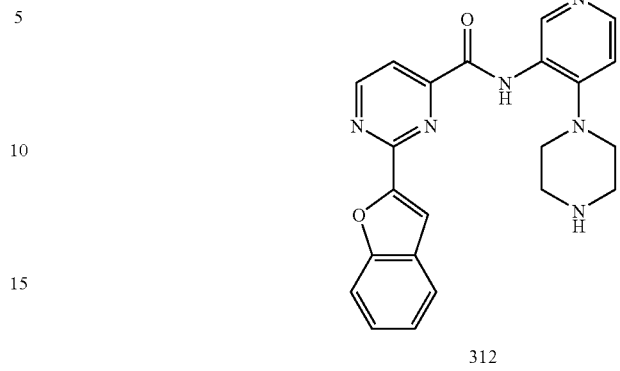

312

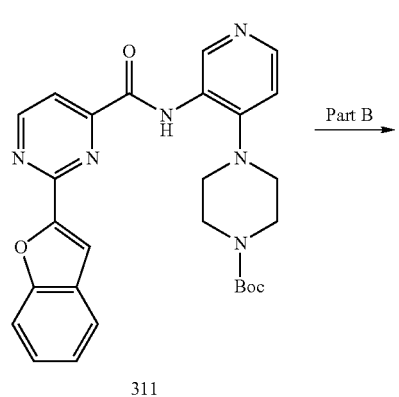

311

Compound 311:

A 10 mL microwave vial was charged with compound 249 (100 mg, 0.24 mmol), benzofuran-2-boronic acid (58 mg, 0.36 mmol), Pd(dppf)Cl$_2$ (19 mg, 0.024 mmol), triethylamine (73 mg, 0.72 mmol) and methanol (1 mL). The mixture was irradiated at 120° C. for 30 minutes, then concentrated and eluted over a short silica gel column, using ethyl acetate, to afford crude compound 311. HPLC-MS t$_R$=0.93 min (UV$_{254\ nm}$); Mass calculated for C$_{22}$H$_{20}$N$_6$O$_2$: 500.2; Observed m/z: 501.2 (M+H).

Compound 312:

The crude intermediate 311 was dissolved in 10% TFA/DCM and stirred at room temperature for 2 hours, at which time it was concentrated and purified by preparative LC to afford compound 312. HPLC-MS t$_R$=1.61 min (UV$_{254\ nm}$); Mass calculated for C$_{22}$H$_{20}$N$_6$O$_2$: 400.2; Observed m/z: 401.2 (M+H).

Compounds 313-350:

By essentially the same procedure given in Preparative Example 311, compounds 313-353 given in Column 2 of Table 14 can be prepared from compound 249.

TABLE 14

| Compound # | Structure | Exact Mass | MS; m/z | HPLC; MS tR |
|---|---|---|---|---|
| 313 | 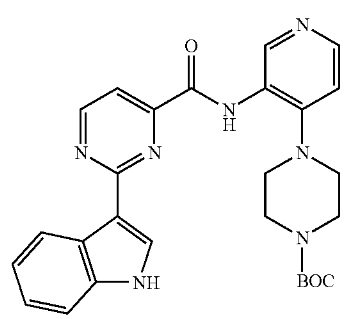 | 499.2 | 500.2 | 1.61 |

TABLE 14-continued

| Compound # | Structure | Exact Mass | MS; m/z | HPLC; MS tR |
|---|---|---|---|---|
| 314 | 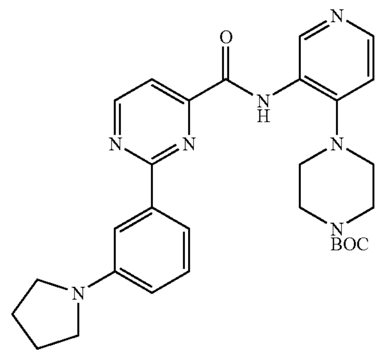 | 629.3 | 630.3 | 1.71 |
| 315 | 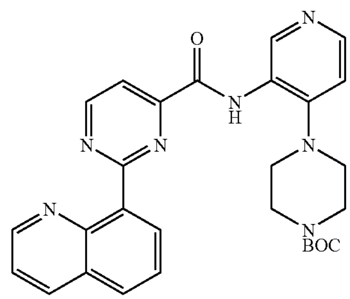 | 511.2 | 512.2 | 1.05 |
| 316 | 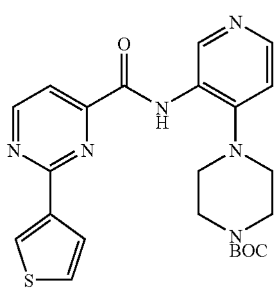 | 466.1 | 467.1 | 1.45 |
| 317 | 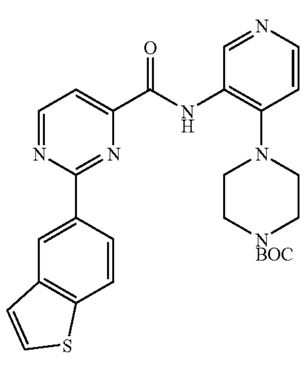 | 516.2 | 517.2 | 1.69 |

TABLE 14-continued

| Compound # | Structure | Exact Mass | MS; m/z | HPLC; MS tR |
|---|---|---|---|---|
| 318 | 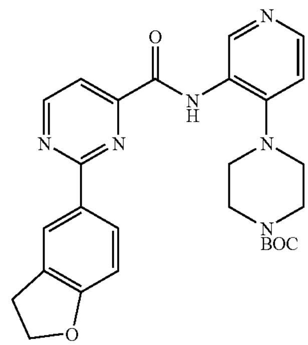 | 502.2 | 503.2 | 1.69 |
| 319 | 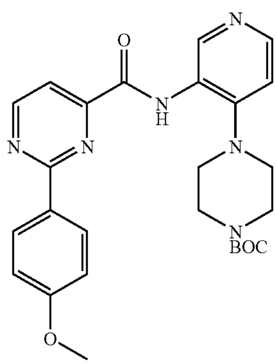 | 490.2 | 491.2 | 1.68 |
| 320 | 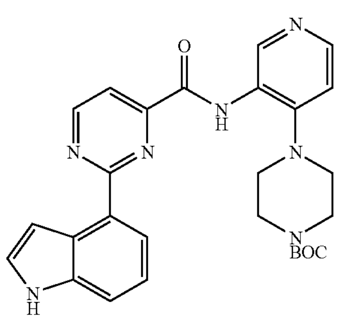 | 499.2 | 500.2 | 1.56 |
| 321 | 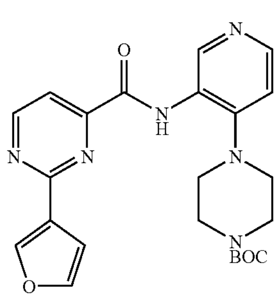 | 450.1 | 451.1 | 1.54 |

TABLE 14-continued

| Compound # | Structure | Exact Mass | MS; m/z | HPLC; MS tR |
|---|---|---|---|---|
| 322 | 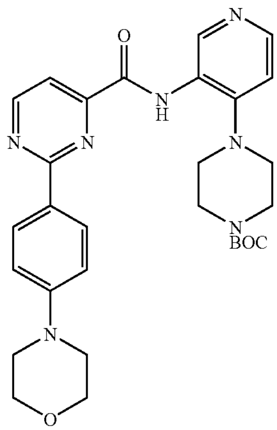 | 545.3 | 546.3 | 1.49 |
| 323 | 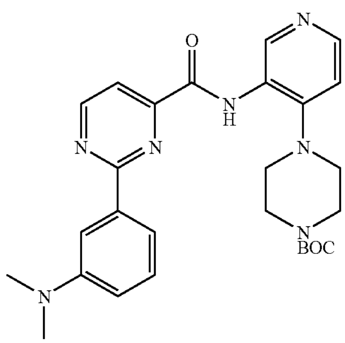 | 503.2 | 504.2 | 1.34 |
| 324 | 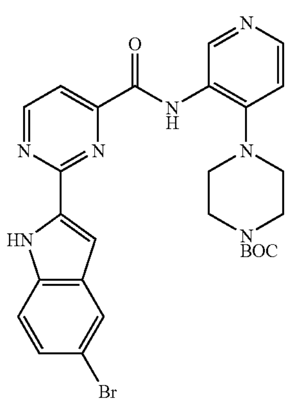 | 577.1 | 578.1 | 1.58 |
| 325 | 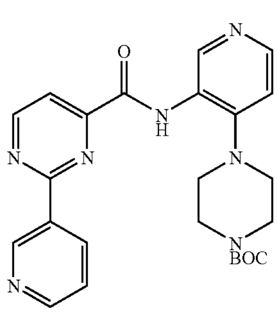 | 461.3 | 462.2 | 1.07 |

TABLE 14-continued
| Compound # | Structure | Exact Mass | MS; m/z | HPLC; MS tR |
|---|---|---|---|---|
| 326 | 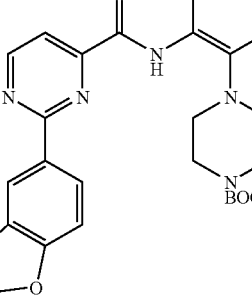 | 500.2 | 501.2 | 1.60 |
| 327 | 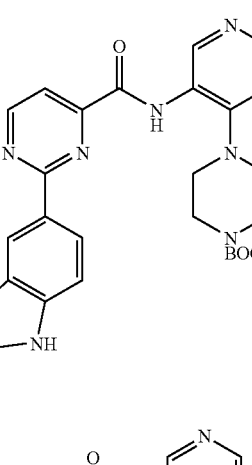 | 499.2 | 500.2 | 1.46 |
| 328 | 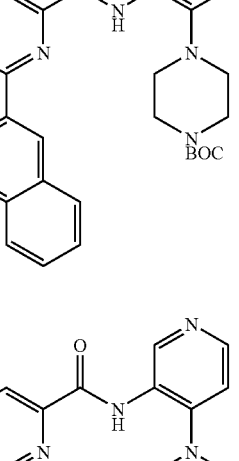 | 511.2 | 412.2 | 0.77 |
| 329 | 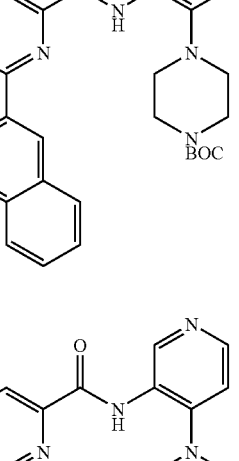 | 491.2 | 392.2 | 0.82 |

TABLE 14-continued

| Compound # | Structure | Exact Mass | MS; m/z | HPLC; MS tR |
|---|---|---|---|---|
| 330 | 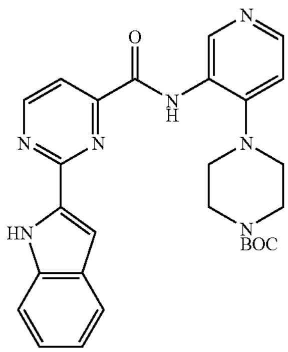 | 499.2 | 500.2 | 1.49 |
| 331 | 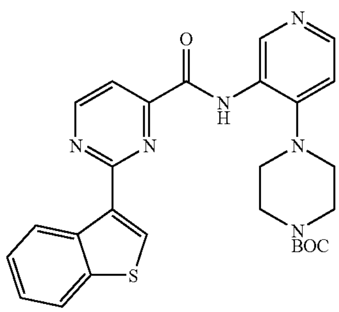 | 516.2 | 517.2 | 1.71 |
| 332 | 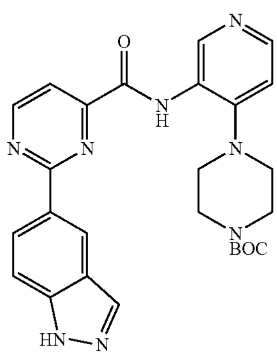 | 500.2 | 501.2 | 1.28 |
| 333 | 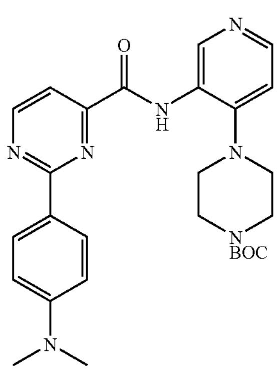 | 503.2 | 504.2 | 1.54 |

TABLE 14-continued

| Compound # | Structure | Exact Mass | MS; m/z | HPLC; MS tR |
|---|---|---|---|---|
| 334 | 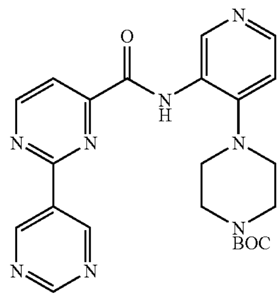 | 462.2 | 463.2 | 1.34 |
| 335 | 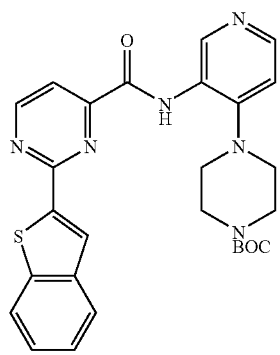 | 516.2 | 517.2 | 1.79 |
| 336 | 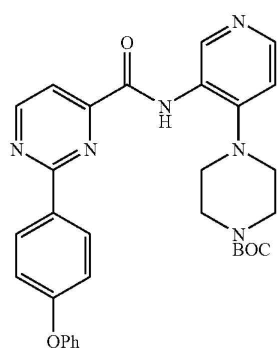 | 552.2 | 553.2 | 1.81 |
| 337 | 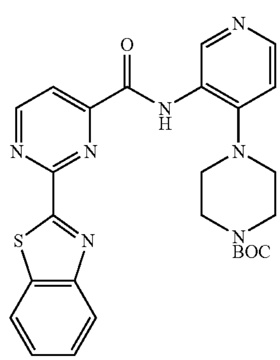 | 517.2 | 518.2 | 1.55 |

TABLE 14-continued

| Compound # | Structure | Exact Mass | MS; m/z | HPLC; MS tR |
|---|---|---|---|---|
| 338 | 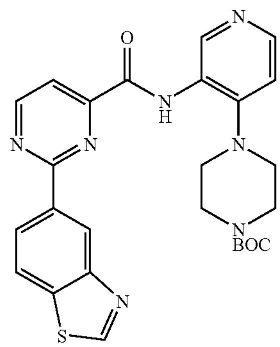 | 517.2 | 418.2 | 1.44 |
| 339 | 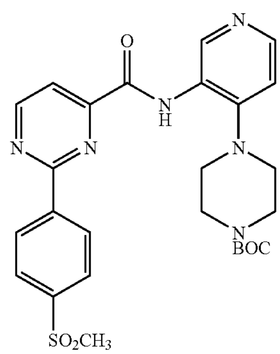 | 538.1 | 539.1 | 1.35 |
| 340 | 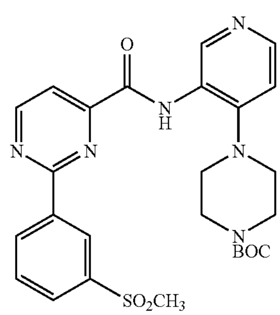 | 538.1 | 539.1 | 1.35 |
| 341 | 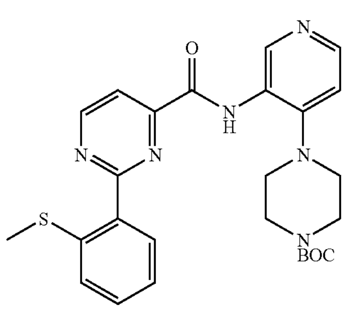 | 506.2 | 507.2 | 1.57 |

TABLE 14-continued

| Compound # | Structure | Exact Mass | MS; m/z | HPLC; MS tR |
|---|---|---|---|---|
| 342 | 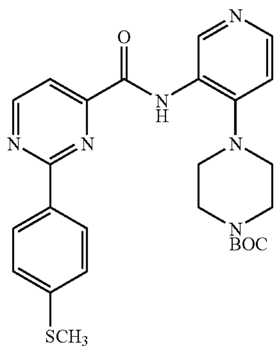 | 506.2 | 507.2 | 1.65 |
| 343 | 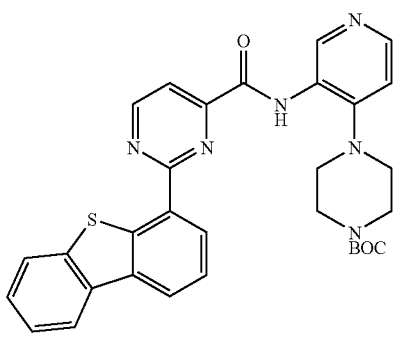 | 566.2 | 567.2 | 1.87 |
| 344 | 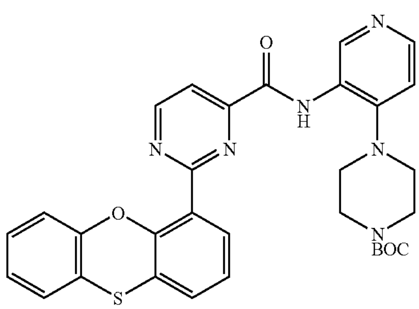 | 582.2 | 583.2 | 1.79 |
| 345 | 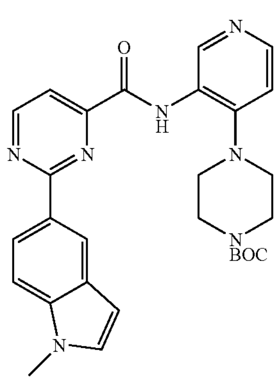 | 513.2 | 514.2 | 1.72 |

TABLE 14-continued

| Compound # | Structure | Exact Mass | MS; m/z | HPLC; MS tR |
|---|---|---|---|---|
| 346 | 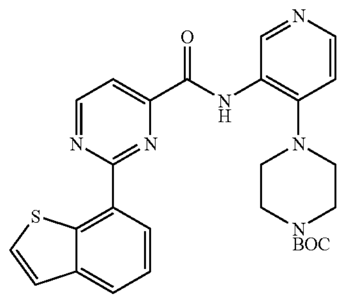 | 516.2 | 517.2 | 1.69 |
| 347 | 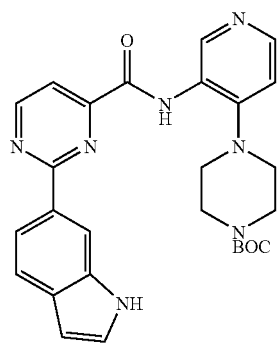 | 499.2 | 500.2 | 1.52 |
| 348 | 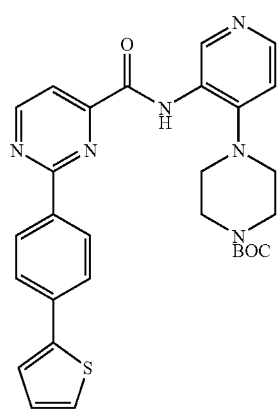 | 542.1 | 543.1 | 1.78 |
| 349 | 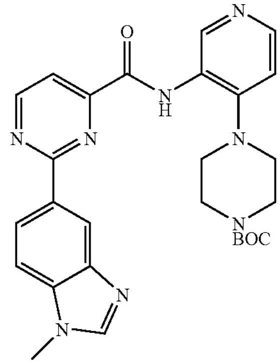 | 514.2 | 515.2 | 1.07 |

TABLE 14-continued

| Compound # | Structure | Exact Mass | MS; m/z | HPLC; MS tR |
|---|---|---|---|---|
| 350 | 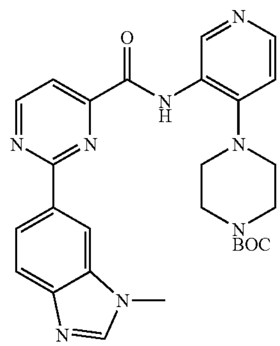 | 514.2 | 515.2 | 1.06 |
| 351 | 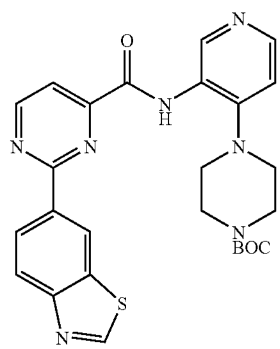 | 517.2 | 518.2 | 1.47 |
| 352 | 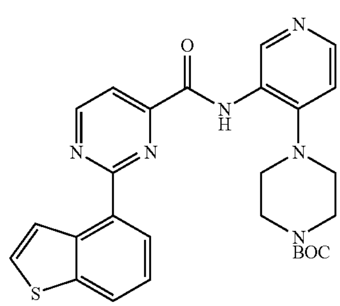 | 516.2 | 517.2 | 1.72 |
| 353 | 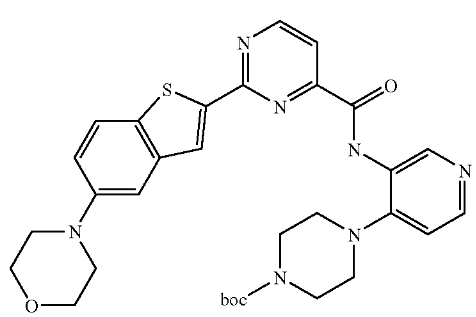 | 601.25 | 602.20 | 1.65 |

Compounds 354-397:

By essentially the same procedure given in Preparative Example 312 (Part B), compounds 354-397 given in Column 2 of Table 15 can be prepared from compound 249.

TABLE 15
| Compound # | Structure | Exact Mass | MS; m/z | HPLC; MS tR |
|---|---|---|---|---|
| 354 | 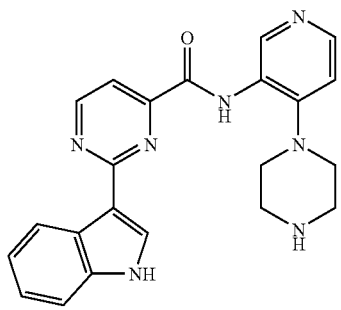 | 399.2 | 400.2 | 2.22 |
| 355 | 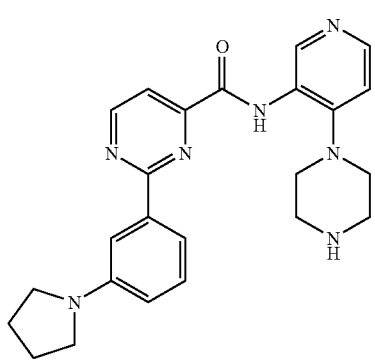 | 529.3 | 530.3 | 4.59 |
| 356 | 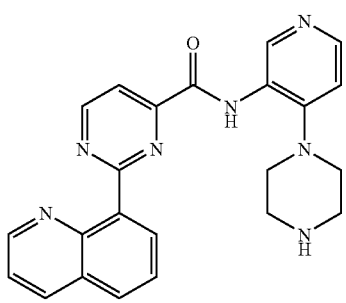 | 511.2 | 512.2 | 2.64 |
| 357 | 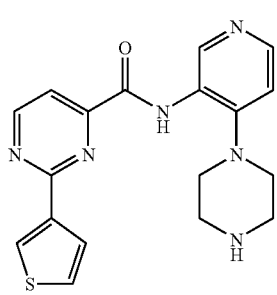 | 366.1 | 367.1 | 1.82 |

TABLE 15-continued

| Compound # | Structure | Exact Mass | MS; m/z | HPLC; MS tR |
|---|---|---|---|---|
| 358 | 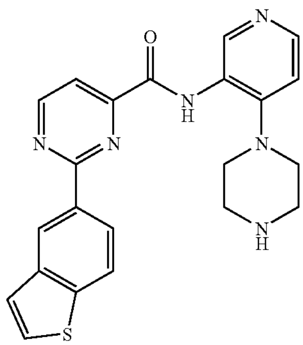 | 416.1 | 417.1 | 2.51 |
| 359 | 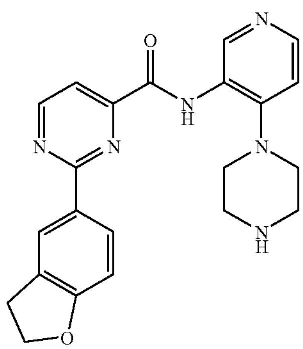 | 402.2 | 403.2 | 2.12 |
| 360 | 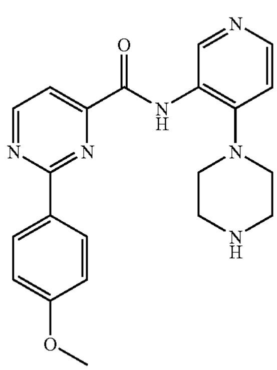 | 390.2 | 391.2 | 2.13 |
| 361 | 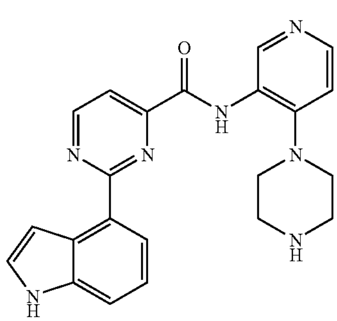 | 399.2 | 400.2 | 1.98 |

TABLE 15-continued

| Compound # | Structure | Exact Mass | MS; m/z | HPLC; MS tR |
|---|---|---|---|---|
| 362 | 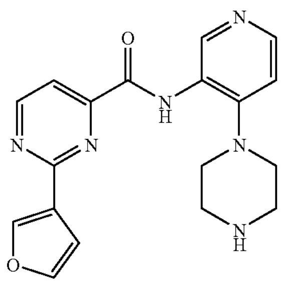 | 350.1 | 351.1 | 1.64 |
| 363 | 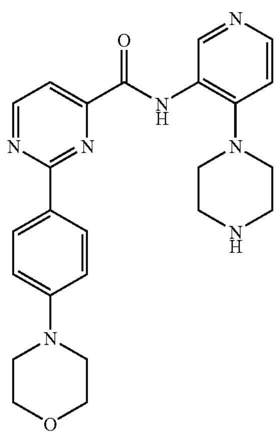 | 445.2 | 446.2 | 2.19 |
| 364 | 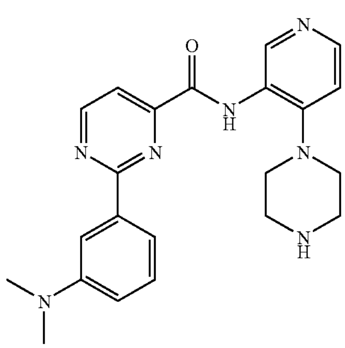 | 403.2 | 404.2 | 1.60 |
| 365 | 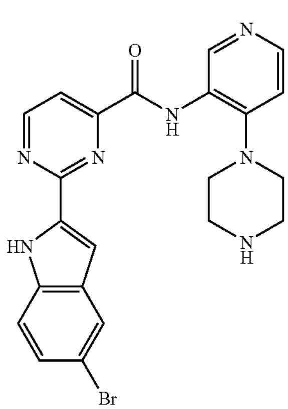 | 477.1 | 478.1 | 2.95 |

TABLE 15-continued

| Compound # | Structure | Exact Mass | MS; m/z | HPLC; MS tR |
|---|---|---|---|---|
| 366 | 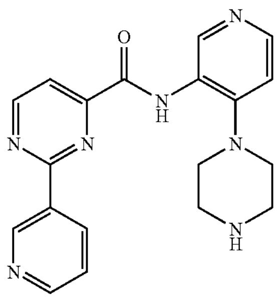 | 361.2 | 362.2 | 1.12 |
| 367 | 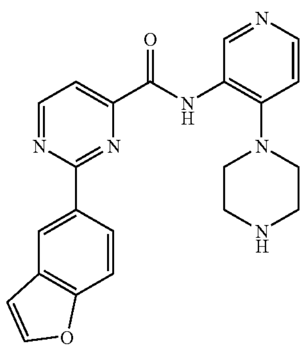 | 400.2 | 401.2 | 2.4 |
| 368 | 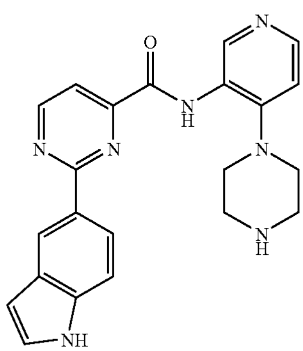 | 399.2 | 400.2 | 2.11 |
| 369 | 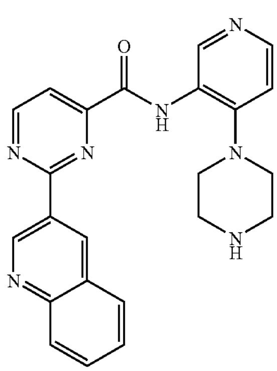 | 411.2 | 412.2 | 1.87 |

TABLE 15-continued
| Compound # | Structure | Exact Mass | MS; m/z | HPLC; MS tR |
|---|---|---|---|---|
| 370 | 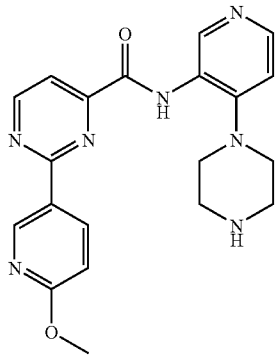 | 391.2 | 392.2 | 1.94 |
| 371 | 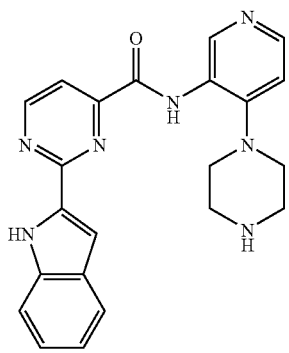 | 399.2 | 400.2 | 2.42 |
| 372 | 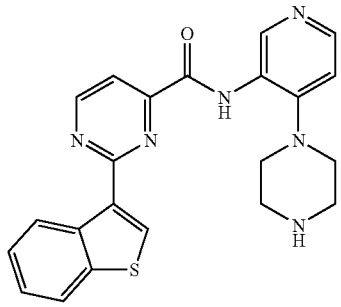 | 416.1 | 417.1 | 2.61 |
| 373 | 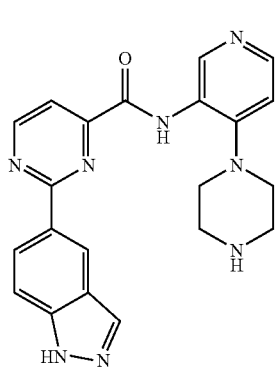 | 400.2 | 401.2 | 1.78 |

TABLE 15-continued

| Compound # | Structure | Exact Mass | MS; m/z | HPLC; MS tR |
|---|---|---|---|---|
| 374 | 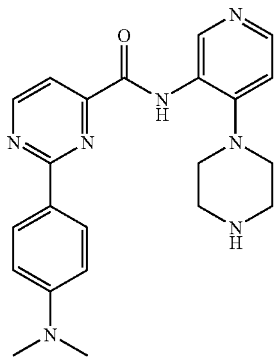 | 403.2 | 404.2 | 2.16 |
| 375 | 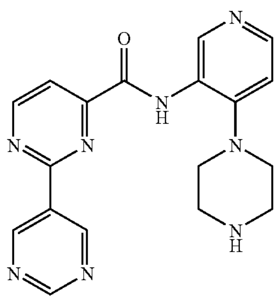 | 362.2 | 363.2 | 1.28 |
| 376 | 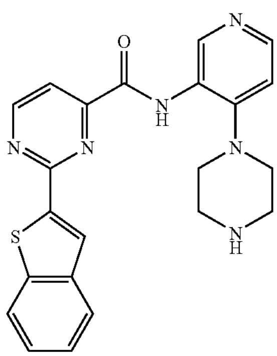 | 416.1 | 417.1 | 2.66 |
| 377 | 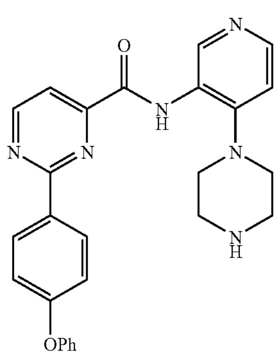 | 452.2 | 453.2 | 3.05 |

TABLE 15-continued

| Compound # | Structure | Exact Mass | MS; m/z | HPLC; MS tR |
|---|---|---|---|---|
| 378 | 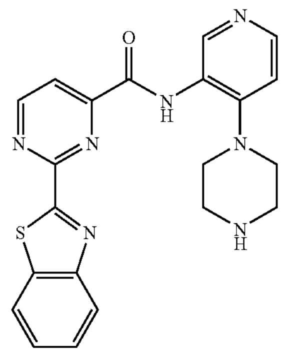 | 417.1 | 418.1 | 2.23 |
| 379 | 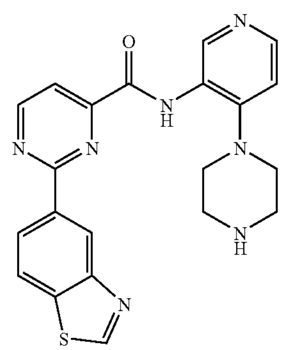 | 417.1 | 418.1 | 2.07 |
| 380 | 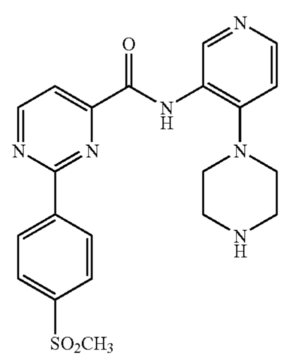 | 438.1 | 439.1 | 1.78 |
| 381 | 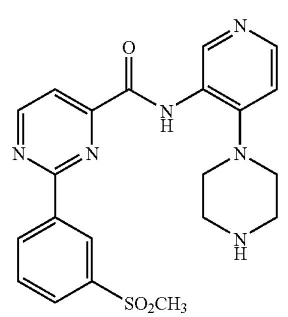 | 438.1 | 439.1 | 1.76 |

TABLE 15-continued
| Compound # | Structure | Exact Mass | MS; m/z | HPLC; MS tR |
|---|---|---|---|---|
| 382 | 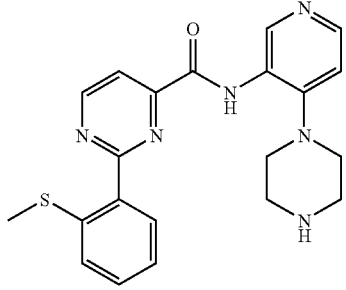 | 406.2 | 407.2 | 2.23 |
| 383 | 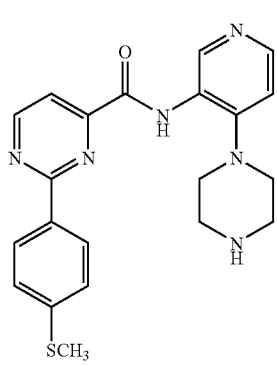 | 406.2 | 407.2 | 2.51 |
| 384 | 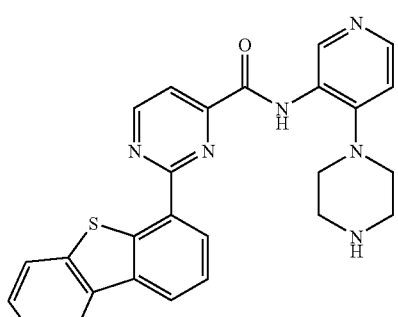 | 466.2 | 467.2 | 3.18 |
| 385 | 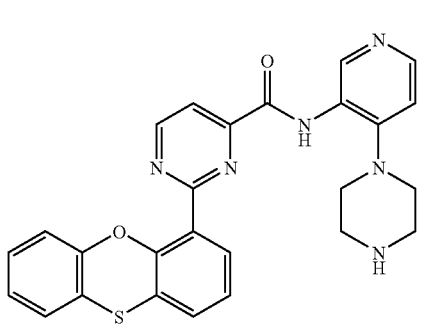 | 482.2 | 483.2 | 2.9 |

TABLE 15-continued

| Compound # | Structure | Exact Mass | MS; m/z | HPLC; MS tR |
|---|---|---|---|---|
| 386 | 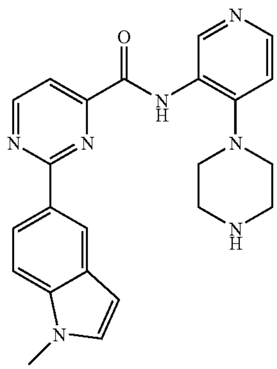 | 413.2 | 414.2 | 2.42 |
| 387 | 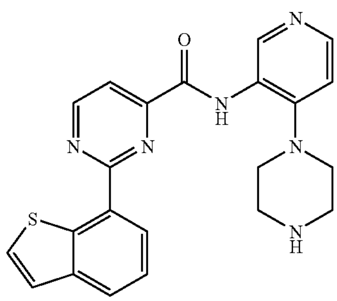 | 416.1 | 417.1 | 2.59 |
| 388 | 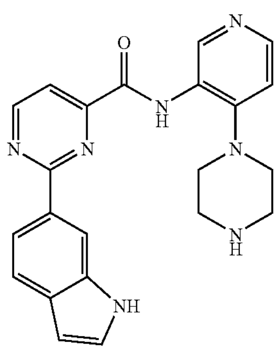 | 399.2 | 400.2 | 2.21 |
| 389 | 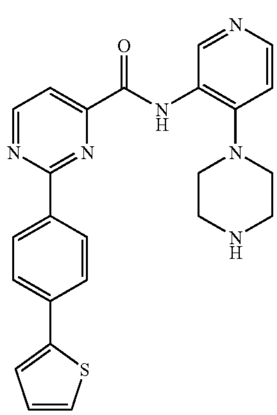 | 442.2 | 443.2 | 2.96 |

TABLE 15-continued
| Compound # | Structure | Exact Mass | MS; m/z | HPLC; MS tR |
|---|---|---|---|---|
| 390 | 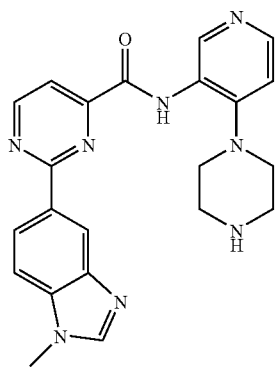 | 414.2 | 415.2 | 1.37 |
| 391 | 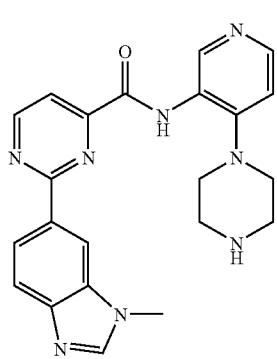 | 414.2 | 415.2 | 1.32 |
| 392 | 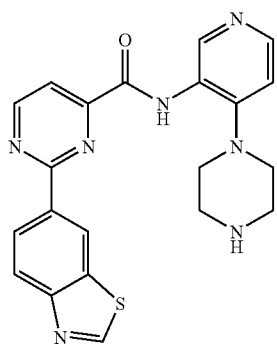 | 417.1 | 418.1 | 2.06 |
| 393 | 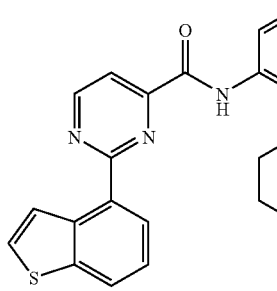 | 416.1 | 417.1 | 1.16 |

TABLE 15-continued
| Compound # | Structure | Exact Mass | MS; m/z | HPLC; MS tR |
|---|---|---|---|---|
| 394 | 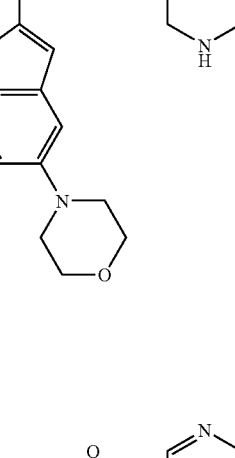 | 501.19 | 502.20 | 0.90 |
| 395 | 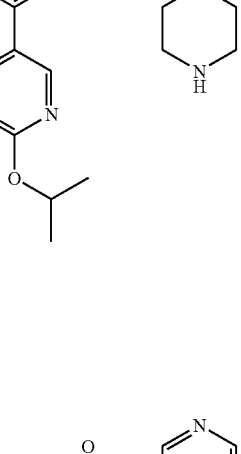 | 419.21 | 420.20 | 0.85 |
| 396 | 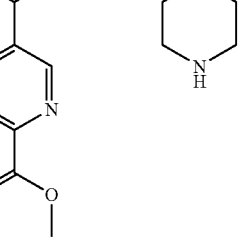 | 419.17 | 420.10 | 1.10 |

TABLE 15-continued

| Compound # | Structure | Exact Mass | MS; m/z | HPLC; MS tR |
|---|---|---|---|---|
| 397 | 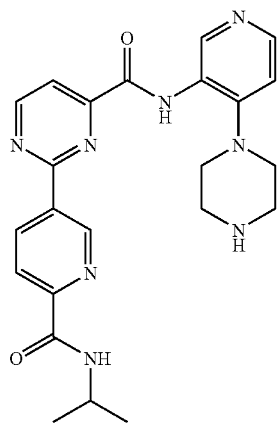 | 446.22 | 447.20 | 1.25 |
| 398 | 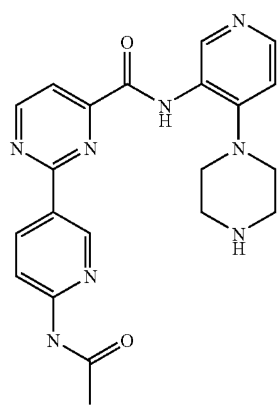 | 418.19 | 419.20 | 1.00 |
| 399 | 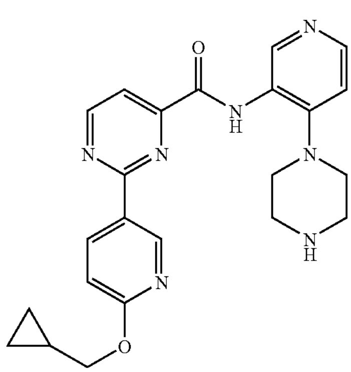 | 431.21 | 432.20 | 1.10 |

TABLE 15-continued

| Compound # | Structure | Exact Mass | MS; m/z | HPLC; MS tR |
|---|---|---|---|---|
| 400 | 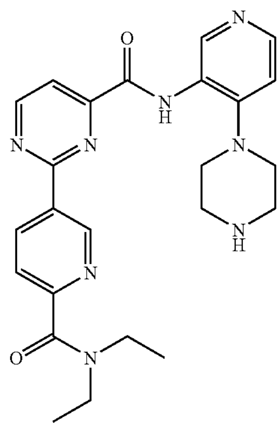 | 460.23 | 461.20 | 1.25 |
| 401 | 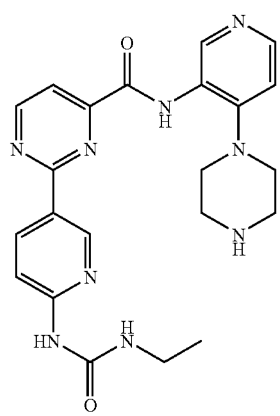 | 432.20 | 433.10 | 1.10 |
| 402 | 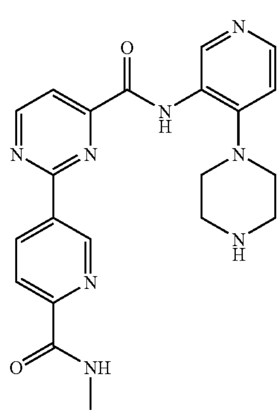 | 418.19 | 419.20 | 1.00 |

Compound 405:

Scheme 26

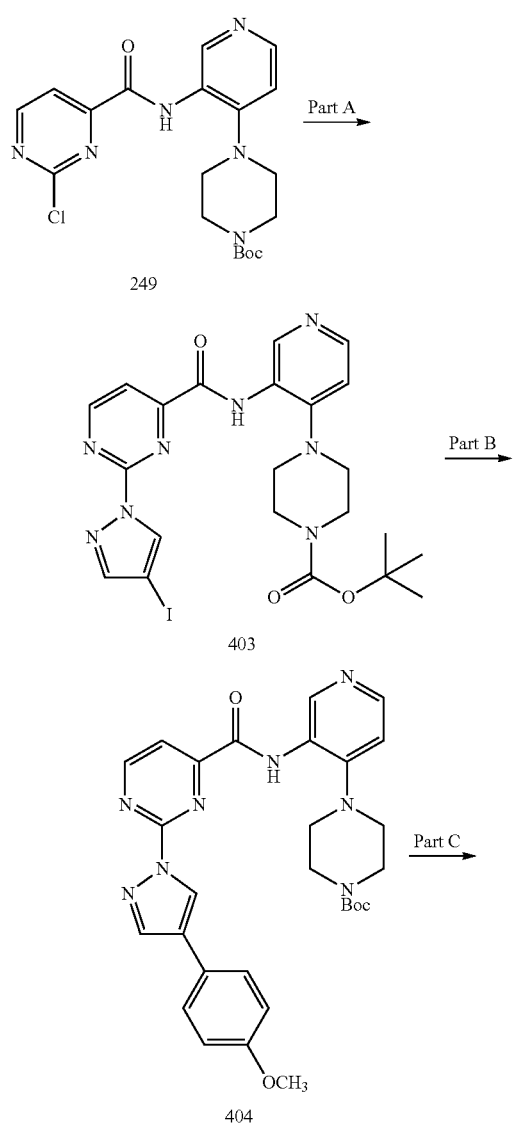

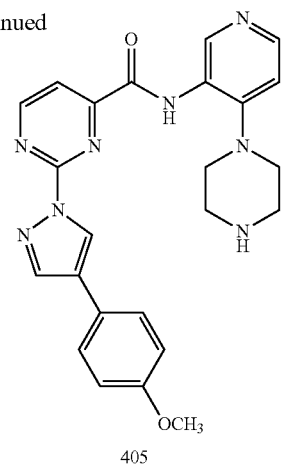

405

Compound 403:

A 10 mL microwave vial was charged with compound 249 (100 mg, 0.17 mmol), 4-iodopyrazole (66 mg, 0.34 mmol), triethylamine (52 mg, 0.51 mmol) and acetonitrile (1 mL). The mixture was irradiated at 120° C. for 30 minutes, then concentrated and purified by silica gel chromatography (100% ethyl acetate), affording intermediate 403 as a colorless solid. HPLC-MS $t_R$=1.63 min (UV$_{254\ nm}$); Mass calculated for $C_{22}H_{25}IN_8O_3$: 576.2; Observed m/z: 577.2 (M+H).

Compound 404:

A 10 mL microwave vial was charged with compound 403 (98 mg, 0.17 mmol), 4-methoxyphenylboronic acid (51 mg, 0.34 mmol), Pd(dppf)Cl$_2$ (14 mg, 0.017 mmol), triethylamine (52 mg, 0.51 mmol) and methanol (1 mL). The mixture was irradiated at 120° C. for 30 minutes, then concentrated and eluted over a short silica gel column, using ethyl acetate, affording the intermediate compound 404. HPLC-MS $t_R$=1.58 min (UV$_{254\ nm}$); Mass calculated for $C_{29}H_{32}N_8O_4$: 556.2; Observed m/z: 557.2 (M+H).

Compound 405:

The intermediate compound 404 was dissolved in 10% TFA/DCM and stirred at room temperature for 2 hours, at which time it was concentrated and purified by preparative LC to afford compound 405. HPLC-MS $t_R$=2.66 min (UV$_{254\ nm}$); Mass calculated for $C_{24}H_{24}N_8O_2$: 456.2; Observed m/z: 457.2 (M+H).

Compounds 406-408:

By essentially the same procedure given in Preparative Example 405 (Part B), compounds 406-408 given in Column 2 of Table 16 can be prepared from compound 100.

TABLE 16

| Example | Column 2 | Exact mass | MS m/z (M + H) | HPLC MS $t_R$ |
|---------|----------|------------|----------------|---------------|
| 406 | 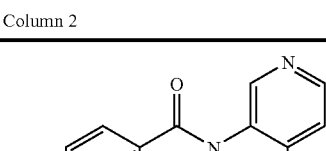 | 532.2 | 533.2 | 1.57 |

TABLE 16-continued
| Example | Column 2 | Exact mass | MS m/z (M + H) | HPLC MS $t_R$ |
|---|---|---|---|---|
| 407 | 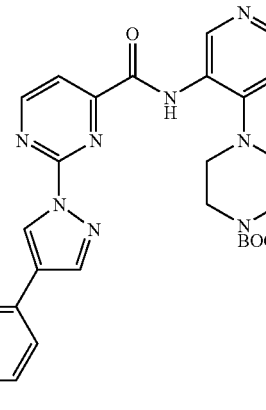 | 586.2 | 587.2 | 1.51 |
| 408 | 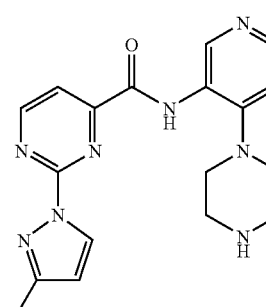 | 586.2 | 587.2 | 1.54 |
Compounds 409-412:
By essentially the same procedure given in Preparative Example 405 (Part B), compounds 409-412 given in Column 2 of Table 17 can be prepared from compound 249.
TABLE 17
| Example | Column 2 | Exact mass | MS m/z (M + H) | HPLC MS $t_R$ |
|---|---|---|---|---|
| 409 | | 432.1 | 433.1 | 2.51 |

TABLE 17-continued
| Example | Column 2 | Exact mass | MS m/z (M + H) | HPLC MS $t_R$ |
|---|---|---|---|---|
| 410 | | 486.2 | 487.2 | 2.46 |
| 411 | | 486.2 | 487.2 | 2.43 |
Compound 417:
Scheme-27:
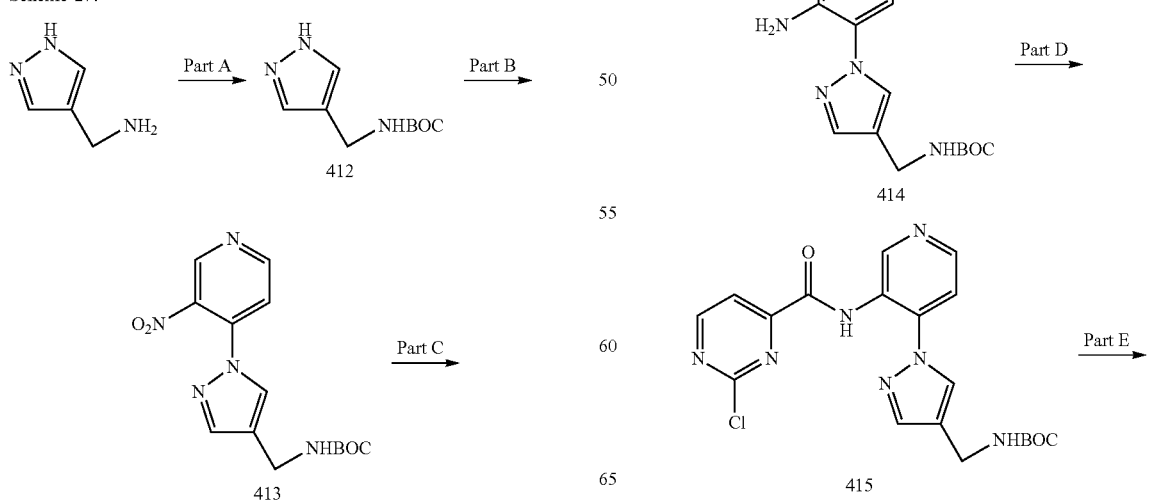

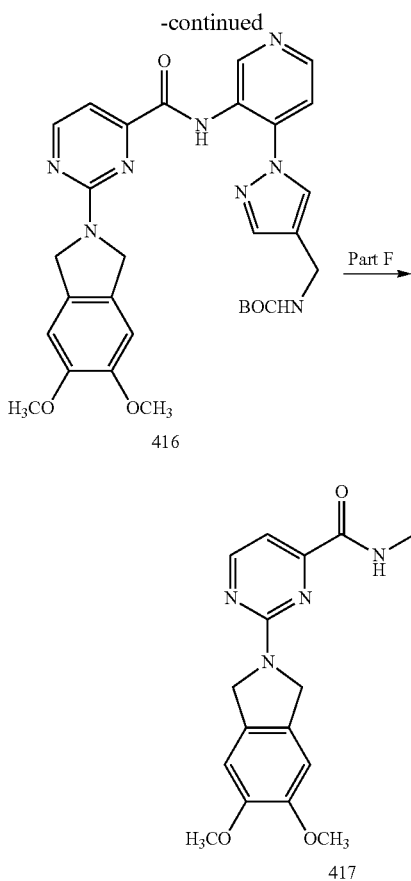

416

417

Compound 417

Compound 412:

To a flask containing the compound 1H-pyrazole-4-methanamine (1 g, 10.3 mmol) and dichloromethane (50 mL) was added di-tert-butyldicarbonate (2.25 g, 10.3 mmol). The reaction was stirred overnight, stripped of solvent and finally purfied by silica gel chromatography (50:50 EtOAc/Hexane) to yield compound 412 as a colorless solid. HPLC-MS $t_R$=1.16 min (ELSD); Mass calculated for $C_9H_{15}N_3O_2$: 197.1; Observed m/z: 198.1 (M+H).

Compound 413:

To a flask containing 4-chloro-3-nitropyridine (1 g, 6.3 mmol) and compound 412 (1.24 g, 6.3 mmol) in DMF (30 mL) was added sodium hydride (60% dispersion in mineral oil; 277 mg, 6.9 mmol). The reaction was stirred overnight, then quenched with saturated $NaHCO_3$ solution and extracted with EtOAc. The organic extract was concentrated and purfied by silica gel chromatography (50:50 EtOAc/Hexane) to yield compound 413 as a colorless solid. HPLC-MS $t_R$=1.55 min ($UV_{254\ nm}$); Mass calculated for $C_{14}H_{17}N_5O_4$: 319.1; Observed m/z: 320.2 (M+H).

Compound 414:

A solution of compound 413 (2 g, 6.3 mmol) in ethanol (100 mL) was degassed with bubbling Ar, then charged with 10% Pd/C (200 mg) and stirred under $H_2$ (1 atm) for 8 hours. The reaction was purged with bubbling $N_2$ and filtered over celite. Concentration of the reaction afforded compound 414 as a waxy solid. HPLC-MS $t_R$=0.91 min ($UV_{254\ nm}$); Mass calculated for $C_{14}H_{19}N_5O_2$: 289.2; Observed m/z: 290.2 (M+H).

Compound 415:

The compound 2-chloropyrimidine-4-carboxylic acid (317 mg, 2.0 mmol) was combined with compound 414 (578 mg, 2.0 mmol) and HATU (760 mg, 2.0 mmol) and then dissolved in DMF (5 mL), and DIEA (350 uL, 2.0 mmol). The mixture was stirred at room temperature over night, then diluted with water and extracted with EtOAc. The organic extract was concentrated and purfied by silica gel chromatography (50:50 EtOAc/Hexane) to yield compound 415 as a yellow solid. HPLC-MS $t_R$=0.234 min (ELSD); Mass calculated for $C_{19}H_{20}ClN_7O_3$: 429.9; Observed m/z: 430.9 (M+H).

Compound 416:

In a 10 mL microwave tube, compound 415 (100 mg, 0.23 mmol) was combined with 5,6-dimethoxyisoindoline (42 mg, 0.23 mmol), triethylamine (69 mg, 0.69 mmol) and acetonitrile (2 mL). The solution was irradiated for 30 minutes at 100° C., then diluted with EtOAc and filtered over a short plug of silica gel, rinsing with EtOAc, to afford the intermediate compound 416. HPLC-MS $t_R$=1.71 min ($UV_{254\ nm}$); Mass calculated for $C_{24}H_{24}N_8O_3$: 572.3; Observed m/z: 573.3 (M+H).

Compound 417:

The compound 416 was dissolved in 10% TFA/DCM. After stirring for 2 hours, the reaction was concentrated and then purified by preparative LC to afford compound 417. HPLC-MS $t_R$=3.00 min ($UV_{254\ nm}$); Mass calculated for $C_{24}H_{24}N_8O_3$: 472.3; Observed m/z: 473.3 (M+H).

Compound 418:

Scheme-28:

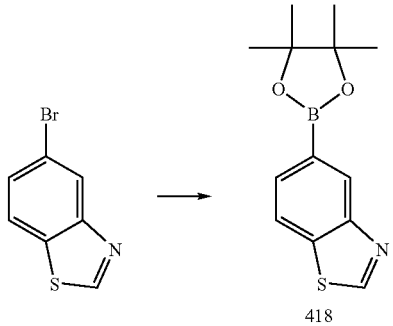

418

Compound 418:

A 10 mL microwave vial was charged with 5-bromobenzothiazole (214 mg, 1 mmol), bis(pinacolato)diboron (381 mg, 1.5 mmol), $Pd(ddpf)Cl_2$ (40 mg, 0.05 mmol), potassium acetate (490 mg, 5 mmol) and DMSO (5 mL). The reaction was irradiated with stirring for 30 minutes at 100° C. The reaction was partitioned between water and EtOAc. The organic phase was separated and concentrated, then purified by silica gel chromatography (1:9 EtOAc/Hexane) to yield compound 418 as a waxy solid. HPLC-MS $t_R$=2.01 min (ELSD); Mass calculated for $C_{13}H_{16}BNO_2S$: 261.1; Observed m/z: 262.1 (M+H).

Compounds 419-421:

By essentially the same procedure given in Preparative Example 418, compounds 419-421 given in Column 2 of Table 18 can be prepared.

TABLE 18
| Example | Column 2 | Exact mass | MS m/z (M + H) | HPLC MS $t_R$ |
|---|---|---|---|---|
| 419 | 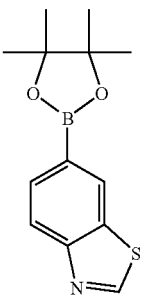 | 261.1 | 262.1 | 2.05 |
| 420 | 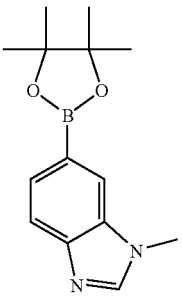 | 258.2 | 259.2 | 1.32 |
| 421 | 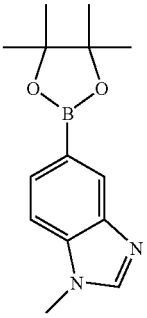 | 258.1 | 259.1 | 1.18 |
| 422 | 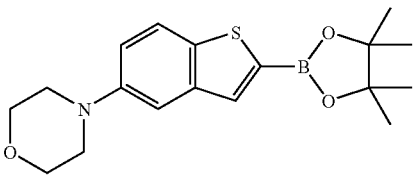 | 345.16 | 346.20 | 1.10 |
Preparation of Compound 426:
Scheme 29
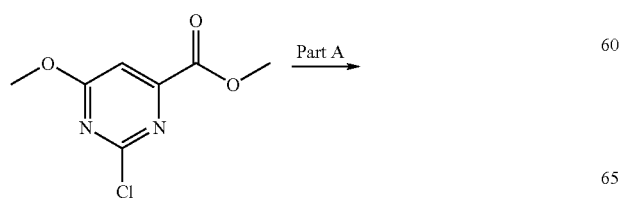 Part A

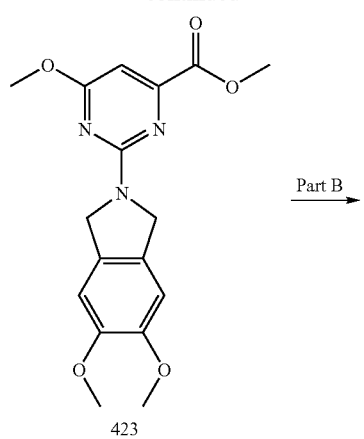

423

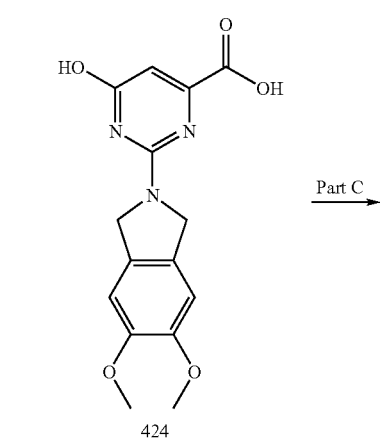

424

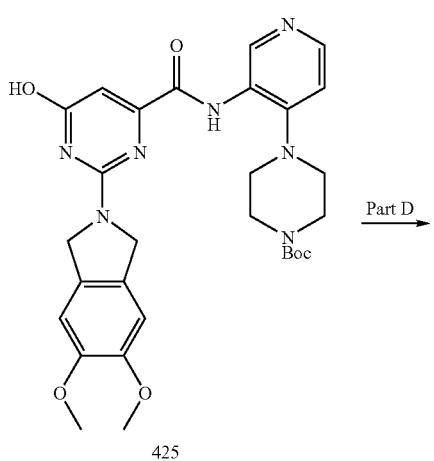

425

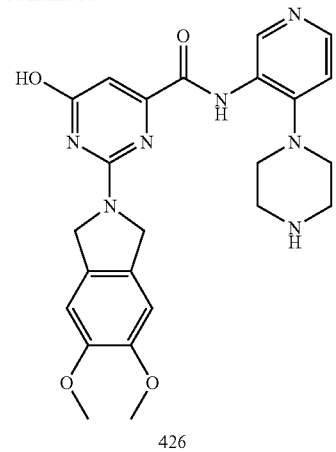

426

Compound 423:

Compound 423 has been synthesized with the same amination condition used in example 250 started from methyl 2-chloro-4-methoxy pyrimidne-6-carboxylate. HPLC-MS $t_R$=1.87 min (UV$_{254\ nm}$); mass calculated for formula $C_{17}H_{19}N_3O_5$ 345.1, observed LCMS m/z 346.1 (M+H).

Compound 424:

Compound 423 (20 mg) was mixed with concentrated HCl (1.5 mL) and the mixture was refluxed for 1 hour. The solvent was removed with concentration under vacuum and the crude product 424 was used in the next step without any further purification. HPLC-MS $t_R$=0.87 min (UV$_{254\ nm}$); mass calculated for formula $C_{15}H_{15}N_3O_5$ 317.1, observed LCMS m/z 318.1 (M+H).

Compound 425:

Compound 424 was prepared using the conditions described in example 251 started from compound 424. HPLC-MS $t_R$=1.27 min (UV$_{254\ nm}$); mass calculated for formula $C_{29}H_{35}N_7O_6$ 577.3, observed LCMS m/z 578.2 (M+H).

Compound 426:

Compound 426 was prepared using the same condition described in part B of Scheme 22, started from compound 425. HPLC-MS $t_R$=0.74 min (UV$_{254\ nm}$); mass calculated for formula $C_{24}H_{27}N_7O_4$ 477.2, observed LCMS m/z 478.1 (M+H).

Preparation of Compound 431:

Scheme 30

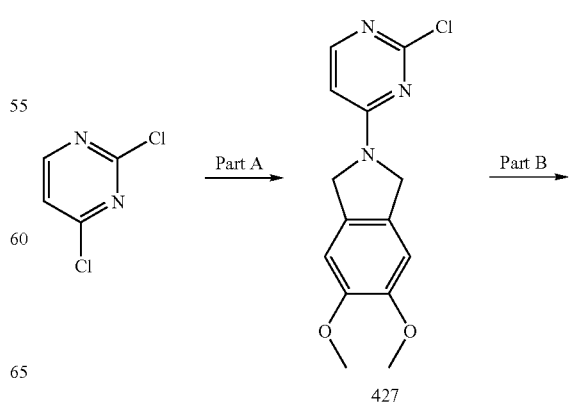

427

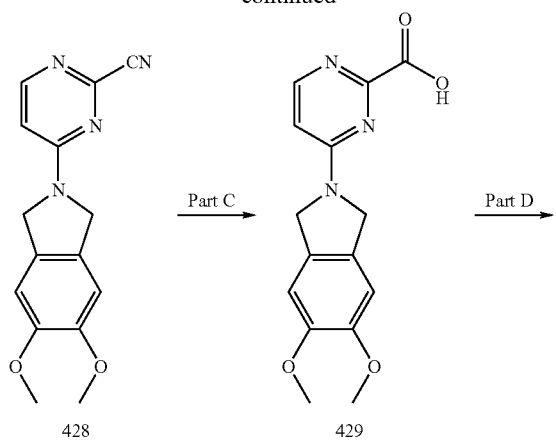

428     429

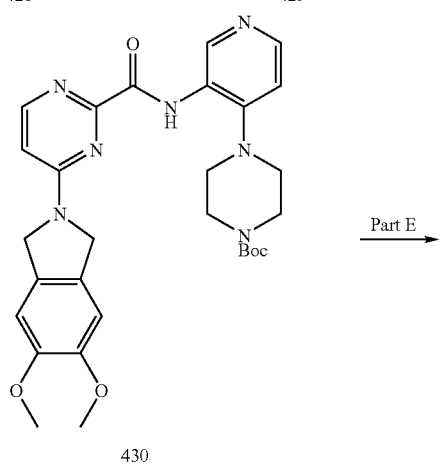

430

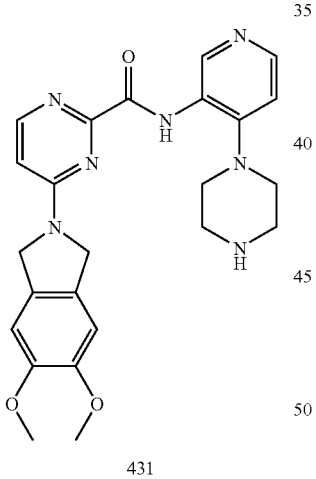

431

Compound 427:

Dichloropyrimidine (298 mg, 2.0 mmol) was dissolved in dry THF (10 mL) with Et$_3$N (280 uL, 2.0 mmol). The mixture was cooled to 0° C., and isoindoline (380 mg, 2.1 mmol) was added. The resulting mixture was warmed to room temperature and stirred for 3 hours. The EtOAc was added to dilute the mixture and the organics was washed with water, brine and dried over Na$_2$SO$_4$. After concentration, the residue was purified with column (silica gel, EtOAc/Hexane=30:70) to give the product 427 (311 mg) as light yellow solid. HPLC-MS $t_R$=1.49 min (UV$_{254\ nm}$); mass calculated for formula C$_{14}$H$_{14}$ClN$_3$O$_2$ 291.1, observed LCMS m/z 292.1 (M+H).

Compound 428:

The compound 427 (100 mg, 0.34 mmol) was dissolved in DMF (5 mL) and KCN (100 mg) was added. The mixture was heated up to 150° C. and stirred overnight. After cooling to room temperature, EtOAc was added to dilute the mixture and the organics was washed with water, brine and dried over Na$_2$SO$_4$. After concentration, the residue was purified with column (silica gel, EtOAc/Hexane=30:70) to give the product 428 (69 mg) as light yellow solid. HPLC-MS $t_R$=1.56 min (UV$_{254\ nm}$); mass calculated for formula C$_{15}$H$_{14}$N$_4$O$_2$ 282.1, observed LCMS m/z 283.1 (M+H).

Compound 429:

Compound 428 (28 mg, 0.1 mmol) was mixed with 15% NaOH (2 mL) and the mixture was heated to reflux and stirred for 2 hours. After cooling to room temperature, 6N HCl was added to adjust the pH to 5~6. The solid (429) was collected with filtration and used in the next step without any further purification. HPLC-MS $t_R$=0.76 min (UV$_{254\ nm}$); mass calculated for formula C$_{15}$H$_{15}$N$_3$O$_4$ 301.1, observed LCMS m/z 282.2 (M+H).

Compound 430:

Compound 430 was prepared with the same condition described in the example for making compound 250 (Scheme-22). HPLC-MS $t_R$=1.22 min (UV$_{254\ nm}$); mass calculated for formula C$_{29}$H$_{35}$N$_7$O$_5$ 561.3, observed LCMS m/z 562.2 (M+H).

Compound 431:

Compound 431 was prepared using the same condition described in part B of Scheme 22 (preparation of compound 251), starting from compound 430. HPLC-MS $t_R$=0.75 min (UV$_{254\ nm}$); mass calculated for formula C$_{24}$H$_{27}$N$_7$O$_3$ 461.2, observed LCMS m/z 462.3 (M+H).

Preparation of Compound 432:

Scheme 31

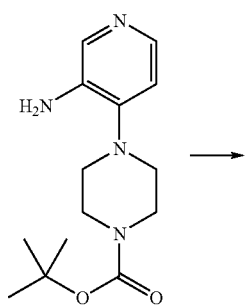

-continued

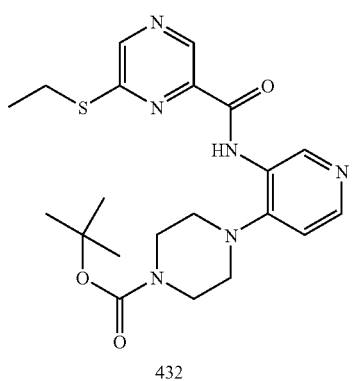

432

To a solution of compound 6-ethylthio pyrazine-2carboxilic acid (184 mg, 1 mmol) in DMF (4 ml) was added HATU (1.2 equivalents). The reaction mixture was stirred at room temperature for 10 minutes, and then added amine, 4-(3-Amino-pyridin-4-yl)-piperazine-1-carboxylic acid tert-butyl ester (333.6 mg, 1.2 equivalents) and diisopropylethylamine (3 equivalents). The reaction mixture was stirred at room temperature for 12 hours. The reaction mixture was concentrated under vacuum and purification by column chromatography (SiO2, Hexane/ethyl acetate) afforded compound 432 as a solid (310 mg, 70% yield). HPLC-MS tR=1.25 min (UV254 nm); mass calculated for formula C21H28N6O3S 444.19, observed LCMS m/z 445.15 (M+H).

Compound 433:

Scheme 32:

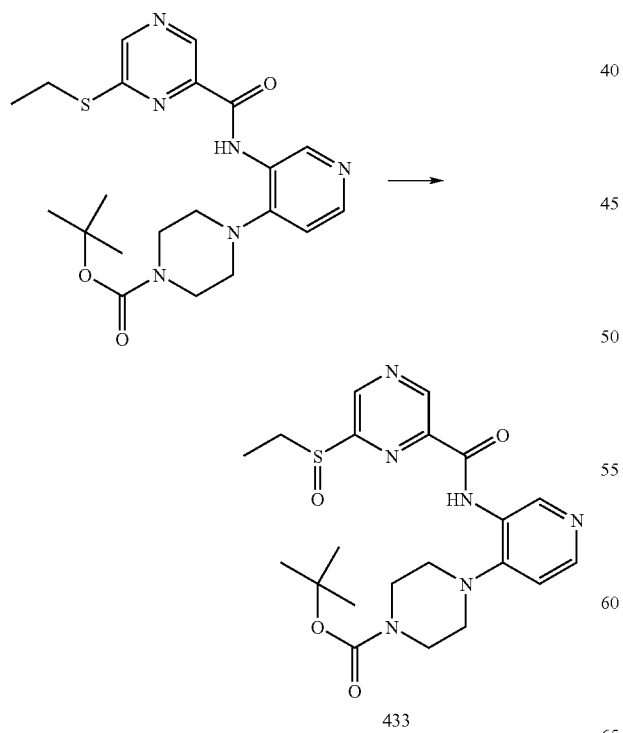

The mixture of compound 432 (93 mg, 0.210 mmol) and m-CPBA (51 mg, 77%, 1.1 mmol) in DCM (3 mL) was stirred at room temperature for 30 min and diluted with EtOAc (100 mL). The organics were washed with NaHCO$_3$ (sat. aq., 20 mL×2), brine and dried over Na$_2$SO$_4$. After concentration, the crude product 433 (90 mg, 93%) was used in the next step directly without further purification. HPLC-MS $t_R$=0.95 min (UV$_{254\ nm}$); mass calculated for formula $C_{21}H_{28}N_6O_4S$ 460.19, observed LCMS m/z 461.2 (M+H).

Compound 434:

Scheme 33

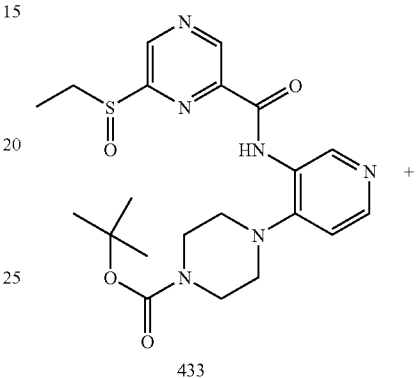

433

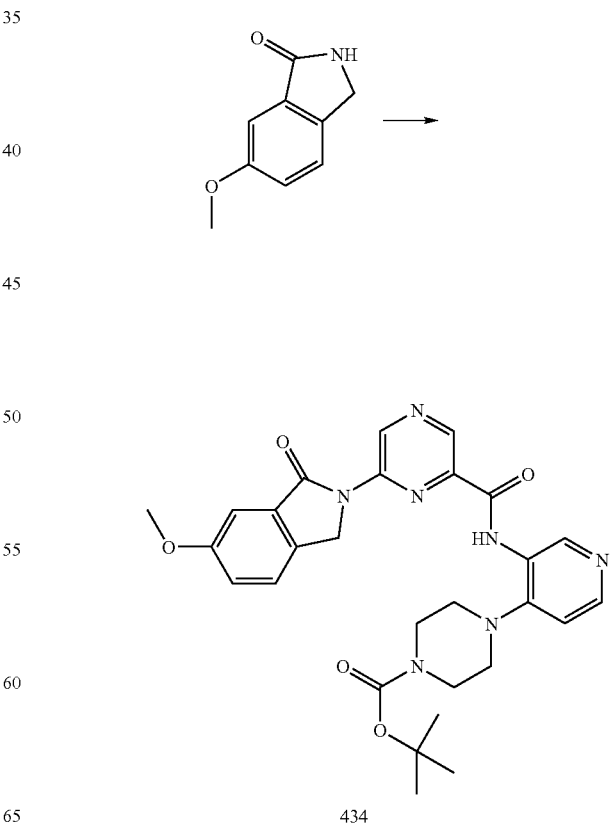

434

A solution of compound 6-methoxy-2,3-dihydro-isoindol-1-one (2 equivalents) in DMSO (1 mL) was treated with NaH (60% dispersion in oil, 2 equivalents) for 15 minutes at room temperature. Compound 433 (1 equivalent) was then added to this solution at room temperature and this solution was stirred at room temperature for 16 hour. LCMS analysis indicated that the reaction was complete. The reaction mixture was quenched with sat. Ammonium chloride (0.5 mL) and acetonitrile (0.5 mL). Purification by Prep-LC afforded compound 434. HPLC-MS $t_R$=3.56 min ($UV_{254\ nm}$); mass calculated for formula $C_{28}H_{31}N_7O_5$ 545.24, observed LCMS m/z 546.2 (M+H).

Compound 435:

Scheme 34

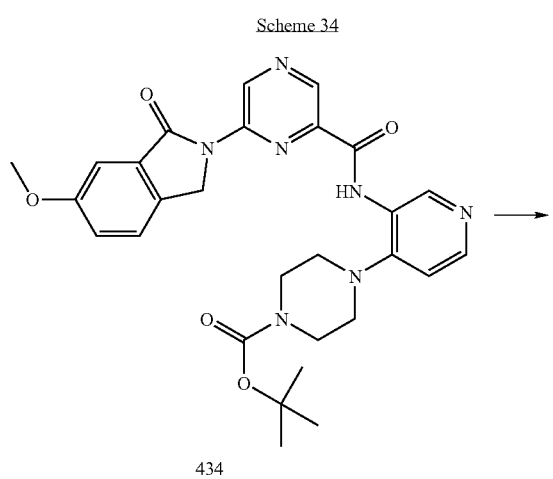

434

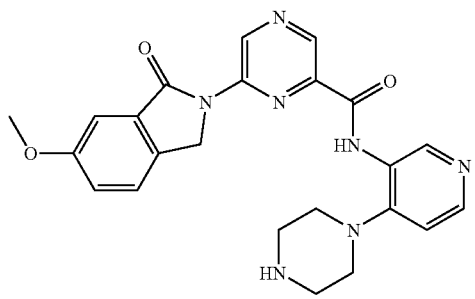

435

Compound 434 from prep LC was concentrated under vacuum and the residue was dissolved in dioxane (2 mL). To this solution added 4 N HCl in dioxane (2 mL) and stirred for 1 hour. After the completion of the reaction (LCMS analysis), concentrated and lyophilized to obtain compound 435 as a solid. HPLC-MS $t_R$=0.9 min ($UV_{254\ nm}$); mass calculated for formula $C_{23}H23N_7O_3$ 445.19, observed LCMS m/z 446.2 (M+H).

Compounds 436 and 437, listed in Table 19 below were synthesized by essentially utilizing the experimental details described for compounds 432 through 435

TABLE 19

| Compound # | Structure | MW | LCMS MH+ m/z | HPLC MS $t_R$ |
|---|---|---|---|---|
| 436 | 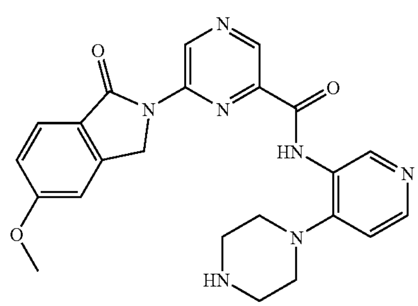 | 445.19 | 446.2 | 0.95 |
| 437 | 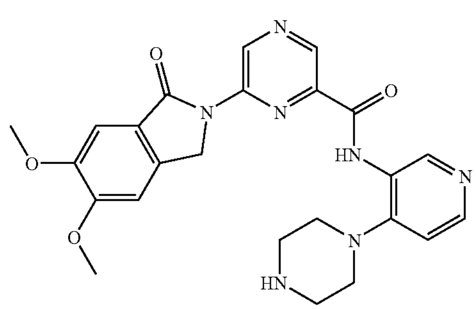 | 475.20 | 476.2 | 0.95 |

Compound, 438 listed in table 20 essentially is synthesized following the procedures described in for compounds through 432 through 435

TABLE 20

| Compound # | Structure | MW | LCMS MH+ m/z | HPLC MS $t_R$ |
|---|---|---|---|---|
| 438 | 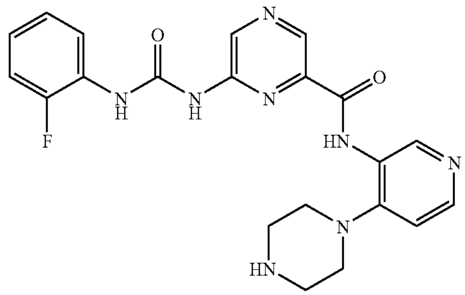 | | | |

Assays

CHK1 SPA Assay

An in vitro assay was developed that utilizes recombinant His-CHK1 expressed in the baculovirus expression system as an enzyme source and a biotinylated peptide based on CDC25C as substrate (biotin-RSGLYRSPSMPENLNRPR).

Materials and Reagents:
1) CDC25C Ser 216 C-term Biotinylated peptide substrate (25 mg), stored at 31 20° C., Custom Synthesis by Research Genetics: biotin-RSGLYRSPSMPENLNRPR 2595.4 MW
2) His-CHK1 In House lot P976, 235 µg/mL, stored at −80° C.
3) D-PBS (without CaCl and MgCl): GIBCO, Cat. #14190-144
4) SPA beads: Amersham, Cat. #SPQ0032: 500 mg/vial
   Add 10 mL of D-PBS to 500 mg of SPA beads to make a working concentration of 50 mg/mL. Store at 4° C. Use within 2 week after hydration.
5) 96-Well White Microplate with Bonded GF/B filter: Packard, Cat. #6005177
6) Top seal-A 96 well Adhesive Film: Perkin Elmer, Cat. #6005185
7) 96-well Non-Binding White Polystyrene Plate: Corning, Cat. #6005177
8) MgCl$_2$: Sigma, Cat. #M-8266
9) DTT: Promega, Cat. #V3155
10) ATP, stored at 4° C.: Sigma, Cat. #A-5394
11) γ$^{33}$P-ATP, 1000-3000 Ci/mMol: Amersham, Cat. #AH9968
12) NaCl: Fisher Scientific, Cat. #BP358-212
13) H$_3$PO$_4$ 85% Fisher, Cat. #A242-500
14) Tris-HCL pH 8.0: Bio-Whittaker, Cat. #16-015V
15) Staurosporine, 100 µg: CALBIOCHEM, Cat. #569397
16) Hypure Cell Culture Grade Water, 500 mL: HyClone, Cat. #SH30529.02

Reaction Mixtures:
1) Kinase Buffer: 50 mM Tris pH 8.0; 10 mM MgCl$_2$; 1 mM DTT
2) His-CHK1, In House Lot P976, MW ~30 KDa, stored at −80° C.
   6 nM is required to yield positive controls of ~5,000 CPM. For 1 plate (100 rxn): dilute 8 µL of 235 µg/mL (7.83 µM) stock in 2 mL Kinase Buffer. This makes a 31 nM mixture. Add 20 µL/well. This makes a final reaction concentration of 6 nM.
3) CDC25C Biotinylated peptide.
   Dilute CDC25C to 1 mg/mL (385 µM) stock and store at −20° C. For 1 plate (100 rxn): dilute 10 µL of 1 mg/mL peptide stock in 2 mL Kinase Buffer. This gives a 1.925 µM mix. Add 20 µL/rxn. This makes a final reaction concentration of 385 nM.
4) ATP Mix.
   For 1 plate (100 rxn): dilute 10 µL of 1 mM ATP (cold) stock and 2 µL fresh P33-ATP (20 µCi) in 5 mL Kinase Buffer. This gives a 2 µM ATP (cold) solution; add 50 µL/well to start the reaction. Final volume is 100 µL/rxn so the final reaction concentrations will be 1 µM ATP (cold) and 0.2 µCi/rxn.
5) Stop Solution:
   For 1 plate add: To 10 mL Wash Buffer 2 (2M NaCl 1% H$_3$PO$_4$):1 mL SPA bead slurry (50 mg); Add 100 µL/well
6) Wash buffer 1: 2 M NaCl
7) Wash buffer 2: 2 M NaCl, 1% H$_3$PO$_4$ Assay Procedure:

| Assay Component | Final Concentration | Volume |
|---|---|---|
| CHK1 | 6 nM | 20 µl/rxn |
| Compound (10% DMSO) | — | 10 µl/rxn |
| CDC25C | 0.385 µM | 20 µl/rxn |
| γ$^{33}$p-ATP | 0.2 µCi/rxn | 50 µl/rxn |
| Cold ATP | 1 µM | |
| Stop solution SPA beads | 0.5 mg/rxn | 100 µl/rxn* |
| | | 200 µl/rxn** |

*Total reaction volume for assay.
**Final reaction volume at termination of reaction (after addition of stop solution).

1) Dilute compounds to desired concentrations in water/10% DMSO—this will give a final DMSO concentration of 1% in the rxn. Dispense 10 µL/rxn to appropriate wells. Add 10 µL 10% DMSO to positive (CHK1+CDC25C+ATP) and negative (CHK1+ATP only) control wells.
2) Thaw enzyme on ice—dilute enzyme to proper concentration in kinase buffer (see Reaction Mixtures) and dispense 20 µL to each well.
3) Thaw the Biotinylated substrate on ice and dilute in kinase buffer (see Reaction Mixtures). Add 20 µL/well except to negative control wells. Instead, add 20 µL Kinase Buffer to these wells.

4) Dilute ATP (cold) and P33-ATP in kinase buffer (see Reaction Mixtures). Add 50 μL/well to start the reaction.
5) Allow the reaction to run for 2 hours at room temperature.
6) Stop reaction by adding 100 μL of the SPA beads/stop solution (see Reaction Mixtures) and leave to incubate for 15 minutes before harvest
7) Place a blank Packard GF/B filter plate into the vacuum filter device (Packard plate harvester) and aspirate 200 mL water through to wet the system.
8) Take out the blank and put in the Packard GF/B filter plate.
9) Aspirate the reaction through the filter plate.
10) Wash: 200 mL each wash; 1× with 2M NaCl; 1× with 2M NaCl/1% $H_3PO_4$
11) Allow filter plate to dry 15 min.
12) Put TopSeal-A adhesive on top of filter plate.
13) Run filter plate in Top Count
   Settings: Data mode: CPM
      Radio nuclide: Manual SPA:P33
      Scintillator: Liq/plast
      Energy Range: Low $IC_{50}$ DETERMINATIONS: Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values were derived by nonlinear regression analysis.

CDK2 Assay

BACULOVIRUS CONSTRUCTIONS: Cyclin E was cloned into pVL1393 (Pharmingen, La Jolla, Calif.) by PCR, with the addition of 5 histidine residues at the amino-terminal end to allow purification on nickel resin. The expressed protein was approximately 45 kDa. CDK2 was cloned into pVL1393 by PCR, with the addition of a haemaglutinin epitope tag at the carboxy-terminal end (YDVPDYAS). The expressed protein was approximately 34 kDa in size.

ENZYME PRODUCTION: Recombinant baculoviruses expressing cyclin E and CDK2 were co-infected into SF9 cells at an equal multiplicity of infection (MOI=5), for 48 hrs. Cells were harvested by centrifugation at 1000 RPM for 10 minutes, then pellets lysed on ice for 30 minutes in five times the pellet volume of lysis buffer containing 50 mM Tris pH 8.0, 150 mM NaCl, 1% NP40, 1 mM DTT and protease inhibitors (Roche Diagnostics GmbH, Mannheim, Germany). Lysates were spun down at 15000 RPM for 10 minutes and the supernatant retained. 5 mL of nickel beads (for one liter of SF9 cells) were washed three times in lysis buffer (Qiagen GmbH, Germany). Imidazole was added to the baculovirus supernatant to a final concentration of 20 mM, then incubated with the nickel beads for 45 minutes at 4° C. Proteins were eluted with lysis buffer containing 250 mM imidazole. Eluate was dialyzed overnight in 2 liters of kinase buffer containing 50 mM Tris pH 8.0, 1 mM DTT, 10 mM $MgCl_2$, 100 μM sodium orthovanadate and 20% glycerol. Enzyme was stored in aliquots at −70° C.

In Vitro Cyclin E/CDK2 Kinase Assay

Cyclin E/CDK2 kinase assays were performed in low protein binding 96-well plates (Corning Inc, Corning, N.Y.). Enzyme was diluted to a final concentration of 50 μg/mL in kinase buffer containing 50 mM Tris pH 8.0, 10 mM $MgCl_2$, 1 mM DTT, and 0.1 mM sodium orthovanadate. The substrate used in these reactions was a biotinylated peptide derived from Histone H1 (from Amersham, UK). The substrate was thawed on ice and diluted to 2 μM in kinase buffer. Compounds were diluted in 10% DMSO to desirable concentrations. For each kinase reaction, 20 μL of the 50 μg/mL enzyme solution (1 μg of enzyme) and 20 μl of the 2 μM substrate solution were mixed, then combined with 10 μL of diluted compound in each well for testing. The kinase reaction was started by addition of 50 μL of 2 μM ATP and 0.1 μCi of 33P-ATP (from Amersham, UK). The reaction was allowed to run for 1 hour at room temperature. The reaction was stopped by adding 200 μL of stop buffer containing 0.1% Triton X-100, 1 mM ATP, 5 mM EDTA, and 5 mg/mL streptavidine coated SPA beads (from Amersham, UK) for 15 minutes. The SPA beads were then captured onto a 96-well GF/B filter plate (Packard/Perkin Elmer Life Sciences) using a Filtermate universal harvester (Packard/Perkin Elmer Life Sciences.). Non-specific signals were eliminated by washing the beads twice with 2M NaCl then twice with 2 M NaCl with 1% phosphoric acid. The radioactive signal was then measured using a TopCount 96 well liquid scintillation counter (from Packard/Perkin Elmer Life Sciences).

$IC_{50}$ DETERMINATIONS: Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values were derived by nonlinear regression analysis.

MEK1 Kinase Assay

Full-length active phosphorylated MEK1 was expressed as a 6× histidine tagged protein ($His_6$-MEK1) by baculovirus infection of Hi-Five cells co-infected with a baculovirus expressing untagged constitutively active Raf-1. Several milligrams of active $His_6$-MEK1 was then purified by Ni-NTA affinity chromatography followed by gel filtration chromatography. Full-length murine catalytically inactive ERK2KR, which had the lysine in subdomain II mutated to arginine was used as a substrate. ERK2KR was expressed from vector pET32aRC in IPTG-induced BL21 D3 *E. coli* as a biotinylated, 6× histidine and thioredoxin tagged fusion protein and purified by Ni-NTA affinity chromatography followed by Mono Q ion exchange chromatography. Kinase reactions were performed in duplicate in a 96-well plate, 33 μL per well at 25° C. for 15 mins, and consisted of 20 nM $His_6$-MEK1, 2 μM ERK2KR, 2 μM ATP, 10 μCi/μL [γ-$^{33}$P]-ATP, 10 mM $MgCl_2$, 0.01% β-octylglucoside, 1 mM DTT, 20 mM HEPES pH 7.5, 3% DMSO and test compounds ranging from 20 μM down to 0.08 nM. Kinase reactions were stopped by addition of 30 μL of 1.5% o-phosphoric acid, transferred to Millipore Multiscreen-PH plates and incubated for 5 minutes to allow ERK2KR binding. Non-specific activity was estimated from pre-inactivated reactions wherein 30 μL of 1.5% o-phosphoric acid was added per well before addition of enzyme. Stopped plates were washed three times by vacuum filtration with 0.75% o-phosphoric acid followed by two washes with 100% ethanol and air dried. 50 μL of scintillation cocktail was added to each well and $^{33}$P incorporated into ERK2KR was detected using a Wallac Microbeta 1450 JET scintillation counter. Percentage inhibition, $IC_{50}$ and Hill slope values were calculated using ActivityBase software.

General Procedure for MEK1 TdF Assays

1 μM protein was mixed with micromolar concentrations (usually 1-50 μM) of compounds in 20 μl of assay buffer (25 mM HEPES, pH 7.4, 300 mM NaCl, 1 mM DTT, 2% DMSO, Sypro Orange 5×) in a white 96-well PCR plate. The plate is sealed by clear strips and placed in a thermocycler (Chromo4, BioRad). The fluorescence intensities are monitored at every 0.5° C. increment during melting from 25° C. to 95° C. The data are exported into an excel sheet and subject to a custom curve fitting algorithm to derive TdF Kd values. All TdF Kd values have an error margin of ~50% due to uncertainty with the enthalpy change of binding.

In Vitro Aurora TdF Assays

Aurora A Assay

Aurora A kinase assays were performed in low protein binding 384-well plates (Corning Inc). All reagents were thawed on ice. Test compounds were diluted in 100% DMSO to desirable concentrations. Each reaction consisted of 8 nM enzyme (Aurora A, Upstate cat #14-511), 100 nM Tamra-PKAtide (Molecular Devices, 5TAMRA-GRTGRRNSI-COOH), 25 µM ATP (Roche), 1 mM DTT (Pierce), and kinase buffer (10 mM Tris, 10 mM MgCl2, 0.01% Tween 20). For each reaction, 14 µl containing TAMRA-PKAtide, ATP, DTT and kianse buffer were combined with 1 µl diluted compound. The kinase reaction was started by the addition of 5 µl diluted enzyme. The reaction was allowed to run for 2 hours at room temperature. The reaction was stopped by adding 60 µl IMAP beads (1:400 beads in progressive (94.7% buffer A: 5.3% buffer B) 1× buffer, 24 mM NaCl). After an additional 2 hours, fluorescent polarization was measured using an Analyst AD (Molecular devices).

Aurora B Assay

Aurora A kinase assays were performed in low protein binding 384-well plates (Corning Inc). All reagents were thawed on ice. Compounds were diluted in 100% DMSO to desirable concentrations. Each reaction consisted of 26 nM enzyme (Aurora B, Invitrogen cat #pv3970), 100 nM Tamra-PKAtide (Molecular Devices, 5TAMRA-GRTGRRNSI-COOH), 50 µM ATP (Roche), 1 mM DTT (Pierce), and kinase buffer (10 mM Tris, 10 mM $MgCl_2$, 0.01% Tween 20). For each reaction, 14 µl containing TAMRA-PKAtide, ATP, DTT and kianse buffer were combined with 1 µl diluted compound. The kinase reaction was started by the addition of 5 µl diluted enzyme. The reaction was allowed to run for 2 hours at room temperature. The reaction was stopped by adding 60 µl IMAP beads (1:400 beads in progressive (94.7% buffer A: 5.3% buffer B) 1× buffer, 24 mM NaCl). After an additional 2 hours, fluorescent polarization was measured using an Analyst AD (Molecular devices).

$IC_{50}$ Determinations

Dose-response curves were plotted from inhibition data generated each in duplicate, from 8-point serial dilutions of test compounds. Concentration of compound was plotted against kinase activity, calculated by degree of fluorescent polarization. To generate $IC_{50}$ values, the dose-response curves were then fitted to a standard sigmoidal curve and $IC_{50}$ values were derived by nonlinear regression analysis.

The compounds of the present invention have Chk1 $IC_{50}$ values ranging from about 1 nM to about 50 µM or higher, Chk2 $IC_{50}$ values ranging from about 0.8 µM to about 50 µM or higher, CDK2 $IC_{50}$ values ranging from about 2.3 µM to about 50 µM or higher, and Chk1 $EC_{50}$ values ranging from about 0.15 µM to about 1.5 µM or higher.

The compounds of the present invention can be useful for treating or preventing a proliferative disease, such as cancer; an autoimmune disease; a viral disease; a fungal disease; a neurological or neurodegenerative disorder (e.g., Alzheimer's disease or Parkinson's disease); arthritis; inflammation; an ischemic injury; an anti-proliferative disorder (e.g., ocular retinopathy); a neuronal disease; alopecia; or a cardiovascular disease. Specific diseases and disorders treatable by administration of at least one compound of present invention include, but are not limited to, those disclosed in U.S. Pat. No. 6,413,974, which is incorporated by reference herein.

The compounds of the present invention have pharmacological properties. In one embodiment, the present compounds (i.e. those of Formula I-VI) can be inhibitors, regulators or modulators of protein kinases. Accordingly, the present compounds are useful for treating or preventing diseases and disorders related to the activity of one or more protein kinases. Non-limiting examples of protein kinases that can be inhibited, regulated or modulated by the compounds of the present invention include cyclin-dependent kinases (CDKs) such as CDK1, CDK2, CDK3, CDK4, CDK5, CDK6 and CDK7, CDK8; aurora kinases such as Aurora-A, Aurora-B and Aurora-C; mitogen activated protein kinase (MAPK/ERK); glycogen synthase kinase 3 (GSK3beta); c-Met kinases, such as c-Met; Pim-1 kinases; checkpoint kinases, such as Chk1 and Chk2; tyrosine kinases, such as the HER subfamily (including, for example, EGFR (HER1), HER2, HER3 and HER4), the insulin subfamily (including, for example, INS-R, IGF-IR, IR, and IR-R), the PDGF subfamily (including, for example, PDGF-alpha and beta receptors, CSFIR, c-kit and FLK-II), the FLK family (including, for example, kinase insert domain receptor (KDR), fetal liver kinase-1 (FLK-1), fetal liver kinase-4 (FLK-4) and the fms-like tyrosine kinase-1 (flt-1)); non-receptor protein tyrosine kinases, for example LCK, Src, Frk, Btk, Csk, Abl, Zap70, Fes/Fps, Fak, Jak, Ack, and LIMK; and growth factor receptor tyrosine kinases such as VEGF-R2, FGF-R, TEK, Akt kinases and the like.

The present compounds can be useful for inhibiting oncogenes that encode for protein kinases. Non-limiting examples of such oncogenes include C-Met.

The present compounds can be useful for treating or preventing a proliferative disease. Illustrative examples of proliferative diseases that can be treated or prevented according to the present methods include, but are not limited to, cancer, atherosclerosis, arthritis, psoriasis, idiopathic pulmonary fibrosis, scleroderma and cirrhosis of the liver.

Due to the key role of CDKs in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The present compounds may also be useful in the treatment of Alzheimer's disease, as suggested by the recent finding that CDK5 is involved in the phosphorylation of tau protein (J. Biochem, (1995) 117, 741-749).

The present compounds may induce or inhibit apoptosis. The apoptotic response is aberrant in a variety of human diseases. The present compounds, as modulators of apoptosis, will be useful in the treatment of cancer (including but not limited to those types mentioned hereinabove), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The present compounds, as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

The present compounds may also act as inhibitors of other protein kinases, e.g., protein kinase C, her2, raf 1, MEK1, MAP kinase, EGF receptor, PDGF receptor, IGF receptor, PI3 kinase, wee1 kinase, Src, Abl and thus be effective in the treatment of diseases associated with other protein kinases.

Accordingly, one aspect of this invention is a method for treating a disease or disorder in a patient, wherein the disease or disorder is associated with one or more protein kinases, the method comprising administering to the patient a therapeutically effective amount of at least one compound of the present invention, or a pharmaceutically acceptable salt, solvate, ester or prodrug thereof.

In a specific embodiment, the compounds of the present invention can be useful in the treatment or prevention of a variety of cancers and metastases thereof, including (but not limited to) the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including brain tumors such as an astrocytoma, a neuroblastoma, a glioma (such as glioblastoma multiforme) or a schwannoma; and other tumors, including melanoma, seminoma, teratocarcinoma, osteosarcoma, xenoderoma pigmentosum, keratoctanthoma, thyroid follicular cancer and Kaposi's sarcoma. The present compounds are useful for treating primary and/or metastatic tumors.

The present compounds may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

The present compounds may also be useful in inhibiting tumor angiogenesis and metastasis.

The compounds of this invention may also be useful in combination (administered together or sequentially in any order) with one or more separate anticancer treatments such as radiation therapy, and/or at least one anticancer agent different from the present compounds. The compounds of the present invention can be present in the same dosage unit as the anticancer agent or in separate dosage units.

Another aspect of the present invention is a method of treating one or more diseases associated with a cyclin dependent kinase, comprising administering to a patient in need of such treatment an amount of a first compound, which is a compound of Formula I-VI, or a pharmaceutically acceptable salt, solvate, ester, prodrug or stereoisomer thereof; and an amount of at least one second compound, the second compound being an anticancer agent different from the present compounds, wherein the amounts of the first compound and the second compound result in a therapeutic effect.

Non-limiting examples of additional anticancer agents (also known as anti-neoplastic agents) suitable for use in combination with the compounds of the present invention include cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide or teniposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoehtyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other useful additional anticancer agents include but are not limited to Uracil mustard, Chlormethine, Ifosfamide, Melphalan, Chlorambucil, Pipobroman, Triethylenemelamine, ara-C, adriamycin, cytoxan, Clofarabine (Clolar® from Genzyme Oncology, Cambridge, Mass.), cladribine (Leustat® from Janssen-Cilag Ltd.), aphidicolon, rituxan (from Genentech/Biogen Idec), sunitinib (Sutent® from Pfizer), dasatinib (or BMS-354825 from Bristol-Myers Squibb), tezacitabine (from Aventis Pharma), Sml1, fludarabine (from Trigan Oncology Associates), pentostatin (from BC Cancer Agency), triapine (from Vion Pharmaceuticals), didox (from Bioseeker Group), trimidox (from ALS Therapy Development Foundation), amidox, 3-AP (3-aminopyridine-2-carboxaldehyde thiosemicarbazone), MDL-101,731 ((E)-2'-deoxy-2'-(fluoromethylene)cytidine) and gemcitabine.

Other useful additional anticancer agents include but are not limited to Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Oxaliplatin, Aroplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, Herceptin, Bexxar, Velcade, Zevalin, Trisenox, Xeloda, Vinorelbine, Profimer, Erbitux, Liposomal, Thiotepa, Altretamine, Melphalan, Trastuzumab, Lerozole, Fulvestrant, Exemestane, Fulvestrant, Ifosfomide, Rituximab, C225 and Campath.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. The compounds of the present invention may also be administered sequentially with known anticancer or cytotoxic agents when a combination formulation is inappropriate. The invention is not limited in the sequence of administration; the present compounds may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in one aspect, this invention includes methods for treating cancer in a patient, comprising administering to the patient an amount of at least one compound of the present invention, or a pharmaceutically acceptable salt, solvate, ester, prodrug or stereoisomer thereof, and one or more other anticancer treatment modalities, wherein the amounts of the present compound(s)/other treatment modality result in the desired therapeutic effect. In one embodiment, the at least one compound of the present invention and the one or more other treatment modalities act synergistically. In one embodiment, the at least one compound of the present invention and the one or more other treatment modalities act additively.

In one embodiment, the other treatment modality is surgery.

In another embodiment, the other treatment modality is radiation therapy.

In another embodiment, the other treatment modality is biological therapy, such as hormonal therapy or anticancer vaccine therapy.

In another embodiment, the present invention provides a method of inhibiting one or more Checkpoint kinases in a patient in need thereof, comprising administering to the patient a therapeutically effective amount of at least one compound of the present invention or a pharmaceutically acceptable salt, solvate, ester, prodrug or stereoisomer thereof.

Another aspect of the present invention is a method of treating, or slowing the progression of, a disease associated with one or more Checkpoint kinases in a patient in need thereof, comprising administering a therapeutically effective amount of at least one compound of the present invention or a pharmaceutically acceptable salt, solvate, ester, prodrug or stereoisomer thereof.

Yet another aspect of the present invention is a method of treating one or more diseases associated with Checkpoint kinase, comprising administering to a patient in need of such treatment at least one compound of the present invention, or a pharmaceutically acceptable salt, solvate, ester, prodrug or stereoisomer thereof; and at least one additional anticancer agent, wherein the amounts of the at least one compound of the present invention and the at least one anticancer agent result in a therapeutic effect.

Another aspect of the present invention is a method of treating, or slowing the progression of, a disease associated with one or more Checkpoint kinases in a patient in need thereof, comprising administering a therapeutically effective amount of a pharmaceutical composition comprising in combination at least one pharmaceutically acceptable carrier and at least one compound of the present invention, or a pharmaceutically acceptable salt, solvate, ester, prodrug or stereoisomer thereof.

In the above methods, the checkpoint kinase to be inhibited can be Chk1 and/or Chk2.

Another aspect of the present invention is a method of inhibiting one or more tyrosine kinases in a patient in need thereof, comprising administering to the patient a therapeutically effective amount of at least one compound of the present invention or a pharmaceutically acceptable salt, solvate, ester, prodrug or stereoisomer thereof.

Yet another aspect of the present invention is a method of treating, or slowing the progression of, a disease associated with one or more tyrosine kinases in a patient in need thereof, comprising administering a therapeutically effective amount of at least one compound of the present invention or a pharmaceutically acceptable salt, solvate, ester, prodrug or stereoisomer thereof.

Another aspect of the present invention is a method of treating one or more diseases associated with tyrosine kinase, comprising administering to a patient in need of such treatment at least one compound of the present invention, or a pharmaceutically acceptable salt, solvate, ester, prodrug or stereoisomer thereof; and at least one additional anticancer agent, wherein the amounts of the at least one one compound of the present invention and the at least one anticancer agent result in a therapeutic effect.

Another aspect of the present invention is a method of treating, or slowing the progression of, a disease associated with one or more tyrosine kinases in a patient in need thereof, comprising administering a therapeutically effective amount of a pharmaceutical composition comprising in combination at least one pharmaceutically acceptable carrier and at least one compound of the present invention or a pharmaceutically acceptable salt, solvate, ester, prodrug or stereoisomer thereof.

In the above methods, the tyrosine kinase can be VEGFR (VEGF-R2), EGFR, HER2, SRC, JAK and/or TEK.

Another aspect of the present invention is a method of inhibiting one or more Pim-1 kinases in a patient in need thereof, comprising administering to the patient a therapeutically effective amount of at least one compound of the present invention or a pharmaceutically acceptable salt, solvate, ester, prodrug or stereoisomer thereof.

Yet another aspect of the present invention is a method of treating, or slowing the progression of, a disease associated with one or more Pim-1 kinases in a patient in need thereof, comprising administering a therapeutically effective amount of at least one compound of the present invention or a pharmaceutically acceptable salt, solvate, ester, prodrug or stereoisomer thereof.

Another aspect of the present invention is a method of treating one or more diseases associated with Pim-1 kinase, comprising administering to a patient in need of such treatment at least one compound of the present invention, or a pharmaceutically acceptable salt, solvate, ester, prodrug or stereoisomer thereof; and at least one additional anticancer agent, wherein the amounts of the at least one compound of the present invention and the at least one anticancer agent result in a therapeutic effect.

Another aspect of the present invention is a method of treating, or slowing the progression of, a disease associated with one or more Pim-1 kinases in a patient in need thereof, comprising administering a therapeutically effective amount of a pharmaceutical composition comprising in combination at least one pharmaceutically acceptable carrier and at least one compound of the present invention or a pharmaceutically acceptable salt, solvate, ester, prodrug or stereoisomer thereof.

Another aspect of the present invention is a method of treating one or more diseases associated with an Aurora kinase, comprising administering to a patient in need of such treatment at least one compound of the present invention, or a pharmaceutically acceptable salt, solvate, ester, prodrug or stereoisomer thereof; and at least one additional anticancer agent, wherein the amounts of the at least one compound of the present invention and the at least one anticancer agent result in a therapeutic effect.

Another aspect of the present invention is a method of treating, or slowing the progression of, a disease associated with one or more Aurora kinases in a patient in need thereof, comprising administering a therapeutically effective amount of a pharmaceutical composition comprising in combination at least one pharmaceutically acceptable carrier and at least one compound of the present invention or a pharmaceutically acceptable salt, solvate, ester, prodrug or stereoisomer thereof.

The pharmacological properties of the compounds of this invention may be confirmed by a number of pharmacological assays. The exemplified pharmacological assays which are described herein below have been carried out with compounds according to the invention and their salts, solvates, esters or prodrugs.

This invention is also directed to pharmaceutical compositions which comprise at least one compound of the present invention, or a pharmaceutically acceptable salt, solvate, ester or prodrug of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously or intrathecally or some suitable combination(s) thereof.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 500 mg. In one embodiment, the quantity of active compound in a unit dose of preparation is from about 0.01 mg to about 250 mg. In another embodiment, the quantity of active compound in a unit dose of preparation is from about 0.1 mg to about 100 mg. In another embodiment, the quantity of active compound in a unit dose of preparation is from about 1.0 mg to about 100 mg. In another embodiment, the quantity of active compound in a unit dose of preparation is from about 1.0 mg to about 50 mg. In still another embodiment, the quantity of active compound in a unit dose of preparation is from about 1.0 mg to about 25 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.01 mg/day to about 2000 mg/day of the compounds of the present invention. In one embodiment, a daily dosage regimen for oral administration is from about 1 mg/day to 1000 mg/day. In another embodiment, a daily dosage regimen for oral administration is from about 1 mg/day to 500 mg/day. In another embodiment, a daily dosage regimen for oral administration is from about 100 mg/day to 500 mg/day. In another embodiment, a daily dosage regimen for oral administration is from about 1 mg/day to 250 mg/day. In another embodiment, a daily dosage regimen for oral administration is from about 100 mg/day to 250 mg/day. In still another embodiment, a daily dosage regimen for oral administration is from about 1 mg/day to 100 mg/day. In still another embodiment, a daily dosage regimen for oral administration is from about 50 mg/day to 100 mg/day. In a further embodiment, a daily dosage regimen for oral administration is from about 1 mg/day to 50 mg/day. In another embodiment, a daily dosage regimen for oral administration is from about 25 mg/day to 50 mg/day. In a further embodiment, a daily dosage regimen for oral administration is from about 1 mg/day to 25 mg/day. The daily dosage may be administered in a single dosage or can be divided into from two to four divided doses.

In one aspect, the present invention provides a kit comprising a therapeutically effective amount of at least one compound of the present invention, or a pharmaceutically acceptable salt, solvate, ester or prodrug of said compound and a pharmaceutically acceptable carrier, vehicle or diluent.

In another aspect the present invention provides a kit comprising an amount of at least one compound of the present invention, or a pharmaceutically acceptable salt, solvate, ester or prodrug of said compound and an amount of at least one anticancer therapy and/or additional anticancer agent listed above, wherein the amounts of the two or more ingredients result in desired therapeutic effect.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

A number of references have been cited, the entire disclosures of which have been incorporated herein in their entirety.

What is claimed is:

1. A compound according to the following Formula:

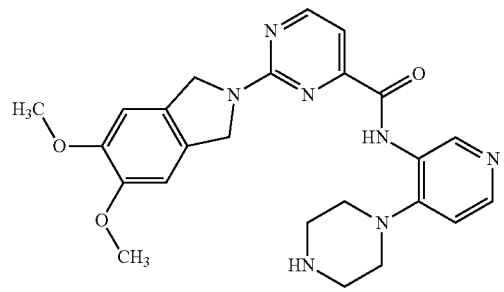

or a pharmaceutically acceptable salt thereof.

2. A pharmaceutical composition comprising a therapeutically effective amount of the compound of claim 1 or a pharmaceutically acceptable salt thereof, in combination with at least one pharmaceutically acceptable carrier.

* * * * *